(12) United States Patent
Markowitz et al.

(10) Patent No.: US 12,404,538 B2
(45) Date of Patent: Sep. 2, 2025

(54) COMPOSITIONS AND METHODS FOR PRESERVING DNA METHYLATION

(71) Applicant: Case Western Reserve University, Cleveland, OH (US)

(72) Inventors: Sanford D. Markowitz, Pepper Pike, OH (US); Helen Moinova, Beachwood, OH (US); Joseph Ready, Carrollton, TX (US)

(73) Assignee: Case Western Reserve University, Cleveland, OH (US)

( * ) Notice: Subject to any disclaimer, the term of this patent is extended or adjusted under 35 U.S.C. 154(b) by 120 days.

(21) Appl. No.: 17/927,525

(22) PCT Filed: May 26, 2021

(86) PCT No.: PCT/US2021/034274
§ 371 (c)(1),
(2) Date: Nov. 23, 2022

(87) PCT Pub. No.: WO2021/242872
PCT Pub. Date: Dec. 2, 2021

(65) Prior Publication Data
US 2024/0417775 A1 Dec. 19, 2024

Related U.S. Application Data

(60) Provisional application No. 63/172,279, filed on Apr. 8, 2021, provisional application No. 63/030,407, filed on May 27, 2020.

(51) Int. Cl.
*C12N 15/10* (2006.01)
*A01N 1/00* (2006.01)
*C12Q 1/6806* (2018.01)

(52) U.S. Cl.
CPC ............. *C12Q 1/6806* (2013.01); *A01N 1/00* (2013.01); *C12N 15/10* (2013.01); *C12Q 2600/154* (2013.01)

(58) Field of Classification Search
None
See application file for complete search history.

(56) References Cited

U.S. PATENT DOCUMENTS

| | | |
|---|---|---|
| 4,499,183 A | 2/1985 | Sujansky et al. |
| 4,714,606 A | 12/1987 | Kass |

(Continued)

FOREIGN PATENT DOCUMENTS

| | | |
|---|---|---|
| CA | 2314695 A1 | 3/2001 |
| CA | 2667790 A1 | 6/2008 |

(Continued)

OTHER PUBLICATIONS

ThinPrep® PreservCyt® Solution Material Safety Data Sheet (MSDS), Feb. 2010, https://www.rmlonline.com/images/data/attachments/0000/1967/Hologic_Thinprep_SDS.pdf.*

(Continued)

*Primary Examiner* — Aaron A Priest
(74) *Attorney, Agent, or Firm* — Greenberg Traurig, LLP; Chinh Pham; Natalie Salem

(57) ABSTRACT

The disclosure provides methods for storage solutions for preserving DNA methylation patterns over a period of time. The disclosure also provides for methods of using methylated DNA stored in such storage solutions.

18 Claims, 41 Drawing Sheets

Specification includes a Sequence Listing.

(56) References Cited

U.S. PATENT DOCUMENTS

| | | | |
|---|---|---|---|
| 4,870,002 | A | 9/1989 | Kiel |
| 5,786,146 | A | 7/1998 | Herman et al. |
| 6,017,704 | A | 1/2000 | Herman et al. |
| 6,200,756 | B1 | 3/2001 | Herman et al. |
| 6,265,171 | B1 | 7/2001 | Herman et al. |
| 6,821,725 | B1 | 11/2004 | Carrasco et al. |
| 9,580,754 | B2 | 2/2017 | Markowitz et al. |
| 2002/0168763 | A1 | 11/2002 | Yan et al. |
| 2003/0211452 | A1 | 11/2003 | Vincek et al. |
| 2004/0115692 | A1 | 6/2004 | Linder et al. |
| 2004/0137551 | A1 | 7/2004 | Markovic et al. |
| 2007/0298431 | A1 | 12/2007 | Mai |
| 2009/0286237 | A1 | 11/2009 | Fitzgerald et al. |
| 2010/0248250 | A1 | 9/2010 | Tanigami et al. |
| 2013/0171622 | A1 | 7/2013 | Luk et al. |
| 2014/0193848 | A1 | 7/2014 | Kaufman |
| 2014/0296079 | A1 | 10/2014 | Albitar |
| 2016/0058713 | A1 | 3/2016 | Singh |
| 2016/0083791 | A1 | 3/2016 | Gillespie et al. |
| 2016/0317132 | A1 | 11/2016 | Markowitz et al. |
| 2019/0309372 | A1 | 10/2019 | Markowitz et al. |
| 2022/0073994 | A1* | 3/2022 | Szyf .................. G16B 20/20 |
| 2022/0243281 | A1 | 8/2022 | Markowitz et al. |

FOREIGN PATENT DOCUMENTS

| | | | |
|---|---|---|---|
| CA | 2741650 | A1 | 6/2010 |
| CN | 101952460 | A | 1/2011 |
| CN | 106222142 | A | 12/2016 |
| CN | 109757109 | A | 5/2019 |
| CN | 110859177 | A | 3/2020 |
| EP | 0212403 | A2 | 3/1987 |
| EP | 266077 | A1 | 5/1988 |
| EP | 344808 | B1 | 3/1995 |
| EP | 846761 | A1 | 6/1998 |
| EP | 2218792 | A1 | 8/2010 |
| FR | 2634211 | A1 | 1/1990 |
| JP | 2004511209 | A | 4/2004 |
| WO | 1985004587 | A1 | 10/1985 |
| WO | 1987006617 | A2 | 11/1987 |
| WO | 1987007912 | A1 | 12/1987 |
| WO | 1989005981 | A1 | 6/1989 |
| WO | 1993005177 | A1 | 3/1993 |
| WO | 1995023223 | A1 | 8/1995 |
| WO | 1997008345 | A1 | 3/1997 |
| WO | 1999031273 | A2 | 6/1999 |
| WO | 2001002599 | A2 | 1/2001 |
| WO | 2004033622 | A2 | 4/2004 |
| WO | 2004047747 | A2 | 6/2004 |
| WO | 2005040351 | A2 | 5/2005 |
| WO | 2005121373 | A2 | 12/2005 |
| WO | 2006089163 | A2 | 8/2006 |
| WO | 2007106425 | A2 | 9/2007 |
| WO | 2009011892 | A1 | 1/2009 |
| WO | 2010102632 | A2 | 9/2010 |
| WO | 2011146683 | A1 | 11/2011 |
| WO | 2013050950 | A2 | 4/2013 |
| WO | 2014036040 | A2 | 3/2014 |
| WO | 2014134570 | A1 | 9/2014 |
| WO | 2017002861 | A1 | 1/2017 |
| WO | 2017205560 | A1 | 11/2017 |
| WO | 2018009535 | A1 | 1/2018 |
| WO | 2018083646 | A3 | 6/2018 |
| WO | 2018170359 | A1 | 9/2018 |
| WO | 2019092718 | A1 | 9/2018 |
| WO | 2019160059 | A1 | 8/2019 |
| WO | 2020243240 | A1 | 12/2020 |

OTHER PUBLICATIONS

Hologic, ThinPrep PreservCyt Solution Material Safety Data Sheet.
Kapoore et al., "Influence of Washing and Quenching in Profiling the Metabolome of Adherent Mammalian Cells: A Case Study with the Metastatic Breast Cancer Cell Line MDA-MB-231" Analyst, vol. 142, No. 11, pp. 2038-2049, May 5, 2017.
Staunstrup et al., "The Genome-Wide DNA Methylation Profile of Peripheral Blood is not Systematially Changed by Short-Time Storage at Room Temperature" Epigenomes, vol. 1, No. 23, pp. 1-11, 2017.
Extended European Search Report and Opinion in EP Patent Application 20 814 329.7 dated Sep. 22, 2023 (11 pages).
Altschul et al., "Basic Local Alignment Search Tool," Journal of Molecular Biology, Oct. 5, 1990, vol. 215, No. 3, pp. 403-410.
Altschul et al., "Gapped BLAST and PSI-BLAST: A New Generation of Protein Database Search Programs.," Nucleic Acids Research, Sep. 1, 1997, vol. 25, No. 17, pp. 3389-3402.
Beaulaurier et al., "Deciphering Bacterial Epigenomes Using Modern Sequencing Technologies," Nature Reviews. Genetics, Mar. 2019, vol. 20, No. 3, pp. 157-172.
Camacho-Sanchez et al., "Preservation of RNA and DNA from mammal samples under field conditions," Molecular Ecology Resources, Jul. 2013, vol. 13, No. 4, pp. 663-673.
Carrillo et al., "The Multiple Sequence Alignment Problem in Biology," SIAM Journal on Applied Mathematics, Oct. 1988, vol. 48, No. 5, pp. 1073-1082.
Devereux et al., "A Comprehensive Set of Sequence Analysis Programs for the VAX," Nucleic Acids Research, Jan. 11, 1984, vol. 12, No. 1 Pt 1, pp. 387-395.
Godhe et al., "PCR Amplification of Microalgal DNA for Sequencing and Species Identification: Studies on Fixatives and Algal Growth Stages," Harmful Algae, Dec. 2002, vol. 1, No. 4, pp. 375-382.
Gonzalgo et al., "Rapid Quantitation of Methylation Differences at Specific Sites Using Methylation-Sensitive Single Nucleotide Primer Extension (Ms-SNuPE)," Nucleic Acids Research, Jun. 1, 1997, vol. 25, No. 12, pp. 2529-2531.
Henning et al., "Isolation and Taxonomic Identity of Bacteriocin-Producing Lactic Acid Bacteria from Retail Foods and Animal Sources," Microorganisms, Mar. 19, 2015, vol. 3, No. 1, pp. 80-93.
Herman et al., "Methylation-Specific PCR: A Novel PCR Assay for Methylation Status of CpG Islands," Proceedings of the National Academy of Sciences of the United States of America, Sep. 3, 1996, vol. 93, No. 18, pp. 9821-9826.
Herranz-Jusdado, J. G. et al., "Comparison of European eel sperm cryopreservation protocols with standardization as a target", Aquaculture, 2019, vol. 498, pp. 539-544, published Jan. 1, 2019.
Kane et al., "Methylation of the HMLH1 Promoter Correlates with Lack of Expression of HMLH1 in Sporadic Colon Tumors and Mismatch Repair-Defective Human Tumor Cell Lines1," Cancer Research, Mar. 1, 1997, vol. 57, No. 5, pp. 808-811.
Li, P. et al., "DNA integrity of Polydon spathula cryopreserved sperm," J. Appl. Ichthyol., 2008, vol. 24, pp. 121-125 Summary; Materials and Methods; Fig. 1.
Moinova et al., Science translational medicine, 2018;10 (424), PMCID:PMC5789768.
"Motility Diagnostic Services | UC Davis Health", Health.ucdavis.edu/internalmedicine/gastro/esophmanometry.html, 2 pages, printed on Apr. 25, 2023. (Year: 2023).
Van Dam et al., "Comparative Evaluation of Fresh, Fixed, and Cryopreserved Solid Tumor Cells for Reliable Flow Cytometry of DNA and Tumor Associated Antigen," Cytometry, 1992, vol. 13, No. 7, pp. 722-729.
Velinov et al., "PCR-Based Methylation Testing for Prader-Willi or Angelman Syndromes Using Archived Fixed-Cell Suspensions," Genetic Testing, 2001, vol. 5, No. 2, pp. 153-155.
Xiong et al., "COBRA: A Sensitive and Quantitative DNA Methylation Assay," Nucleic Acids Research, Jun. 15, 1997, vol. 25, No. 12, pp. 2532-2534.
Zou et al., "Quantification of Methylated Markers with a Multiplex Methylation-Specific Technology," Clinical Chemistry, Feb. 2012, vol. 58, No. 2, pp. 375-383.
Alles et al., "Cell Fixation and Preservation for Droplet-Based Single-Cell Transcriptomics," BMC Biology, May 19, 2017, vol. 15, No. 44, pp. 1-14.

(56) References Cited

OTHER PUBLICATIONS

Henning et al., "Identification of Multiple Bacteriocins in *Enterococcus* spp. Using an Enterococcus-Specific Bacteriocin PCR Array," Microorganisms, Feb. 4, 2015, vol. 3, pp. 1-16.

Yuan et al., "Optimized Protocol of Methanol Treatment for Immunofluorescent Staining in Fixed Brain Slices," Appl. Immunohistochem Mol. Morphol., Mar. 2017, vol. 25, No. 3, pp. 221-224.

Maatouk et al., "DNA Methylation is a Primary Mechanism for Silencing Postmigratory Primordial Germ Cell Genes in Both Germ Cell and Somatic Cell Lineages," Development, Jun. 2006, vol. 133, No. 17, pp. 3411-3418.

Ren et al., "Methanol Fixed Fibroblasts Serve as Feeder Cells to Maintain Stem Cells in the Pluripotent State in Vitro," Scientific Reports, May 17, 2018, vol. 8, No. 1, pp. 7780-7790.

Enright et al., "Methylation and Acetylation Characteristics of Cloned Bovine Embryos from Donor Cells Treated with 5-asa-2'—Deoxycytidine," Biology of Reproduction, Apr. 1, 2005, vol. 72, No. 4, pp. 944-948.

Chen et al., "PBMC Fixation and Processing for Chromium Single-Cell RNA Sequencing," Journal of Translational Medicine, Dec. 2018, vol. 16, pp. 1-11.

International Search Report issued for International Application No. PCT /US2021/034274, mailed Aug. 16, 2021 (7 pages).

Josipovic et al., "Antagonistic and Synergistic Epigenetic Modulation Using Orthologous CRISPR/dCas9-based Modular System," Nucleic Acids Research, vol. 47, No. 18, pp. 9637-9657, 2019.

Marinus et al., "DNA Methylation," EcoSal Plus, vol. 6, No. 1, pp. 1-62, May 2014.

Extended European Search Report dated May 3, 2024 in corresponding European Patent Application No. 21813179.5 (10 pages).

\* cited by examiner

COMPOSITIONS AND METHODS FOR PRESERVING DNA METHYLATION

RELATED APPLICATIONS

This application is a national stage filing under 35 U.S.C. § 371 of International Application No. PCT/US2021/034274, filed on May 26, 2021, which claims the benefit of and priority to U.S. Provisional Application No. 63/030,407, filed on May 27, 2020 and U.S. Provisional Application No. 63/172,279, filed on Apr. 8, 2021. The specifications of each of the foregoing applications are hereby incorporated herein by reference in their entirety.

FUNDING

This invention was made with government support under Grant CA152756 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Nov. 22, 2022, is named 1848493-100-301_Seq.txt and is 25,944 bytes in size.

BACKGROUND

Cytosine methylation is frequently referred to as being the "fifth base" in DNA of eukaryotic genomes. Altered patterns of DNA cytosine methylation are recognized as an accompaniment, a biomarker, and a sometimes causal element in multiple human disease states, including various metaplasias, neoplasias and cancers. However, while DNA polynucleotide sequences are stable at room temperature for extended periods of time, methylation patterns are more likely to deviate from original methylation patterns when stored at room temperature for an extended period of time. As such, there is a need for new storage conditions for preserving DNA methylation patterns for prolonged periods of time.

SUMMARY OF THE DISCLOSURE

In some embodiments, the disclosure provides for a composition comprising a biological sample comprising a methylated DNA sequence; and a storage solution comprising methanol and tris(hydroxymethyl)aminomethane (tris); wherein methylation patterns of the methylated DNA sequence are preserved. In certain embodiments, the tris has a pH of from 7.0 to 9.0. In certain embodiments, the tris has a pH of from 7.0 to 8.0. In certain embodiments, the tris has a pH of from 7.5 to 8.5. In certain embodiments, the tris has a pH of from 7.5 to 8.0. In certain embodiments, the tris is present in a concentration of from 1 mM to 250 mM. In certain embodiments, the tris is present in a concentration of from 1 mM to 100 mM. In certain embodiments, the tris is present in a concentration of from 5 mM to 50 mM. In certain embodiments, the tris is present in a concentration of from 5 mM to 20 mM. In certain embodiments, the tris is present in a concentration of from 20 mM to 250 mM. In certain embodiments, the tris is present in a concentration of from 20 mM to 100 mM. In certain embodiments, the tris is present in a concentration of from 30 mM to 70 mM. In certain embodiments, the tris is present in a concentration of from 30 mM to 50 mM. In certain embodiments, the tris is present in a concentration of 10 mM. In certain embodiments, the tris is present in a concentration of 50 mM. In certain embodiments, the storage solution further comprises butylated hydroxytoluene (BHT). In certain such embodiments, the BHT is present in an amount from 1 to 500 ppm. In certain embodiments, the BHT is present in an amount from 20 to 200 ppm. In certain embodiments, the BHT is present in an amount from 25 to 100 ppm. In some embodiments, the disclosure provides for a composition comprising a biological sample and a storage solution; wherein the biological sample comprises a methylated DNA sequence; wherein the storage solution comprises methanol and BHT; and wherein the composition preserves the methylation pattern of the biological sample. In certain such embodiments, the BHT is present in an amount from 1 to 500 ppm. In certain embodiments, the BHT is present in an amount from 20 to 200 ppm. In certain embodiments, the BHT is present in an amount from 25 to 100 ppm. In some embodiments, the methylation pattern is preserved for at least 2 weeks. In some embodiments, the methylation pattern is preserved for at least 3 weeks. In some embodiments, the methylation pattern is preserved at room temperature. In some embodiments, the methylation pattern of the biological sample in the storage solution is preserved by at least 60% in comparison to the methylation pattern in the biological sample prior to storage. In some embodiments, the methylation pattern of the biological sample in the storage solution is preserved by at least 65% in comparison to the methylation pattern in the biological sample prior to storage. In some embodiments, the methylation pattern of the biological sample in the storage solution is preserved by at least 70% in comparison to the methylation pattern in the biological sample prior to storage. In some embodiments, the methylation pattern of the biological sample in the storage solution is preserved by at least 75% in comparison to the methylation pattern in the biological sample prior to storage. In some embodiments, the methylation pattern of the biological sample in the storage solution is preserved by at least 80% in comparison to the methylation pattern in the biological sample prior to storage. In some embodiments, the methylation pattern of the biological sample in the storage solution is preserved by at least 85% in comparison to the methylation pattern in the biological sample prior to storage. In some embodiments, the methylation pattern of the biological sample in the storage solution is preserved by at least 90% in comparison to the methylation pattern in the biological sample prior to storage. In some embodiments, the methylation pattern of the biological sample in the storage solution is preserved by at least 95% in comparison to the methylation pattern in the biological sample prior to storage. In some embodiments, the sample is a human biological sample. In some embodiments, the biological sample is a sample from any of: gastrointestinal tract, aerodigestive tract, respiratory tract, genitourinary tract, or a body fluid. In certain such embodiments, the body fluid is any of: blood, urine, sputum, saliva, stool, bile, pancreatic juice, nasal secretions, tears, semen, vaginal secretions, cerebrospinal fluid, pleural fluid, peritoneal fluid, gastric juice, pericardial fluid, sweat, lymph, cyst fluid, pancreatic cyst fluid, synovial fluid, joint fluid, menstrual fluid, endometrial washing, breast aspirate, or amniotic fluid. In some embodiments, the biological sample is a sample from any of: esophagus, stomach, colon, small intestine, pancreas, liver, oral cavity, oropharynx, trachea, bronchial tree, lung, or breast. In some embodiments, the biological sample is an esophageal biological sample. In some embodiments, the storage solution comprises tris and 100% methanol. In some embodiments, the storage solution comprises tris and 10% to 100% methanol admixed with water. In some embodiments, the storage solution comprises tris and 10-95% methanol admixed with water. In some embodiments, the storage solution comprises tris and 10-90% methanol admixed with water. In some embodiments, the storage solution comprises tris and 15-90% methanol admixed with water. In some embodiments, the storage solution comprises tris and 20-90% methanol admixed with water. In some embodiments, the storage solution comprises tris and 25-90% methanol admixed with water. In some embodiments, the storage solution comprises tris and 30-90% methanol admixed with water. In some embodiments, the storage solution comprises tris and 30-85% methanol admixed with water. In some embodiments, the storage solution comprises tris and 30-80% methanol admixed with water. In some embodiments, the storage solution comprises tris and 35-80% methanol admixed with water. In some embodiments, the storage solution comprises tris and 35-75% methanol admixed with water. In some embodiments, the storage solution comprises tris and 35-70% methanol admixed with water. In some embodiments, the storage solution comprises tris and 30-70% methanol admixed with water. In some embodiments, the storage solution comprises tris and 40-70% methanol admixed with water. In some embodiments, the storage solution comprises tris and 40-65% methanol admixed with water. In some embodiments, the storage solution comprises tris and 40-60% methanol admixed with water. In some embodiments, the storage solution comprises tris and 40-55% methanol admixed with water. In some embodiments, the storage solution comprises tris and 45-55% methanol admixed with water. In some embodiments, the storage solution comprises tris and 50% methanol admixed with water. In some embodiments, the storage solution comprises BHT and 100% methanol. In some embodiments, the storage solution comprises BHT and 10% to 100% methanol admixed with water. In some embodiments, the storage solution comprises BHT and 10-95% methanol admixed with water. In some embodiments, the storage solution comprises BHT and 10-90% methanol admixed with water. In some embodiments, the storage solution comprises BHT and 15-90% methanol admixed with water. In some embodiments, the storage solution comprises BHT and 20-90% methanol admixed with water. In some embodiments, the storage solution comprises BHT and 25-90% methanol admixed with water. In some embodiments, the storage solution comprises BHT and 30-90% methanol admixed with water. In some embodiments, the storage solution comprises BHT and 30-85% methanol admixed with water. In some embodiments, the storage solution comprises BHT and 30-80% methanol admixed with water. In some embodiments, the storage solution comprises BHT and 35-80% methanol admixed with water. In some embodiments, the storage solution comprises BHT and 35-75% methanol admixed with water. In some embodiments, the storage solution comprises BHT and 35-70% methanol admixed with water. In some embodiments, the storage solution comprises BHT and 30-70% methanol admixed with water. In some embodiments, the storage solution comprises BHT and 40-70% methanol admixed with water. In some embodiments, the storage solution comprises BHT and 40-65% methanol admixed with water. In some embodiments, the storage solution comprises BHT and 40-60% methanol admixed with water. In some embodiments, the storage solution comprises BHT and 40-55% methanol admixed with water. In some embodiments, the storage solution comprises BHT and 45-55% methanol admixed with water. In some embodiments, the storage solution comprises BHT and 50% methanol admixed with water. In some embodiments, the storage solution comprises tris, BHT and 100% methanol. In some embodiments, the storage solution comprises tris, BHT and 10% to 100% methanol admixed with water. In some embodiments, the storage solution comprises tris, BHT and 10-95% methanol admixed with water. In some embodiments, the storage solution comprises tris, BHT and 10-90% methanol admixed with water. In some embodiments, the storage solution comprises tris, BHT and 15-90% methanol admixed with water. In some embodiments, the storage solution comprises tris, BHT and 20-90% methanol admixed with water. In some embodiments, the storage solution comprises tris, BHT and 25-90% methanol admixed with water. In some embodiments, the storage solution comprises tris, BHT and 30-90% methanol admixed with water. In some embodiments, the storage solution comprises tris, BHT and 30-85% methanol admixed with water. In some embodiments, the storage solution comprises tris, BHT and 30-80% methanol admixed with water. In some embodiments, the storage solution comprises tris, BHT and 35-80% methanol admixed with water. In some embodiments, the storage solution comprises tris, BHT and 35-75% methanol admixed with water. In some embodiments, the storage solution comprises tris, BHT and 35-70% methanol admixed with water. In some embodiments, the storage solution comprises tris, BHT and 30-70% methanol admixed with water. In some embodiments, the storage solution comprises tris, BHT and 40-70% methanol admixed with water. In some embodiments, the storage solution comprises tris, BHT and 40-65% methanol admixed with water. In some embodiments, the storage solution comprises tris, BHT and 40-60% methanol admixed with water. In some embodiments, the storage solution comprises tris, BHT and 40-55% methanol admixed with water. In some embodiments, the storage solution comprises tris, BHT and 45-55% methanol admixed with water. In some embodiments, the storage solution comprises tris, BHT and 50% methanol admixed with water. In some embodiments, the storage solution consists essentially of tris and 100% methanol. In some embodiments, the storage solution consists essentially of tris and 10% to 100% methanol admixed with water. In some embodiments, the storage solution consists essentially of tris and 10-95% methanol admixed with water. In some embodiments, the storage solution consists essentially of tris and 10-90% methanol admixed with water. In some embodiments, the storage solution consists essentially of tris and 15-90% methanol admixed with water. In some embodiments, the storage solution consists essentially of tris and 20-90% methanol admixed with water. In some embodiments, the storage solution consists essentially of tris and 25-90% methanol admixed with water. In some embodiments, the storage solution consists essentially of tris and 30-90% methanol admixed with water. In some embodiments, the storage solution consists essentially of tris and 30-85% methanol admixed with water. In some embodiments, the storage solution consists essentially of tris and 30-80% methanol admixed with water. In some embodiments, the storage solution consists essentially of tris and 35-80% methanol admixed with water. In some embodiments, the storage solution consists essentially of tris and 35-75% methanol admixed with water. In some embodiments, the storage solution consists essentially of tris and 35-70% methanol admixed with water. In some embodiments, the storage solution consists essentially of tris and 30-70% methanol admixed with water. In some embodiments, the storage solution consists essentially of tris and 40-70% methanol admixed with water. In some embodiments, the storage solution consists essentially of tris and 40-65% methanol admixed with water. In some embodiments, the storage solution consists essentially of tris and 40-60% methanol admixed with water. In some embodiments, the storage solution consists essentially of tris and 40-55% methanol admixed with water. In some embodiments, the storage solution consists essentially of tris and 45-55% methanol admixed with water. In some embodiments, the storage solution consists essentially of tris and 50% methanol admixed with water. In some embodiments, the storage solution consists essentially of BHT and 100% methanol. In some embodiments, the storage solution consists essentially of BHT and 10% to 100% methanol admixed with water. In some embodiments, the storage solution consists essentially of BHT and 10-95% methanol admixed with water. In some embodiments, the storage solution consists essentially of BHT and 10-90% methanol admixed with water. In some embodiments, the storage solution consists essentially of BHT and 15-90% methanol admixed with water. In some embodiments, the storage solution consists essentially of BHT and 20-90% methanol admixed with water. In some embodiments, the storage solution consists essentially of BHT and 25-90% methanol admixed with water. In some embodiments, the storage solution consists essentially of BHT and 30-90% methanol admixed with water. In some embodiments, the storage solution consists essentially of BHT and 30-85% methanol admixed with water. In some embodiments, the storage solution consists essentially of BHT and 30-80% methanol admixed with water. In some embodiments, the storage solution consists essentially of BHT and 35-80% methanol admixed with water. In some embodiments, the storage solution consists essentially of BHT and 35-75% methanol admixed with water. In some embodiments, the storage solution consists essentially of BHT and 35-70% methanol admixed with water. In some embodiments, the storage solution consists essentially of BHT and 30-70% methanol admixed with water. In some embodiments, the storage solution consists essentially of BHT and 40-70% methanol admixed with water. In some embodiments, the storage solution consists essentially of BHT and 40-65% methanol admixed with water. In some embodiments, the storage solution consists essentially of BHT and 40-60% methanol admixed with water. In some embodiments, the storage solution consists essentially of BHT and 40-55% methanol admixed with water. In some embodiments, the storage solution consists essentially of BHT and 45-55% methanol admixed with water. In some embodiments, the storage solution consists essentially of BHT and 50% methanol admixed with water. In some embodiments, the storage solution consists essentially of tris, BHT and 100% methanol. In some embodiments, the storage solution consists essentially of tris, BHT and 10% to 100% methanol admixed with water. In some embodiments, the storage solution consists essentially of tris, BHT and 10-95% methanol admixed with water. In some embodiments, the storage solution consists essentially of tris, BHT and 10-90% methanol admixed with water. In some embodiments, the storage solution consists essentially of tris, BHT and 15-90% methanol admixed with water. In some embodiments, the storage solution consists essentially of tris, BHT and 20-90% methanol admixed with water. In some embodiments, the storage solution consists essentially of tris, BHT and 25-90% methanol admixed with water. In some embodiments, the storage solution consists essentially of tris, BHT and 30-90% methanol admixed with water. In some embodiments, the storage solution consists essentially of tris, BHT and 30-85% methanol admixed with water. In some embodiments, the storage solution consists essentially of tris, BHT and 30-80% methanol admixed with water. In some embodiments, the storage solution consists essentially of tris, BHT and 35-80% methanol admixed with water. In some embodiments, the storage solution consists essentially of tris, BHT and 35-75% methanol admixed with water. In some embodiments, the storage solution consists essentially of tris, BHT and 35-70% methanol admixed with water. In some embodiments, the storage solution consists essentially of tris, BHT and 30-70% methanol admixed with water. In some embodiments, the storage solution consists essentially of tris, BHT and 40-70% methanol admixed with water. In some embodiments, the storage solution consists essentially of tris, BHT and 40-65% methanol admixed with water. In some embodiments, the storage solution consists essentially of tris, BHT and 40-60% methanol admixed with water. In some embodiments, the storage solution consists essentially of tris, BHT and 40-55% methanol admixed with water. In some embodiments, the storage solution consists essentially of tris, BHT and 45-55% methanol admixed with water. In some embodiments, the storage solution consists essentially of tris, BHT and 50% methanol admixed with water. In some embodiments, the storage solution consists of tris and 100% methanol. In some embodiments, the storage solution consists of tris and 10% to 100% methanol admixed with water. In some embodiments, the storage solution consists of tris and 10-95% methanol admixed with water. In some embodiments, the storage solution consists of tris and 10-90% methanol admixed with water. In some embodiments, the storage solution consists of tris and 15-90% methanol admixed with water. In some embodiments, the storage solution consists of tris and 20-90% methanol admixed with water. In some embodiments, the storage solution consists of tris and 25-90% methanol admixed with water. In some embodiments, the storage solution consists of tris and 30-90% methanol admixed with water. In some embodiments, the storage solution consists of tris and 30-85% methanol admixed with water. In some embodiments, the storage solution consists of tris and 30-80% methanol admixed with water. In some embodiments, the storage solution consists of tris and 35-80% methanol admixed with water. In some embodiments, the storage solution consists of tris and 35-75% methanol admixed with water. In some embodiments, the storage solution consists of tris and 35-70% methanol admixed with water. In some embodiments, the storage solution consists of tris and 30-70% methanol admixed with water. In some embodiments, the storage solution consists of tris and 40-70% methanol admixed with water. In some embodiments, the storage solution consists of tris and 40-65% methanol admixed with water. In some embodiments, the storage solution consists of tris and 40-60% methanol admixed with water. In some embodiments, the storage solution consists of tris and 40-55% methanol admixed with water. In some embodiments, the storage solution consists of tris and 45-55% methanol admixed with water. In some embodiments, the storage solution consists of tris and 50% methanol admixed with water. In some embodiments, the storage solution consists of BHT and 100% methanol. In some embodiments, the storage solution consists of BHT and 10% to 100% methanol admixed with water. In some embodiments, the storage solution consists of BHT and 10-95% methanol admixed with water. In some embodiments, the storage solution consists of BHT and 10-90% methanol admixed with water. In some embodiments, the storage solution consists of BHT and 15-90% methanol admixed with water. In some embodiments, the storage solution consists of BHT and 20-90% methanol admixed with water. In some embodiments, the storage solution consists of BHT and 25-90% methanol admixed with water. In some embodiments, the storage solution consists of BHT and 30-90% methanol admixed with water. In some embodiments, the storage solution consists of BHT and 30-85% methanol admixed with water. In some embodiments, the storage solution consists of BHT and 30-80% methanol admixed with water. In some embodiments, the storage solution consists of BHT and 35-80% methanol admixed with water. In some embodiments, the storage solution consists of BHT and 35-75% methanol admixed with water. In some embodiments, the storage solution consists of BHT and 35-70% methanol admixed with water. In some embodiments, the storage solution consists of BHT and 30-70% methanol admixed with water. In some embodiments, the storage solution consists of BHT and 40-70% methanol admixed with water. In some embodiments, the storage solution consists of BHT and 40-65% methanol admixed with water. In some embodiments, the storage solution consists of BHT and 40-60% methanol admixed with water. In some embodiments, the storage solution consists of BHT and 40-55% methanol admixed with water. In some embodiments, the storage solution consists of BHT and 45-55% methanol admixed with water. In some embodiments, the storage solution consists of BHT and 50% methanol admixed with water. In some embodiments, the storage solution consists of tris, BHT and 100% methanol. In some embodiments, the storage solution consists of tris, BHT and 10% to 100% methanol admixed with water. In some embodiments, the storage solution consists of tris, BHT and 10-95% methanol admixed with water. In some embodiments, the storage solution consists of tris, BHT and 10-90% methanol admixed with water. In some embodiments, the storage solution consists of tris, BHT and 15-90% methanol admixed with water. In some embodiments, the storage solution consists of tris, BHT and 20-90% methanol admixed with water. In some embodiments, the storage solution consists of tris, BHT and 25-90% methanol admixed with water. In some embodiments, the storage solution consists of tris, BHT and 30-90% methanol admixed with water. In some embodiments, the storage solution consists of tris, BHT and 30-85% methanol admixed with water. In some embodiments, the storage solution consists of tris, BHT and 30-80% methanol admixed with water. In some embodiments, the storage solution consists of tris, BHT and 35-80% methanol admixed with water. In some embodiments, the storage solution consists of tris, BHT and 35-75% methanol admixed with water. In some embodiments, the storage solution consists of tris, BHT and 35-70% methanol admixed with water. In some embodiments, the storage solution consists of tris, BHT and 30-70% methanol admixed with water. In some embodiments, the storage solution consists of tris, BHT and 40-70% methanol admixed with water. In some embodiments, the storage solution consists of tris, BHT and 40-65% methanol admixed with water. In some embodiments, the storage solution consists of tris, BHT and 40-60% methanol admixed with water. In some embodiments, the storage solution consists of tris, BHT and 40-55% methanol admixed with water. In some embodiments, the storage solution consists of tris, BHT and 45-55% methanol admixed with water. In some embodiments, the storage solution consists of tris, BHT and 50% methanol admixed with water. In some embodiments, the methanol is peroxide free or at a level less than or equal to 0.001%. In some embodiments, the water is purified by distillation, or ultra-filtration, or reverse osmosis. In some embodiments, the water is free of DNAse and/or RNAse activity. In some embodiments, the methylated DNA sequence comprises a polynucleotide sequence that is at least 60%, 65%, 70%, 75%, 80%, 85%, 90%, 91%, 92%, 93%, 94%, 95%, 96%, 97%, 98%, 99%, or 100% identical to any of the nucleotide sequences of vimentin, CCNA1, Up10, Up35-1, Up35-2, FER1L4, VAV3, DOCK10, ADCY1, BMP3, CD1D, ELMO1, ELOVL2, LRRC4, NDRG4, SFMBT2, ST8SIA1, TSPYL5, ZNF568, ZNF569, ZNF610, ZNF671, ZNF682, CDKN2A, DI03, and HUNK genes, or any fragments and/or complements thereof. In some embodiments, the methylated DNA sequence comprises a polynucleotide sequence that is at least 60%, 65%, 70%, 75%, 80%, 85%, 90%, 91%, 92%, 93%, 94%, 95%, 96%, 97%, 98%, 99%, or 100% identical to any one of SEQ ID NOs: 1-45, or any fragments and/or complements thereof. In some embodiments, the methylated DNA patterns are preserved for at least 1 hour, 2 hours, 3 hours, 4 hours, 5 hours, 6 hours, 7 hours, 10 hours, 12 hours, 16 hours, 20 hours, 24 hours, 2 days, 3 days, 4 days, 5 days, 6 days, 7 days, 10 days, two weeks, 15 days, 16 days, 17 days, 18 days, 19 days, 20 days, 21 days, 22 days, 23 days, 24 days, 25 days, 26 days, 27 days, 28 days, 29 days, 30 days, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 1 year, 18 months or 2 years in the composition when stored at room temperature (23° C.). In some embodiments, the methylated DNA patterns are preserved for at least 1 hour, 2 hours, 3 hours, 4 hours, 5 hours, 6 hours, 7 hours, 10 hours, 12 hours, 16 hours, 20 hours, 24 hours, 2 days, 3 days, 4 days, 5 days, 6 days, 7 days, 10 days, two weeks, 15 days, 16 days, 17 days, 18 days, 19 days, 20 days, 21 days, 22 days, 23 days, 24 days, 25 days, 26 days, 27 days, 28 days, 29 days, 30 days, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 1 year, 18 months or 2 years in the composition when stored at 4° C. In some embodiments, the methylated DNA patterns are preserved for at least 1 hour, 2 hours, 3 hours, 4 hours, 5 hours, 6 hours, 7 hours, 10 hours, 12 hours, 16 hours, 20 hours, 24 hours, 2 days, 3 days, 4 days, 5 days, 6 days, 7 days, 10 days, two weeks, 15 days, 16 days, 17 days, 18 days, 19 days, 20 days, 21 days, 22 days, 23 days, 24 days, 25 days, 26 days, 27 days, 28 days, 29 days, 30 days, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 1 year, 18 months or 2 years in the composition when stored at temperatures ranging between −30° C. to 50° C. In some embodiments, the methylated DNA patterns are preserved for at least 1 hour, 2 hours, 3 hours, 4 hours, 5 hours, 6 hours, 7 hours, 10 hours, 12 hours, 16 hours, 20 hours, 24 hours, 2 days, 3 days, 4 days, 5 days, 6 days, 7 days, 10 days, two weeks, 15 days, 16 days, 17 days, 18 days, 19 days, 20 days, 21 days, 22 days, 23 days, 24 days, 25 days, 26 days, 27 days, 28 days, 29 days, 30 days, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 1 year, 18 months or 2 years in the composition when stored at temperatures ranging between −30° C. to 30° C. In some embodiments, the methylated DNA patterns are preserved for at least 1 hour, 2 hours, 3 hours, 4 hours, 5 hours, 6 hours, 7 hours, 10 hours, 12 hours, 16 hours, 20 hours, 24 hours, 2 days, 3 days, 4 days, 5 days, 6 days, 7 days, 10 days, two weeks, 15 days, 16 days, 17 days, 18 days, 19 days, 20 days, 21 days, 22 days, 23 days, 24 days, 25 days, 26 days, 27 days, 28 days, 29 days, 30 days, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 1 year, 18 months or 2 years in the composition when stored at temperatures ranging between −10° C. to 30° C.

In some embodiments, the disclosure provides for a method of preserving the methylation pattern of methylated DNA molecule in a biological sample, comprising treating the biological sample with a storage solution, wherein the storage solution comprises methanol and tris. In certain embodiments, the tris has a pH of from 7.0 to 9.0. In certain embodiments, the tris has a pH of from 7.0 to 8.0. In certain embodiments, the tris has a pH of from 7.5 to 8.5. In certain embodiments, the tris has a pH of from 7.5 to 8.0. In certain embodiments, the tris is present in a concentration of from 1 mM to 250 mM. In certain embodiments, the tris is present in a concentration of from 1 mM to 100 mM. In certain embodiments, the tris is present in a concentration of from 5 mM to 50 mM. In certain embodiments, the tris is present in a concentration of from 5 mM to 20 mM. In certain embodiments, the tris is present in a concentration of from 20 mM to 250 mM. In certain embodiments, the tris is present in a concentration of from 20 mM to 100 mM. In certain embodiments, the tris is present in a concentration of from 30 mM to 70 mM. In certain embodiments, the tris is present in a concentration of from 30 mM to 50 mM. In certain embodiments, the tris is present in a concentration of 10 mM. In certain embodiments, the tris is present in a concentration of 50 mM. In certain embodiments, the storage solution further comprises butylated hydroxytoluene (BHT). In certain such embodiments, the BHT is present in an amount from 1 to 500 ppm. In certain embodiments, the BHT is present in an amount from 20 to 200 ppm. In certain embodiments, the BHT is present in an amount from 25 to 100 ppm. In some embodiments, the disclosure provides for a method of preserving the methylation pattern of methylated DNA molecule in a biological sample, comprising treating the biological sample with a storage solution, wherein the storage solution comprises methanol and BHT. In certain such embodiments, the BHT is present in an amount from 1 to 500 ppm. In certain embodiments, the BHT is present in an amount from 20 to 200 ppm. In certain embodiments, the BHT is present in an amount from 25 to 100 ppm. In some embodiments, the methylation pattern is preserved at room temperature. In some embodiments, the methylation pattern is preserved for at least two weeks. In some embodiments, the methylation pattern of the biological sample in the storage solution is preserved by at least 60% in comparison to the methylation pattern in the biological sample prior to storage. In some embodiments, the methylation pattern of the biological sample in the storage solution is preserved by at least 65% in comparison to the methylation pattern in the biological sample prior to storage. In some embodiments, the methylation pattern of the biological sample in the storage solution is preserved by at least 70% in comparison to the methylation pattern in the biological sample prior to storage. In some embodiments, the methylation pattern of the biological sample in the storage solution is preserved by at least 75% in comparison to the methylation pattern in the biological sample prior to storage. In some embodiments, the methylation pattern of the biological sample in the storage solution is preserved by at least 80% in comparison to the methylation pattern in the biological sample prior to storage. In some embodiments, the methylation pattern of the biological sample in the storage solution is preserved by at least 85% in comparison to the methylation pattern in the biological sample prior to storage. In some embodiments, the methylation pattern of the biological sample in the storage solution is preserved by at least 90% in comparison to the methylation pattern in the biological sample prior to storage. In some embodiments, the methylation pattern of the biological sample in the storage solution is preserved by at least 95% in comparison to the methylation pattern in the biological sample prior to storage. In some embodiments, the biological sample is stored in the storage solution. In some embodiments, the sample is from a human tissue or body fluid. In some embodiments, the sample is from any of: gastrointestinal tract, aerodigestive tract, respiratory tract, genitourinary tract, or a body fluid. In certain such embodiments, the body fluid is any of: blood, urine, sputum, saliva, stool, bile, pancreatic juice, nasal secretions, tears, semen, vaginal secretions, cerebrospinal fluid, pleural fluid, peritoneal fluid, gastric juice, pericardial fluid, sweat, lymph, cyst fluid, pancreatic cyst fluid, synovial fluid, joint fluid, menstrual fluid, endometrial washing, breast aspirate, or amniotic fluid. In some embodiments, the sample is from any of: esophagus, stomach, colon, small intestine, pancreas, liver, oral cavity, oropharynx, trachea, bronchial tree, lung, or breast. In some embodiments, the sample is an esophageal sample. In some embodiments, the storage solution comprises tris and 100% methanol. In some embodiments, the storage solution comprises tris and 10% to 100% methanol admixed with water. In some embodiments, the storage solution comprises tris and 10-95% methanol admixed with water. In some embodiments, the storage solution comprises tris and 10-90% methanol admixed with water. In some embodiments, the storage solution comprises tris and 15-90% methanol admixed with water. In some embodiments, the storage solution comprises tris and 20-90% methanol admixed with water. In some embodiments, the storage solution comprises tris and 25-90% methanol admixed with water. In some embodiments, the storage solution comprises tris and 30-90% methanol admixed with water. In some embodiments, the storage solution comprises tris and 30-85% methanol admixed with water. In some embodiments, the storage solution comprises tris and 30-80% methanol admixed with water. In some embodiments, the storage solution comprises tris and 35-80% methanol admixed with water. In some embodiments, the storage solution comprises tris and 35-75% methanol admixed with water. In some embodiments, the storage solution comprises tris and 35-70% methanol admixed with water. In some embodiments, the storage solution comprises tris and 30-70% methanol admixed with water. In some embodiments, the storage solution comprises tris and 40-70% methanol admixed with water. In some embodiments, the storage solution comprises tris and 40-65% methanol admixed with water. In some embodiments, the storage solution comprises tris and 40-60% methanol admixed with water. In some embodiments, the storage solution comprises tris and 40-55% methanol admixed with water. In some embodiments, the storage solution comprises tris and 45-55% methanol admixed with water. In some embodiments, the storage solution comprises tris and 50% methanol admixed with water. In some embodiments, the storage solution comprises BHT and 100% methanol. In some embodiments, the storage solution comprises BHT and 10% to 100% methanol admixed with water. In some embodiments, the storage solution comprises BHT and 10-95% methanol admixed with water. In some embodiments, the storage solution comprises BHT and 10-90% methanol admixed with water. In some embodiments, the storage solution comprises BHT and 15-90% methanol admixed with water. In some embodiments, the storage solution comprises BHT and 20-90% methanol admixed with water. In some embodiments, the storage solution comprises BHT and 25-90% methanol admixed with water. In some embodiments, the storage solution comprises BHT and 30-90% methanol admixed with water. In some embodiments, the storage solution comprises BHT and 30-85% methanol admixed with water. In some embodiments, the storage solution comprises BHT and 30-80% methanol admixed with water. In some embodiments, the storage solution comprises BHT and 35-80% methanol admixed with water. In some embodiments, the storage solution comprises BHT and 35-75% methanol admixed with water. In some embodiments, the storage solution comprises BHT and 35-70% methanol admixed with water. In some embodiments, the storage solution comprises BHT and 30-70% methanol admixed with water. In some embodiments, the storage solution comprises BHT and 40-70% methanol admixed with water. In some embodiments, the storage solution comprises BHT and 40-65% methanol admixed with water. In some embodiments, the storage solution comprises BHT and 40-60% methanol admixed with water. In some embodiments, the storage solution comprises BHT and 40-55% methanol admixed with water. In some embodiments, the storage solution comprises BHT and 45-55% methanol admixed with water. In some embodiments, the storage solution comprises BHT and 50% methanol admixed with water. In some embodiments, the storage solution comprises tris, BHT and 100% methanol. In some embodiments, the storage solution comprises tris, BHT and 10% to 100% methanol admixed with water. In some embodiments, the storage solution comprises tris, BHT and 10-95% methanol admixed with water. In some embodiments, the storage solution comprises tris, BHT and 10-90% methanol admixed with water. In some embodiments, the storage solution comprises tris, BHT and 15-90% methanol admixed with water. In some embodiments, the storage solution comprises tris, BHT and 20-90% methanol admixed with water. In some embodiments, the storage solution comprises tris, BHT and 25-90% methanol admixed with water. In some embodiments, the storage solution comprises tris, BHT and 30-90% methanol admixed with water. In some embodiments, the storage solution comprises tris, BHT and 30-85% methanol admixed with water. In some embodiments, the storage solution comprises tris, BHT and 30-80% methanol admixed with water. In some embodiments, the storage solution comprises tris, BHT and 35-80% methanol admixed with water. In some embodiments, the storage solution comprises tris, BHT and 35-75% methanol admixed with water. In some embodiments, the storage solution comprises tris, BHT and 35-70% methanol admixed with water. In some embodiments, the storage solution comprises tris, BHT and 30-70% methanol admixed with water. In some embodiments, the storage solution comprises tris, BHT and 40-70% methanol admixed with water. In some embodiments, the storage solution comprises tris, BHT and 40-65% methanol admixed with water. In some embodiments, the storage solution comprises tris, BHT and 40-60% methanol admixed with water. In some embodiments, the storage solution comprises tris, BHT and 40-55% methanol admixed with water. In some embodiments, the storage solution comprises tris, BHT and 45-55% methanol admixed with water. In some embodiments, the storage solution comprises tris, BHT and 50% methanol admixed with water. In some embodiments, the storage solution consists essentially of tris and 100% methanol. In some embodiments, the storage solution consists essentially of tris and 10% to 100% methanol admixed with water. In some embodiments, the storage solution consists essentially of tris and 10-95% methanol admixed with water. In some embodiments, the storage solution consists essentially of tris and 10-90% methanol admixed with water. In some embodiments, the storage solution consists essentially of tris and 15-90% methanol admixed with water. In some embodiments, the storage solution consists essentially of tris and 20-90% methanol admixed with water. In some embodiments, the storage solution consists essentially of tris and 25-90% methanol admixed with water. In some embodiments, the storage solution consists essentially of tris and 30-90% methanol admixed with water. In some embodiments, the storage solution consists essentially of tris and 30-85% methanol admixed with water. In some embodiments, the storage solution consists essentially of tris and 30-80% methanol admixed with water. In some embodiments, the storage solution consists essentially of tris and 35-80% methanol admixed with water. In some embodiments, the storage solution consists essentially of tris and 35-75% methanol admixed with water. In some embodiments, the storage solution consists essentially of tris and 35-70% methanol admixed with water. In some embodiments, the storage solution consists essentially of tris and 30-70% methanol admixed with water. In some embodiments, the storage solution consists essentially of tris and 40-70% methanol admixed with water. In some embodiments, the storage solution consists essentially of tris and 40-65% methanol admixed with water. In some embodiments, the storage solution consists essentially of tris and 40-60% methanol admixed with water. In some embodiments, the storage solution consists essentially of tris and 40-55% methanol admixed with water. In some embodiments, the storage solution consists essentially of tris and 45-55% methanol admixed with water. In some embodiments, the storage solution consists essentially of tris and 50% methanol admixed with water. In some embodiments, the storage solution consists essentially of BHT and 100% methanol. In some embodiments, the storage solution consists essentially of BHT and 10% to 100% methanol admixed with water. In some embodiments, the storage solution consists essentially of BHT and 10-95% methanol admixed with water. In some embodiments, the storage solution consists essentially of BHT and 10-90% methanol admixed with water. In some embodiments, the storage solution consists essentially of BHT and 15-90% methanol admixed with water. In some embodiments, the storage solution consists essentially of BHT and 20-90% methanol admixed with water. In some embodiments, the storage solution consists essentially of BHT and 25-90% methanol admixed with water. In some embodiments, the storage solution consists essentially of BHT and 30-90% methanol admixed with water. In some embodiments, the storage solution consists essentially of BHT and 30-85% methanol admixed with water. In some embodiments, the storage solution consists essentially of BHT and 30-80% methanol admixed with water. In some embodiments, the storage solution consists essentially of BHT and 35-80% methanol admixed with water. In some embodiments, the storage solution consists essentially of BHT and 35-75% methanol admixed with water. In some embodiments, the storage solution consists essentially of BHT and 35-70% methanol admixed with water. In some embodiments, the storage solution consists essentially of BHT and 30-70% methanol admixed with water. In some embodiments, the storage solution consists essentially of BHT and 40-70% methanol admixed with water. In some embodiments, the storage solution consists essentially of BHT and 40-65% methanol admixed with water. In some embodiments, the storage solution consists essentially of BHT and 40-60% methanol admixed with water. In some embodiments, the storage solution consists essentially of BHT and 40-55% methanol admixed with water. In some embodiments, the storage solution consists essentially of BHT and 45-55% methanol admixed with water. In some embodiments, the storage solution consists essentially of BHT and 50% methanol admixed with water. In some embodiments, the storage solution consists essentially of tris, BHT and 100% methanol. In some embodiments, the storage solution consists essentially of tris, BHT and 10% to 100% methanol admixed with water. In some embodiments, the storage solution consists essentially of tris, BHT and 10-95% methanol admixed with water. In some embodiments, the storage solution consists essentially of tris, BHT and 10-90% methanol admixed with water. In some embodiments, the storage solution consists essentially of tris, BHT and 15-90% methanol admixed with water. In some embodiments, the storage solution consists essentially of tris, BHT and 20-90% methanol admixed with water. In some embodiments, the storage solution consists essentially of tris, BHT and 25-90% methanol admixed with water. In some embodiments, the storage solution consists essentially of tris, BHT and 30-90% methanol admixed with water. In some embodiments, the storage solution consists essentially of tris, BHT and 30-85% methanol admixed with water. In some embodiments, the storage solution consists essentially of tris, BHT and 30-80% methanol admixed with water. In some embodiments, the storage solution consists essentially of tris, BHT and 35-80% methanol admixed with water. In some embodiments, the storage solution consists essentially of tris, BHT and 35-75% methanol admixed with water. In some embodiments, the storage solution consists essentially of tris, BHT and 35-70% methanol admixed with water. In some embodiments, the storage solution consists essentially of tris, BHT and 30-70% methanol admixed with water. In some embodiments, the storage solution consists essentially of tris, BHT and 40-70% methanol admixed with water. In some embodiments, the storage solution consists essentially of tris, BHT and 40-65% methanol admixed with water. In some embodiments, the storage solution consists essentially of tris, BHT and 40-60% methanol admixed with water. In some embodiments, the storage solution consists essentially of tris, BHT and 40-55% methanol admixed with water. In some embodiments, the storage solution consists essentially of tris, BHT and 45-55% methanol admixed with water. In some embodiments, the storage solution consists essentially of tris, BHT and 50% methanol admixed with water. In some embodiments, the storage solution consists of tris and 100% methanol. In some embodiments, the storage solution consists of tris and 10% to 100% methanol admixed with water. In some embodiments, the storage solution consists of tris and 10-95% methanol admixed with water. In some embodiments, the storage solution consists of tris and 10-90% methanol admixed with water. In some embodiments, the storage solution consists of tris and 15-90% methanol admixed with water. In some embodiments, the storage solution consists of tris and 20-90% methanol admixed with water. In some embodiments, the storage solution consists of tris and 25-90% methanol admixed with water. In some embodiments, the storage solution consists of tris and 30-90% methanol admixed with water. In some embodiments, the storage solution consists of tris and 30-85% methanol admixed with water. In some embodiments, the storage solution consists of tris and 30-80% methanol admixed with water. In some embodiments, the storage solution consists of tris and 35-80% methanol admixed with water. In some embodiments, the storage solution consists of tris and 35-75% methanol admixed with water. In some embodiments, the storage solution consists of tris and 35-70% methanol admixed with water. In some embodiments, the storage solution consists of tris and 30-70% methanol admixed with water. In some embodiments, the storage solution consists of tris and 40-70% methanol admixed with water. In some embodiments, the storage solution consists of tris and 40-65% methanol admixed with water. In some embodiments, the storage solution consists of tris and 40-60% methanol admixed with water. In some embodiments, the storage solution consists of tris and 40-55% methanol admixed with water. In some embodiments, the storage solution consists of tris and 45-55% methanol admixed with water. In some embodiments, the storage solution consists of tris and 50% methanol admixed with water. In some embodiments, the storage solution consists of BHT and 100% methanol. In some embodiments, the storage solution consists of BHT and 10% to 100% methanol admixed with water. In some embodiments, the storage solution consists of BHT and 10-95% methanol admixed with water. In some embodiments, the storage solution consists of BHT and 10-90% methanol admixed with water. In some embodiments, the storage solution consists of BHT and 15-90% methanol admixed with water. In some embodiments, the storage solution consists of BHT and 20-90% methanol admixed with water. In some embodiments, the storage solution consists of BHT and 25-90% methanol admixed with water. In some embodiments, the storage solution consists of BHT and 30-90% methanol admixed with water. In some embodiments, the storage solution consists of BHT and 30-85% methanol admixed with water. In some embodiments, the storage solution consists of BHT and 30-80% methanol admixed with water. In some embodiments, the storage solution consists of BHT and 35-80% methanol admixed with water. In some embodiments, the storage solution consists of BHT and 35-75% methanol admixed with water. In some embodiments, the storage solution consists of BHT and 35-70% methanol admixed with water. In some embodiments, the storage solution consists of BHT and 30-70% methanol admixed with water. In some embodiments, the storage solution consists of BHT and 40-70% methanol admixed with water. In some embodiments, the storage solution consists of BHT and 40-65% methanol admixed with water. In some embodiments, the storage solution consists of BHT and 40-60% methanol admixed with water. In some embodiments, the storage solution consists of BHT and 40-55% methanol admixed with water. In some embodiments, the storage solution consists of BHT and 45-55% methanol admixed with water. In some embodiments, the storage solution consists of BHT and 50% methanol admixed with water. In some embodiments, the storage solution consists of tris, BHT and 100% methanol. In some embodiments, the storage solution consists of tris, BHT and 10% to 100% methanol admixed with water. In some embodiments, the storage solution consists of tris, BHT and 10-95% methanol admixed with water. In some embodiments, the storage solution consists of tris, BHT and 10-90% methanol admixed with water. In some embodiments, the storage solution consists of tris, BHT and 15-90% methanol admixed with water. In some embodiments, the storage solution consists of tris, BHT and 20-90% methanol admixed with water. In some embodiments, the storage solution consists of tris, BHT and 25-90% methanol admixed with water. In some embodiments, the storage solution consists of tris, BHT and 30-90% methanol admixed with water. In some embodiments, the storage solution consists of tris, BHT and 30-85% methanol admixed with water. In some embodiments, the storage solution consists of tris, BHT and 30-80% methanol admixed with water. In some embodiments, the storage solution consists of tris, BHT and 35-80% methanol admixed with water. In some embodiments, the storage solution consists of tris, BHT and 35-75% methanol admixed with water. In some embodiments, the storage solution consists of tris, BHT and 35-70% methanol admixed with water. In some embodiments, the storage solution consists of tris, BHT and 30-70% methanol admixed with water. In some embodiments, the storage solution consists of tris, BHT and 40-70% methanol admixed with water. In some embodiments, the storage solution consists of tris, BHT and 40-65% methanol admixed with water. In some embodiments, the storage solution consists of tris, BHT and 40-60% methanol admixed with water. In some embodiments, the storage solution consists of tris, BHT and 40-55% methanol admixed with water. In some embodiments, the storage solution consists of tris, BHT and 45-55% methanol admixed with water. In some embodiments, the storage solution consists of tris, BHT and 50% methanol admixed with water. In some embodiments, the methanol is peroxide free or at a level less than or equal to 0.001%. In some embodiments, the water is purified by distillation, or ultrafiltration, or reverse osmosis. In some embodiments, the water is free of DNAse and/or RNAse activity. In some embodiments, the disclosure provides for a method of preserving the DNA methylation pattern of a biological sample in which the biological sample is treated with and/or stored in DNA/RNA Shield. In some embodiments, the pattern of DNA methylation is assayed within a differentially methylated domain of the vimentin gene or a differentially methylated domain of the CCNA1 gene. In some embodiments, the differentially methylated domain of vimentin comprises a nucleotide sequence that is at least 60%, 65%, 70%, 75%, 80%, 85%, 90%, 91%, 92%, 93%, 94%, 95%, 96%, 97%, 98%, 99%, or 100% identical to any one of SEQ ID NOs: 1-5, or SEQ ID NO: 18 corresponding to chr10:17,270,838-17,271,717, or complements and/or fragments thereof. In some embodiments, the differentially methylated domain of vimentin comprises a nucleotide sequence that is at least 60%, 65%, 70%, 75%, 80%, 85%, 90%, 91%, 92%, 93%, 94%, 95%, 96%, 97%, 98%, 99%, or 100% identical to any one of SEQ ID NOs: 1-5, a complement thereof, or a fragment thereof. In some embodiments, the differentially methylated domain of CCNA1 comprises a nucleotide sequence that is at least 60%, 65%, 70%, 75%, 80%, 85%, 90%, 91%, 92%, 93%, 94%, 95%, 96%, 97%, 98%, 99%, or 100% identical to SEQ ID NO: 6 or 7, a complement thereof, or a fragment thereof. In some embodiments, the pattern of DNA methylation is assayed within a differentially methylated domain of an Up10, Up35-1 and/or Up35-2 nucleotide sequence. In some embodiments, the differentially methylated domain of Up10 comprises a nucleotide sequence that is at least 60%, 65%, 70%, 75%, 80%, 85%, 90%, 91%, 92%, 93%, 94%, 95%, 96%, 97%, 98%, 99%, or 100% identical to any one of SEQ ID NOs: 8-11, a complement thereof, or a fragment thereof. In some embodiments, the differentially methylated domain of Up35-1 comprises a nucleotide sequence that is at least 60%, 65%, 70%, 75%, 80%, 85%, 90%, 91%, 92%, 93%, 94%, 95%, 96%, 97%, 98%, 99%, or 100% identical to any one of SEQ ID NOs: 12-15, a complement thereof, or a fragment thereof. In some embodiments, the differentially methylated domain of Up35-2 comprises a nucleotide sequence that is at least 60%, 65%, 70%, 75%, 80%, 85%, 90%, 91%, 92%, 93%, 94%, 95%, 96%, 97%, 98%, 99%, or 100% identical to any one of SEQ ID NOs: 12-13 and 16-17, a complement thereof, or a fragment thereof. In some embodiments, the nucleotide sequence, the complement, or the fragment is at least 20 nucleotides in length. In some embodiments, the pattern of DNA methylation is assayed within a differentially methylated domain associated with a DNA molecule comprising a nucleotide sequence that is at least 60%, 65%, 70%, 75%, 80%, 85%, 90%, 91%, 92%, 93%, 94%, 95%, 96%, 97%, 98%, 99%, or 100% identical to any of the nucleotide sequences of the vimentin, CCNA1, FER1L4, VAV3, DOCK10, ADCY1, BMP3, CD1D, ELMO1, ELOVL2, LRRC4, NDRG4, SFMBT2, ST8SIA1, TSPYL5, ZNF568, ZNF569, ZNF610, ZNF671, ZNF682, CDKN2A, DI03, and/or HUNK genes, or any fragments and/or complements thereof. In some embodiments, the differentially methylated domains are associated with a DNA molecule comprising a nucleotide sequence that is at least 60%, 65%, 70%, 75%, 80%, 85%, 90%, 91%, 92%, 93%, 94%, 95%, 96%, 97%, 98%, 99%, or 100% identical to any of the nucleotide sequences specified by genomic coordinates:

| Gene name | Chromosome No. | DMR Start and End Position (hg19) | DMR2 | DMR3 | DMR4 |
|---|---|---|---|---|---|
| ADCY1 | 7 | 45613877-45614572 | | | |
| BMP3 | 4 | 81952348-81952402 | 81031173-81031262 | | |
| CD1D | 1 | 158150797-158151205 | | | |
| CDKN2A | 9 | 21974710-21974763 | 21975053-21975199 | | |
| DIO3 | 14 | 102026104-102026204 | | | |
| DOCK10 | 2 | 225907226-225907322 | | | |
| ELMO1 | 7 | 37487755-37488477 | | | |
| ELOVL2 | 6 | 11044395-11044834 | | | |
| FER1L4 | 20 | 34189488-34189693 | 34189488-34189693 | | |
| HUNK | 21 | 33246580-33246650 | | | |
| LRRC4 | 7 | 127671993-127672310 | | | |
| NDRG4 | 16 | 58497395-58497451 | | | |
| SFMBT2 | 10 | 7452885-7452956 | 7451771-7451869 | 7452029-7452452 | 7450242-7450831 |
| ST8SIA1 | 12 | 22487528-22487620 | | | |
| TSPYL5 | 8 | 98289858-98290220 | | | |
| VAV3 | 1 | 108507608-108507679 | | | |
| ZNF568 | 19 | 37407197-37407284 | 37407197-37407365 | | |
| ZNF569 | 19 | 37957760-37958046 | | | |
| ZNF610 | 19 | 52839503-52840013 | | | |
| ZNF671 | 19 | 58238810-58238955 | | | |

-continued

| Gene name | Chromo-some No. | DMR Start and End Position (hg19) | DMR2 | DMR3 | DMR4 |
|---|---|---|---|---|---|
| ZNF682 | 19 | 20149796-20149923 | | | | the complements thereof, or the fragments thereof. In some embodiments, the differentially methylated domain of ADCY1 comprises a nucleotide sequence that is at least 60%, 65%, 70%, 75%, 80%, 85%, 90%, 91%, 92%, 93%, 94%, 95%, 96%, 97%, 98%, 99%, or 100% identical to SEQ ID NO: 19, a complement thereof, or a fragment thereof. In some embodiments, the differentially methylated domain of BMP3 comprises a nucleotide sequence that is at least 60%, 65%, 70%, 75%, 80%, 85%, 90%, 91%, 92%, 93%, 94%, 95%, 96%, 97%, 98%, 99%, or 100% identical to SEQ ID NO: 20 or 21, a complement thereof, or a fragment thereof. In some embodiments, the differentially methylated domain of CD1D comprises a nucleotide sequence that is at least 60%, 65%, 70%, 75%, 80%, 85%, 90%, 91%, 92%, 93%, 94%, 95%, 96%, 97%, 98%, 99%, or 100% identical to SEQ ID NO: 22, a complement thereof, or a fragment thereof. In some embodiments, the differentially methylated domain of CDKN2A comprises a nucleotide sequence that is at least 60%, 65%, 70%, 75%, 80%, 85%, 90%, 91%, 92%, 93%, 94%, 95%, 96%, 97%, 98%, 99%, or 100% identical to SEQ ID NO: 23 or 24, a complement thereof, or a fragment thereof. In some embodiments, the differentially methylated domain of DIO3 comprises a nucleotide sequence that is at least 60%, 65%, 70%, 75%, 80%, 85%, 90%, 91%, 92%, 93%, 94%, 95%, 96%, 97%, 98%, 99%, or 100% identical to SEQ ID NO: 25, a complement thereof, or a fragment thereof. In some embodiments, the differentially methylated domain of DOCK10 comprises a nucleotide sequence that is at least 60%, 65%, 70%, 75%, 80%, 85%, 90%, 91%, 92%, 93%, 94%, 95%, 96%, 97%, 98%, 99%, or 100% identical to SEQ ID NO: 26, a complement thereof, or a fragment thereof. In some embodiments, the differentially methylated domain of ELMO1 comprises a nucleotide sequence that is at least 60%, 65%, 70%, 75%, 80%, 85%, 90%, 91%, 92%, 93%, 94%, 95%, 96%, 97%, 98%, 99%, or 100% identical to SEQ ID NO: 27, a complement thereof, or a fragment thereof. In some embodiments, the differentially methylated domain of ELOVl2 comprises a nucleotide sequence that is at least 60%, 65%, 70%, 75%, 80%, 85%, 90%, 91%, 92%, 93%, 94%, 95%, 96%, 97%, 98%, 99%, or 100% identical to SEQ ID NO: 28, a complement thereof, or a fragment thereof. In some embodiments, the differentially methylated domain of FER1L4 comprises a nucleotide sequence that is at least 60%, 65%, 70%, 75%, 80%, 85%, 90%, 91%, 92%, 93%, 94%, 95%, 96%, 97%, 98%, 99%, or 100% identical to SEQ ID NO: 29, a complement thereof, or a fragment thereof. In some embodiments, the differentially methylated domain of HUNK comprises a nucleotide sequence that is at least 60%, 65%, 70%, 75%, 80%, 85%, 90%, 91%, 92%, 93%, 94%, 95%, 96%, 97%, 98%, 99%, or 100% identical to SEQ ID NO: 30, a complement thereof, or a fragment thereof. In some embodiments, the differentially methylated domain of LRRC4 comprises a nucleotide sequence that is at least 60%, 65%, 70%, 75%, 80%, 85%, 90%, 91%, 92%, 93%, 94%, 95%, 96%, 97%, 98%, 99%, or 100% identical to SEQ ID NO: 31, a complement thereof, or a fragment thereof. In some embodiments, the differentially methylated domain of NDRG4 comprises a nucleotide sequence that is at least 60%, 65%, 70%, 75%, 80%, 85%, 90%, 91%, 92%, 93%, 94%, 95%, 96%, 97%, 98%, 99%, or 100% identical to SEQ ID NO: 32, a complement thereof, or a fragment thereof. In some embodiments, the differentially methylated domain of SFMBT2 comprises a nucleotide sequence that is at least 60%, 65%, 70%, 75%, 80%, 85%, 90%, 91%, 92%, 93%, 94%, 95%, 96%, 97%, 98%, 99%, or 100% identical to any one of SEQ ID NOs: 33, 34, 35 or 36, a complement thereof, or a fragment thereof. In some embodiments, the differentially methylated domain of ST8S1A1 comprises a nucleotide sequence that is at least 60%, 65%, 70%, 75%, 80%, 85%, 90%, 91%, 92%, 93%, 94%, 95%, 96%, 97%, 98%, 99%, or 100% identical to SEQ ID NO: 37, a complement thereof, or a fragment thereof. In some embodiments, the differentially methylated domain of TSPYL5 comprises a nucleotide sequence that is at least 60%, 65%, 70%, 75%, 80%, 85%, 90%, 91%, 92%, 93%, 94%, 95%, 96%, 97%, 98%, 99%, or 100% identical to SEQ ID NO: 38, a complement thereof, or a fragment thereof. In some embodiments, the differentially methylated domain of VAV3 comprises a nucleotide sequence that is at least 60%, 65%, 70%, 75%, 80%, 85%, 90%, 91%, 92%, 93%, 94%, 95%, 96%, 97%, 98%, 99%, or 100% identical to SEQ ID NO: 39, a complement thereof, or a fragment thereof. In some embodiments, the differentially methylated domain of ZNF568 comprises a nucleotide sequence that is at least 60%, 65%, 70%, 75%, 80%, 85%, 90%, 91%, 92%, 93%, 94%, 95%, 96%, 97%, 98%, 99%, or 100% identical to SEQ ID NO: 40 or 41, a complement thereof, or a fragment thereof. In some embodiments, the differentially methylated domain of ZNF569 comprises a nucleotide sequence that is at least 60%, 65%, 70%, 75%, 80%, 85%, 90%, 91%, 92%, 93%, 94%, 95%, 96%, 97%, 98%, 99%, or 100% identical to SEQ ID NO: 42, a complement thereof, or a fragment thereof. In some embodiments, the differentially methylated domain of ZNF610 comprises a nucleotide sequence that is at least 60%, 65%, 70%, 75%, 80%, 85%, 90%, 91%, 92%, 93%, 94%, 95%, 96%, 97%, 98%, 99%, or 100% identical to SEQ ID NO: 43, a complement thereof, or a fragment thereof. In some embodiments, the differentially methylated domain of ZNF671 comprises a nucleotide sequence that is at least 60%, 65%, 70%, 75%, 80%, 85%, 90%, 91%, 92%, 93%, 94%, 95%, 96%, 97%, 98%, 99%, or 100% identical to SEQ ID NO: 44, a complement thereof, or a fragment thereof. In some embodiments, the differentially methylated domain of ZNF682 comprises a nucleotide sequence that is at least 60%, 65%, 70%, 75%, 80%, 85%, 90%, 91%, 92%, 93%, 94%, 95%, 96%, 97%, 98%, 99%, or 100% identical to SEQ ID NO: 45, a complement thereof, or a fragment thereof. In some embodiments, such nucleotide sequence, complements, or such fragments are at least 20 nucleotides in length. In some embodiments, the pattern of DNA methylation is assayed by a step that includes treatment of the DNA with a bisulfite compound that converts cytosine bases to uracil. In some embodiments, the methylated DNA patterns are preserved for at least 1 hour, 2 hours, 3 hours, 4 hours, 5 hours, 6 hours, 7 hours, 10 hours, 12 hours, 16 hours, 20 hours, 24 hours, 2 days, 3 days, 4 days, 5 days, 6 days, 7 days, 10 days, two weeks, 15 days, 16 days, 17 days, 18 days, 19 days, 20 days, 21 days, 22 days, 23 days, 24 days, 25 days, 26 days, 27 days, 28 days, 29 days, 30 days, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 1 year, 18 months or 2 years in the composition when stored at room temperature (23° C.). In some embodiments, the methylated DNA patterns are preserved for at least 1 hour, 2 hours, 3 hours, 4 hours, 5 hours, 6 hours, 7 hours, 10 hours, 12 hours, 16 hours, 20 hours, 24 hours, 2 days, 3 days, 4 days, 5 days, 6 days, 7 days, 10 days, two weeks, 15 days, 16 days, 17 days, 18 days, 19 days, 20 days, 21 days, 22 days, 23 days, 24 days, 25 days, 26 days, 27 days, 28 days, 29 days, 30 days, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 1 year, 18 months or 2 years in the composition when stored at 4° C. In some embodiments, the methylated DNA patterns are preserved for at least 1 hour, 2 hours, 3 hours, 4 hours, 5 hours, 6 hours, 7 hours, 10 hours, 12 hours, 16 hours, 20 hours, 24 hours, 2 days, 3 days, 4 days, 5 days, 6 days, 7 days, 10 days, two weeks, 15 days, 16 days, 17 days, 18 days, 19 days, 20 days, 21 days, 22 days, 23 days, 24 days, 25 days, 26 days, 27 days, 28 days, 29 days, 30 days, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 1 year, 18 months or 2 years in the composition at temperatures ranging between −30° C. to 50° C. In some embodiments, the methylated DNA patterns are preserved for at least 1 hour, 2 hours, 3 hours, 4 hours, 5 hours, 6 hours, 7 hours, 10 hours, 12 hours, 16 hours, 20 hours, 24 hours, 2 days, 3 days, 4 days, 5 days, 6 days, 7 days, 10 days, two weeks, 15 days, 16 days, 17 days, 18 days, 19 days, 20 days, 21 days, 22 days, 23 days, 24 days, 25 days, 26 days, 27 days, 28 days, 29 days, 30 days, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 1 year, 18 months or 2 years in the composition at temperatures ranging between −30° C. to 30° C. In some embodiments, the methylated DNA patterns are preserved for at least 1 hour, 2 hours, 3 hours, 4 hours, 5 hours, 6 hours, 7 hours, 10 hours, 12 hours, 16 hours, 20 hours, 24 hours, 2 days, 3 days, 4 days, 5 days, 6 days, 7 days, 10 days, two weeks, 15 days, 16 days, 17 days, 18 days, 19 days, 20 days, 21 days, 22 days, 23 days, 24 days, 25 days, 26 days, 27 days, 28 days, 29 days, 30 days, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 1 year, 18 months or 2 years in the composition at temperatures ranging between −20° C. to 50° C. In some embodiments, the methylated DNA patterns are preserved for at least 1 hour, 2 hours, 3 hours, 4 hours, 5 hours, 6 hours, 7 hours, 10 hours, 12 hours, 16 hours, 20 hours, 24 hours, 2 days, 3 days, 4 days, 5 days, 6 days, 7 days, 10 days, two weeks, 15 days, 16 days, 17 days, 18 days, 19 days, 20 days, 21 days, 22 days, 23 days, 24 days, 25 days, 26 days, 27 days, 28 days, 29 days, 30 days, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 1 year, 18 months or 2 years in the composition at temperatures ranging between −20° C. to 30° C. In some embodiments, the methylated DNA patterns are preserved for at least 1 hour, 2 hours, 3 hours, 4 hours, 5 hours, 6 hours, 7 hours, 10 hours, 12 hours, 16 hours, 20 hours, 24 hours, 2 days, 3 days, 4 days, 5 days, 6 days, 7 days, 10 days, two weeks, 15 days, 16 days, 17 days, 18 days, 19 days, 20 days, 21 days, 22 days, 23 days, 24 days, 25 days, 26 days, 27 days, 28 days, 29 days, 30 days, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 1 year, 18 months or 2 years in the composition at temperatures ranging between −10° C. to 30° C.

The present invention further provides a method of increasing accuracy of a DNA methylation assay, comprising obtaining a sample from a subject; treating the sample with a storage solution (e.g., a storage solution as disclosed herein); and assaying the sample to determine DNA methylation patterns in a nucleic acid sequence of interest, wherein the treatment with the storage solution increases methylation assay accuracy. In certain such embodiments of the foregoing method, the rate of erroneous diagnosis is reduced. In certain embodiments, the sample is an esophageal sample. In certain such embodiments, the sample is obtained by contacting the esophagus with a cytology brush or a balloon. In certain embodiments, the nucleic acid sequence of interest is a vimentin gene or a CCNA1 gene, or a fragment thereof.

DETAILED DESCRIPTION OF THE INVENTION

Figure 1:
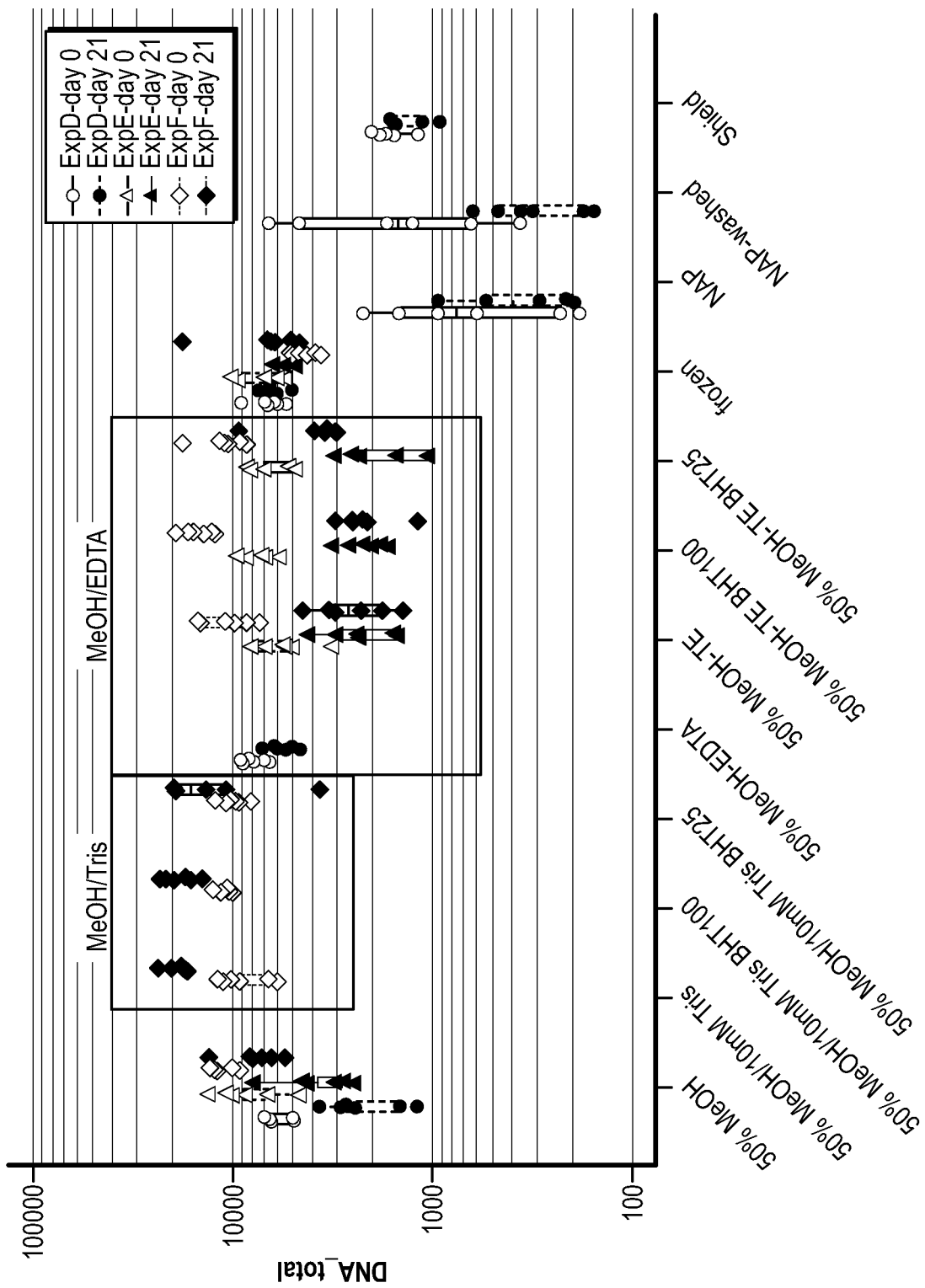
FIG. 1: DNA amount recovered from samples fixed in indicated preservatives from Experiments D, E, and F.

In general, neoplasias may develop through one of at least three different pathways, termed chromosomal instability, microsatellite instability, and the CpG island methylator phenotype (CIMP). Although there is some overlap, these pathways tend to present somewhat different biological behavior. By understanding the pathway of tumor or metaplasia development, the target genes involved, and the mechanisms underlying the genetic instability, it is possible to implement strategies to detect and treat the different types of neoplasias or metaplasias.

Certain target genes may be silenced or inactivated by the differential methylation of CpG islands in the 5' flanking or promoter regions of the target gene. CpG islands are clusters of cytosine-guanosine residues in a DNA sequence, which are prominently represented in the 5'-flanking region or promoter region of about half the genes in our genome. This disclosure is based at least in part on the recognition that certain storage solutions surprisingly preserve DNA methylation patterns in a sample as compared to other solutions.

A. Definitions

For convenience, certain terms employed in the specification, examples, and appended claims are collected here. Unless defined otherwise, all technical and scientific terms used herein have the same meaning as commonly understood by one of ordinary skill in the art to which this invention belongs.

Although methods and materials similar or equivalent to those described herein can be used in the practice or testing of the present invention, suitable methods and materials are described below. The materials, methods and examples are illustrative only, and are not intended to be limiting. All publications, patents and other documents mentioned herein are incorporated by reference in their entirety.

Each embodiment of the invention described herein may be taken alone or in combination with one or more other embodiments of the invention.

Throughout this specification, the word "comprise" or variations such as "comprises" or "comprising" will be understood to imply the inclusion of a stated integer or groups of integers but not the exclusion of any other integer or group of integers.

The articles "a" and "an" are used herein to refer to one or to more than one (i.e., to at least one) of the grammatical object of the article. By way of example, "an element" means one element or more than one element.

The term "about" or "approximately" means within an acceptable error range for the particular value as determined by one of ordinary skill in the art, which will depend in part on how the value is measured or determined, i.e., the limitations of the measurement system. For example, "about" can mean within one or more than one standard deviation, per the practice in the art. Alternatively, "about" can mean a range of up to 20%, up to 15%, up to 10%, up to 5%, or up to 1% above or below a given value.

The terms "adenoma" is used herein to describe any precancerous neoplasia or benign tumor of epithelial tissue, for example, a precancerous neoplasia of the gastrointestinal tract, pancreas, and/or the bladder.

The term "blood-derived fraction" herein refers to a component or components of whole blood. Whole blood comprises a liquid portion (i.e., plasma) and a solid portion (i.e., blood cells). The liquid and solid portions of blood are each comprised of multiple components; e.g., different proteins in plasma or different cell types in the solid portion. One of these components or a mixture of any of these components is a blood-derived fraction as long as such fraction is missing one or more components found in whole blood.

The term "esophagus" is intended to encompass the upper portion of the digestive system spanning from the back of the oral cavity, passing downwards through the rear part of the mediastinum, through the diaphragm and into the stomach.

The term "esophageal cancer" is used herein to refer to any cancerous neoplasia of the esophagus.

"Barrett's esophagus" as used herein refers to an abnormal change (metaplasia) in the cells of the lower portion of the esophagus. Barrett's is characterized by the finding of intestinal metaplasia in the esophagus.

A "brushing" of the esophagus, as referred to herein, may be obtained using any of the means known in the art. In some embodiments, a brushing is obtained by contacting the esophagus with a brush, a cytology brush, a sponge, a balloon, or with any other device or substance that contacts the esophagus and obtains an esophageal sample.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The terms "compound", "test compound," "agent", and "molecule" are used herein interchangeably and are meant to include, but are not limited to, peptides, nucleic acids, carbohydrates, small organic molecules, natural product extract libraries, and any other molecules (including, but not limited to, chemicals, metals, and organometallic compounds).

The term "compound-converted DNA" herein refers to DNA that has been treated or reacted with a chemical compound that converts unmethylated C bases in DNA to a different nucleotide base. For example, one such compound is sodium bisulfite, which converts unmethylated C to U. If DNA that contains conversion-sensitive cytosine is treated with sodium bisulfite, the compound-converted DNA will contain U in place of C. If the DNA which is treated with sodium bisulfite contains only methylcytosine, the compound-converted DNA will not contain uracil in place of the methylcytosine.

The term "de-methylating agent" as used herein refers to agents that restore activity and/or gene expression of target genes silenced by methylation upon treatment with the agent. Examples of such agents include without limitation 5-azacytidine and 5-aza-2'-deoxycytidine.

The term "detection" is used herein to refer to any process of observing a marker, or a change in a marker (such as for example the change in the methylation state of the marker), in a biological sample, whether or not the marker or the change in the marker is actually detected. In some embodiments, the act of probing a sample for a marker or a change in the marker, is a "detection" even if the marker is determined to be not present or below the level of sensitivity. Detection may be a quantitative, semi-quantitative or non-quantitative observation.

The term "differentially methylated nucleotide sequence" or a "differentially methylated domain" refers to a region of a genomic loci/target gene that is found to be methylated in cancer tissues or cell lines, but not methylated in the normal tissues or cell lines, or refers to a region of a genomic loci/target gene that is found to be less methylated in cancer tissues or cell lines, than in the normal tissues or cell lines.

The term "neoplasia" as used herein refers to an abnormal growth of tissue. As used herein, the term "neoplasia" may be used to refer to cancerous and non-cancerous tumors, as well as to Barrett's esophagus (which may also be referred to herein as a metaplasia) and Barrett's esophagus with dysplasia. In some embodiments, the Barrett's esophagus with dysplasia is Barrett's esophagus with high grade dysplasia. In some embodiments, the Barrett's esophagus with dysplasia is Barrett's esophagus with low grade dysplasia. In some embodiments, the neoplasia is a cancer (e.g., esophageal adenocarcinoma).

"Gastrointestinal neoplasia" refers to neoplasia of the upper and lower gastrointestinal tract. As commonly understood in the art, the upper gastrointestinal tract includes the esophagus, stomach, and duodenum; the lower gastrointestinal tract includes the remainder of the small intestine and all of the large intestine.

The terms "healthy", "normal," and "non-neoplastic" are used interchangeably herein to refer to a subject or particular cell or tissue that is devoid (at least to the limit of detection) of a disease condition, such as a neoplasia.

"Homology" or "identity" or "similarity" refers to sequence similarity between two peptides or between two nucleic acid molecules. Homology and identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. A sequence which is "unrelated or "non-homologous" shares, in some embodiments, less than 40% identity, and in particular embodiments, less than 25% identity with a sequence of the present invention. In comparing two sequences, the absence of residues (amino acids or nucleic acids) or presence of extra residues also decreases the identity and homology/similarity.

The term "homology" describes a mathematically based comparison of sequence similarities which is used to identify genes or proteins with similar functions or motifs. The nucleic acid and protein sequences of the present invention may be used as a "query sequence" to perform a search against public databases to, for example, identify other family members, related sequences or homologs. Such searches can be performed using the NBLAST and XBLAST programs (version 2.0) of Altschul, et al. (1990) *J Mol. Biol.* 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and BLAST) can be used. See www.ncbi.nlm.nih.gov.

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in (*Computational Molecular Biology*, Lesk, A.

M., ed., Oxford University Press, New York, 1988; Biocomputing: Informatics and Genome Projects, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM J. Applied Math., 48: 1073, 1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., *Nucleic Acids Research* 12(1): 387 (1984)), BLASTP, BLASTN, and FASTA (Altschul, S. F. et al., *J. Molec. Biol.* 215: 403-410 (1990) and Altschul et al. *Nuc. Acids Res.* 25: 3389-3402 (1997)). The BLAST X program is publicly available from NCBI and other sources (*BLAST Manual*, Altschul, S., et al., NCBI NLM NIH Bethesda, Md. 20894; Altschul, S., et al., *J. Mol. Biol.* 215: 403-410 (1990)). The well-known Smith Waterman algorithm may also be used to determine identity.

The term "including" is used herein to mean, and is used interchangeably with, the phrase "including but not limited to."

The term "isolated" as used herein with respect to nucleic acids, such as DNA or RNA, refers to molecules in a form which does not occur in nature. Moreover, an "isolated nucleic acid" is meant to include nucleic acid fragments which are not naturally occurring as fragments and would not be found in the natural state.

The term "methylation-specific PCR" ("MSP") herein refers to a polymerase chain reaction in which amplification of the compound-converted template sequence is performed. Two sets of primers are designed for use in MSP. Each set of primers comprises a forward primer and a reverse primer. In some embodiments, one set of primers, called methylation-specific primers, will amplify the compound-converted template sequence if C bases in CpG dinucleotides within the DNA are methylated. In some embodiments, another set of primers, called unmethylation-specific primers or primers for unmethylated sequences and the like, will amplify the compound-converted template sequences if C bases in CpG dinucleotides within the DNA are not methylated.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides.

"Operably linked" when describing the relationship between two DNA regions simply means that they are functionally related to each other. For example, a promoter or other transcriptional regulatory sequence is operably linked to a coding sequence if it controls the transcription of the coding sequence.

The term "or" is used herein to mean, and is used interchangeably with, the term "and/or", unless context clearly indicates otherwise.

The terms "proteins" and "polypeptides" are used interchangeably herein.

A "sample" includes any material that is obtained or prepared for detection of a molecular marker or a change in a molecular marker such as, for example, the methylation state, or any material that is contacted with a detection reagent or detection device for the purpose of detecting a molecular marker or a change in the molecular marker.

As used herein, "obtaining a sample" includes directly retrieving a sample from a subject to be assayed, or directly retrieving a sample from a subject to be stored (e.g., in any of the storage solutions described herein) and assayed at a later time. Alternatively, a sample may be obtained via a second party. That is, a sample may be obtained via, e.g., shipment, from another individual who has retrieved the sample, or otherwise obtained the sample.

A "storage solution" is any solution that preserves methylation patterns in a DNA molecule over a period of time. A storage solution may also be referred to herein as a "preservative."

A "subject" is any organism of interest, generally a mammalian subject, such as a mouse, and in particular embodiments, a human subject.

As used herein, the term "specifically hybridizes" refers to the ability of a nucleic acid probe/primer of the invention to hybridize to at least 12, 15, 20, 25, 30, 35, 40, 45, 50 or 100 consecutive nucleotides of a target sequence, or a sequence complementary thereto, or naturally occurring mutants thereof, such that it has, in some embodiments, less than 15%, less than 10%, or less than 5% background hybridization to a cellular nucleic acid (e.g., mRNA or genomic DNA) other than the target gene. A variety of hybridization conditions may be used to detect specific hybridization, and the stringency is determined primarily by the wash stage of the hybridization assay. Generally high temperatures and low salt concentrations give high stringency, while low temperatures and high salt concentrations give low stringency. Low stringency hybridization is achieved by washing in, for example, about 2.0×SSC at 50° C., and high stringency is achieved with about 0.2×SSC at 50° C. Further descriptions of stringency are provided herein.

As applied to polypeptides, the term "substantial sequence identity" means that two peptide sequences, when optimally aligned such as by the programs GAP or BESTFIT using default gap, share at least 90 percent sequence identity, in some embodiments, at least 95 percent sequence identity, or at least 99 percent sequence identity or more. In some embodiments, residue positions which are not identical differ by conservative amino acid substitutions. For example, the substitution of amino acids having similar chemical properties such as charge or polarity is not likely to affect the properties of a protein. Examples include glutamine for asparagine or glutamic acid for aspartic acid.

The term "Up10" as used herein refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 8, or fragments or reverse complements thereof. The term "Up10" as used herein also refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 9, or fragments or reverse complements thereof. The term "Up10" as used herein also refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 10, or fragments or reverse complements thereof. The term "Up10" as used herein also refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 11, or fragments or reverse complements thereof.

The term "Up35-1" as used herein refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 12, or fragments or reverse complements thereof. The term "Up35-1" as used herein also refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 13, or fragments or reverse complements thereof. The term "Up35-1" as used herein also refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 14, or fragments or reverse complements thereof. The term "Up35-1" as used herein also refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 15, or fragments or reverse complements thereof.

The term "Up35-2" as used herein refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 12, or fragments or reverse complements thereof. The term "Up35-2" as used herein also refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 13, or fragments or reverse complements thereof. The term "Up35-2" as used herein also refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 16, or fragments or reverse complements thereof. The term "Up35-2" as used herein also refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 17, or fragments or reverse complements thereof.

B. Storage Solutions

In some embodiments, the disclosure provides for a storage solution for preserving DNA methylation patterns in cellular samples.

In some embodiments, the solution comprises an organic solvent. In some embodiments, the organic solvent is any one of or combination of methanol, ethanol, isopropanol, or chloroform. In some embodiments, the storage solution comprises methanol. In some embodiments, the storage solution comprises ethanol. In some embodiments, the storage solution comprises isopropanol. In some embodiments, the storage solution comprises chloroform. In some embodiments, the storage solution is diluted with water. In some embodiments, the storage solution comprises any of the organic solvents disclosed herein and water. In some embodiments, the storage solution comprises tris and/or BHT, and at least 30%, 35%, 40%, 45%, 50%, 55%, 60%, 65%, 70%, 75%, 80%, 85%, 90%, 95%, or 97% of an organic solvent. In some embodiments, the storage solution comprises tris and/or BHT and less than 70%, 65%, 60%, 55%, 50%, 45%, 40%, 35%, 30%, 25%, 20%, 15%, 10%, 5% or 3% water. In some embodiments, the storage solution comprises tris and/or BHT and 95% of an organic solvent and 5% water. In some embodiments, the storage solution comprises tris and/or BHT and about 90% of an organic solvent and about 10% water. In some embodiments, the storage solution comprises tris and/or BHT and about 85% of an organic solvent and about 15% water. In some embodiments, the storage solution comprises tris and/or BHT and about 80% of an organic solvent and about 20% water. In some embodiments, the storage solution comprises tris and/or BHT and about 75% of an organic solvent and about 25% water. In some embodiments, the storage solution comprises tris and/or BHT and about 70% of an organic solvent and 30% water. In some embodiments, the storage solution comprises tris and/or BHT and about 65% of an organic solvent and about 35% water. In some embodiments, the storage solution comprises tris and/or BHT and about 60% of an organic solvent and about 40% water. In some embodiments, the storage solution comprises tris and/or BHT and about 55% of an organic solvent and about 45% water. In some embodiments, the storage solution comprises tris and/or BHT and about 50% of an organic solvent and about 50% water. In some embodiments, the storage solution comprises tris and/or BHT and about 45% of an organic solvent and about 55% water. In some embodiments, the storage solution comprises tris and/or BHT and about 40% of an organic solvent and about 60% water. In some embodiments, the storage solution comprises tris and/or BHT and about 35% of an organic solvent and about 65% water. In some embodiments, the storage solution comprises tris and/or BHT and about 30% of an organic solvent and about 70% water. In some embodiments, the storage solution comprises tris and/or BHT and about 25% of an organic solvent and about 75% water. In some embodiments, the storage solution comprises tris and/or BHT and about 20% of an organic solvent and about 80% water. In some embodiments, the storage solution comprises tris and/or BHT and about 15% of an organic solvent and about 85% water. In some embodiments, the storage solution comprises tris and/or BHT and about 10% of an organic solvent and about 90% water. In some embodiments, the storage solution consists essentially of tris and/or BHT and 95% of an organic solvent and 5% water. In some embodiments, the storage solution consists essentially of tris and/or BHT and about 90% of an organic solvent and about 10% water. In some embodiments, the storage solution consists essentially of tris and/or BHT and about 85% of an organic solvent and about 15% water. In some embodiments, the storage solution consists essentially of tris and/or BHT and about 80% of an organic solvent and about 20% water. In some embodiments, the storage solution consists essentially of tris and/or BHT and about 75% of an organic solvent and about 25% water. In some embodiments, the storage solution consists essentially of tris and/or BHT and about 70% of an organic solvent and 30% water. In some embodiments, the storage solution consists essentially of tris and/or BHT and about 65% of an organic solvent and about 35% water. In some embodiments, the storage solution consists essentially of tris and/or BHT and about 60% of an organic solvent and about 40% water. In some embodiments, the storage solution consists essentially of tris and/or BHT and about 55% of an organic solvent and about 45% water. In some embodiments, the storage solution consists essentially of tris and/or BHT and about 50% of an organic solvent and about 50% water. In some embodiments, the storage solution consists essentially of tris and/or BHT and about 45% of an organic solvent and about 55% water. In some embodiments, the storage solution consists essentially of tris and/or BHT and about 40% of an organic solvent and about 60% water. In some embodiments, the storage solution consists essentially of tris and/or BHT and about 35% of an organic solvent and about 65% water. In some embodiments, the storage solution consists essentially of tris and/or BHT and about 30% of an organic solvent and about 70% water. In some embodiments, the storage solution consists essentially of tris and/or BHT and about 25% of an organic solvent and about 75% water. In some embodiments, the storage solution consists essentially of tris and/or BHT and about 20% of an organic solvent and about 80% water. In some embodiments, the storage solution consists essentially of tris and/or BHT and about 15% of an organic solvent and about 85% water. In some embodiments, the storage solution consists essentially of tris and/or BHT and about 10% of an organic solvent and about 90% water. In some embodiments, the storage solution consists of tris and/or BHT and 95% of an organic solvent and 5% water. In some embodiments, the storage solution consists of tris and/or BHT and about 90% of an organic solvent and about 10% water. In some embodiments, the storage solution consists of tris and/or BHT and about 85% of an organic solvent and about 15% water. In some embodiments, the storage solution consists of tris and/or BHT and about 80% of an organic solvent and about 20% water. In some embodiments, the storage solution consists of tris and/or BHT and about 75% of an organic solvent and about 25% water. In some embodiments, the storage solution consists of tris and/or BHT and about 70% of an organic solvent and 30% water. In some embodiments, the storage solution consists of tris and/or BHT and about 65% of an organic solvent and about 35% water. In some embodiments, the storage solution consists of tris and/or BHT and about 60% of an organic solvent and about 40% water. In some embodiments, the storage solution consists of tris and/or BHT and about 55% of an organic solvent and about 45% water. In some embodiments, the storage solution consists of tris and/or BHT and about 50% of an organic solvent and about 50% water. In some embodiments, the storage solution consists of tris and/or BHT and about 45% of an organic solvent and about 55% water. In some embodiments, the storage solution consists of tris and/or BHT and about 40% of an organic solvent and about 60% water. In some embodiments, the storage solution consists of tris and/or BHT and about 35% of an organic solvent and about 65% water. In some embodiments, the storage solution consists of tris and/or BHT and about 30% of an organic solvent and about 70% water. In some embodiments, the storage solution consists of tris and/or BHT and about 25% of an organic solvent and about 75% water. In some embodiments, the storage solution consists of tris and/or BHT and about 20% of an organic solvent and about 80% water. In some embodiments, the storage solution consists of tris and/or BHT and about 15% of an organic solvent and about 85% water. In some embodiments, the storage solution consists of tris and/or BHT and about 10% of an organic solvent and about 90% water. In some embodiments, the storage solution comprises tris and/or BHT and 10-90% of an organic solvent. In some embodiments, the storage solution comprises tris and/or BHT and 20-80% of an organic solvent. In some embodiments, the storage solution comprises tris and/or BHT and 25-75% of an organic solvent. In some embodiments, the storage solution comprises tris and/or BHT and 30-70% of an organic solvent. In some embodiments, the storage solution comprises tris and/or BHT and 35-65% of an organic solvent. In some embodiments, the storage solution comprises tris and/or BHT and 40-60% of an organic solvent. In some embodiments, the storage solution comprises tris and/or BHT and 45-55% of an organic solvent. In certain embodiments of the foregoing, the storage solution does not comprise ethylenediaminetetraacetic acid (EDTA).

In some embodiments, the storage solution comprises tris and/or BHT and methanol. In some embodiments, the storage solution is a methanol-based buffer. In some embodiments, the storage solution comprises tris and/or BHT and 100% methanol. In some embodiments, the methanol is peroxide-free. In some embodiments, the methanol is Peroxide-Free/Sequencing methanol (Fisher BioReagents). In some embodiments, the methanol is ultrapure methanol. In some embodiments, the storage solution comprises a mixture of tris and/or BHT, methanol and another liquid. In some embodiments, the other liquid is water. In some embodiments, the storage solution comprises tris and/or BHT and at least 30%, 35%, 40%, 45%, 50%, 55%, 60%, 65%, 70%, 75%, 80%, 85%, 90%, 95%, or 97% methanol. In some embodiments, the storage solution comprises less than 70%, 65%, 60%, 55%, 50%, 45%, 40%, 35%, 30%, 25%, 20%, 15%, 10%, 5% or 3% water. In some embodiments, the storage solution comprises tris and/or BHT, 95% methanol and 5% water. In some embodiments, the storage solution comprises tris and/or BHT, about 90% methanol and about 10% water. In some embodiments, the storage solution comprises tris and/or BHT, about 85% methanol and about 15% water. In some embodiments, the storage solution comprises tris and/or BHT, about 80% methanol and about 20% water. In some embodiments, the storage solution comprises tris and/or BHT, about 75% methanol and about 25% water. In some embodiments, the storage solution comprises tris and/or BHT, about 70% methanol and 30% water. In some embodiments, the storage solution comprises tris and/or BHT, about 65% methanol and about 35% water. In some embodiments, the storage solution comprises tris and/or BHT, about 60% methanol and about 40% water. In some embodiments, the storage solution comprises tris and/or BHT, about 55% methanol and about 45% water. In some embodiments, the storage solution comprises tris and/or BHT, about 50% methanol and about 50% water. In some embodiments, the storage solution comprises tris and/or BHT, about 45% methanol and about 55% water. In some embodiments, the storage solution comprises tris and/or BHT, about 40% methanol and about 60% water. In some embodiments, the storage solution comprises tris and/or BHT, about 35% methanol and about 65% water. In some embodiments, the storage solution comprises tris and/or BHT, about 30% methanol and about 70% water. In some embodiments, the storage solution comprises tris and/or BHT, about 25% methanol and about 75% water. In some embodiments, the storage solution comprises tris and/or BHT, about 20% methanol and about 80% water. In some embodiments, the storage solution comprises tris and/or BHT, about 15% methanol and about 85% water. In some embodiments, the storage solution comprises tris and/or BHT, about 10% methanol and about 90% water. In some embodiments, the storage solution consists essentially of tris and/or BHT, 95% methanol and 5% water. In some embodiments, the storage solution consists essentially of tris and/or BHT, about 90% methanol and about 10% water. In some embodiments, the storage solution consists essentially of tris and/or BHT, about 85% methanol and about 15% water. In some embodiments, the storage solution consists essentially of tris and/or BHT, about 80% methanol and about 20% water. In some embodiments, the storage solution consists essentially of tris and/or BHT, about 75% methanol and about 25% water. In some embodiments, the storage solution consists essentially of tris and/or BHT, about 70% methanol and 30% water. In some embodiments, the storage solution consists essentially of tris and/or BHT, about 65% methanol and about 35% water. In some embodiments, the storage solution consists essentially of tris and/or BHT, about 60% methanol and about 40% water. In some embodiments, the storage solution consists essentially of tris and/or BHT, about 55% methanol and about 45% water. In some embodiments, the storage solution consists essentially of tris and/or BHT, about 50% methanol and about 50% water. In some embodiments, the storage solution consists essentially of tris and/or BHT, about 45% methanol and about 55% water. In some embodiments, the storage solution consists essentially of tris and/or BHT, about 40% methanol and about 60% water. In some embodiments, the storage solution consists essentially of tris and/or BHT, about 35% methanol and about 65% water. In some embodiments, the storage solution consists essentially of tris and/or BHT, about 30% methanol and about 70% water. In some embodiments, the storage solution consists essentially of tris and/or BHT, about 25% methanol and about 75% water. In some embodiments, the storage solution consists essentially of tris and/or BHT, about 20% methanol and about 80% water. In some embodiments, the storage solution consists essentially of tris and/or BHT, about 15% methanol and about 85% water. In some embodiments, the storage solution consists essentially of tris and/or BHT, about 10% methanol and about 90% water. In some embodiments, the storage solution consists of tris and/or BHT, 95% methanol and 5% water. In some embodiments, the storage solution consists of tris and/or BHT, about 90% methanol and about 10% water. In some embodiments, the storage solution consists of tris and/or BHT, about 85% methanol and about 15% water. In some embodiments, the storage solution consists of tris and/or BHT, about 80% methanol and about 20% water. In some embodiments, the storage solution consists of tris and/or BHT, about 75% methanol and about 25% water. In some embodiments, the storage solution consists of tris and/or BHT, about 70% methanol and 30% water. In some embodiments, the storage solution consists of tris and/or BHT, about 65% methanol and about 35% water. In some embodiments, the storage solution consists of tris and/or BHT, about 60% methanol and about 40% water. In some embodiments, the storage solution consists of tris and/or BHT, about 55% methanol and about 45% water. In some embodiments, the storage solution consists of tris and/or BHT, about 50% methanol and about 50% water. In some embodiments, the storage solution consists of tris and/or BHT, about 45% methanol and about 55% water. In some embodiments, the storage solution consists of tris and/or BHT, about 40% methanol and about 60% water. In some embodiments, the storage solution consists of tris and/or BHT, about 35% methanol and about 65% water. In some embodiments, the storage solution consists of tris and/or BHT, about 30% methanol and about 70% water. In some embodiments, the storage solution consists of tris and/or BHT, about 25% methanol and about 75% water. In some embodiments, the storage solution consists of tris and/or BHT, about 20% methanol and about 80% water. In some embodiments, the storage solution consists of tris and/or BHT, about 15% methanol and about 85% water. In some embodiments, the storage solution consists of tris and/or BHT, about 10% methanol and about 90% water. In some embodiments, the storage solution comprises tris and/or BHT and 10-90% of methanol. In some embodiments, the storage solution comprises tris and/or BHT and 20-80% of methanol. In some embodiments, the storage solution comprises tris and/or BHT and 25-75% of methanol. In some embodiments, the storage solution comprises tris and/or BHT and 30-70% of methanol. In some embodiments, the storage solution comprises tris and/or BHT and 35-65% of methanol. In some embodiments, the storage solution comprises tris and/or BHT and 40-60% of methanol. In some embodiments, the storage solution comprises tris and/or BHT and 45-55% of methanol. In some embodiments, the water is purified by distillation. In some embodiments, the water is purified by ultrafiltration. In some embodiments, the water is purified by reverse osmosis. In some embodiments, the water is free of DNase and/or DNase activity. In some embodiments, the water is free of RNase and/or RNase activity. In some embodiments, the water is UltraPure™ DNase/RNase-Free Distilled Water (ThermoFischer Invitrogen). In certain embodiments of the foregoing, the storage solution does not comprise EDTA.

In certain embodiments, the tris is present in the storage solution at a concentration of from about 1 mM to about 250 mM. In some embodiments, the tris is present in the storage solution at a concentration of from about 1 mM to about 100 mM. In some embodiments, the tris is present in the storage solution at a concentration of from about 1 mM to about 90 mM. In some embodiments, the tris is present in the storage solution at a concentration of from about 1 mM to about 80 mM. In some embodiments, the tris is present in the storage solution at a concentration of from about 1 mM to about 70 mM. In some embodiments, the tris is present in the storage solution at a concentration of from about 1 mM to about 60 mM. In some embodiments, the tris is present in the storage solution at a concentration of from about 1 mM to about 50 mM. In some embodiments, the tris is present in the storage solution at a concentration of from about 1 mM to about 40 mM. In some embodiments, the tris is present in the storage solution at a concentration of from about 1 mM to about 30 mM. In some embodiments, the tris is present in the storage solution at a concentration of from about 1 mM to about 20 mM. In some embodiments, the tris is present in the storage solution at a concentration of from about 5 mM to about 20 mM. In certain embodiments, the tris is present in the storage solution at a concentration of from about 5 mM to about 50 mM. In some embodiments, the tris is present in the storage solution at a concentration of from about 10 mM to about 20 mM. In certain embodiments, the tris is present in the storage solution at a concentration of from about 20 mM to about 250 mM. In certain embodiments, the tris is present in the storage solution at a concentration of from about 20 mM to about 100 mM. In certain embodiments, the tris is present in the storage solution at a concentration of from about 30 mM to about 70 mM. In certain embodiments, the tris is present in the storage solution at a concentration of from about 30 mM to about 50 mM. In some embodiments, the tris is present in the storage solution at a concentration of about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, or about 20 mM. In some embodiments, the tris is present in the storage solution at a concentration of about 10 mM. In certain embodiments, the tris is present in the storage solution at a concentration of about 15 mM, about 20 mM, about 25 mM, about 30 mM, about 35 mM, about 40 mM, about 45 mM, about 50 mM, about 55 mM, about 60 mM, about 65 mM, about 70 mM, or about 75 mM. In certain embodiments, the tris is present in the storage solution at a concentration of about 50 mM.

In some embodiments, the BHT is present in the storage solution at a concentration of from about 1 ppm (e.g., mg/mL) to about 500 ppm (e.g., mg/mL). In some embodiments, the BHT is present in the storage solution at a concentration of from about 1 ppm to about 450 ppm. In some embodiments, the BHT is present in the storage solution at a concentration of from about 1 ppm to about 400 ppm. In some embodiments, the BHT is present in the storage solution at a concentration of from about 1 ppm to about 350 ppm. In some embodiments, the BHT is present in the storage solution at a concentration of from about 1 ppm to about 300 ppm. In some embodiments, the BHT is present in the storage solution at a concentration of from about 1 ppm to about 250 ppm. In some embodiments, the BHT is present in the storage solution at a concentration of from about 1 ppm to about 200 ppm. In some embodiments, the BHT is present in the storage solution at a concentration of from about 1 ppm to about 150 ppm. In some embodiments, the BHT is present in the storage solution at a concentration of from about 10 ppm to about 200 ppm. In some embodiments, the BHT is present in the storage solution at a concentration of from about 20 ppm to about 200 ppm. In some embodiments, the BHT is present in the storage solution at a concentration of from about 20 ppm to about 150 ppm. In some embodiments, the BHT is present in the storage solution at a concentration of from about 20 ppm to about 125 ppm. In some embodiments, the BHT is present in the storage solution at a concentration of from about 20 ppm to about 100 ppm. In some embodiments, the BHT is present in the storage solution at a concentration of from about 25 ppm to about 100 ppm.

In some embodiments, the storage solution comprises a detergent. In some embodiments, the storage solution comprises a chaotropic agent. In some embodiments, the chaotropic agent comprises urea. In some embodiments, the chaotropic agent is guanidine.

In some embodiments, the storage solution is free of metal ions (e.g., calcium, iron, magnesium, or zinc). In some embodiments, the storage solution is free of calcium. In some embodiments, the storage solution is free of magnesium. In some embodiments, the storage solution is free of zinc. In some embodiments, the storage solution is free of iron.

In some embodiments, the storage solution is at a neutral pH. In some embodiments, the storage solution is not at an acidic pH. In some embodiments, the storage solution is at a pH of between 5-9. In some embodiments the storage solution has a pH greater than 5.5. In some embodiments the storage solution is at pH between 6-9. In some embodiments the storage solution is at pH between 7-9. In some embodiments the storage solution is at pH between 7-8. In some embodiments the storage solution is at pH between 7.4-7.5. In some embodiments, the storage solution is at a pH of between 6-8. In some embodiments, the storage solution is at a pH of between 6.2 and 7.8. In some embodiments, the storage solution is at a pH of between 6.5 and 7.5. In some embodiments, the storage solution is at a pH of between 6.8 and 7.2. In some embodiments, the pH is 7.0. In some embodiments, the pH is 7.1. In some embodiments, the pH is 7.2. In some embodiments, the pH is 7.3. In some embodiments, the pH is 7.4. In some embodiments, the pH is 7.5. In some embodiments, the pH is 7.6. In some embodiments, the pH is 8.0. In some embodiments, the storage solution is at a physiological pH.

In some embodiments, the storage solution is peroxide free. In some embodiments, the storage solution comprises less than 0.1%, 0.05%, 0.01%, 0.005% or 0.001% peroxide.

In some embodiments, any of the storage solutions disclosed herein is capable of preserving methylation patterns in a target DNA sequence/target gene in a biological sample for at least 1 hour, 2 hours, 3 hours, 4 hours, 5 hours, 6 hours, 7 hours, 10 hours, 12 hours, 16 hours, 20 hours, 24 hours, 2 days, 3 days, 4 days, 5 days, 6 days, 7 days, 10 days, two weeks, 15 days, 16 days, 17 days, 18 days, 19 days, 20 days, 21 days, 22 days, 23 days, 24 days, 25 days, 26 days, 27 days, 28 days, 29 days, 30 days, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 1 year, 18 months or 2 years at room temperature (23° C.). In some embodiments, any of the storage solutions disclosed herein is capable of preserving DNA methylation patterns in a target DNA sequence/target gene in a biological sample for at least 1 hour, 2 hours, 3 hours, 4 hours, 5 hours, 6 hours, 7 hours, 10 hours, 12 hours, 16 hours, 20 hours, 24 hours, 2 days, 3 days, 4 days, 5 days, 6 days, 7 days, 10 days, two weeks, 15 days, 16 days, 17 days, 18 days, 19 days, 20 days, 21 days, 22 days, 23 days, 24 days, 25 days, 26 days, 27 days, 28 days, 29 days, 30 days, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 1 year, 18 months or 2 years at 4° C. In some embodiments, any of the storage solutions disclosed herein is capable of preserving DNA methylation patterns in a target DNA sequence/target gene in a biological sample for at least 1 hour, 2 hours, 3 hours, 4 hours, 5 hours, 6 hours, 7 hours, 10 hours, 12 hours, 16 hours, 20 hours, 24 hours, 2 days, 3 days, 4 days, 5 days, 6 days, 7 days, 10 days, two weeks, 15 days, 16 days, 17 days, 18 days, 19 days, 20 days, 21 days, 22 days, 23 days, 24 days, 25 days, 26 days, 27 days, 28 days, 29 days, 30 days, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 1 year, 18 months or 2 years at −10° C. In certain embodiments, the storage solution is maintained at a temperature below 50° C. In certain embodiments, the storage solution is maintained at a temperature below 45° C. In certain embodiments, the storage solution is maintained at a temperature below 40° C. In certain embodiments, the storage solution is maintained at a temperature below 37° C. In certain embodiments, the storage solution is maintained at a temperature below 35° C. In certain embodiments, the storage solution is maintained at a temperature below 30° C. In certain embodiments, the storage solution is maintained at a temperature below 25° C.

In some embodiments, any of the storage solutions disclosed herein preserves DNA methylation patterns in a target DNA sequence/target gene in a biological sample obtained from a subject. In some embodiments, methylation patterns are preserved in the target DNA sequence/target gene of at least 75%, 80%, 85%, 90%, 95% or 100% of the copies of the target DNA sequence/target gene in a biological sample have the same or nearly the same methylation pattern after a period of time (e.g., 21 days) in any of the storage solutions described herein as compared to the methylation patterns associated with a reference target DNA sequence (e.g., a reference differentially methylated domain). In some embodiments, a target DNA sequence/target gene stored in a storage solution for a period of time is considered to have nearly the same methylation pattern of a reference target DNA molecule if the target sequence in a DNA molecule that has been stored in a storage solution for a period of time (e.g., 21 days) has a methylation pattern that is at least 75%, 80%, 85%, 90%, 95%, or 100% the same as the methylation pattern of a reference target DNA sequence (e.g., a reference differentially methylated domain). In some embodiments, the reference target DNA molecule or reference target DNA sequence is a DNA molecule/sequence for which the methylation pattern has been previously determined for a reference cell (e.g., a healthy control cell). In some embodiments, the reference target DNA molecule or reference target DNA sequence is a DNA molecule/sequence for which the methylation pattern is determined in a sample after isolation of the sample from a subject. In some embodiments, the methylation pattern of the reference target DNA sequence is determined prior to storage of the reference target DNA sequence for more than 1 hour, 2 hours, 4 hours, 6 hours, 12 hours, 18 hours, or 1 day following obtaining the sample comprising the reference target DNA sequence from a subject. In preferred embodiments, the reference target DNA sequence/molecule is from the same cell type (e.g., an esophageal neoplastic cell) as the cell type from which the stored target DNA sequence/molecule is compared.

In some embodiments, the methylation pattern of a differentially methylated domain in a DNA molecule stored in a storage solution is considered to be preserved if at least 70%, 75%, 80%, 85%, 90%, 95%, or 100% of the CpGs known to be methylated in a reference differentially methylated domain of a reference DNA molecule are methylated in the differentially methylated domain of the stored DNA molecule after a period of time (e.g., 21 days). In some embodiments, at least 50%, 60%, 70%, 80%, 90%, or 100% of the DNA molecules in a sample stored in any of the storage solutions disclosed herein for a period of time (e.g., 21 days) have a preserved methylation pattern.

C. Target Genes

In some embodiments, any of the storage solutions described herein may be used to preserve the methylation patterns of any of the target genes disclosed herein. As used herein, the term "target gene" includes all non-coding and coding regions associated with a particular gene, as well as complements and/or fragments thereof. For example, the term "target gene" comprises regulatory sequences upstream of the coding sequence for any particular gene. In some embodiments, a target gene comprises promoters, repressors, enhancers, silencers, introns, and exons of a particular gene of interest (e.g., vimentin or CCNA1). In particular embodiments, the target gene comprises the 5' flanking or promoter regions of the target gene, as CpG islands are prominently represented in the 5'-flanking region or promoter region of about half the genes in our genome. In some embodiments, the methylation patterns of a target gene are only determined for a fragment of a particular gene of interest, e.g., for a portion of the 5' flanking or promoter regions of the target gene. In particular embodiments, the term "target gene" refers to a differentially methylated domain of a gene.

In some embodiments, the target gene is any one or more of vimentin, CCNA1, FER1L4, VAV3, DOCK1, ADCY1, BMP3, M13D, ELM, ELOVL2, LRRC4, NDRG4, SFMBT2, ST8SIA1, TSPYL5, ZNF568, ZNF569, ZNF610, ZNF671, ZNF682, CDKN2A, DI03, HUNK, Up35-1, Up35-2 or Up10, or a fragment and/or complement thereof. In some embodiments, the target gene may be a gene in which differential methylation may be used for distinguishing or detecting a tissue metaplasia or neoplasia, as for example, but not limited to, a metaplasia or neoplasia of the esophagus. Examples of differentially methylated domains (DMR) of other genomic loci are represented in Table 1:

TABLE 1

| Gene name | Chromosome No. | DMR Start and End Position (hg19) | DMR2 | DMR3 | DMR4 |
|---|---|---|---|---|---|
| ADCY1 | 7 | 45613877-45614572 | | | |
| BMP3 | 4 | 81952348-81952402 | 81031173-81031262 | | |
| CD1D | 1 | 158150797-158151205 | | | |
| CDKN2A | 9 | 21974710-21974763 | 21975053-21975199 | | |
| DIO3 | 14 | 102026104-102026204 | | | |
| DOCK10 | 2 | 225907226-225907322 | | | |
| ELMO1 | 7 | 37487755-37488477 | | | |
| ELOVL2 | 6 | 11044395-11044834 | | | |
| FER1L4 | 20 | 34189488-34189693 | 34189488-34189693 | | |
| HUNK | 21 | 33246580-33246650 | | | |
| LRRC4 | 7 | 127671993-127672310 | | | |
| NDRG4 | 16 | 58497395-58497451 | | | |
| SFMBT2 | 10 | 7452885-7452956 | 7451771-7451869 | 7452029-7452452 | 7450242-7450831 |
| ST8SIA1 | 12 | 22487528-22487620 | | | |
| TSPYL5 | 8 | 98289858-98290220 | | | |
| VAV3 | 1 | 108507608-108507679 | | | |
| ZNF568 | 19 | 37407197-37407284 | 37407197-37407365 | | |
| ZNF569 | 19 | 37957760-37958046 | | | |
| ZNF610 | 19 | 52839503-52840013 | | | |
| ZNF671 | 19 | 58238810-58238955 | | | |
| ZNF682 | 19 | 20149796-20149923 | | | |

In some embodiments, a target gene comprises a nucleotide sequence that is at least 60%, 65%, 70%, 75%, 80%, 85%, 90%, 91%, 92%, 93%, 94%, 95%, 96%, 97%, 98%, 99%, or 100% identical to any of the nucleotide sequences disclosed in Table 1, or any fragments and/or complements thereof.

In some embodiments, the target gene comprises at least a portion of a vimentin gene. In some embodiments, the target gene comprises a nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 1, or a fragment and/or complement thereof. In some embodiments, the target gene comprises a nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 2, or a fragment and/or complement thereof. In some embodiments, the target gene comprises a nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 3, or a fragment or a fragment and/or complement thereof. In some embodiments, the target gene comprises a nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 4, or a fragment and/or complement thereof. In some embodiments, the target gene comprises a nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 5, or a fragment and/or complement thereof. In some embodiments, the target gene comprises a nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 18, or a fragment and/or complement thereof. In some embodiments, the target gene comprises the nucleotide sequence of any one of the vimentin nucleotide sequences disclosed in U.S. Pat. No. 9,580,754 (which patent is incorporated herein by reference in its entirety), or a fragment and/or complement thereof.

In some embodiments, the target gene comprises a vimentin nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence corresponding to Hg19 coordinates: chr10:17,270,838-17,271,347, or any fragments and/or complements thereof. In some embodiments, the target gene comprises a vimentin nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence corresponding to Hg19 coordinates: chr10:17,270,838-17, 271,717, or any fragments and/or complements thereof.

In some embodiments, the target gene comprises a vimentin nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence corresponding to Hg19 coordinates: chr10:17271442-17271547, or any fragments and/or complements thereof. In some embodiments, the target gene comprises a vimentin nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 5, or any fragments and/or complements thereof.

In some embodiments, the target gene comprises a CCNA1 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence corresponding to Hg19 coordinates chr13: 37005805-37006194, or a fragment and/or complement thereof. In some embodiments, the target gene comprises a CCNA1 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence corresponding to Hg19 coordinates chr13: 37005856-37006031, or a fragment and/or complement thereof. In some embodiments, the target gene comprises a CCNA1 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 6, or a fragment and/or complement thereof. In some embodiments, the target gene comprises a CCNA1 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 7, or a fragment and/or complement thereof.

In some embodiments, the target gene comprises an Up10 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 8, or a fragment and/or complement thereof. In some embodiments, the target gene comprises an Up10 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 9, or a fragment and/or complement thereof. In some embodiments, the target gene comprises an Up10 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 10, or a fragment and/or complement thereof. In some embodiments, the target gene comprises an Up10 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 11, or a fragment and/or complement thereof.

In some embodiments, the target gene comprises an Up35-1 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 12, or a fragment and/or complement thereof. In some embodiments, the target gene comprises an Up35-1 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 13, or a fragment and/or complement thereof. In some embodiments, the target gene comprises an Up35-1 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 14, or a fragment and/or complement thereof. In some embodiments, the target gene comprises an Up35-1 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 15, or a fragment and/or complement thereof.

In some embodiments, the target gene comprises an Up35-2 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 12, or a fragment and/or complement thereof. In some embodiments, the target gene comprises an Up35-2 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 13, or a fragment and/or complement thereof. In some embodiments, the target gene comprises an Up35-2 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 16, or a fragment and/or complement thereof. In some embodiments, the target gene comprises an Up35-2 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 17, or a fragment and/or complement thereof.

In some embodiments, the target gene comprises an ADCY1 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 19, or a fragment and/or complement thereof.

In some embodiments, the target gene comprises a BMP3 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 20, or a fragment and/or complement thereof. In some embodiments, the target gene comprises a BMP3 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 21, or a fragment and/or complement thereof.

In some embodiments, the target gene comprises a CD1D nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 22, or a fragment and/or complement thereof.

In some embodiments, the target gene comprises a CDKN2A nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 23, or a fragment and/or complement thereof. In some embodiments, the target gene comprises a CDKN2A nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 24, or a fragment and/or complement thereof.

In some embodiments, the target gene comprises a DI03 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 25, or a fragment and/or complement thereof.

In some embodiments, the target gene comprises a DOCK10 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 26, or a fragment and/or complement thereof.

In some embodiments, the target gene comprises a ELMO1 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 27, or a fragment and/or complement thereof.

In some embodiments, the target gene comprises a ELOVL2 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 28, or a fragment and/or complement thereof.

In some embodiments, the target gene comprises a FER1L4 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 29, or a fragment and/or complement thereof.

In some embodiments, the target gene comprises a HUNK nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 30, or a fragment and/or complement thereof.

In some embodiments, the target gene comprises a LRRC4 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 31, or a fragment and/or complement thereof.

In some embodiments, the target gene comprises a NDRG4 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 32, or a fragment and/or complement thereof.

In some embodiments, the target gene comprises a SFMBT2 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 33, or a fragment and/or complement thereof. In some embodiments, the target gene comprises a SFMBT2 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 34, or a fragment and/or complement thereof. In some embodiments, the target gene comprises a SFMBT2 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 35, or a fragment and/or complement thereof. In some embodiments, the target gene comprises a SFMBT2 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 36, or a fragment and/or complement thereof.

In some embodiments, the target gene comprises a ST8S1A1 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 37, or a fragment and/or complement thereof.

In some embodiments, the target gene comprises a TSPYL5 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 38, or a fragment and/or complement thereof.

In some embodiments, the target gene comprises a VAV3 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 39, or a fragment and/or complement thereof.

In some embodiments, the target gene comprises a ZNF568 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 40, or a fragment and/or complement thereof. In some embodiments, the target gene comprises a ZNF568 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 41, or a fragment and/or complement thereof.

In some embodiments, the target gene comprises a ZNF569 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 42, or a fragment and/or complement thereof.

In some embodiments, the target gene comprises a ZNF610 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 43, or a fragment and/or complement thereof.

In some embodiments, the target gene comprises a ZNF671 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 44, or a fragment and/or complement thereof.

In some embodiments, the target gene comprises a ZNF682 nucleotide sequence that is at least 60%, 65%, 70%, 75%, 80%, 85%, 90%, 91%, 92%, 93%, 94%, 95%, 96%, 97%, 98%, 99%, or 100% identical to the nucleotide sequence of SEQ ID NO: 45, or a fragment and/or complement thereof.

In some embodiments, any of the target gene fragments disclosed herein is at least 10, 20, 30, 40, 50, 60, 70, 80, 90, 100, 200, 250, 300, 350, 400, 450, 500, 550, 600, 700, 800, 900, or 1000 nucleotides in length. In particular embodiments, the fragment is at least 20 nucleotides in length. In some embodiments, any of the target gene fragments disclosed herein is between 10-1000, between 10-500, between 10-250, between 10-200, between 10-150, between 10-100, between 10-50, between 10-25, between 10-20, between 25-50, between 50-75, between 25-100, between 50-100, between 50-150, between 100-200, between 50-250, or between 100-250 nucleotides in length.

D. Biological Samples

In some embodiments, any of the storage solutions described herein is for use in storing any of the biological samples disclosed herein. Samples may be essentially any biological material of interest, e.g., a collection of cells taken from a subject. For example, a sample may be a bodily fluid sample from a subject, a tissue sample from a subject, a solid or semi-solid sample from a subject, a primary cell culture or tissue culture of materials derived from a subject, cells from a cell line, or medium or other extracellular material from a cell or tissue culture, or a xenograft (meaning a sample of a cancer from a first subject, e.g., a human, that has been cultured in a second subject, e.g., an immunocompromised mouse). The term "sample" as used herein is intended to encompass both a biological material obtained directly from a subject (which may be described as the primary sample) as well as any manipulated forms or portions of a primary sample. A sample may also be obtained by contacting a biological material with an exogenous liquid, resulting in the production of a lavage liquid containing some portion of the contacted biological material. Furthermore, the term "sample" is intended to encompass the primary sample after it has been mixed with one or more additive, such as preservatives, chelators, anti-clotting factors, etc. In some embodiments, a sample is obtained by means of a cytology brushing and/or a balloon. In some embodiments, the sample is obtained from a subject's gastroesophageal junction.

In certain embodiments, a bodily fluid sample is a blood sample. In this case, the term "sample" is intended to encompass not only the blood as obtained directly from the patient but also fractions of the blood, such as plasma, serum, cell fractions (e.g., platelets, erythrocytes, and lymphocytes), protein preparations, nucleic acid preparations, etc. In some embodiments, the bodily fluid may be derived from the stomach, for example, gastric secretions, acid reflux, or vomit. In other embodiments, the bodily fluid may be a fluid secreted by the pancreas or bladder. In other embodiments, the body fluid may be saliva, spit, or an esophageal washing. In certain embodiments, a tissue sample is a biopsy taken from the mucosa of the gastrointestinal tract. In other embodiments, a tissue sample is the brushings from, e.g., the esophagus of a subject.

In some embodiments, the biological sample is a sample from any of: gastrointestinal tract, aerodigestive tract, respiratory tract, genitourinary tract, or a body fluid. In certain such embodiments, the body fluid is any of: blood, urine, sputum, saliva, stool, bile, pancreatic juice, nasal secretions, tears, semen, vaginal secretions, cerebrospinal fluid, pleural fluid, peritoneal fluid, gastric juice, pericardial fluid, sweat, lymph, cyst fluid, pancreatic cyst fluid, synovial fluid, joint fluid, menstrual fluid, endometrial washing, breast aspirate, or amniotic fluid. In some embodiments, the biological sample is a sample from any of: esophagus, stomach, colon, small intestine, pancreas, liver, oral cavity, oropharynx, trachea, bronchial tree, lung, or breast.

In some embodiments, the biological sample is at least a portion of a cell, tissue, or organ from a subject. In some embodiments, the sample is a tissue sample from the gastrointestinal tract. In some embodiments, the sample is a tissue sample from the upper gastrointestinal tract. In some embodiments, the sample is a tissue from the lower gastrointestinal tract. In some embodiments, the sample is a cell or tissue sample from the esophagus. In some embodiments, the sample is a cell or tissue sample from the stomach. In some embodiments, the sample is a cell or tissue sample from the intestine. In some embodiments, the sample is a cell or tissue sample from the colon.

In some embodiments, the sample comprises cells of any one or more of the following cell types: urinary bladder, pancreatic epithelial, pancreatic alpha, pancreatic beta, pancreatic endothelial, bone marrow lymphoblast, bone marrow B lymphoblast, bone marrow macrophage, bone marrow erythroblast, bone marrow dendritic, bone marrow adipocyte, bone marrow osteocyte, bone marrow chondrocyte, promyeloblast, bone marrow megakaryoblast, bladder, brain B lymphocyte, brain glial, neuron, brain astrocyte, neuroectoderm, brain macrophage, brain microglia, brain epithelial, cardiomyocyte, cortical neuron, brain fibroblast, breast epithelial, colon epithelial, colon B lymphocyte, esophagus epithelial, mammary epithelial, mammary myoepithelial, mammary fibroblast, colon enterocyte, cervix epithelial, ovary epithelial, ovary fibroblast, breast duct epithelial, tongue epithelial, tonsil dendritic, tonsil B lymphocyte, peripheral blood lymphoblast, peripheral blood T lymphoblast, peripheral blood cutaneous T lymphocyte, peripheral blood natural killer, peripheral blood B lymphoblast, peripheral blood monocyte, peripheral blood myeloblast, peripheral blood monoblast, peripheral blood promyeloblast, peripheral blood macrophage, peripheral blood basophil, liver endothelial, liver mast, liver epithelial, liver B lymphocyte, spleen endothelial, spleen epithelial, spleen B lymphocyte, liver hepatocyte, liver Alexander, liver fibroblast, lung epithelial, bronchus epithelial, lung fibroblast, lung B lymphocyte, lung Schwann, lung squamous, lung macrophage, lung osteoblast, neuroendocrine, lung alveolar, stomach epithelial, and stomach fibroblast.

In some embodiments, the sample comprises one or more neoplastic cells. In some embodiments, the sample comprises one or more metaplastic cells. In some embodiments, the sample comprises one or more cancer cells. In some embodiments, the sample comprises one or more cancer cells, wherein the cancer cells are associated with any one or more of the following cancers: Acute Lymphoblastic Leukemia (ALL), Acute Myeloid Leukemia (AML), Adrenocortical Carcinoma Childhood Adrenocortical Carcinoma, AIDS-Related Cancers Kaposi Sarcoma (Soft Tissue Sarcoma), AIDS-Related Lymphoma (Lymphoma), Primary CNS Lymphoma (Lymphoma), Anal Cancer, Appendix Cancer, Gastrointestinal Carcinoid Tumors, Astrocytomas, brain cancer, Atypical Teratoid/Rhabdoid Tumor, skin cancer, Basal Cell Carcinoma, Bile Duct Cancer, Bladder Cancer Childhood Bladder Cancer, Bone Cancer, Ewing Sarcoma and Osteosarcoma and Malignant Fibrous Histiocytoma, Brain Tumors, Breast Cancer, Bronchial Tumors, Burkitt Lymphoma, Non-Hodgkin Lymphoma, Carcinoid Tumor, cardiac cancer, Primary CNS Lymphoma, Cervical Cancer, Cholangiocarcinoma, Bile Duct Cancer, Chordoma, Chronic Lymphocytic Leukemia (CLL), Chronic Myelogenous Leukemia (CML), Chronic Myeloproliferative Neoplasms, colon cancer, Colorectal Cancer, Craniopharyngioma, Cutaneous T-Cell Lymphoma, Ductal Carcinoma In Situ (DCIS), Endometrial Cancer, Uterine Cancer, Ependymoma, Esophageal cancer, Esthesioneuroblastoma, Head and Neck Cancer, Ewing Sarcoma, Bone Cancer, Extracranial Germ Cell Tumor, Extragonadal Germ Cell Tumor, Eye Cancer Childhood Intraocular Melanoma, Intraocular Melanoma, Retinoblastoma, Fallopian Tube Cancer, Fibrous Histiocytoma of Bone, Malignant, and Osteosarcoma, Gallbladder Cancer, Gastric Cancer, Gastrointestinal Carcinoid Tumor, Ovarian Cancer, Testicular Cancer, Gestational Trophoblastic Disease, Hairy Cell Leukemia, Head and Neck Cancer, Heart Tumors, Liver Cancer, Hodgkin Lymphoma, Hypopharyngeal Cancer, Intraocular Melanoma, Islet Cell Tumors, Pancreatic Neuroendocrine Tumors, Kaposi Sarcoma, Soft Tissue Sarcoma, Renal Cancer, Langerhans Cell Histiocytosis, Laryngeal Cancer, Leukemia, Lip and Oral Cavity Cancer, Lung Cancer (Non-Small Cell and Small Cell), Lymphoma, Male Breast Cancer, Malignant Fibrous Histiocytoma of Bone and Osteosarcoma. Melanoma, Skin Cancer, Merkel Cell Carcinoma, Mesothelioma, Metastatic Cancer, Metastatic Squamous Neck Cancer with Occult Primary, Midline Tract Carcinoma With NUT Gene Changes, Mouth Cancer, Multiple Endocrine Neoplasia Syndromes, Multiple Myeloma/Plasma Cell Neoplasms, Mycosis Fungoides, Myelodysplastic Syndromes, Myelodysplastic/Myeloproliferative Neoplasms, Myelogenous Leukemia, Chronic (CML), Myeloid Leukemia, Acute (AML), Myeloproliferative Neoplasms, Nasal Cavity and Paranasal Sinus Cancer, Nasopharyngeal Cancer, Neuroblastoma, Non-Hodgkin Lymphoma, Non-Small Cell Lung Cancer, Oral Cancer, Lip and Oral Cavity Cancer and Oropharyngeal Cancer, Osteosarcoma and Malignant Fibrous Histiocytoma of Bone, Ovarian Cancer, Pancreatic Cancer, Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Pregnancy and Breast Cancer, Primary Central Nervous System (CNS) Lymphoma, Primary Peritoneal Cancer, Prostate Cancer, Rectal Cancer, Retinoblastoma, Rhabdomyosarcoma, Salivary Gland Cancer, Sarcoma Childhood Rhabdomyosarcoma, Childhood Vascular Tumors, Ewing Sarcoma, Kaposi Sarcoma, Osteosarcoma, Soft Tissue Sarcoma, Uterine Sarcoma, Sézary Syndrome, Small Cell Lung Cancer, Small Intestine Cancer, Soft Tissue Sarcoma, Squamous Cell Carcinoma of the Skin, Squamous Neck Cancer with Occult Primary, Stomach Cancer, T-Cell Lymphoma, Testicular Cancer, Throat Cancer, Nasopharyngeal Cancer, Oropharyngeal Cancer, Hypopharyngeal Cancer, Thymoma and Thymic Carcinoma, Thyroid Cancer, Transitional Cell Cancer of the Renal Pelvis and Ureter, Urethral Cancer, Uterine Cancer, Endometrial Cancer, Uterine Sarcoma, Vaginal Cancer, Vulvar Cancer, and/or Wilms Tumor. In particular embodiments, the sample comprises one or more esophageal cancer cells. In some embodiments, the sample comprises one or more colon cancer cells. In some embodiments, the sample comprises one or more Barrett's esophagus cells.

In some embodiments, the sample comprises cells and/or tissue from a subject suspected of having any of the neoplasias disclosed herein (e.g., esophageal adenocarcinoma), any of the cancers disclosed herein, or any of the metaplasias disclosed herein (e.g., Barrett's esophagus). Alternatively, a subject may be undergoing routine screening and may not necessarily be suspected of having such metaplasia or neoplasia.

A subject is in some embodiments a human subject. In other embodiments, a subject is a non-human animal.

In certain embodiments, it may be possible to detect a biomarker described herein (e.g., DNA methylation or protein expression level) directly in an organism without obtaining a separate portion of biological material. In such instances, the term "sample" is intended to encompass that portion of biological material that is contacted with a reagent or device involved in the detection process.

In certain embodiments, DNA comprising a target gene of interest is obtained from a bodily fluid sample. Examples of bodily fluids are blood, saliva, spit or an esophageal washing. Other body fluids can also be used. Because they can be easily obtained from a subject and can be used to screen for multiple diseases, blood or blood-derived fractions may be especially useful. Blood-derived fractions can comprise blood, serum, plasma, or other fractions. For example, a cellular fraction can be prepared as a "buffy coat" (i.e., leukocyte-enriched blood portion) by centrifuging 5 ml of whole blood for 10 min at 800 times gravity at room temperature. Red blood cells sediment most rapidly and are present as the bottom-most fraction in the centrifuge tube. The buffy coat is present as a thin creamy white colored layer on top of the red blood cells. The plasma portion of the blood forms a layer above the buffy coat. Fractions from blood can also be isolated in a variety of other ways. One method is by taking a fraction or fractions from a gradient used in centrifugation to enrich for a specific size or density of cells.

In some embodiments, DNA is isolated from samples. In some embodiments, the term "biological sample" or "sample" is used to refer to DNA isolated from a cell sample or tissue sample or bodily fluid sample or stool sample from a subject. Procedures for isolation of DNA from such samples are well known to those skilled in the art. Commonly, such DNA isolation procedures comprise lysis of any cells present in the samples using detergents, for example. After cell lysis, proteins are commonly removed from the DNA using various proteases. RNA is removed using RNase. The DNA is then commonly extracted with phenol, precipitated in alcohol and dissolved in an aqueous solution.

E. Methods of Use

In some embodiments, the disclosure provides for a method of preserving DNA methylation patterns in any of the target genes disclosed herein (or fragments thereof) in any of the biological samples disclosed herein. In some embodiments, the method comprises administering any of the biological samples disclosed herein to any of the storage solutions described herein. In some embodiments, the method comprises mixing any of the biological samples disclosed herein with any of the storage solutions described herein. In some embodiments, the method comprises treating any of the biological samples disclosed herein with any of the storage solutions described herein. In some embodiments, the method comprises storing any of the biological samples disclosed herein in any of the storage solutions described herein. In some embodiments, the method comprises storing the sample in the storage solution for at least 1 hour, 2 hours, 3 hours, 4 hours, 5 hours, 6 hours, 7 hours, 10 hours, 12 hours, 16 hours, 20 hours, 24 hours, 2 days, 3 days, 4 days, 5 days, 6 days, 7 days, 10 days, two weeks, 15 days, 16 days, 17 days, 18 days, 19 days, 20 days, 21 days, 22 days, 23 days, 24 days, 25 days, 26 days, 27 days, 28 days, 29 days, 30 days, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 1 year, 18 months or 2 years. In some embodiments, the method comprises storing the sample in the storage solution at a temperature ranging from −30° C. to 50° C. In some embodiments, the method comprises storing the sample in the storage solution at a temperature ranging from −20° C. to 40° C. In some embodiments, the method comprises storing the sample in the storage solution at a temperature ranging from −10° C. to 30° C. In some embodiments, the method comprises storing the sample in the storage solution at a temperature ranging from 0° C. to 25° C. In some embodiments, the method comprises storing the sample in the storage solution at a temperature ranging from 4° C. to 25° C. In some embodiments, the method comprises storing the sample in the storage solution at a temperature ranging from −10° C. to 10° C. In some embodiments, the method comprises storing the sample in the storage solution at a temperature ranging from 15° C. to 25° C. In some embodiments, the method comprises storing the sample in the storage solution at room temperature. In some embodiments, the method comprises storing the sample in the storage solution for at least 1 hour, 2 hours, 3 hours, 4 hours, 5 hours, 6 hours, 7 hours, 10 hours, 12 hours, 16 hours, 20 hours, 24 hours, 2 days, 3 days, 4 days, 5 days, 6 days, 7 days, 10 days, two weeks, 15 days, 16 days, 17 days, 18 days, 19 days, 20 days, 21 days, 22 days, 23 days, 24 days, 25 days, 26 days, 27 days, 28 days, 29 days, 30 days, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 1 year, 18 months or 2 years at 23° C. In some embodiments, the method comprises storing the sample in the storage solution for at least 1 hour, 2 hours, 3 hours, 4 hours, 5 hours, 6 hours, 7 hours, 10 hours, 12 hours, 16 hours, 20 hours, 24 hours, 2 days, 3 days, 4 days, 5 days, 6 days, 7 days, 10 days, two weeks, 15 days, 16 days, 17 days, 18 days, 19 days, 20 days, 21 days, 22 days, 23 days, 24 days, 25 days, 26 days, 27 days, 28 days, 29 days, 30 days, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 1 year, 18 months or 2 years at 40° C. In some embodiments, the method comprises storing the sample in the storage solution for at least 1 hour, 2 hours, 3 hours, 4 hours, 5 hours, 6 hours, 7 hours, 10 hours, 12 hours, 16 hours, 20 hours, 24 hours, 2 days, 3 days, 4 days, 5 days, 6 days, 7 days, 10 days, two weeks, 15 days, 16 days, 17 days, 18 days, 19 days, 20 days, 21 days, 22 days, 23 days, 24 days, 25 days, 26 days, 27 days, 28 days, 29 days, 30 days, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 1 year, 18 months or 2 years at 50° C. In some embodiments, the method comprises storing the sample in the storage solution for at least 1 hour, 2 hours, 3 hours, 4 hours, 5 hours, 6 hours, 7 hours, 10 hours, 12 hours, 16 hours, 20 hours, 24 hours, 2 days, 3 days, 4 days, 5 days, 6 days, 7 days, 10 days, two weeks, 15 days, 16 days, 17 days, 18 days, 19 days, 20 days, 21 days, 22 days, 23 days, 24 days, 25 days, 26 days, 27 days, 28 days, 29 days, 30 days, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 1 year, 18 months or 2 years at 4° C. In some embodiments, the method comprises storing the sample in the storage solution for at least 1 hour, 2 hours, 3 hours, 4 hours, 5 hours, 6 hours, 7 hours, 10 hours, 12 hours, 16 hours, 20 hours, 24 hours, 2 days, 3 days, 4 days, 5 days, 6 days, 7 days, 10 days, two weeks, 15 days, 16 days, 17 days, 18 days, 19 days, 20 days, 21 days, 22 days, 23 days, 24 days, 25 days, 26 days, 27 days, 28 days, 29 days, 30 days, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 1 year, 18 months or 2 years at −10° C. In some embodiments, the method comprises storing the sample in the storage solution for at least 1 hour, 2 hours, 3 hours, 4 hours, 5 hours, 6 hours, 7 hours, 10 hours, 12 hours, 16 hours, 20 hours, 24 hours, 2 days, 3 days, 4 days, 5 days, 6 days, 7 days, 10 days, two weeks, 15 days, 16 days, 17 days, 18 days, 19 days, 20 days, 21 days, 22 days, 23 days, 24 days, 25 days, 26 days, 27 days, 28 days, 29 days, 30 days, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 1 year, 18 months or 2 years at −30° C. In some embodiments, the method comprises storing the sample in the storage solution for at least 1 hour, 2 hours, 3 hours, 4 hours, 5 hours, 6 hours, 7 hours, 10 hours, 12 hours, 16 hours, 20 hours, 24 hours, 2 days, 3 days, 4 days, 5 days, 6 days, 7 days, 10 days, two weeks, 15 days, 16 days, 17 days, 18 days, 19 days, 20 days, 21 days, 22 days, 23 days, 24 days, 25 days, 26 days, 27 days, 28 days, 29 days, 30 days, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 1 year, 18 months or 2 years at a temperature ranging between −30° C. to 50° C.

In some embodiments, the storage sample is stored in a container. In some embodiments, the container is a vial. In some embodiments, the container is made of glass. In some embodiments, the container is made of plastic. In some embodiments, the container is made of polypropylene. In some embodiments, the container is made of polystyrene. In some embodiments, the container is capable of holding a volume of at least 5 ml, 10 ml, 15 ml, 20 ml, 25 ml, 30 ml, 35 ml, 40 ml, 50 ml, 75 ml or 100 ml. In some embodiments, the container is a centrifuge vial. In some embodiments, if the sample is collected by means of a balloon (e.g., if obtaining an esophageal sample), the centrifuge vial is capable of completely covering the balloon and sample when added to the vial. In some embodiments, if the sample is collected by means of a balloon (e.g., if obtaining an esophageal sample), the centrifuge vial is capable of completely covering the balloon when 60%-70% full and the sample when added to the vial. In particular embodiments, the centrifuge vial is free-standing 30 ml polypropylene tube (see, e.g., Evergreen Scientific).

In some embodiments, the disclosure provides for a kit comprising any of the containers disclosed herein and any of the storage solutions disclosed herein. In some embodiments, the kit further comprises instructions for using the container and storage solution. In some embodiments, the kit further comprises an instrument for obtaining a sample from a subject (e.g., a balloon). In particular embodiments, the kit comprises a storage solution comprising tris and/or BHT and 50:50 methanol:water. In further embodiments, the kit comprises a storage solution comprising tris and/or BHT and 50:50 methanol:water, and the kit further comprises a container that is a 30 ml polypropylene centrifuge vial.

In some embodiments, once any of the samples disclosed herein has been added to any of the containers disclosed herein comprising any of the storage solutions disclosed herein, the container is then placed in a package. In some embodiments, the package is an envelope or a box. In some embodiments, the box is a cardboard box. In some embodiments, the package comprises a mailing label. In some embodiments, the box is shipped to another location for analysis of the sample.

In some embodiments, any of the samples stored in any of the storage solutions described herein may be used in any of the methods disclosed herein. In some embodiments, the sample comprising methylated DNA may be used in an assay for detecting differentially methylated nucleotide sequences. In certain embodiments, the application provides assays for detecting differentially methylated nucleotide sequences (e.g., vimentin and/or CCNA1). Thus, in some embodiments, a differentially methylated nucleotide sequence, in its methylated state, can serve as a target for detection using various methods described herein and the methods that are well within the purview of the skilled artisan in view of the teachings of this application.

In certain aspects, such methods for detecting methylated nucleotide sequences (e.g., vimentin and/or CCNA1) are based on treatment of genomic DNA with a chemical compound which converts non-methylated C, but not methylated C (i.e., 5 mC), to a different nucleotide base. One such compound is sodium bisulfite (also referred to simply as "bisulfite" herein), which converts C, but not 5 mC, to U. Methods for bisulfite treatment of DNA are known in the art (Herman, et al., 1996, Proc Natl Acad Sci USA, 93:9821-6; Herman and Baylin, 1998, Current Protocols in Human Genetics, N. E. A. Dracopoli, ed., John Wiley & Sons, 2:10.6.1-10.6.10; U.S. Pat. No. 5,786,146). To illustrate, when a DNA molecule that contains unmethylated C nucleotides is treated with sodium bisulfite to become a compound-converted DNA, the sequence of that DNA is changed (C→U). Detection of the U in the converted nucleotide sequence is indicative of an unmethylated C.

The different nucleotide base (e.g., U) present in compound-converted nucleotide sequences can subsequently be detected in a variety of ways. In a particular embodiment, the disclosure provides a method of detecting U in compound-converted DNA sequences by using "methylation sensitive PCR" (MSP) (see, e.g., Herman, et al., 1996, *Proc. Natl. Acad. Sci. USA*, 93:9821-9826; U.S. Pat. Nos. 6,265, 171; 6,017,704; 6,200,756). In MSP, one set of primers (i.e., comprising a forward and a reverse primer) amplifies the compound-converted template sequence if C bases in CpG dinucleotides within the DNA are methylated. This set of primers is called "methylation-specific primers." Another set of primers amplifies the compound-converted template sequence if C bases in CpG dinucleotides within the 5' flanking sequence are not methylated. This set of primers is called "unmethylation-specific primers."

In MSP, the reactions use the compound-converted DNA from a sample in a subject. In assays for methylated DNA, methylation-specific primers are used. In the case where C within CpG dinucleotides of the target sequence of the DNA are methylated, the methylation-specific primers will amplify the compound-converted template sequence in the presence of a polymerase and an MSP product will be produced. If C within CpG dinucleotides of the target sequence of the DNA is not methylated, the methylation-specific primers will not amplify the compound-converted template sequence in the presence of a polymerase and an MSP product will not be produced. In some embodiments, any of the bisulfite converted methylated sequences disclosed herein is used as a marker for a particular indication.

In some embodiments, it is also useful to run a control reaction for the detection of unmethylated DNA. The reaction uses the compound-converted DNA from a sample in a subject and unmethylation-specific primers are used. In the case where C within CpG dinucleotides of the target sequence of the DNA are unmethylated, the unmethylation specific primers will amplify the compound-converted template sequence in the presence of a polymerase and an MSP product will be produced. If C within CpG dinucleotides of the target sequence of the DNA is methylated, the unmethylation-specific primers will not amplify the compound-converted template sequence in the presence of a polymerase and an MSP product will not be produced. Note that a biologic sample will often contain a mixture of both neoplastic cells that give rise to a signal with methylation specific primers, and normal cellular elements that give rise to a signal with unmethylation-specific primers. The unmethylation specific signal is often of use as a control reaction, but does not in this instance imply the absence of neoplasia as indicated by the positive signal derived from reactions using the methylation specific primers.

Primers for a MSP reaction are derived from the compound-converted template sequence. Herein, "derived from" means that the sequences of the primers are chosen such that the primers amplify the compound-converted template sequence in a MSP reaction. Each primer comprises a single-stranded DNA fragment which is at least 8 nucleotides in length. In some embodiments, the primers are less than 50 nucleotides in length, or in some embodiments, from 15 to 35 nucleotides in length. Because the compound-converted template sequence can be either the Watson strand or the Crick strand of the double-stranded DNA that is treated with sodium bisulfite, the sequences of the primers is dependent upon whether the Watson or Crick compound-converted template sequence is chosen to be amplified in the MSP. Either the Watson or Crick strand can be chosen to be amplified.

The compound-converted template sequence, and therefore the product of the MSP reaction, is, in some embodiments, between 20 to 3000 nucleotides in length. In other embodiments, the product of the MSP reaction is between 20 to 200 nucleotides in length. In other embodiments, the product of the MSP reaction is between 20 to 100 nucleotides in length. In other embodiments, the product of the MSP reaction is between 30 to 200 nucleotides in length. In other embodiments, the product of the MSP reaction is between 50 to 1000 nucleotides in length. In other embodiments, the product of the MSP reaction is between 50 to 100 nucleotides in length. In other embodiments, the product of the MSP reaction is between 50 to 200 nucleotides in length. In other embodiments, the product of the MSP reaction is between 50 to 500 nucleotides in length. In other embodiments, the product of the MSP reaction is between 80-150 nucleotides in length. In some embodiments, the product of the MSP reaction is at least 20, 30, 40, 50, 60, 70, 80, 90, 100, 110, 120, 130, 140, 150, 160, 170, 180, 190, 200, 210, 220, 230, 240 or 250 nucleotides in length. In some embodiments, the methylation-specific primers result in an MSP product of a different length than the MSP product produced by the unmethylation-specific primers.

A variety of methods can be used to determine if an MSP product has been produced in a reaction assay. One way to determine if an MSP product has been produced in the reaction is to analyze a portion of the reaction by agarose gel electrophoresis. For example, a horizontal agarose gel of from 0.6 to 2.0% agarose is made and a portion of the MSP reaction mixture is electrophoresed through the agarose gel. After electrophoresis, the agarose gel is stained with ethidium bromide. MSP products are visible when the gel is viewed during illumination with ultraviolet light. By comparison to standardized size markers, it is determined if the MSP product is of the correct expected size.

Other methods can be used to determine whether a product is made in an MSP reaction. One such method is called "real-time PCR." Real-time PCR utilizes a thermal cycler (i.e., an instrument that provides the temperature changes necessary for the PCR reaction to occur) that incorporates a fluorimeter (i.e. an instrument that measures fluorescence). The real-time PCR reaction mixture also contains a reagent whose incorporation into a product can be quantified and whose quantification is indicative of copy number of that sequence in the template. One such reagent is a fluorescent dye, called SYBR Green I (Molecular Probes, Inc.; Eugene, Oregon) that preferentially binds double-stranded DNA and whose fluorescence is greatly enhanced by binding of double-stranded DNA. When a PCR reaction is performed in the presence of SYBR Green I, resulting DNA products bind SYBR Green I and fluorescence. The fluorescence is detected and quantified by the fluorimeter. Such technique is particularly useful for quantification of the amount of the product in the PCR reaction. Additionally, the product from the PCR reaction may be quantitated in "real-time PCR" by the use of a variety of probes that hybridize to the product including TaqMan probes and molecular beacons. Quantitation may be on an absolute basis, or may be relative to a constitutively methylated DNA standard, or may be relative to an unmethylated DNA standard. In one instance the ratio of methylated derived product to unmethylated derived product may be constructed.

Methods for detecting methylation of the DNA according to the present disclosure are not limited to MSP, and may cover any assay for detecting DNA methylation. Another example method of detecting methylation of the DNA is by using "methylation-sensitive" restriction endonucleases. Such methods comprise treating the genomic DNA isolated from a subject with a methylation-sensitive restriction endonuclease and then using the restriction endonuclease-treated DNA as a template in a PCR reaction. Herein, methylation-sensitive restriction endonucleases recognize and cleave a specific sequence within the DNA if C bases within the recognition sequence are not methylated. If C bases within the recognition sequence of the restriction endonuclease are methylated, the DNA will not be cleaved. Examples of such methylation-sensitive restriction endonucleases include, but are not limited to HpaII, SmaI, SacII, EagI, BstUI, and BssHII. In this technique, a recognition sequence for a methylation-sensitive restriction endonuclease is located within the template DNA, at a position between the forward and reverse primers used for the PCR reaction. In the case that a C base within the methylation-sensitive restriction endonuclease recognition sequence is not methylated, the endonuclease will cleave the DNA template and a PCR product will not be formed when the DNA is used as a template in the PCR reaction. In the case that a C base within the methylation-sensitive restriction endonuclease recognition sequence is methylated, the endonuclease will not cleave the DNA template and a PCR product will be formed when the DNA is used as a template in the PCR reaction. Therefore, methylation of C bases can be determined by the absence or presence of a PCR product (Kane, et al., 1997, Cancer Res, 57:808-11). In particular embodiments, no sodium bisulfite is used in this technique.

Yet another exemplary method of detecting methylation of the DNA is called the modified MSP, which method utilizes primers that are designed and chosen such that products of the MSP reaction are susceptible to digestion by restriction endonucleases, depending upon whether the compound-converted template sequence contains CpG dinucleotides or UpG dinucleotides.

Yet other methods for detecting methylation of the DNA include the MS-SnuPE methods. This method uses compound-converted DNA as a template in a primer extension reaction wherein the primers used produce a product, dependent upon whether the compound-converted template contains CpG dinucleotides or UpG dinucleotides (see e.g., Gonzalgo, et al., 1997, Nucleic Acids Res., 25:2529-31).

Another exemplary method of detecting methylation of the DNA is called COBRA (i.e., combined bisulfite restriction analysis). This method has been routinely used for DNA methylation detection and is well known in the art (see, e.g., Xiong, et al., 1997, Nucleic Acids Res, 25:2532-4). In this technique, methylation-sensitive restriction endonucleases recognize and cleave a specific sequence within the DNA if C bases within the recognition sequence are methylated. If C bases within the recognition sequence of the restriction endonuclease are not methylated, the DNA will not be cleaved. In some embodiments, the method utilizes methylation-sensitive restriction endonucleases.

Another exemplary method of detecting methylation of DNA requires hybridization of a compound converted DNA to arrays that include probes that hybridize to sequences derived from a methylated template.

Another exemplary method of detecting methylation of DNA includes precipitation of methylated DNA with antibodies that bind methylated DNA or with other proteins that bind methylated DNA, and then detection of DNA sequences in the precipitate. The detection of DNA could be done by PCR based methods, by hybridization to arrays, or by other methods known to those skilled in the art.

Another exemplary method of detecting methylation of DNA is by Quantitative allele-specific real-time target and signal amplification (QuARTS) as performed on bisulfite converted DNA (see e.g., Zou et al., 2012, Clin. Chem., 58:375-83).

Another exemplary method of detecting methylation of DNA is by single molecule, real-time sequencing (SMRT) and nanopore-based sequencing of DNA that can directly detect DNA bases that are modified by methylation (see e.g., Beaulerier et al., Nat Rev Genet, 2019, 20:157-172.). SMRT may in some instances be performed on instrumentation manufactured by Pacific Biosciences (PacBio) (see e.g. https://www.pacb.com/smrt-science/smrt-sequencing/epigenetics/).

Another exemplary method of detecting methylated DNA is bisulfite sequencing that involves amplification of a target region of bisulfite converted DNA using methylation indifferent PCR primers that amplify converted DNAs derived from both methylated and unmethylated templates. The methylation indifferent primers are often designed to be both methylation indifferent and bisulfite specific, i.e. to amplify only bisulfite converted target DNAs and not to amplify non-converted target sequences. In some embodiments, the amplified DNAs then may be characterized by Next Generation Sequencing methods that allow each cytosine base in the original template to be assessed within each DNA sequence read for the presence of methylation (retention of cytosine) or the absence of methylation (conversion to thymidine). The percent of methylation at each cytosine base in the original template can then be calculated by the percent of DNA reads in which the cytosine is preserved as cytosine versus is converted to thymidine. Similarly, the percent of methylation across a region of interest can be assessed by determining a rule for assessing the region as methylated or unmethylated in an individual DNA read (i.e. determining a cutoff for methylation in the region that will categorize the region as "methylated"), and then determining the percent of DNA reads in which the region qualifies as methylated.

In certain embodiments, the disclosure provides methods that involve directly sequencing the product resulting from an MSP reaction to determine if the compound-converted template sequence contains CpG dinucleotides or UpG dinucleotides. Molecular biology techniques such as directly sequencing a PCR product are well known in the art.

In some embodiments, methylation of DNA may be measured as a percentage of total DNA. High levels of methylation may be 1-100% methylation, for example, 1%, 10%, 20%, 30%, 40%, 50%, 60%, 70%, 80%, 90%, or 100% methylation. Low levels of methylation may be 0%-0.99% methylation, for example, 0%, 0.1%, 0.5%, 0.6%, 0.7%, 0.8%, 0.9%. At least some normal tissues, for example, normal esophagus samples, may not have any detectable methylation.

In some embodiments, the methylated DNA stored in any of the storage solutions disclosed herein may encode a polypeptide that, for example, may function as a tumor suppressor gene. Accordingly, the application further provides methods for detecting such polypeptides in the samples. In some embodiments, the disclosure provides detection methods by assaying such polypeptides so as to determine whether a patient has or does not have a disease condition. Further, such a disease condition may be characterized by decreased levels of such polypeptides. In certain embodiments, the disclosure provides methods for determining whether a patient is or is not likely to have cancer by detecting such polypeptides. In further embodiments, the disclosure provides methods for determining whether the patient is having a relapse or determining whether a patient's cancer is responding to treatment.

Optionally, such methods involve obtaining a quantitative measure of the protein in the sample. In view of this specification, one of skill in the art will recognize a wide range of techniques that may be employed to detect and optionally quantitate the presence of a protein. In some embodiments, a protein is detected with an antibody. In many embodiments, an antibody-based detection assay involves bringing the sample and the antibody into contact so that the antibody has an opportunity to bind to proteins having the corresponding epitope. In many embodiments, an antibody-based detection assay also typically involves a system for detecting the presence of antibody-epitope complexes, thereby achieving a detection of the presence of the proteins having the corresponding epitope. Antibodies may be used in a variety of detection techniques, including enzyme-linked immunosorbent assays (ELISAs), immunoprecipitations, Western blots. Antibody-independent techniques for identifying a protein may also be employed. For example, mass spectroscopy, particularly coupled with liquid chromatography, permits detection and quantification of large numbers of proteins in a sample. Two-dimensional gel electrophoresis may also be used to identify proteins, and may be coupled with mass spectroscopy or other detection techniques, such as N-terminal protein sequencing. RNA aptamers with specific binding for the protein of interest may also be generated and used as a detection reagent. Samples should generally be prepared in a manner that is consistent with the detection system to be employed. For example, a sample to be used in a protein detection system should generally be prepared in the absence of proteases. Likewise, a sample to be used in a nucleic acid detection system should generally be prepared in the absence of nucleases. In many instances, a sample for use in an antibody-based detection system will not be subjected to substantial preparatory steps. For example, urine may be used directly, as may saliva and blood, although blood will, in certain embodiments, be separated into fractions such as plasma and serum.

In certain embodiments, a method of the disclosure comprises detecting in any of the samples stored in any of the storage solutions disclosed herein the presence of an expressed nucleic acid, such as an mRNA. Optionally, the method involves obtaining a quantitative measure of the expressed nucleic acid in the sample. In view of this specification, one of skill in the art will recognize a wide range of techniques that may be employed to detect and optionally quantitate the presence of a nucleic acid. Nucleic acid detection systems generally involve preparing a purified nucleic acid fraction of a sample, and subjecting the sample to a direct detection assay or an amplification process followed by a detection assay. Amplification may be achieved, for example, by polymerase chain reaction (PCR), reverse transcriptase (RT) and coupled RT-PCR. Detection of a nucleic acid is generally accomplished by probing the purified nucleic acid fraction with a probe that hybridizes to the nucleic acid of interest, and in many instances, detection involves an amplification as well. Northern blots, dot blots, microarrays, quantitative PCR, and quantitative RT-PCR are all well-known methods for detecting a nucleic acid in a sample.

In certain embodiments, the disclosure provides nucleic acid probes that bind specifically to any of the nucleic acids from any of the samples stored in any of the storage samples disclosed herein. In some embodiments, the disclosure provides nucleic acid probes that bind specifically to a nucleic acid amplified from DNA (which may be optionally pre-treated with a reagent such as bisulfite) from any of the samples stored in any of the storage samples disclosed herein. Such probes may be labeled with, for example, a fluorescent moiety, a radionuclide, an enzyme or an affinity tag such as a biotin moiety. For example, the TaqMan® system employs nucleic acid probes that are labeled in such a way that the fluorescent signal is quenched when the probe is free in solution and bright when the probe is incorporated into a larger nucleic acid.

Immunoscintigraphy using monoclonal antibodies directed at the methylated DNA (e.g., methylated DNA stored in any of the storage solutions described herein), or an amplicon of the methylated DNA (or an amplicon of pre-treated DNA, e.g., with bisulfite), may be used to detect and/or diagnose a cancer. For example, monoclonal antibodies against the methylated target gene (or a bisulfite converted amplicon thereof) labeled with $^{99}$Technetium, $^{111}$Indium, $^{125}$Iodine—may be effectively used for such imaging. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety. Typically 0.1-100 millicuries per dose of imaging agent, 1-10 millicuries, or often 2-5 millicuries are administered. Thus, compositions according to the present invention useful as imaging agents comprising a targeting moiety conjugated to a radioactive moiety comprise 0.1-100 millicuries, in some embodiments 1-10 millicuries, in some embodiments 2-5 millicuries, in some embodiments 1-5 millicuries.

In some embodiments, the disclosure provides for a device useful for detecting the methylation status of any of the target genes, or fragments or complements thereof, disclosed herein. In some embodiments, the disclosure provides for a kit comprising components useful for detecting the methylation status of the target gene, or fragments, or complements thereof, disclosed herein. In some embodiments, the kit comprises a swallowable balloon for collecting an esophageal sample from the subject. In some embodiments, the kit comprises any of the swallowable balloon devices disclosed in published US application 2016/317132, which is incorporated herein in its entirety. In some embodiments, the disclosure provides for a kit comprising primers for amplifying any of the target genes described herein, and instructions for performing any of the methods disclosed herein. In some embodiments, the kit further comprises bisulfite. In some embodiments, the kit further comprises an object suitable for collecting a sample from a subject (e.g., a brush and or balloon). In some embodiments, the disclosure provides for a kit comprising any of the therapeutic agents disclosed herein and instructions for performing any of the therapeutic methods disclosed herein.

A variety of assay formats may be used and, in light of the present disclosure, those not expressly described herein will nevertheless be considered to be within the purview of ordinary skill in the art. Assay formats can approximate such conditions as protein expression level, methylation status of nucleotide sequences, tumor suppressing activity, and may be generated in many different forms. In many embodiments, the disclosure provides assays including both cell-free systems and cell-based assays which utilize intact cells.

In some embodiments, the disclosure provides for a method of diagnosing a subject as having a neoplasia (e.g., esophageal cancer) or a metaplasia (e.g., Barrett's Esophagus) by determining whether a target gene in a sample from the subject is more methylated than a reference target gene. In some embodiments, the subject is determined to have a neoplasia or a metaplasia if the target gene is at least 20%, 30%, 40%, 50%, 60%, 70%, 80%, 90% or 100% more methylated as compared a reference target gene. In some embodiments, the reference target gene is from a healthy control subject.

In some embodiments, the disclosure provides a method for selecting a subject to undergo a treatment or a diagnostic procedure, such as an endoscopy. In some embodiments the disclosure provides a method for selecting a subject to undergo an endoscopy by identifying the subject as at increased risk for harboring an esophageal metaplasia (e.g., Barrett's esophagus) or neoplasia (e.g., esophageal cancer).

In addition to diagnosis, assaying of a marker in a sample from a subject not known to have a metaplasia or neoplasia (e.g., of the upper gastrointestinal tract) can be prognostic for the subject (i.e., indicating the probable course of the disease). To illustrate, subjects having a predisposition to develop a metaplasia or neoplasia of the upper gastrointestinal tract may possess methylated nucleotide sequences. Assaying of methylated target genes (e.g., vimentin and/or CCNA1) in a sample from subjects can also be used to select a particular therapy or therapies which are particularly effective against, e.g., a neoplasia or metaplasia of the upper gastrointestinal tract in the subject, or to exclude therapies that are not likely to be effective.

Assaying of methylated target genes (e.g., vimentin and/or CCNA1) in samples from subjects that are known to have, or to have had, a cancer is also useful. For example, the present methods can be used to identify whether therapy is effective or not for certain subjects. One or more samples are taken from the same subject prior to and following therapy and stored in any of the storage solutions disclosed herein, and assayed for methylation patterns of the target gene. A finding that a target gene is methylated in the sample taken prior to therapy and absent (or at a lower level) after therapy may indicate that the therapy is effective and need not be altered. In those cases where the target gene is methylated in the sample taken before therapy and in the sample taken after therapy, it may be desirable to alter the therapy to increase the likelihood that the cancer will be reduced in the subject. Thus, the present method may obviate the need to perform more invasive procedures which are used to determine a patient's response to therapy.

Cancers frequently recur following therapy in patients with advanced cancers. In this and other instances, the assays of the invention are useful for monitoring over time the status of a cancer associated with silencing of genes located in any of the target genes disclosed herein. In some embodiments, for subjects in whom a cancer is progressing, there can be no DNA methylation in some or all samples when the first sample is taken and then appear in one or more samples when the second sample is taken. In some embodiments, for subjects in which cancer is regressing, DNA methylation may be present in one or a number of samples when the first sample is taken and then be absent in some or all of these samples when the second sample is taken.

The methods described herein help increase the accuracy and accuracy of DNA methylation assays. In certain embodiments, the present invention provides a method of increasing accuracy of a DNA methylation assay, comprising obtaining a sample from a subject; treating the sample with a storage solution (e.g., a storage solution as disclosed herein); and assaying the sample to determine DNA methylation patterns in a nucleic acid sequence of interest, wherein the treatment with the storage solution increases methylation assay accuracy. In certain embodiments of the foregoing method, the rate of erroneous diagnosis is reduced. In certain embodiments, the sample is an esophageal sample. In certain such embodiments, the sample is obtained by contacting the esophagus with a cytology brush or a balloon. In certain embodiments of the foregoing method, the nucleic acid sequence of interest is a vimentin gene or a CCNA1 gene, or a fragment thereof.

EXEMPLIFICATION

The invention now being generally described, it will be more readily understood by reference to the following examples, which are included merely for purposes of illustration of certain aspects and embodiments of the present invention, and are not intended to limit the invention.

Example 1

These studies relate to assays of DNA methylation in the Vimentin (VIM) gene locus and CCNA1 (CCNA1) gene locus as specified in the published study of Moinova et al. Science translational medicine. 2018; 10 (424). H1975 (non-small lung cancer cell line, VIM and CCNA1 fully methylation-negative, available from ATCC® CRL-5908™) and SKGT4 (esophageal cancer cell line, VIM and CCNA1 fully methylation-positive, available from Sigma, Cat #11012001-1VL, comes from ECACC) were used to create starting mixes containing the target amount of methylated and unmethylated cells. Both cell lines were grown in RPMI media supplemented with 10% FBS, according to recommended cell culture guidelines.

On experiment day zero, cells were harvested with TripLE Express enzyme (ThermoFisher Scientific, Cat #12604013), spun down to remove trypsin, counted, and resuspended to $1 \times 10^6$ cells/ml in standard growing media. To create 1% methyl cell line mix, one part SKGT4 cells at $1 \times 10^6$ cells/ml was mixed with 99 parts of H1975 at $1 \times 10^6$ cells/ml. To make 0.5% methyl mix, the 1% mix was diluted 1:2 by mixing equal volumes of the 1% mix with H1975 unmethylated cell line at $1 \times 10^6$ cells/ml. Pure H1975 equaled 0% methyl cell line.

To create individual samples for the experiment, 2 ml cell mixes ($2 \times 10^6$ cells total) were aliquoted into 15 ml or 50 ml conical tubes according to experimental plan for each experiment. 15 ml conical tubes were used for small volume buffer fixation, and 50 ml conical tubes were used for large-volume experiments (See experiment summary). Two independent replicates were used for every condition in every experiment.

Cell aliquots were spun down for 3 min at 1200 rpm. After removing the media, cells were resuspended in fixative buffers (see experimental summary for buffer volumes used in each experiment). In some experiments, a medical grade silicone balloon was added to the mix of cells plus buffer by dropping the balloon into the buffer with cells. Samples were then incubated in respective buffers at indicated temperatures for indicated period of time (see experiment summary)

After the required incubation time, cells were spun down, fixative buffer removed, the cell pellet resuspended in 180 μl buffer ATL with 20 μl Proteinase K. DNA extraction was done using DNeasy Blood and Tissue kit (Qiagen, Cat No./ID: 69506).

In the case of fixative buffer that lysed the cells (DNA/RNA shield) the proteinase K was added directly to the lysis buffer, without the spin step. The amount of proteinase K, and subsequent kit reagents (buffer AL and ethanol) was increased proportionately to account for the fact that there was 5× more fixative lysis buffer, compared to 200 μl of the buffer ATL, used with non-lysing preservatives.

Regardless of preservative used, the column washes and DNA elution steps were identical. DNA was eluted from columns in 100 μl kit elution buffer. 1 μl DNA was used to quantitate DNA concentration using Qubit.

Bisulfite conversion was set up with the goal of 50 ng of starting DNA input per PCR. For example, when doing 4 replicate PCRs for VIM, and 4 replicate PCRs for CCNA, the total amount of DNA in bisulfite conversion was 50×8=400 ng of DNA).

Bisulfite conversion, PCR, library preparation, and sequencing were performed as per the published methods of Moinova et al.

TABLE 2

| | | | Experiment summary | | | |
|---|---|---|---|---|---|---|
| Expt. | Time(s) of incubation in buffer | % methyl cell mixes tested | Incubation temperature | Buffer volume | Balloon added? | Buffers tested |
| A | 0 days<br>3 days<br>7 days<br>14 days<br>21 days | 0%<br>1% | RT and 4° C. (for cytolyt) | 1 ml | no | Cytolyt (4° C.)<br>50% methanol<br>DNA/RNA shield (Zymo)<br>Frozen (−80° C., no buffer) |
| B | 0 days<br>21 days | 0%<br>1% | −20° C.<br>4° C.<br>RT<br>37° C.<br>50° C. | 1 ml | no | 40% methanol<br>50% methanol<br>60% methanol<br>Frozen (−80° C., no buffer) |
| C | 0 days<br>7 days<br>21 days | 0%<br>0.50%<br>1% | RT | 1 ml | no | Cytolyt<br>50% methanol<br>DNA/RNA shield (Zymo)<br>Frozen (−80° C., no buffer) |
| D | 0 days,<br>21 days | 0%<br>0.50%<br>1% | RT | 1 ml | no | NAP buffer1<br>50% methanol with 16 mM EDTA<br>50% methanol<br>DNA/RNA shield (Zymo)<br>Frozen (−80° C., no buffer) |
| E | 0 days,<br>21 days | 0%<br>0.50%<br>1% | RT | 1 ml | no | 50% methanol<br>50% methanol/TE<br>50% methanol/TE + BHT 25 mg/L<br>50% methanol/TE + BHT 100 mg/L<br>Frozen (−80° C., no buffer) |
| F | 0 days,<br>21 days | 0%<br>0.50%<br>1% | RT | 1 ml | no | 50% methanol<br>50% methanol/10 mM Tris pH 7.9<br>50% methanol/10 mM Tris + BHT 25 mg/L pH 7.9<br>50% methanol/10 mM Tris + BHT 100 mg/L pH 7.9<br>50% methanol/10 mM Tris + 1 mM EDTA pH 7.4<br>50% methanol/10 mM Tris + |

TABLE 2-continued

Experiment summary

| Expt. | Time(s) of incubation in buffer | % methyl cell mixes tested | Incubation temperature | Buffer volume | Balloon added? | Buffers tested |
|---|---|---|---|---|---|---|
| | | | | | | 1 mM EDTA pH 7.4 + BHT 25 mg/L |
| | | | | | | 50% methanol/10 mM Tris + 1 mM EDTA pH 7.4 + BHT 100 mg/L |
| | | | | | | Frozen (−80° C., no buffer) |
| G | 0 days, 21 days | 0% 0.50% 1% | RT | 1 ml | no | 50% methanol |
| | | | | | | 50% methanol/10 mM Tris pH 7.9 |
| | | | | | | 50% methanol/10 mM Tris + BHT 25 mg/L pH 7.9 |
| | | | | | | 50% methanol/10 mM Tris + BHT 100 mg/L pH 7.9 |
| | | | | | | Frozen (−80° C., no buffer) |
| H | 0 days, 21 days | 0% 0.50% 1% | RT | 20 ml | yes (+/−) | 50% methanol |
| | | | | | | 50% methanol/10 mM Tris pH 7.9 |
| | | | | | | 50% methanol/10 mM Tris + BHT 100 mg/L pH 7.9 |
| | | | | | | Frozen (−80° C., no buffer) |
| I | 0 days, 3 days | 0% 0.50% 1% | RT | 20 ml | no | 50% methanol |
| | | | | | | 50% methanol/10 mM Tris pH 7.9 |
| | | | | | | 50% methanol/10 mM Tris + BHT 100 mg/L pH 7.9 |
| | | | | | | Frozen (−80° C., no buffer) |
| J | 0 days, 3 days, 21 days | 0% 0.50% 1% | RT | 20 ml | yes (+/−) | 50% methanol |
| | | | | | | 50% methanol/10 mM Tris pH 7.9 |
| | | | | | | 50% methanol/10 mM Tris +BHT 100 mg/L pH 7.9 |
| | | | | | | Frozen (−80° C., no buffer) |
| K | 0 days, 3 days, 21 days | 0% 1% | −20° C. 4° C. RT 37° C. 50° C. | 20 ml | yes (+/−) | 50% methanol/10 mM Tris pH 7.9 |
| | | | | | | 50% methanol/10 mM Tris + BHT 100 mg/L pH 7.9 |
| | | | | | | Frozen (−80° C., no buffer) |
| L | 0 days, 3 days, 21 days | 0% 1% | RT | 20 ml | yes (+balloons in all samples) | 30% methanol/10 mM Tris + BHT 100 mg/L pH 7.9 |
| | | | | | | 40% methanol/10 mM Tris + BHT 100 mg/L pH 7.9 |
| | | | | | | 50% methanol/10 mM Tris + BHT 100 mg/L pH 7.9 |
| | | | | | | 60% methanol/10 mM Tris + BHT 100 mg/L pH 7.9 |
| | | | | | | 70% methanol/10 mM Tris + BHT 100 mg/L pH 7.9 |
| | | | | | | Frozen (−80° C., no buffer) |

Buffer Preparations Tested:

NAP buffer (Preservation of RNA and DNA from mammal samples under field conditions. Camacho-Sanchez M1, Burraco P, Gomez-Mestre I, Leonard JA. Mol Ecol Resour. 2013 July; 13(4):663-73. doi: 10.1111/1755-0998.12108. Epub 2013 Apr. 26)

The NAP buffer consists of 0.019 M ethylenediaminetetraacetic acid (EDTA) disodium salt dihydrate, 0.018 M sodium citrate trisodium salt dihydrate, 3.8 M ammonium sulphate and was adjusted to pH 5.2 with $H_2SO_4$.

The NAP buffer was prepared by combining EDTA, sodium citrate trisodium salt dihydrate, and ammonium sulfate and approximately 700 mL of water in a graduated flask. The solution was stirred on low to moderate heat until the ammonium sulfate dissolved completely, approximately one hour. The solution was then cooled to room temperature, then adjusted pH to 5.2 with $H_2SO_4$. (need ~200-400 µl, add drop-wise while measuring pH), filtered, and stored at room temperature or kept refrigerated.

50% Methanol 500 ml peroxide free methanol and 500 ml UltraPure DNAse/RNase free distilled water were combined.

50% Methanol/16 mM EDTA 500 ml peroxide free methanol and 500 ml of 32 mM EDTA were combined.

To make 32 mM EDTA, 32 ml 0.5M EDTA (324504-500ML EDTA, 500 mM Solution, pH 8.0, ULTROL Grade—CAS 60-00-4—Calbiochem) was diluted to 500 ml with UltraPure DNAse/RNase free distilled water)

50% Methanol/TE (10 mM Tris, 1 mM EDTA)

500 ml peroxide free methanol; 50 ml 20× TE (pH7.5, DNase/RNase free); and 450 ml UltraPure DNAse/RNase free distilled water were combined. Final Conditions: 50% methanol, 10 mM tris, 1 mM EDTA, pH 7.4

50% Methanol/TE/Plus 25 mg/L BHT

To make 100 ml, 25 µl of BHT stock was added to 100 ml of 50% Methanol/TE (see above).

BHT stock of 100 g/L was prepared by dissolving 1 g of BHT (Sigma Cat #B1378-100G) in 10 ml of 100% methanol. Stored at 4° C.

50% Methanol/TE/Plus 100 mg/L BHT

To make 100 ml, 100 µl of BHT stock was added to 100 ml of 50% Methanol/TE (see above).

BHT stock of 100 g/L was prepared by dissolving 1 g of BHT (Sigma Cat #B1378-100G) in 10 ml of 100% methanol. Stored at 4° C.

50% Methanol/10 mM Tris 500 ml peroxide free methanol; 10 ml 1M Tris (pH 8, DNase/RNase free, ThermoFisher Scientific Cat #AM9855G); and 490 ml UltraPure DNAse/RNase free distilled water were combined. pH of the buffer was checked after preparation to make sure it is greater than 7.5 but ≤8.0. Stored at RT.

50% Methanol/10 mM Tris/Plus 25 mg/L BHT

To make 100 ml, 25 µl of BHT stock was added to 100 ml of 50% Methanol/10 mM Tris (see above). pH of the buffer was checked after preparation to make sure it is greater than 7.5 but ≤8.0. Stored at RT.

BHT stock of 100 g/L was prepared by dissolving 1 g of BHT (Sigma Cat #B1378-100G) in 10 ml of 100% methanol. Stored at 4° C.

50% Methanol/10 mM Tris/Plus 100 mg/L BHT

To make 100 ml, 100 µl of BHT stock was added to 100 ml of 50% Methanol/10 mM Tris (see above). pH of the buffer was checked after preparation to make sure it is greater than 7.5 but ≤8.0. Stored at RT.

BHT stock of 100 g/L was prepared by dissolving 1 g of BHT (Sigma Cat #B1378-100G) in 10 ml of 100% methanol. Stored at 4° C.

FIG. 1 provides the DNA amount recovered from samples fixed in indicated preservatives. This figure is the summary of total DNA yield in ng from samples processed in Experiments D, E, and F. Values for Experiment D (circles), Experiment E (triangles) and Experiment F (diamonds) are shown, with samples collected at 0-day timepoint (open symbols), and 21-day timepoint (filled symbols). In this figure, 50% MeOH is 50% Methanol; 50% MeOH/10 mM Tris is 50% Methanol/10 mM Tris; 50% MeOH/10 mM Tris BHT100 is 50% methanol/10 mM Tris +100 mg/L BHT; 50% MeOH/10 mM Tris BHT25 is 50% methanol/10 mM Tris +25 mg/L BHT; 50% MeOH-EDTA is 50% methanol/16 mM EDTA; 50% MeOH-TE is 50% methanol/TE; 50% MeOH-TE BHT100 is 50% methanol/TE+100 mg/L BHT; 50% MeOH-TE BHT25 is 50% methanol/TE+25 mg/L BHT; Frozen refers to cell pellet frozen at −80° C. without any buffer addition; NAP refers to Nucleic Acid Preservation buffer as described above; NAP-washed refers to cells fixed in NAP buffer, but washed with PBS before adding the buffer ATL for DNA extraction; and Shield refers to DNA/RNA shield buffer from Zymo Research.

The data in FIG. 1 shows that NAP buffer is not working, as compared to from frozen cells, because of the low DNA amount recovery from cells after a 21 day incubation. Methanol Buffers containing TE also reduced the DNA recovery after 21 days. Cells incubated for 21 days in Methanol/Tris buffers were closest to Frozen Cells in terms of DNA yield. Addition of BHT to buffers didn't seem to have an effect on DNA yield, regardless of concentration used. Cells incubated in Shield buffer had lower DNA yield than Frozen cells.

Figure 2:
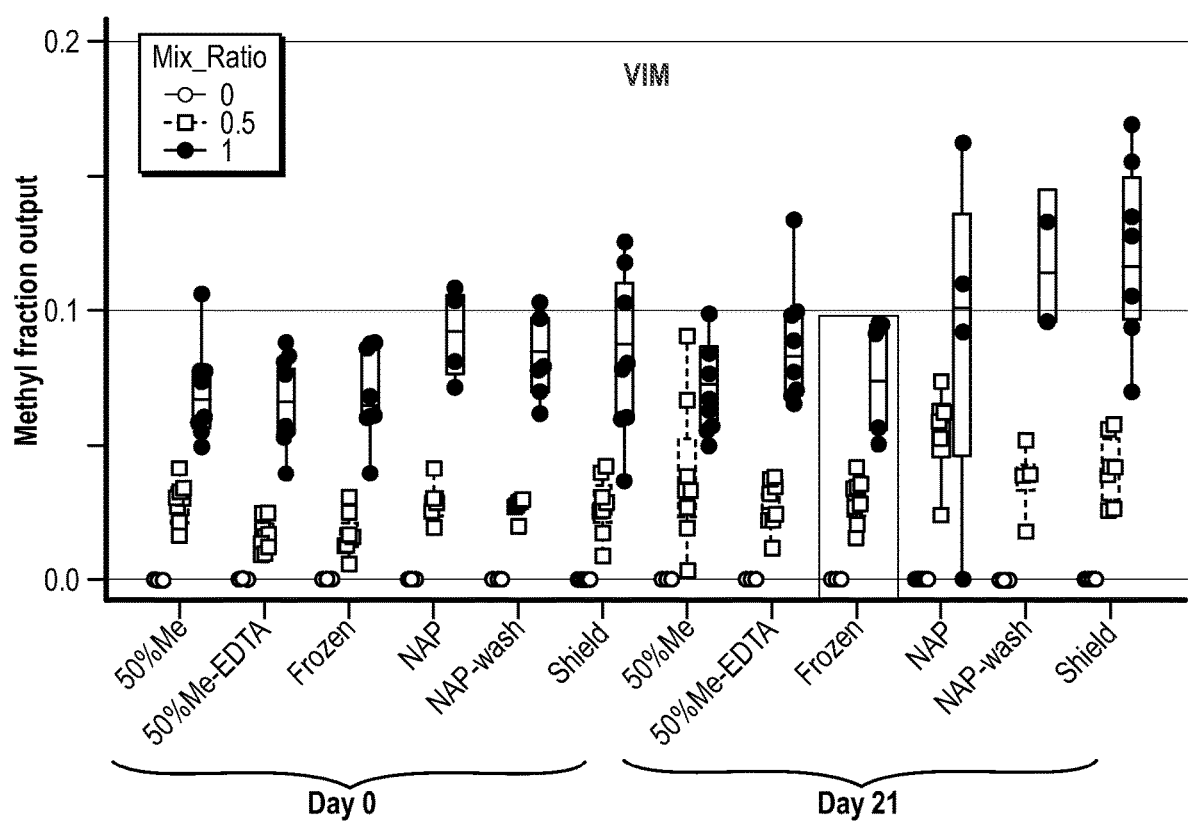
FIG. 2: VIM methylation level assay results in cells fixed in various buffers from Experiment D. "VIM" corresponds to vimentin.
Figure 3:
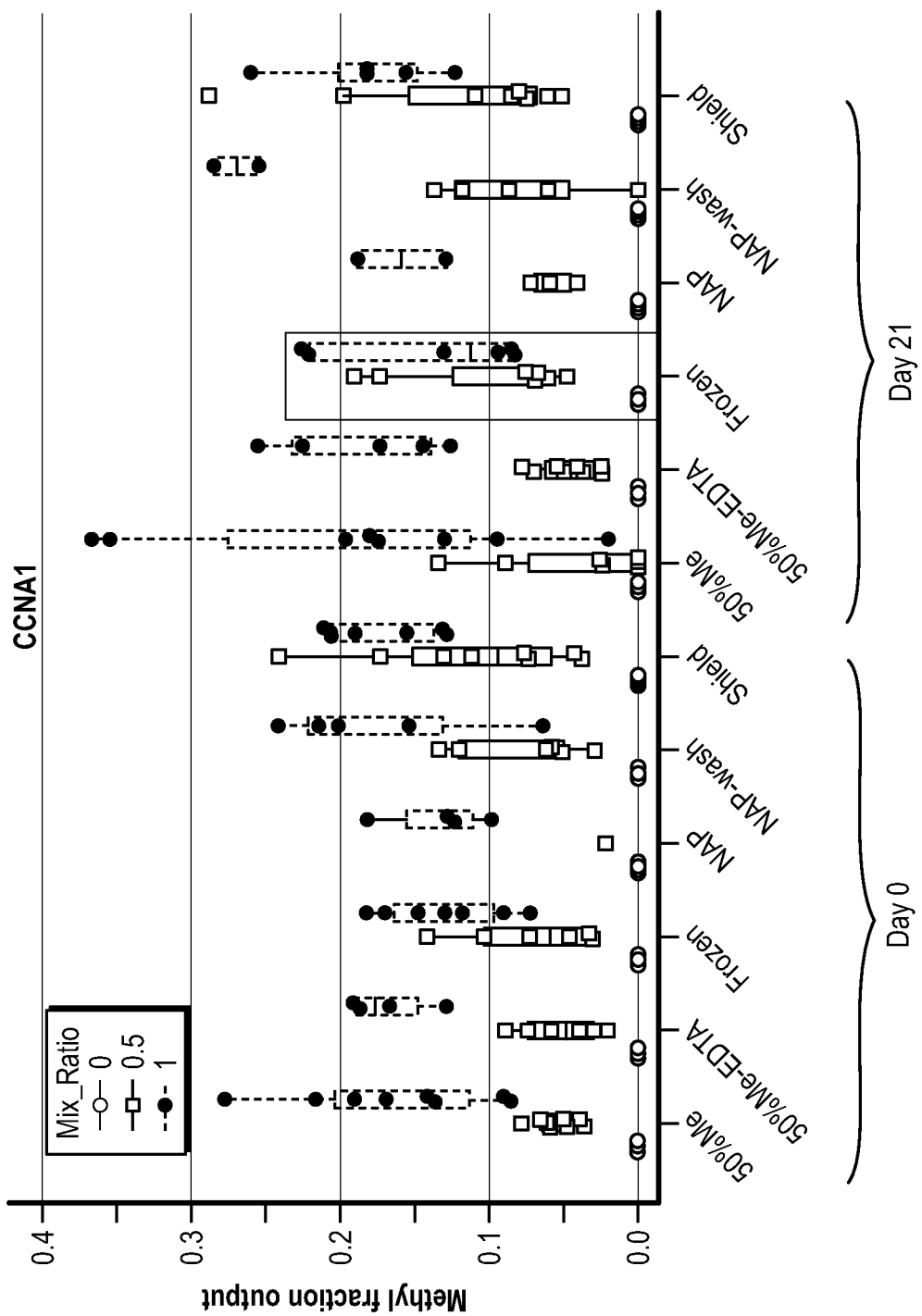
FIG. 3: CCNA1 methylation level assay results in cells fixed in various buffers from Experiment D.

FIGS. 2 and 3 provide methylation level assay results in cells fixed in various buffers from Experiment D. VIM and CCNA1 methylation results are shown in FIGS. 2 and 3, respectively. In these figures, mix ratio refers to the input cell line mixes with 0% (open circles) 0.5% (squares) and 1% (filled circles) methylated cell line, respectively. Methylation signal output (fraction) is shown on the Y axis, while different buffers are displayed on the X axis. In FIGS. 2 and 3, 50% Me is 50% Methanol; 50% Me-EDTA is 50% methanol/16 mM EDTA; Frozen refers to cell pellet frozen at −80° C. without any buffer addition; NAP refers to Nucleic Acid Preservation buffer described above; NAP-washed refers to cells fixed in NAP buffer, but washed with PBS before adding the buffer ATL for DNA extraction; Shield refers to DNA/RNA shield buffer from Zymo Research.

The data in FIGS. 2 and 3 shows that on day 21 of incubation in buffers, there was some increase in methylation signal in cells incubated in buffers versus cells that were frozen, and this increase varied depending on the marker analyzed and buffer used. For VIM (FIG. 2), 50% methanol performed the closest to Frozen (no-preservative) samples. Addition of EDTA to 50% methanol increased the artifactual Vim methylation in cells incubated for 21 days in buffer.

Figure 4:
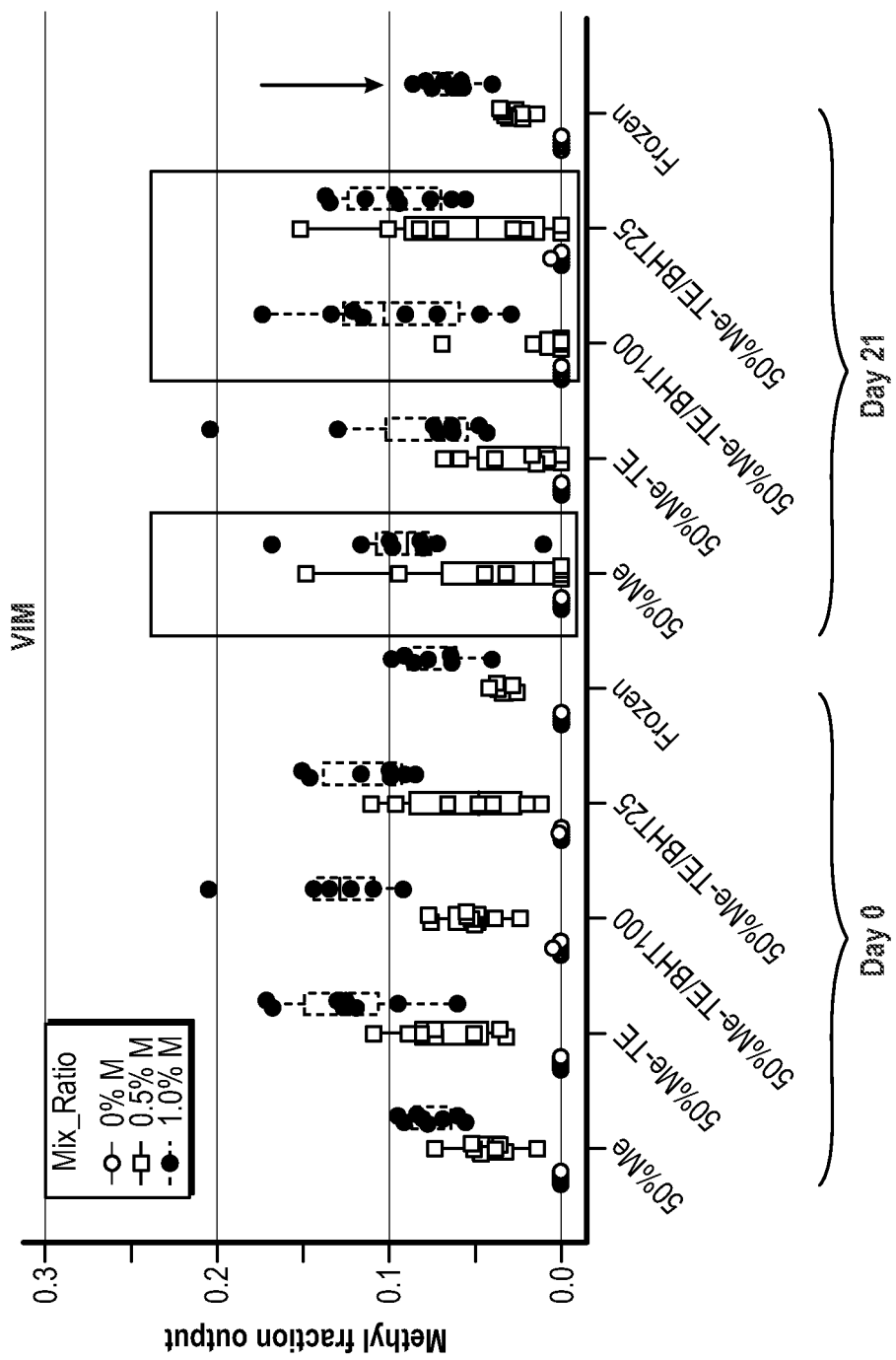
FIG. 4: VIM methylation level assay results in cells fixed in various buffers from Experiment E. "VIM" corresponds to vimentin.
Figure 5:
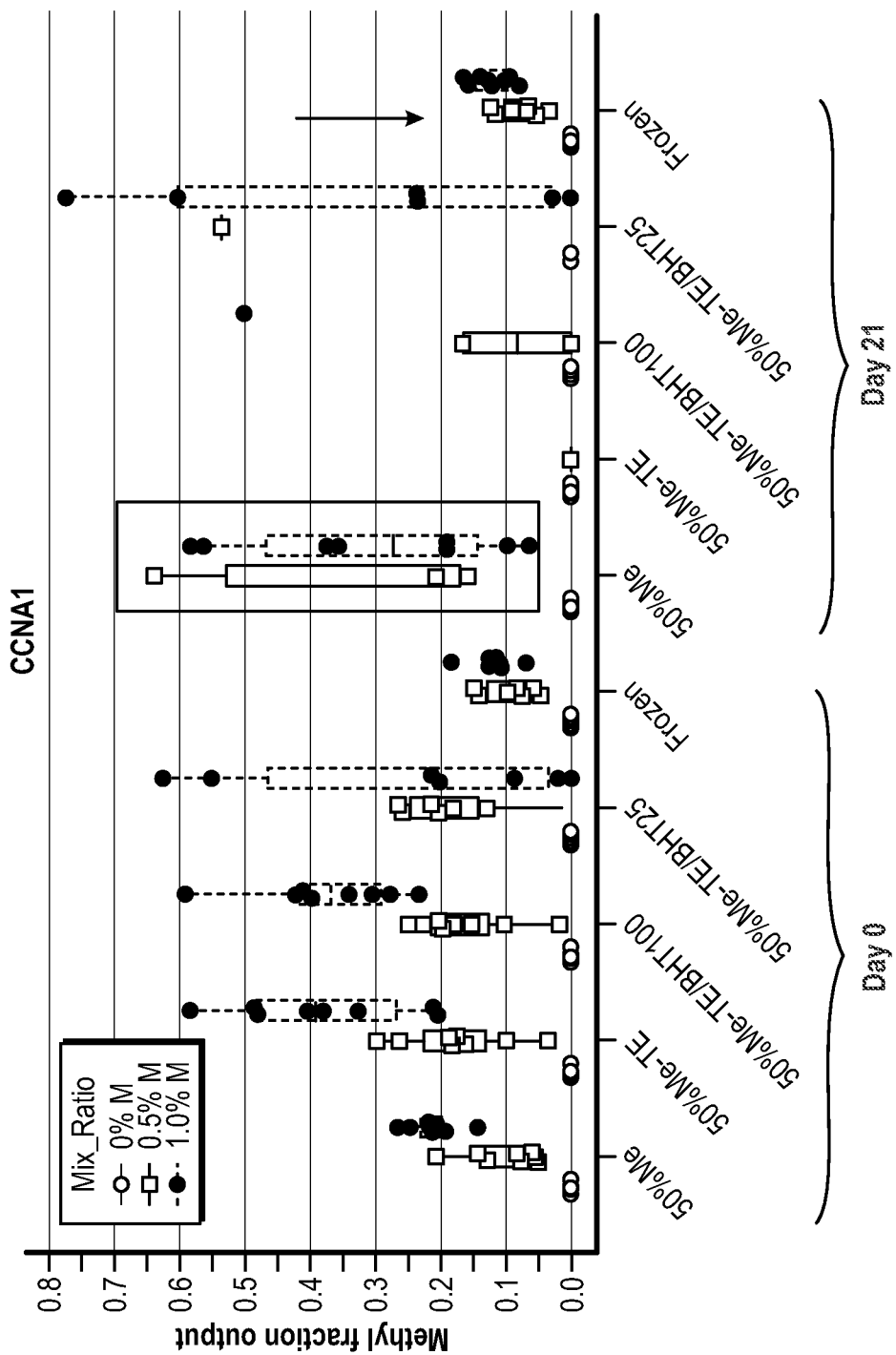
FIG. 5: CCNA1 methylation level assay results in cells fixed in various buffers from Experiment E.

FIGS. 4 and 5 provide methylation level assay results in cells fixed in various buffers from Experiment E. VIM and CCNA1 methylation results are shown in FIGS. 4 and 5, respectively. In these figures, mix ratio refers to the input cell line mixes with 0% (open circles) 0.5% (squares) and 1% (filled circles) methylated cell line, respectively. Methylation signal output (fraction) is shown on the Y axis, while different buffers are displayed on the X axis. In FIGS. 4 and 5, 50% Me is 50% Methanol; 50% Me-TE is 50% methanol/TE; 50% Me-TE BHT100 is 50% methanol/TE+100 mg/L BHT; 50% Me-TE BHT25 is 50% methanol/TE+25 mg/L BHT; Frozen refers to cell pellet frozen at −80° C. without any buffer addition.

The data in FIGS. 4 and 5 show that on day 21, there was some increase in methylation signal, and this increase varied depending on the marker analyzed, and buffer used. For VIM (FIG. 4), 50% methanol and methanol-TE buffers result in higher signal than output observed in frozen samples. For CCNA1 (FIG. 5), all of the buffers that included TE showed a particularly deleterious effect on the signal, which is associated with the particularly lower DNA yield seen in these buffer formulations (see FIG. 1). In FIG. 5, the absence of data for CCNA1 on day 21 samples incubated in 50% methanol with tris and EDTA, and the reduction in data for day 21 samples incubated in 50% methanol with tris and EDTA and 100 mg/L BHT, in both cases reflects a marked reduction in CCNA1 aligned reads obtained from the samples incubated under these buffer conditions.

Figure 6:
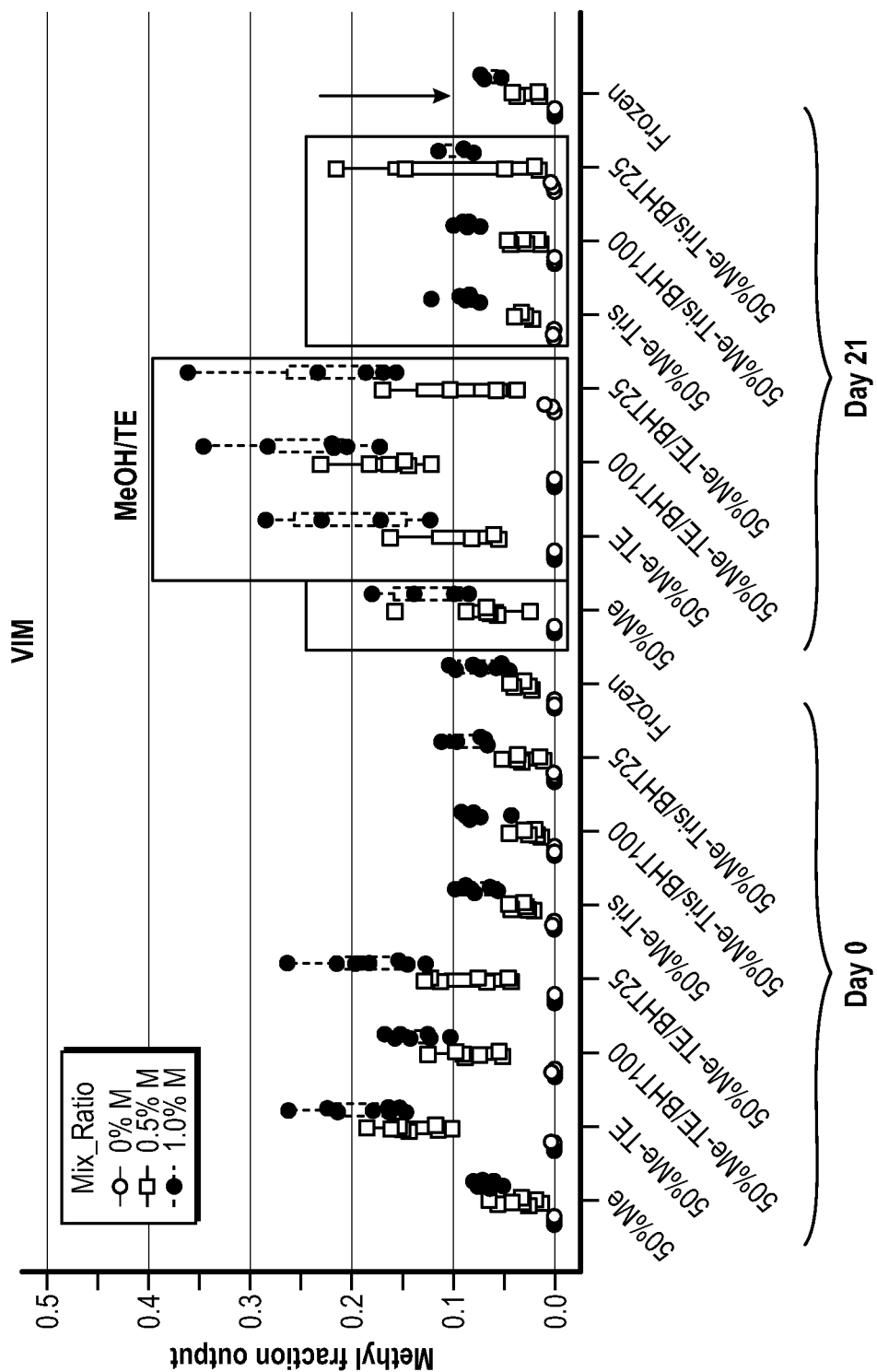
FIG. 6: VIM methylation level assay results in cells fixed in various buffers from Experiment F. "VIM" corresponds to vimentin.
Figure 7:
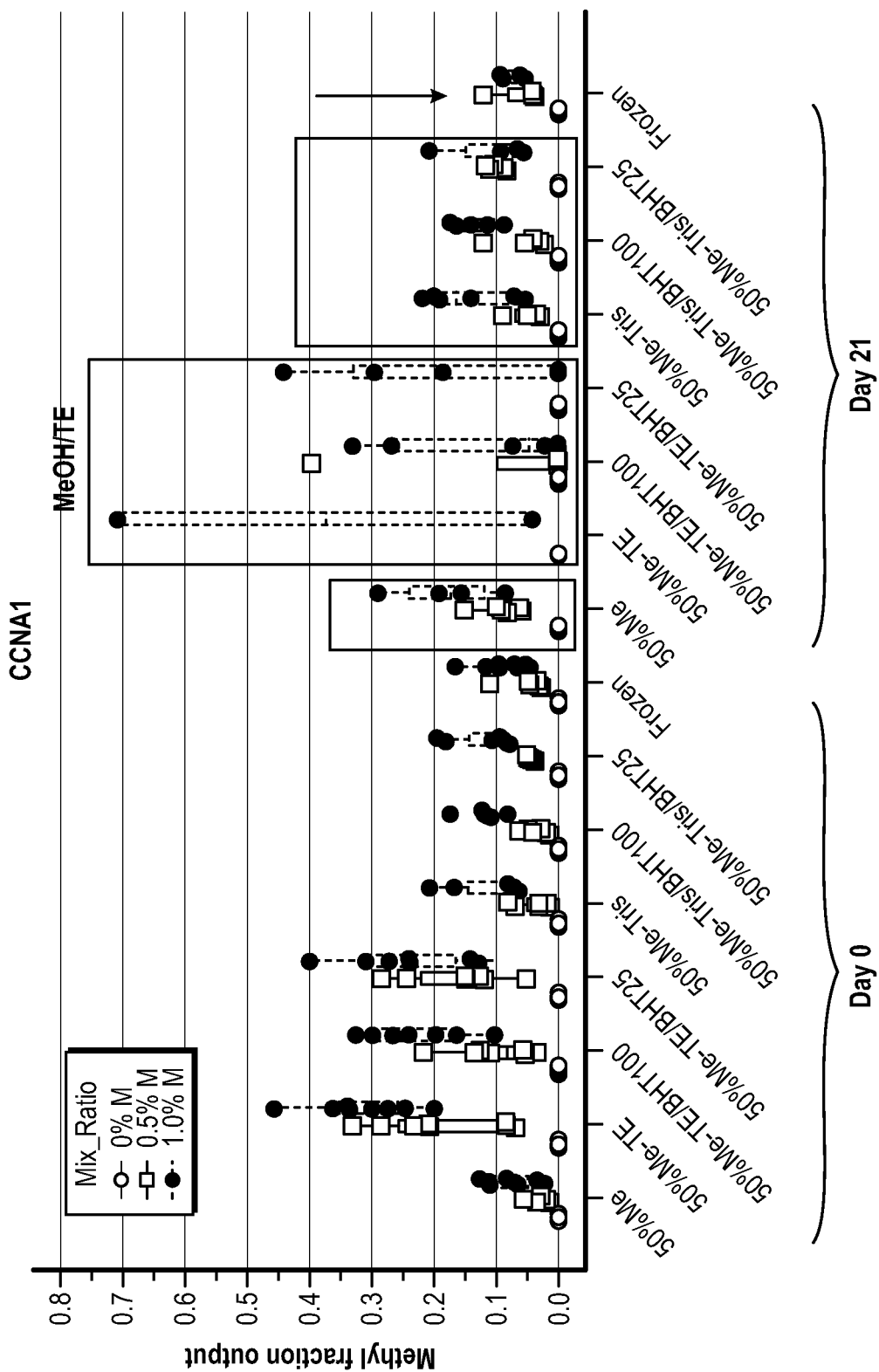
FIG. 7: CCNA1 methylation level assay results in cells fixed in various buffers from Experiment F.

FIGS. 6 and 7 provide methylation level assay results in cells fixed in various buffers from Experiment F. VIM and CCNA1 methylation results are shown in FIGS. 6 and 7, respectively. In these figures, mix ratio refers to the input cell line mixes with 0% (open circles) 0.5% (squares) and 1% (filled circles) methylated cell line, respectively. Methylation signal output (fraction) is shown on the Y axis, while different buffers are displayed on the X axis. In FIGS. 6 and 7, 50% Me is 50% Methanol; 50% Me-TE is 50% methanol/TE; 50% Me-TE BHT100 is 50% methanol/TE+100 mg/L BHT; 50% Me-TE BHT25 is 50% methanol/TE+25 mg/L BHT; 50% Me-Tris is 50% Methanol/10 mM Tris; 50% Me-Tris BHT100 is 50% methanol/10 mM Tris +100 mg/L BHT; 50% Me-Tris BHT25 is 50% methanol/10 mM Tris +25 mg/L BHT; Frozen refers to cell pellet frozen at −80° C. without any buffer addition.

The data in FIGS. 6 and 7 show that on day 21, 50% MeOH-Tris buffers, either with or without BHT, performed closest to Frozen samples in maintaining fidelity of DNA methylation, both for VIM (FIG. 6) and CCNA1 (FIG. 7). The presence of BHT didn't appear to affect magnitude of methylation signal, but may have decreased the variance. This data confirmed that all buffers that contain EDTA (i.e., containing TE) showed higher increases in DNA methylation. These results were also seen in Experiments D and E (FIGS. 2-5).

Figure 8:
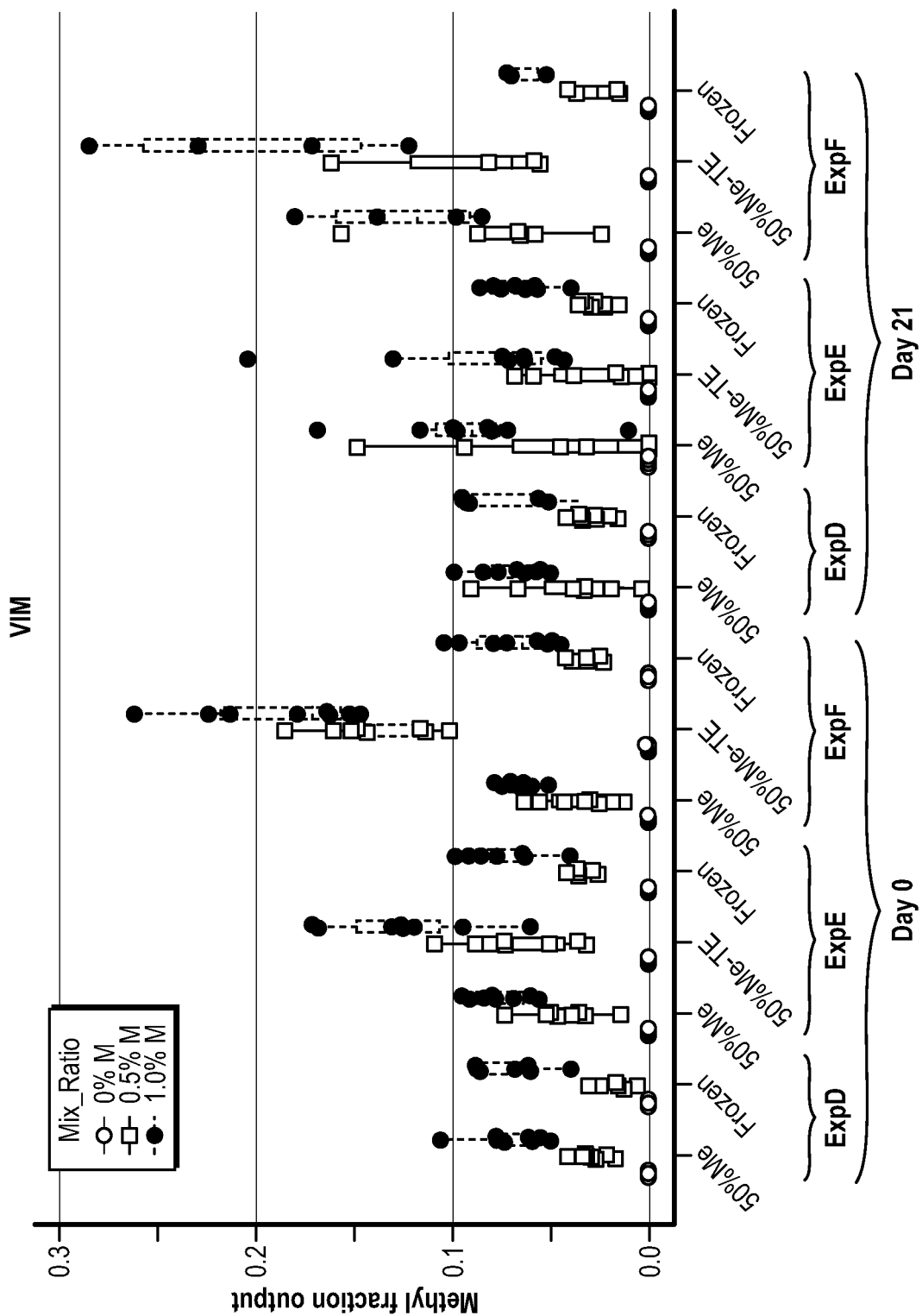
FIG. 8: VIM methylation level assay results in cells fixed in various buffers from Experiments D, E, and F. "VIM" corresponds to vimentin.
Figure 9:
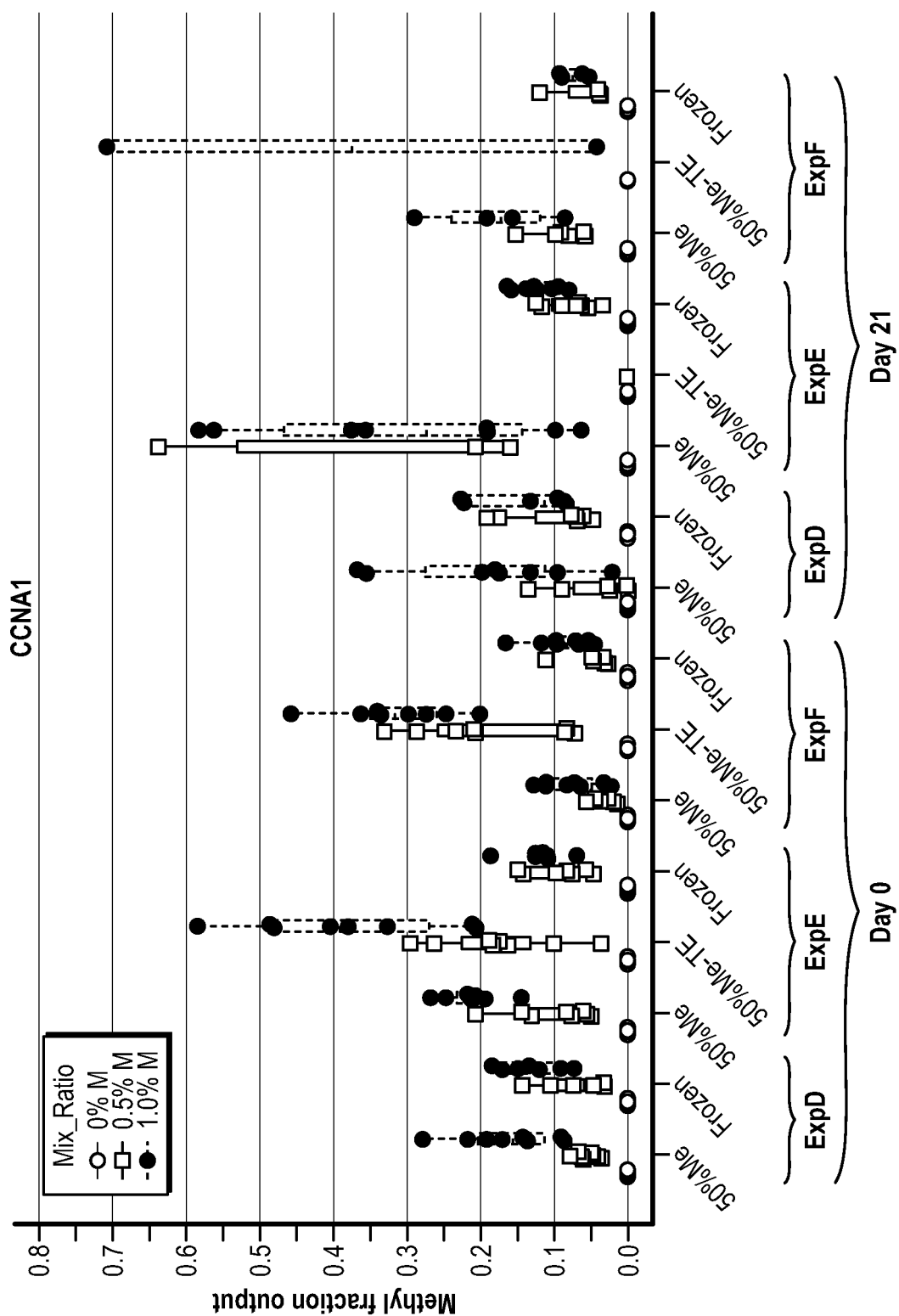
FIG. 9: CCNA1 methylation level assay results in cells fixed in various buffers from Experiments D, E, and F.

FIGS. 8 and 9 provide methylation level assay results in cells fixed in various buffers from Experiments D, E, and F. VIM and CCNA1 methylation results are shown in FIGS. 8 and 9, respectively. The results in these figures extract specifically the data for comparing methanol vs methanol-TE-containing buffers from Experiments D, E, and F, and display them side-by-side on the same graph for ease of comparison. In these figures, mix ratio refers to the input cell line mixes with 0% (open circles) 0.5% (squares) and 1% (filled circles) methylated cell line, respectively. Methylation signal output (fraction) is shown on the Y axis, while different buffers are displayed on the X axis. In FIGS. 8 and 9, 50% Me is 50% Methanol; 50% Me-TE is 50% methanol/TE; 50% Me-Tris is 50% Methanol/10 mM Tris; Frozen refers to cell pellet frozen at −80° C. without any buffer addition.

The data in FIGS. 8 and 9 highlight the finding that all buffers with EDTA (i.e., containing TE) show higher increase in methylation in cells after 21 days of incubation.

Figure 10:
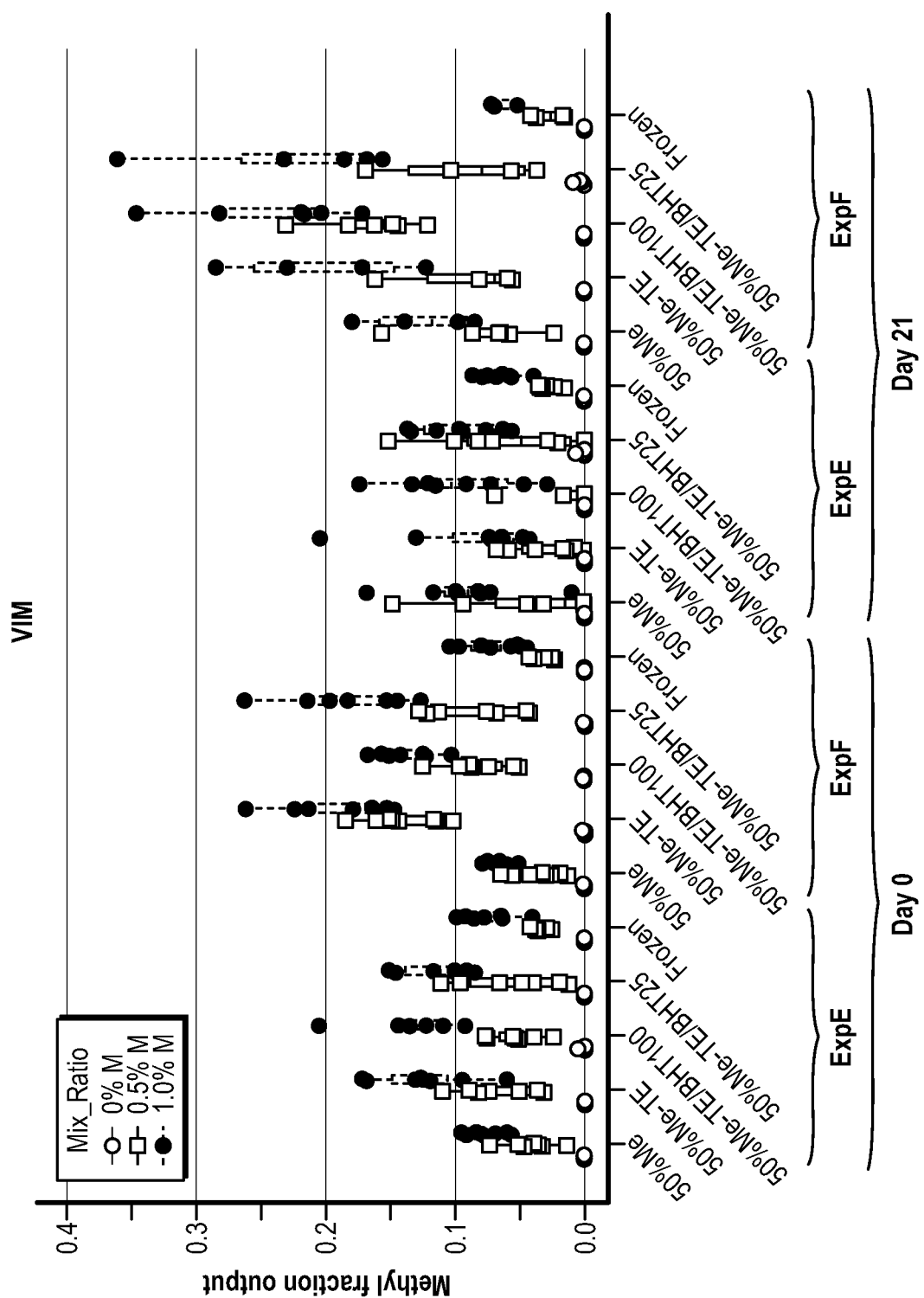
FIG. 10: VIM methylation level assay results in cells fixed in various buffers from Experiments E and F. "VIM" corresponds to vimentin.
Figure 11:
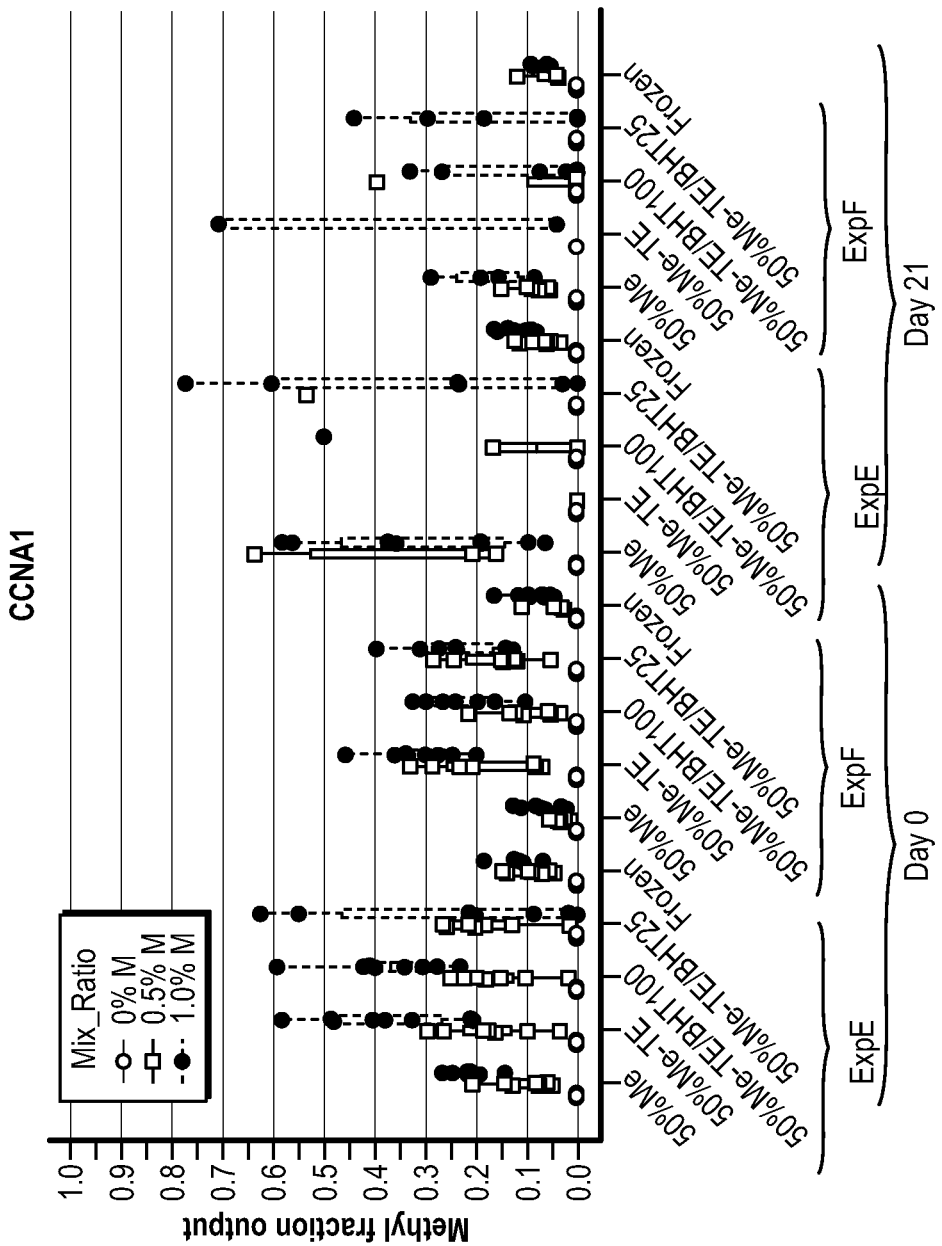
FIG. 11: CCNA1 methylation level assay results in cells fixed in various buffers from Experiments E and F.

FIGS. 10 and 11 provide methylation level assay results in cells fixed in various buffers from Experiments E and F. VIM and CCNA1 methylation results are shown in FIGS. 10 and 11, respectively. The results in these figures extract specifically the data for comparing methanol vs methanol-TE-containing buffers from Experiments E and F, and display them side-by-side on the same graph for ease of comparison. In these figures, mix ratio refers to the input cell line mixes with 0% (open circles) 0.5% (squares) and 1% (filled circles) methylated cell line, respectively. Methylation signal output (fraction) is shown on the Y axis, while different buffers are displayed on the X axis. In FIGS. 10 and 11, 50% Me is 50% Methanol; 50% Me-TE is 50% methanol/TE; 50% Me-TE BHT100 is 50% methanol/TE+100 mg/L BHT; 50% Me-TE BHT25 is 50% methanol/TE+25 mg/L BHT; Frozen refers to cell pellet frozen at −80° C. without any buffer addition.

The data in FIGS. 10 and 11 highlight the finding that all buffers with EDTA (i.e., containing TE) result in higher increases in DNA methylation after 21 days of incubation, and that the addition of BHT, at either high or low concentration, does not counteract the EDTA-related increases in methylation signal.

The data above and as shown in FIGS. 1-10 show that DNA yield in samples incubated for 21 days in different buffers was maximized with formulations comprised of Methanol and Tris, with or without BHT, and without EDTA. In addition, DNA methylation marks were perfectly preserved in samples incubated for 21 days at room temperature with buffer formulations comprised of Methanol plus Tris, with or without BHT, and without EDTA. Improved buffer formulations may increase stability of DNA and of DNA methylation marks in biological samples during shipping and storage thereby improving the accuracy of biomarker assays based on measuring DNA methylation.

Figure 12:
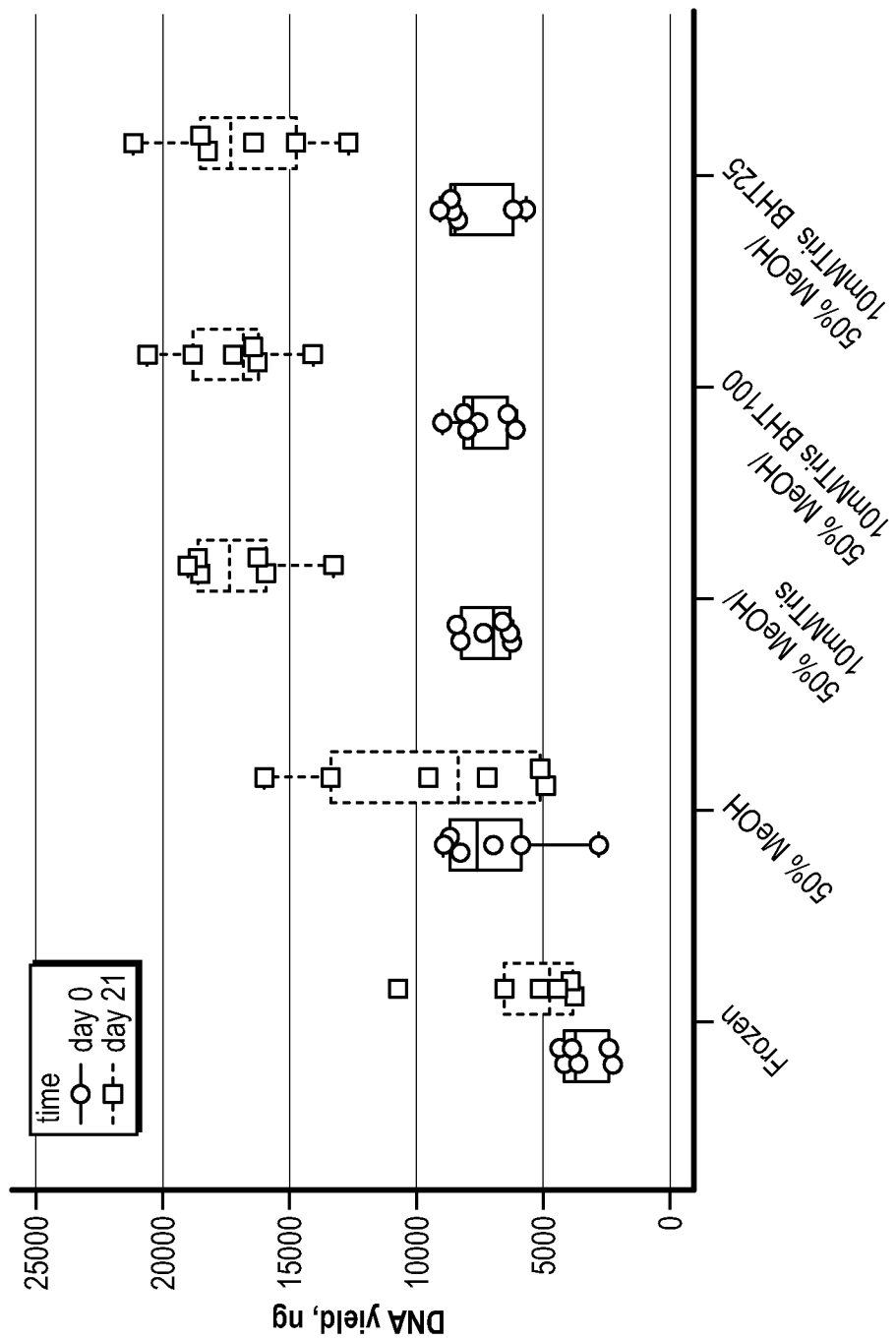
FIG. 12: DNA amount recovered from samples fixed in indicated preservatives from Experiment G.

FIG. 12 provides a summary of total DNA yield in ng from samples processed in Experiment G. DNA amount in ng is displayed on the Y axis, while the X axis shows the buffers tested in this experiment. Open circles denote samples collected at day 0 timepoint, while squares are used to mark DNA processed after 21 days of incubation in indicated buffers. In FIG. 12, Frozen refers to cell pellet frozen at −80° C. without any buffer addition; 50% MeOH is 50% Methanol; 50% MeOH/10 mM Tris is 50% Methanol/10 mM Tris; 50% MeOH/10 mM Tris BHT100 is 50% methanol/10 mM Tris +100 mg/L BHT; 50% MeOH/10 mM Tris BHT25 is 50% methanol/10 mM Tris +25 mg/L BHT.

FIG. 12 shows improved DNA yield after 21 days of incubation in methanol/Tris-containing buffers, relative to cells fixed in 50% methanol without addition of Tris buffer, or in cells frozen without the addition of the preservative buffer. Addition of BHT to the methanol/Tris formulation does not alter the buffer properties relative to the methanol/Tris formulation without BHT.

Figure 13:
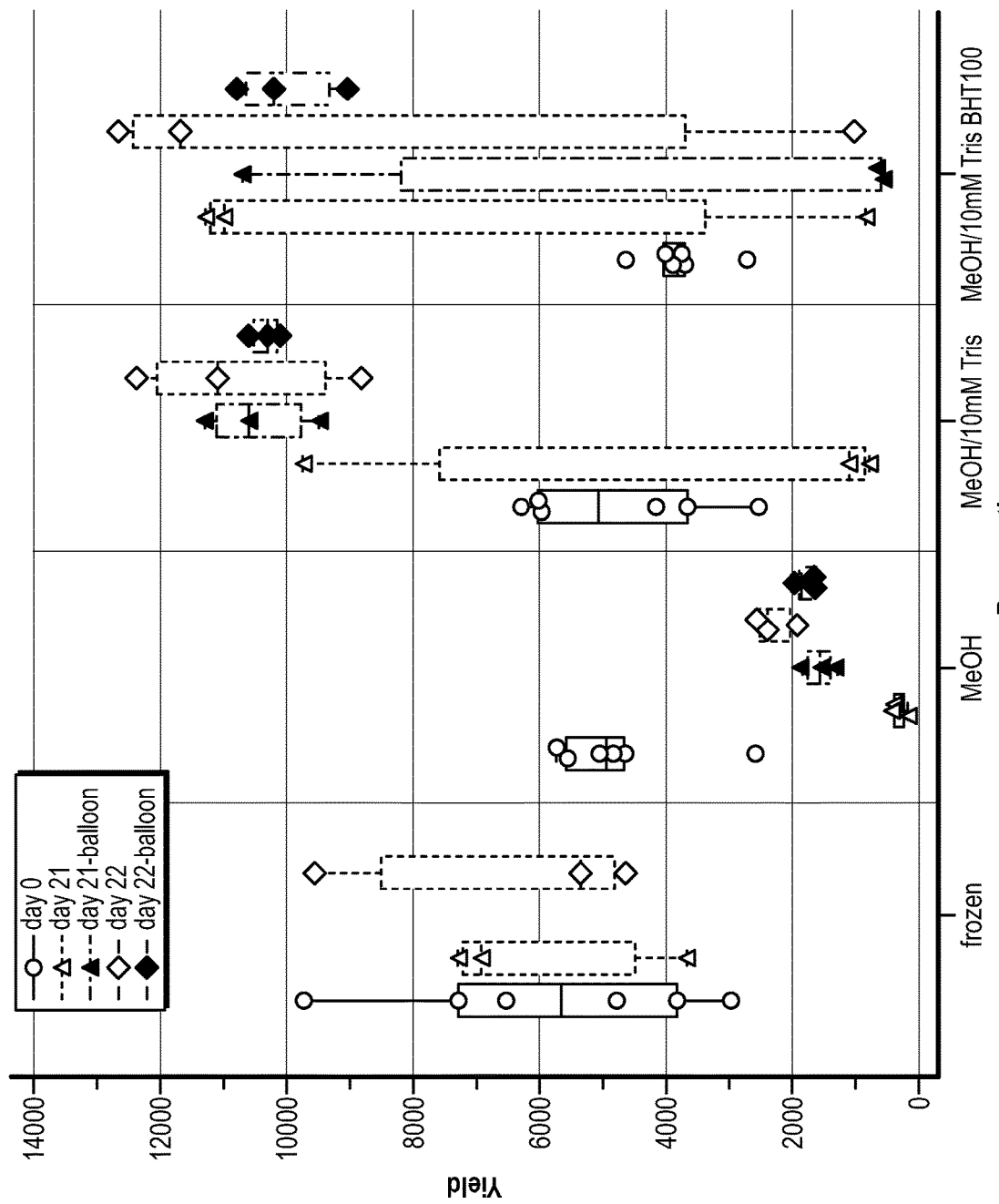
FIG. 13: DNA amount recovered from samples fixed in indicated preservatives from Experiment H.

FIG. 13 provides a summary of total DNA yield in ng from samples processed in Experiment H. DNA amount in ng is displayed on the Y axis, while the X axis shows the buffers tested in this experiment. Open circles denote samples collected at day 0 timepoint, while triangles are used to mark DNA processed after 21 days of incubation in indicated buffers, and diamonds denote samples collected after 22 days of incubation in indicated buffers. Open triangles and diamonds refer to cells incubated for 21 or 22 days, respectively, with buffers only, while the filled triangles and diamonds denote samples that were incubated in buffer in the presence of medical grade silicone balloons. In FIG. 13, Frozen refers to cell pellet frozen at −80 C without any buffer addition; MeOH is 50% Methanol; MeOH/10 mM Tris is 50% Methanol/10 mM Tris; MeOH/10 mM Tris BHT100 is 50% methanol/10 mM Tris +100 mg/L BHT. This experiment was done in 50 mL tubes, with cells fixed in larger 20 mL volume of buffer.

FIG. 13 shows increased DNA yield after 21 days of incubation in methanol/Tris-containing buffers, relative to cells fixed in 50% methanol without addition of Tris buffer, or in cells frozen without the addition of the preservative buffer. The experiment further shows there was no effect on DNA yield of adding a medical grade silicone balloon into the cell plus buffer mixture. The variability of DNA yield was likely due to change of experimental procedures, and switch to larger tubes to accommodate the larger volume of buffer necessitated to cover the balloons. Further experiments have addressed the technique to decrease the variability due to handling of large volumes.

Figure 14:
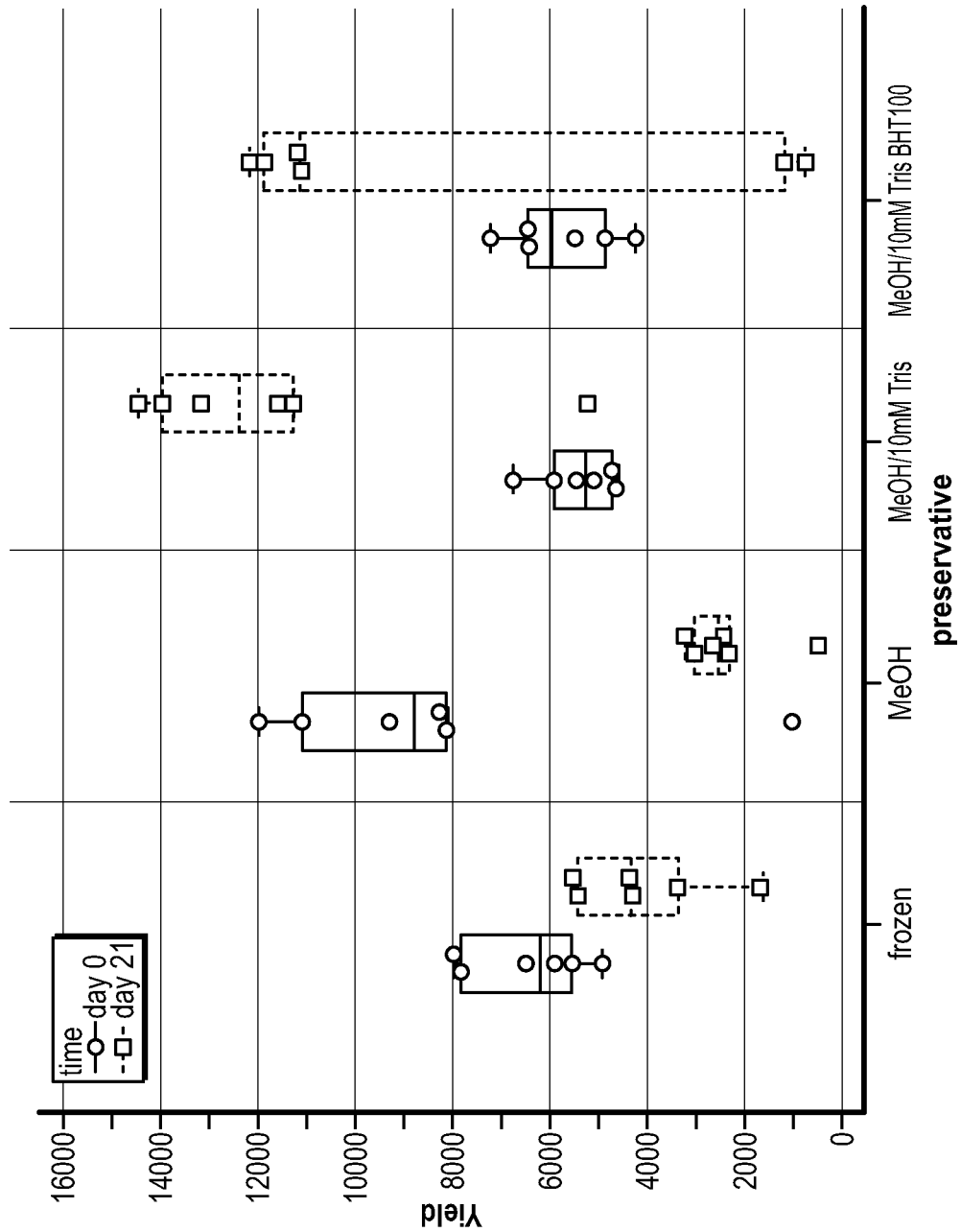
FIG. 14: DNA amount recovered from samples fixed in indicated preservatives from Experiment I for 0 versus 3 days.

FIG. 14 provides a summary of total DNA yield in ng from samples processed in Experiment I. DNA amount in ng is displayed on the Y axis, while the X axis shows the buffers tested in this experiment. Open circles denote samples collected at day 0 timepoint, while squares are used to mark DNA processed after 3 days of incubation in indicated buffers. In FIG. 14, Frozen refers to cell pellet frozen at −80° C. without any buffer addition; MeOH is 50% Methanol; MeOH/10 mM Tris is 50% Methanol/10 mM Tris; MeOH/10 mM Tris BHT100 is 50% methanol/10 mM Tris +100 mg/L BHT. This experiment was done in 50 mL tubes, with cells fixed in larger 20 mL volume of buffer.

FIG. 14 shows increased DNA yield was obtained after only 3 days of incubation in methanol/Tris-containing buffers, relative to cells fixed in 50% methanol without addition of Tris buffer, or in cells frozen without the addition of the preservative buffer. The variability in the study likely reflects the cumbersome nature of handling samples incubated in the larger buffer volumes initiated with Experiment H.

Figure 15:
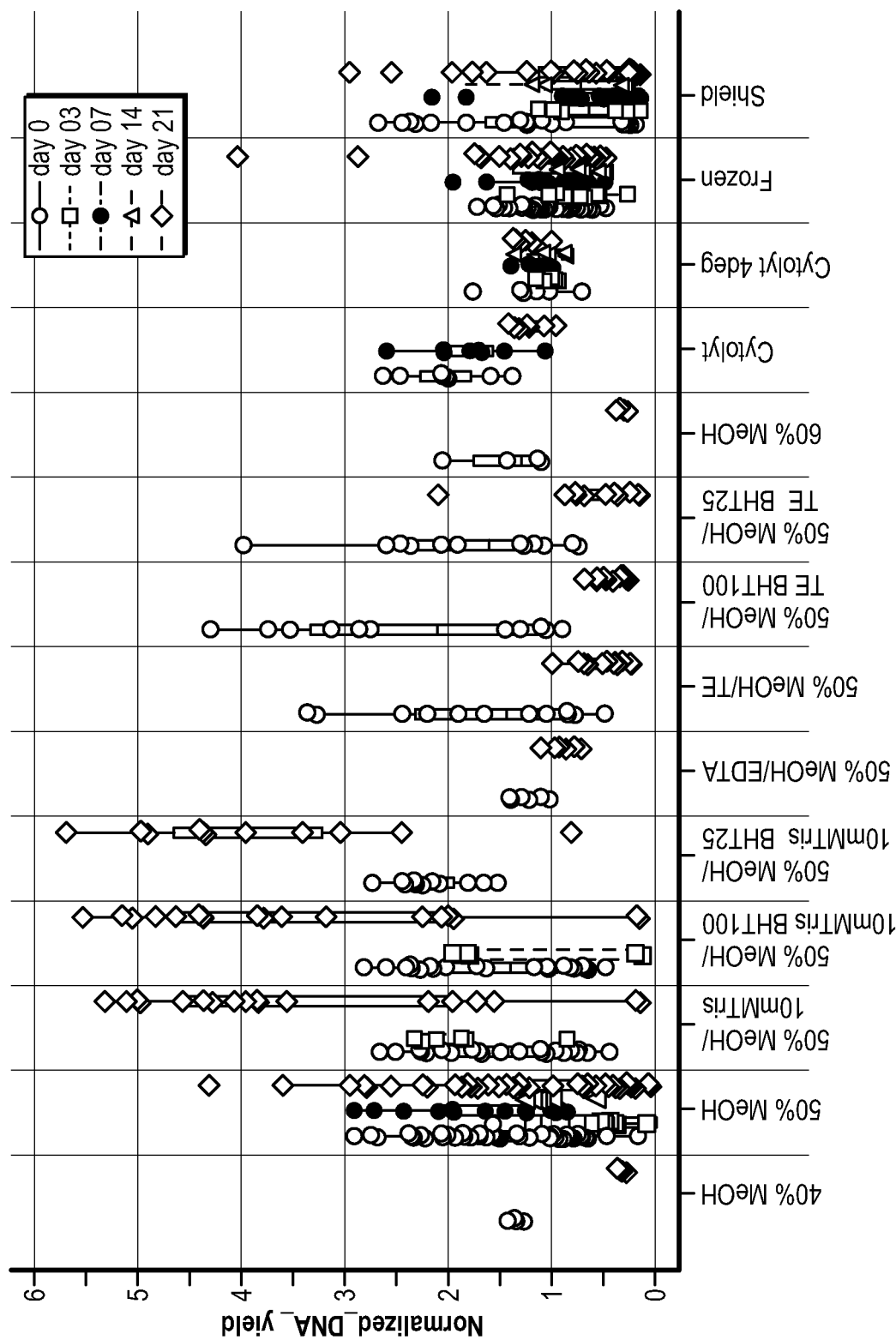
FIG. 15: Normalized DNA amount recovered from samples fixed in indicated preservatives from Experiments A-I.

FIG. 15 provides a summary of total DNA yield from samples processed in Experiments A-I. DNA amount is normalized to median day 0 Frozen sample timepoint in each experiment, and displayed on the Y axis, while the X axis shows the buffers tested in various experiments. Open circles denote samples collected at day 0 timepoint; open squares correspond to DNA processed after 3 days of incubation in indicated buffers; filled circles correspond to DNA processed after 7 days of incubation in indicated buffers; filled triangles correspond to DNA processed after 14 days of incubation in indicated buffers; filled diamonds correspond to DNA processed after 21 days of incubation in indicated buffers. In this figure, 40% MeOH is 40% Methanol; 50% MeOH is 50% Methanol; 60% MeOH is 60% Methanol; 50% MeOH/10 mM Tris is 50% Methanol/10 mM Tris; 50% MeOH/10 mM Tris BHT100 is 50% methanol/10 mM Tris +100 mg/L BHT; 50% MeOH/10 mM Tris BHT25 is 50% methanol/10 mM Tris +25 mg/L BHT; 50% MeOH-EDTA is 50% methanol/16 mM EDTA; 50% MeOH-TE is 50% methanol/TE; 50% MeOH-TE BHT100 is 50% methanol/TE+100 mg/L BHT; 50% MeOH-TE BHT25 is 50% methanol/TE+25 mg/L BHT; Frozen refers to cell pellet frozen at −80° C. without any buffer addition; Cytolyt refers commercially-available fixative CytoLyt (from Hologic); Cytolyt 4 deg refers to cells incubated in CytoLyt at 4° C., instead of room temperature; Shield refers to DNA/RNA shield buffer from Zymo Research.

FIG. 15 shows a reproducible trend towards increased DNA yield after 21 days of incubation in methanol/Tris-containing buffers, in multiple experiments, relative to cells fixed in 50% methanol without addition of Tris buffer, or in cells frozen without the addition of the preservative buffer, and also shows a decrease in DNA recovery in all buffers containing EDTA, either alone, or in combination with Tris.

The above data demonstrated that buffers containing methanol plus tris, with or without BHT, increase DNA yield as compared to buffers of methanol plus water alone, as determined by incubating cells in these buffers from 3-21 days. These effects are evident in incubations as short as 3 days. Adding medical grade silicone balloons into the buffers does not alter DNA yield.

Figure 16:
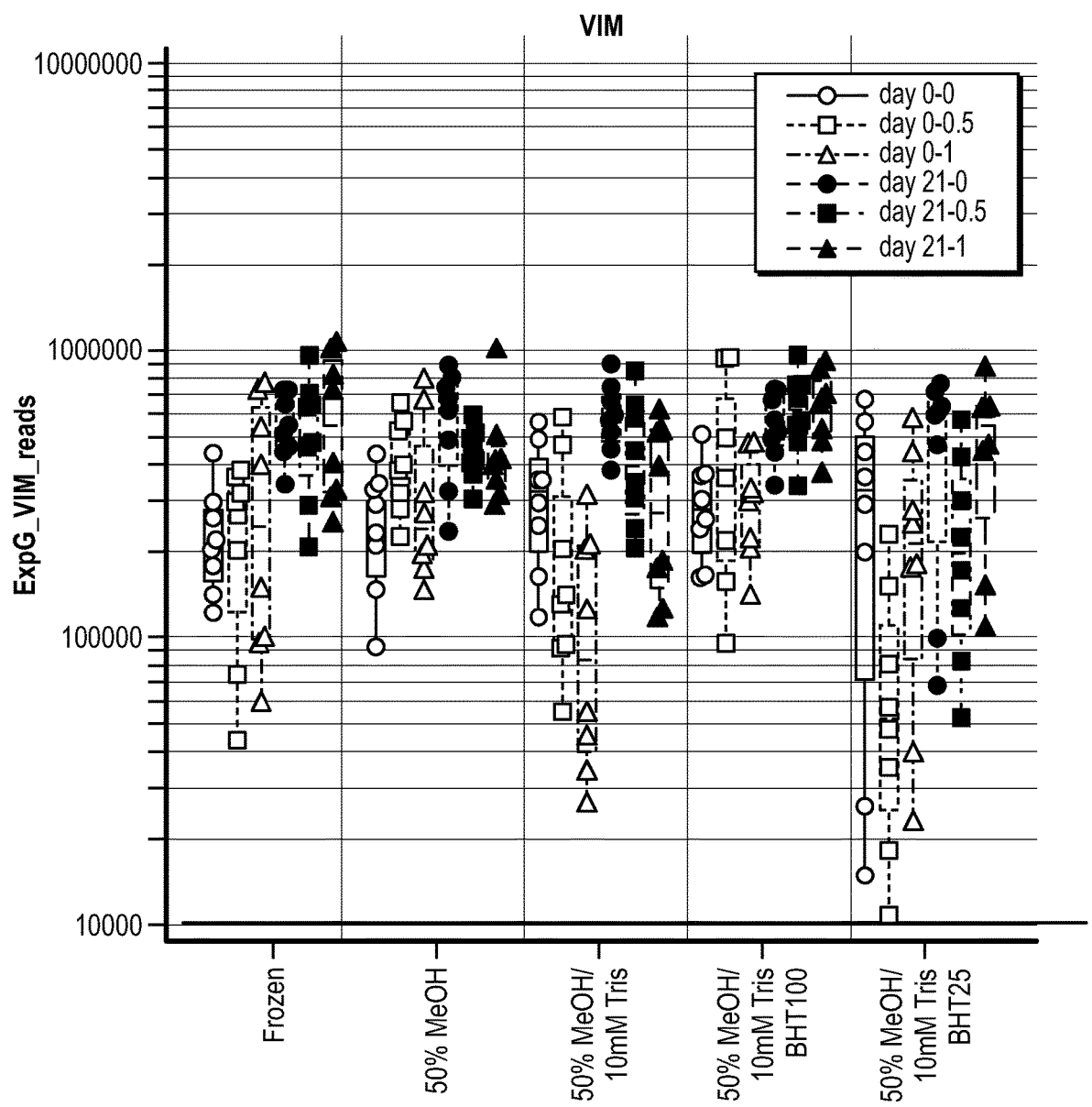
FIG. 16: Total aligned reads to VIM locus obtained after sequencing libraries in Experiment G. "VIM" corresponds to vimentin.
Figure 17:
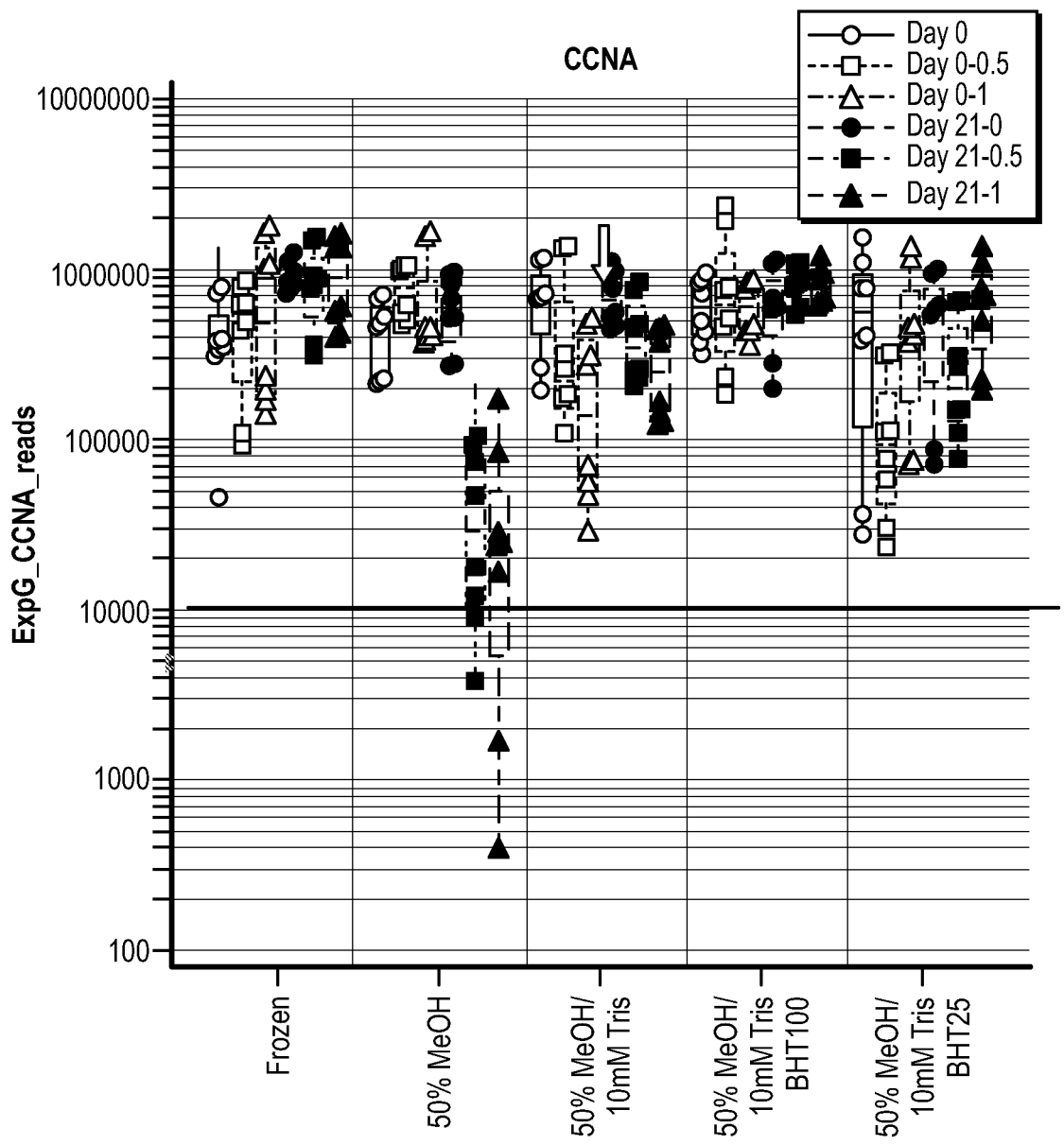
FIG. 17: Total aligned reads to CCNA1 locus obtained after sequencing libraries in Experiment G.

FIGS. 16 and 17 provide the total aligned reads obtained after sequencing the libraries in Experiment G. Number of reads aligned to VIM or CCNA1 locus, FIGS. 16 and 17 respectively, is displayed on the Y axis, while the X axis shows the buffers tested in this experiment. Circles denote samples with 0% Methyl cell line input. Squares denote input samples with 0.5% methylated cell line, and triangles denote samples with 1% methylated cell line input. Open symbols denote samples collected at day 0 timepoint, while filled symbols are used to mark samples processed after 21 days of incubation in indicated buffers. A reference line corresponding to 10000 reads (a minimum number required for sample to be considered diagnostic in a clinical assay) is drawn across the graphs for ease of visualization. In this figure, Frozen refers to cell pellet frozen at −80° C. without any buffer addition; 50% MeOH is 50% Methanol; 50% MeOH/10 mM Tris is 50% Methanol/10 mM Tris; 50% MeOH/10 mM Tris BHT100 is 50% methanol/10 mM Tris +100 mg/L BHT; 50% MeOH/10 mM Tris BHT25 is 50% methanol/10 mM Tris +25 mg/L BHT.

FIG. 17 shows an unexpected loss of analyzable reads for CCNA1 marker specifically in cells fixed for 21 days in 50% methanol buffer (red arrow) but not in 50% methanol buffer supplemented with Tris or Tris plus BHT. This type of loss has of a stochastic element, as it appears in some but not all experiments studying cells fixed in 50% methanol.

Figure 18:
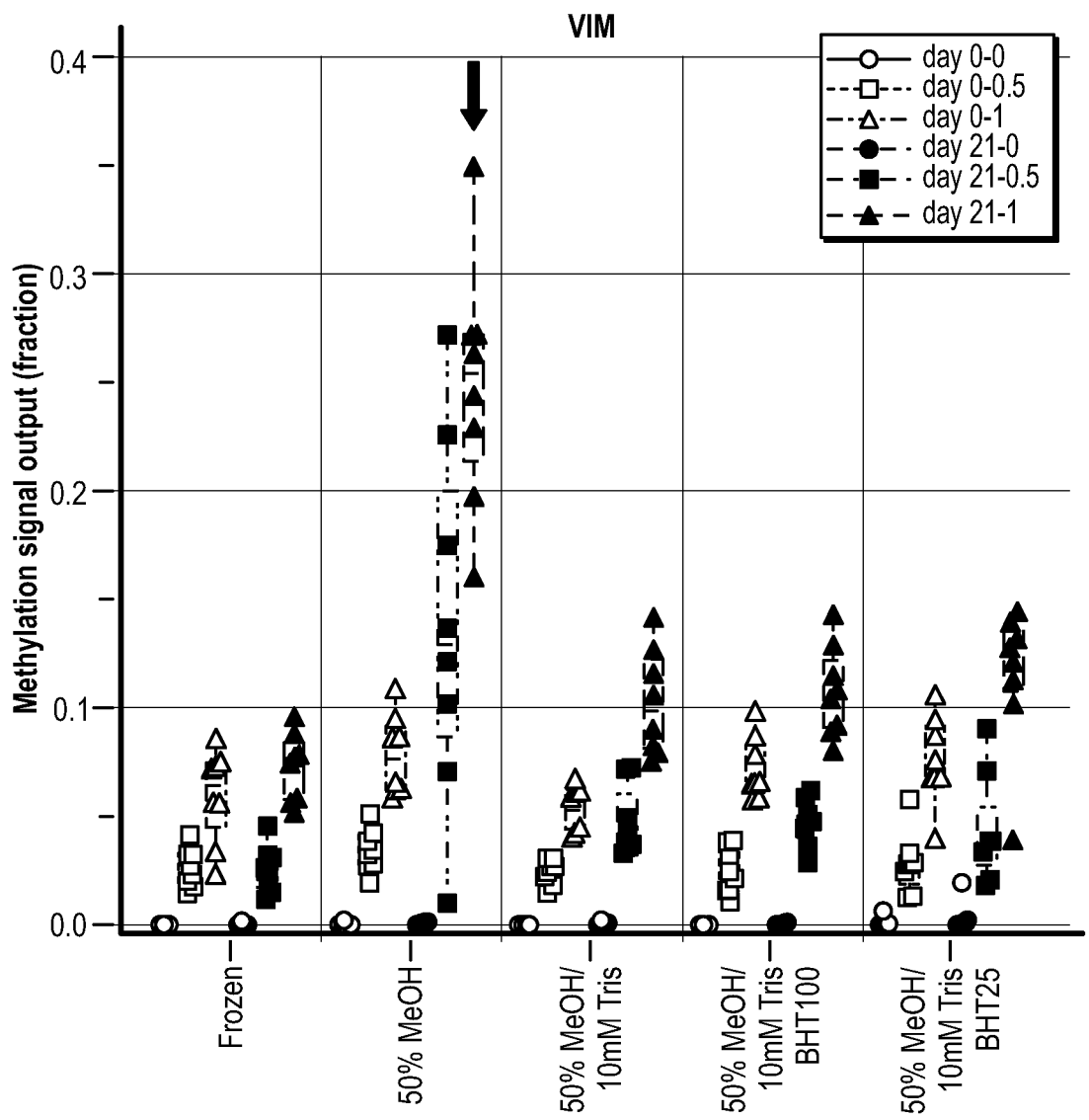
FIG. 18: VIM methylation level assay results in cells fixed in various buffers from Experiment G. "VIM" corresponds to vimentin.
Figure 19:
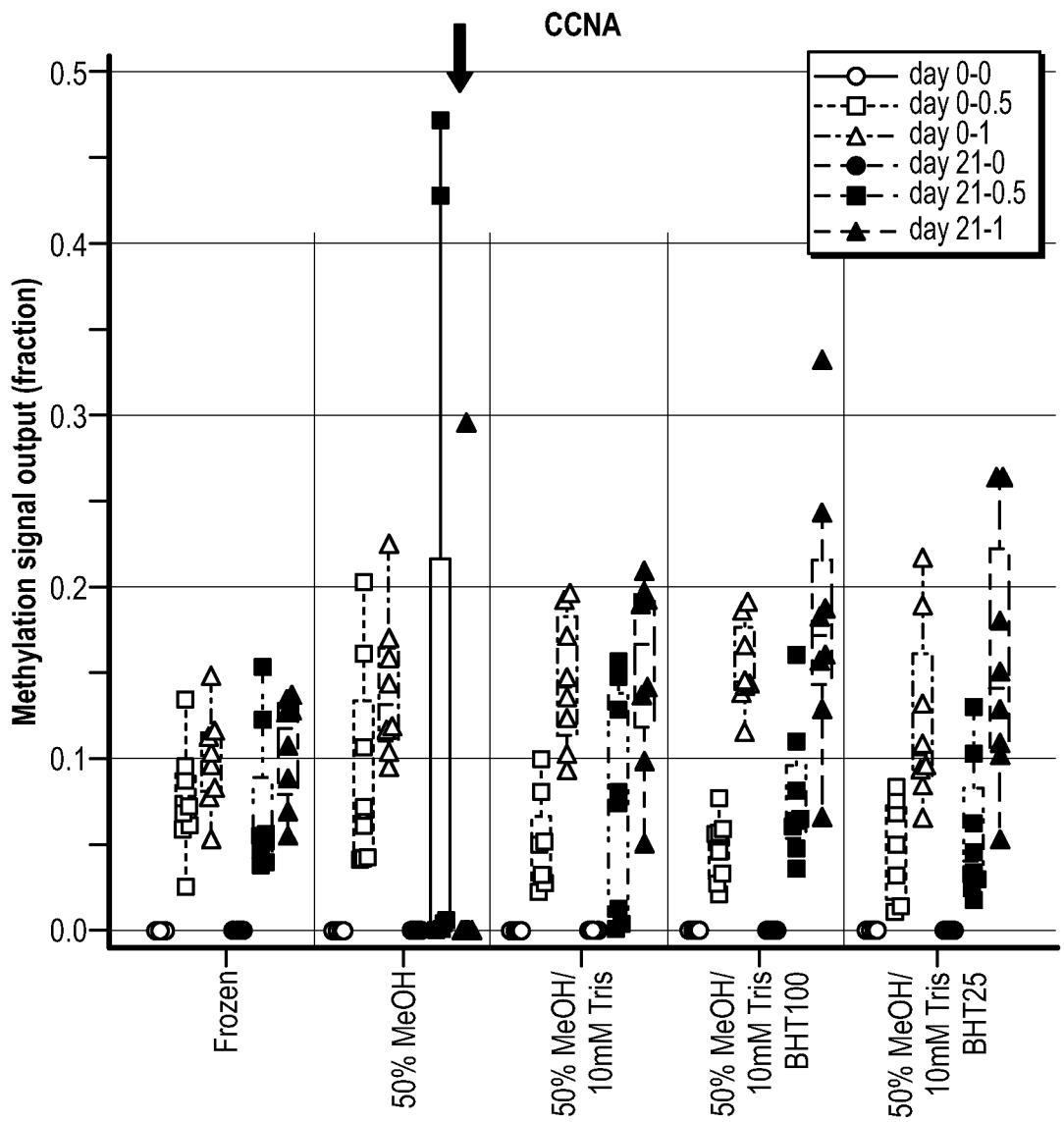
FIG. 19: CCNA1 methylation level assay results in cells fixed in various buffers from Experiment G.

FIGS. 18 and 19 provide methylation level assay results for VIM and CCNA, respectively, in Experiment G. Methylation signal (fraction) is plotted on the Y axis. Circles denote samples with 0% Methyl cell line input. Squares denote input samples with 0.5% methylated cell line, and triangles denote samples with 1% methylated cell line input. Open symbols denote samples collected at day 0 timepoint, while filled symbols are used to mark samples processed after 21 days of incubation in indicated buffers. In these figures, Frozen refers to cell pellet frozen at −80° C. without any buffer addition; 50% MeOH is 50% Methanol; 50% MeOH/10 mM Tris is 50% Methanol/10 mM Tris; 50% MeOH/10 mM Tris BHT100 is 50% methanol/10 mM Tris +100 mg/L BHT; 50% MeOH/10 mM Tris BHT25 is 50% methanol/10 mM Tris +25 mg/L BHT.

FIG. 18 shows a marked artifactual increase of VIM methylation signal after 21 days of incubation in 50% Methanol buffer, but not in buffers supplemented with 10 mM Tris, either with or without further addition of BHT. FIG. 19 shows that CCNA1 methylation in 50% methanol buffer at day 21 shows wide variability, with some samples showing marked increased methylation, and others complete signal collapse, likely due to the very low number of reads in analysis observed in FIGS. 16 and 17, and a consequent "all or none" effect.

In summary, Experiment G reproduced results of prior studies that DNA yield is much increased in cells incubated in 50% methanol plus Tris, with or without BHT, as compared to cells incubated in 50% methanol alone. Incubation of cells in 50% methanol only buffer generates artifactual increased VIM DNA methylation by Day 21. This was prevented in buffers containing 50% methanol plus tris, either with or without the addition of BHT. In addition, incubation of cells in 50% methanol was associated with a marked reduction in obtainable DNA sequencing reads for CCNA1, especially for methylated CCNA1. Consistent with the generation of a bottleneck for capturing methylated DNA reads in a small sample of reads, this was associated with an "all or none" phenomenon in which samples either assayed as showing artifactually increased CCNA1 DNA methylation or hardly any CCNA1 DNA methylation. This was prevented in buffers containing 50% methanol plus Tris, either with or without the addition of BHT. Finally, buffers containing 50% methanol plus 10 nM Tris, or 50% methanol plus 10 mM Tris plus 25 mg/L BHT, or 50% methanol plus 10 mM Tris plus 100 mg/L BHT, all behaved essentially the same.

Figure 20:
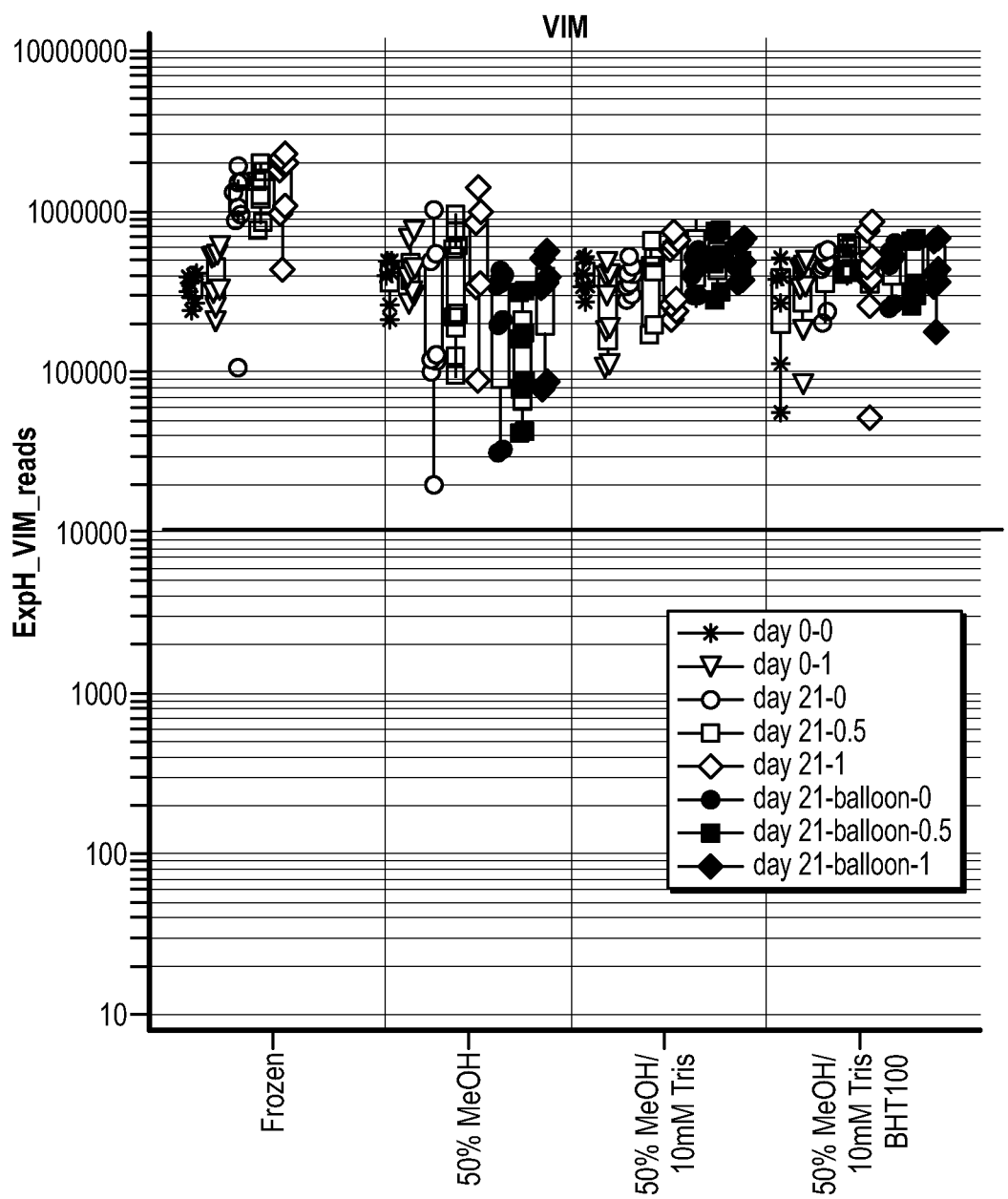
FIG. 20: Total aligned reads to VIM locus obtained after sequencing libraries in Experiment H. "VIM" corresponds to vimentin.
Figure 21:
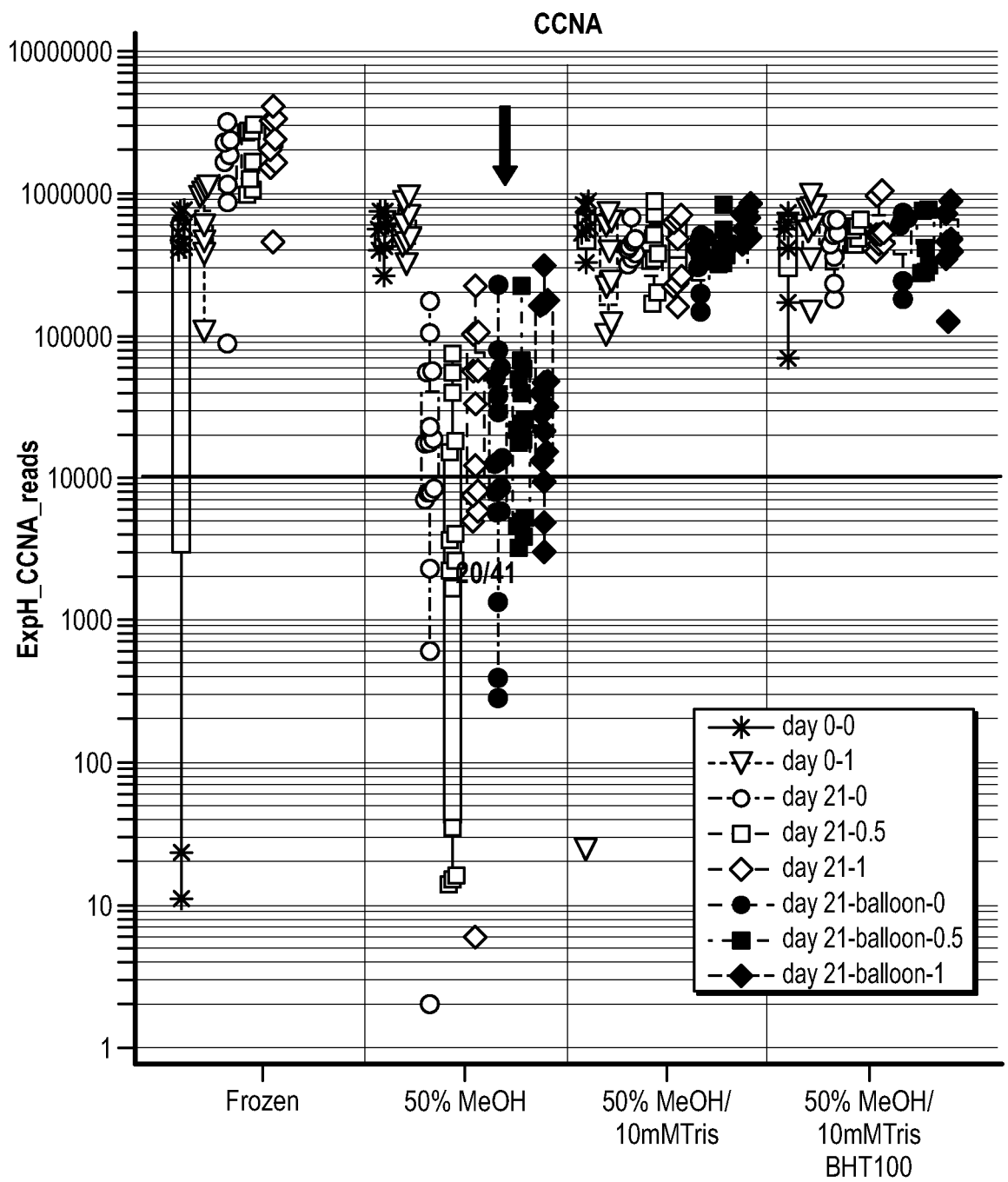
FIG. 21: Total aligned reads to CCNA1 locus obtained after sequencing libraries in Experiment H.

FIGS. 20 and 21 provide the total aligned reads obtained after sequencing the libraries in Experiment H. Number of reads aligned to VIM or CCNA1 locus, FIGS. 20 and 21 respectively, is displayed on the Y axis, while the X axis shows the buffers tested in this experiment. Asterisks denote samples with 0% Methyl cell line input at day 0. filled triangles denote input samples with 1% methylated cell line, also at day 0; Open circles denote samples with 0% methylated cell line input on day 21, without added balloon during incubation; open squares denote samples with 0.5% methylated cell line input on day 21, without added balloon during incubation; open diamonds denote samples with 1% methylated cell line input on day 21, without added balloon during incubation; filled circles denote samples with 0% methylated cell line input on day 21, with added balloon during incubation; filled squares denote samples with 0.5% methylated cell line input on day 21, with added balloon during incubation; filled diamonds denote samples with 1% methylated cell line input on day 21, with added balloon during incubation. A reference line corresponding to 10000 reads (a minimum number required for sample to be considered diagnostic in a clinical assay) is drawn across the graphs for ease of visualization. In these figures, Frozen refers to cell pellet frozen at −80° C. without any buffer addition; 50% MeOH is 50% Methanol; 50% MeOH/10 mM Tris is 50% Methanol/10 mM Tris; 50% MeOH/10 mM Tris BHT100 is 50% methanol/10 mM Tris +100 mg/L BHT; 50% MeOH/10 mM Tris BHT25 is 50% methanol/10 mM Tris +25 mg/L BHT.

FIG. 21 shows an unexpected loss of analyzable DNA reads for CCNA1 marker specifically in cells fixed for 21 days in 50% methanol buffer (red arrow) but not in 50% methanol buffer supplemented with Tris and or BHT. This recapitulated the similar loss noted in Experiment G analyzing cells fixed in 50% methanol. On repeat PCR amplification and analysis of these samples, the loss of DNA reads was again evidenced for the samples incubated in 50% methanol (see FIG. 24).

Figure 22:
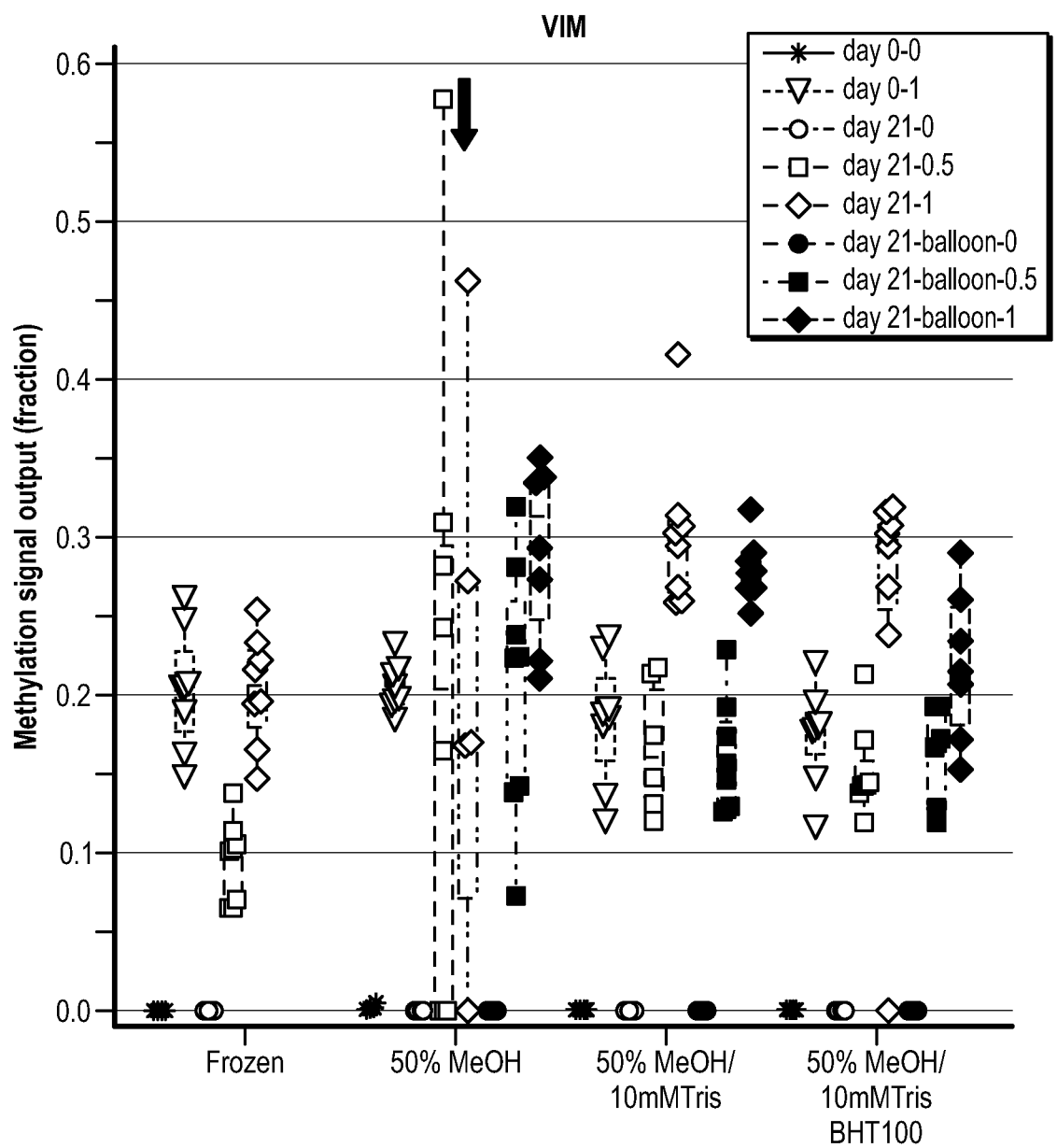
FIG. 22: VIM methylation level assay results in cells fixed in various buffers from Experiment H. "VIM" corresponds to vimentin.
Figure 23:
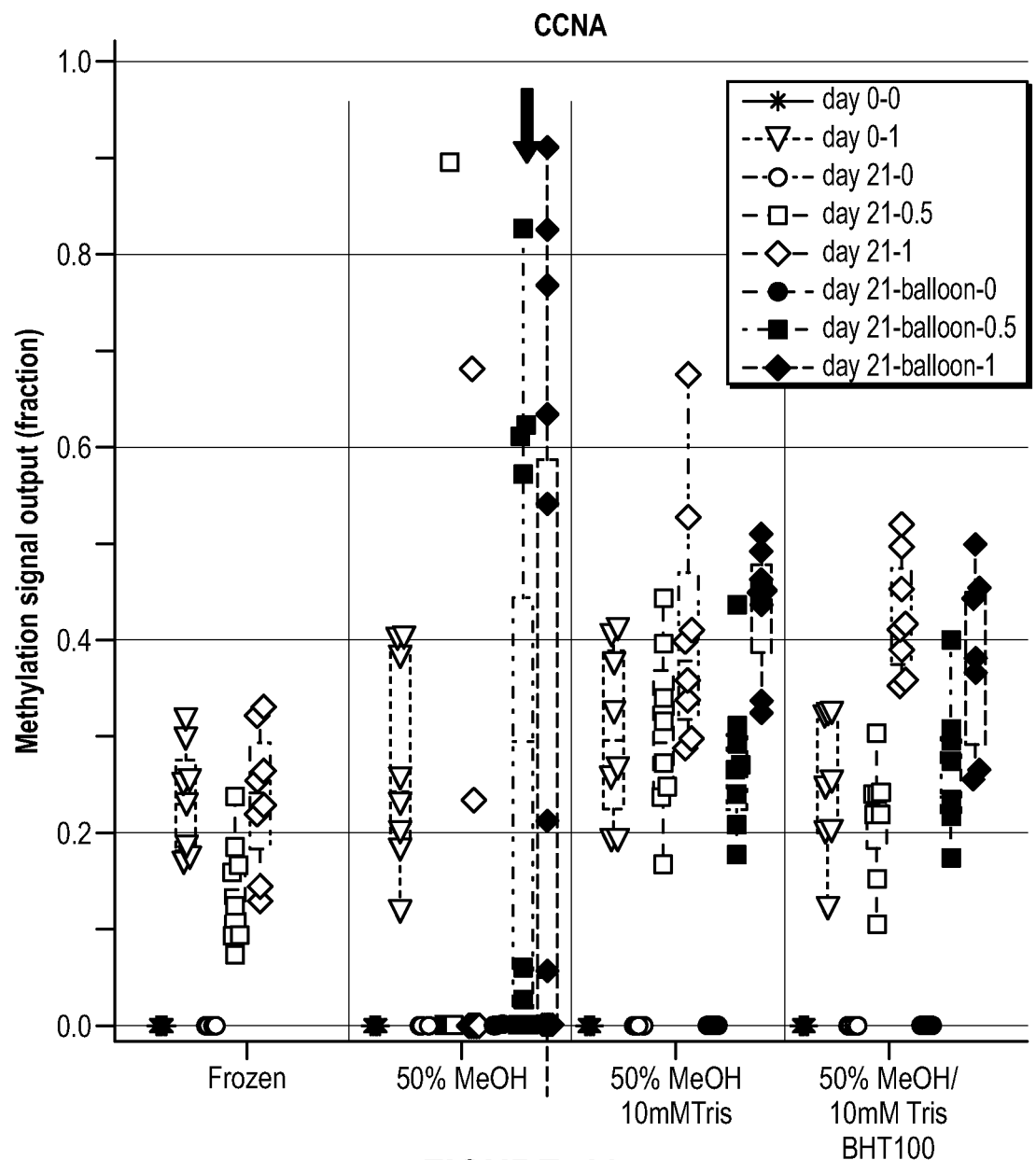
FIG. 23: CCNA1 methylation level assay results in cells fixed in various buffers from Experiment H.

FIGS. 22 and 23 provide methylation level assay results for VIM and CCNA, respectively, in Experiment H. Methylation signal (fraction) is plotted on the Y axis. Asterisks denote samples with 0% Methyl cell line input at day 0. Filled triangles denote input samples with 1% methylated cell line, also at day 0; Open circles denote samples with 0% methylated cell line input on day 21, without added balloon during incubation; Open squares denote samples with 0.5% methylated cell line input on day 21, without added balloon during incubation; Open diamonds denote samples with 1% methylated cell line input on day 21, without added balloon during incubation; Filled circles denote samples with 0% methylated cell line input on day 21, with added balloon during incubation; Filled squares denote samples with 0.5% methylated cell line input on day 21, with added balloon during incubation; Filled diamonds denote samples with 1% methylated cell line input on day 21, with added balloon during incubation In these figures, Frozen refers to cell pellet frozen at −80° C. without any buffer addition; 50% MeOH is 50% Methanol; 50% MeOH/10 mM Tris is 50% Methanol/10 mM Tris; 50% MeOH/10 mM Tris BHT100 is 50% methanol/10 mM Tris +100 mg/L BHT. This experiment was done in 50 mL tubes, with cells fixed in larger 20 mL volume of buffer.

FIGS. 22 and 23 show an artifactual increase of VIM and CCNA1 methylation signal, respectively, after 21 days of incubation in 50% Methanol buffer (red arrows), along with a marked increase in variability in these samples. Both effects were much less evident in buffers supplemented with 10 mM Tris. In this experiment, the presence of BHT further brought the methylation signal at 21 days closer to that observed in the frozen samples. The presence of balloons during the incubation had no effect on the methylation signal.

Figure 24:
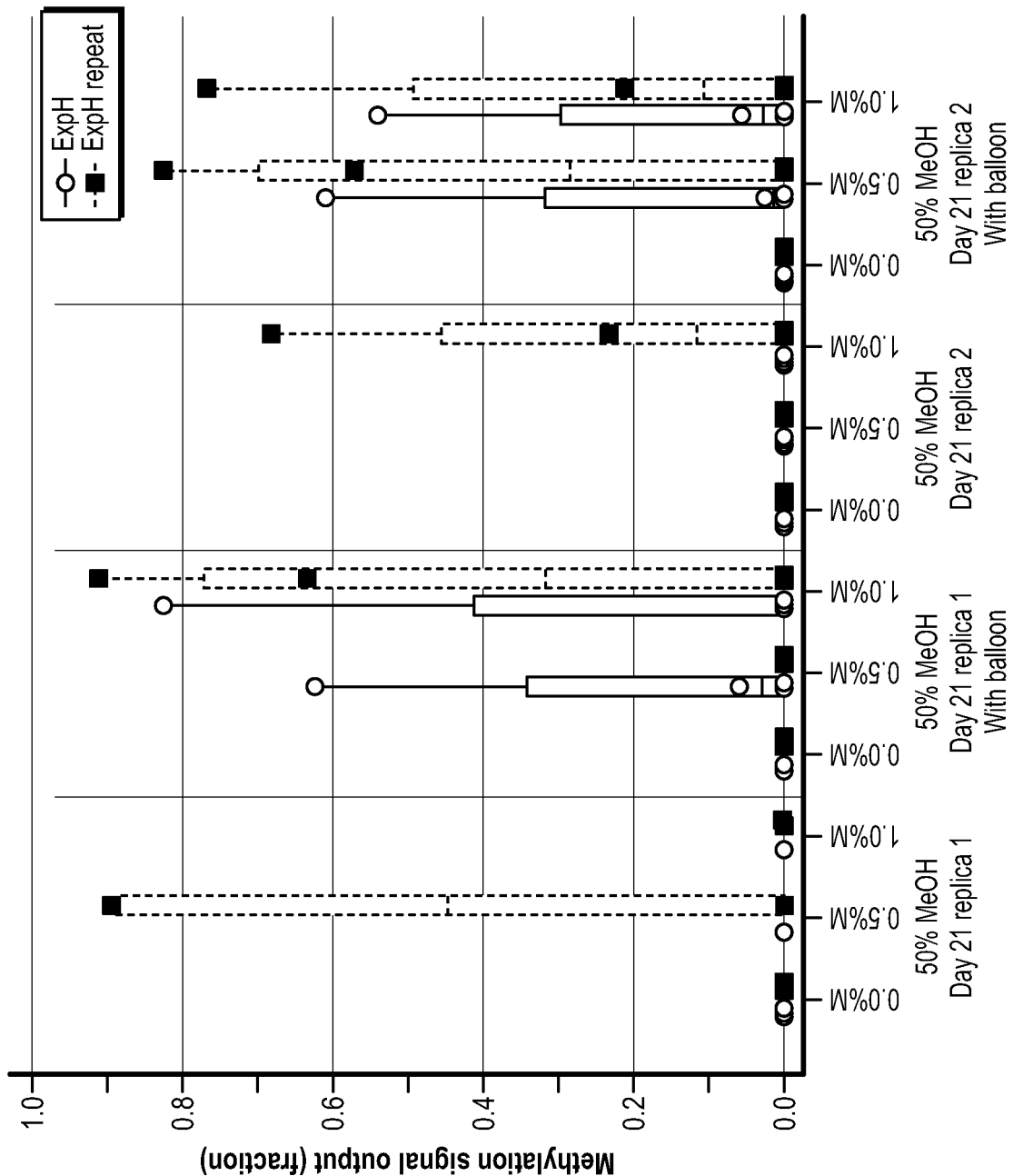
FIG. 24: CCNA1 methylation level assay results in cells fixed in repeated 50% methanol samples from Experiment H.

FIG. 24 provides methylation level assay results for repeated 50% methanol samples assayed for CCNA in Experiment H. Methylation signal (fraction) is plotted on the Y axis. Circles denote the first attempt at CCNA1 assay in originally poorly-amplifying samples from Experiment H. Squares denote an independent repeat of bisulfite treatment and PCR of the same samples. In this figure, 50% MeOH is 50% Methanol.

FIG. 24 shows that the large variability and failure of the CCNA1 assay in some samples incubated in 50% methanol buffer repeated in independent assays performed on different days. It was thus not due to any lab bench factors that occurred during the first attempt.

The above data from Experiment H demonstrates that incubation in 50% methanol only buffers led to much lower DNA yields as compared to samples incubated in 50% methanol containing Tris (either with or without BHT). In addition, incubation in 50% methanol only buffers led to much higher variability of assay of CCNA1 DNA methylation as compared to samples incubated in 50% methanol containing Tris (either with or without BHT). Furthermore, buffers with 50% methanol plus tris plus BHT at 25 mg/L performed similarly to buffers with 50% methanol plus BHT at 100 mg/L. Finally, adding medical grade silicone balloons into the incubation buffer had no observed effect on DNA yield or assay of DNA methylation.

Figure 25:
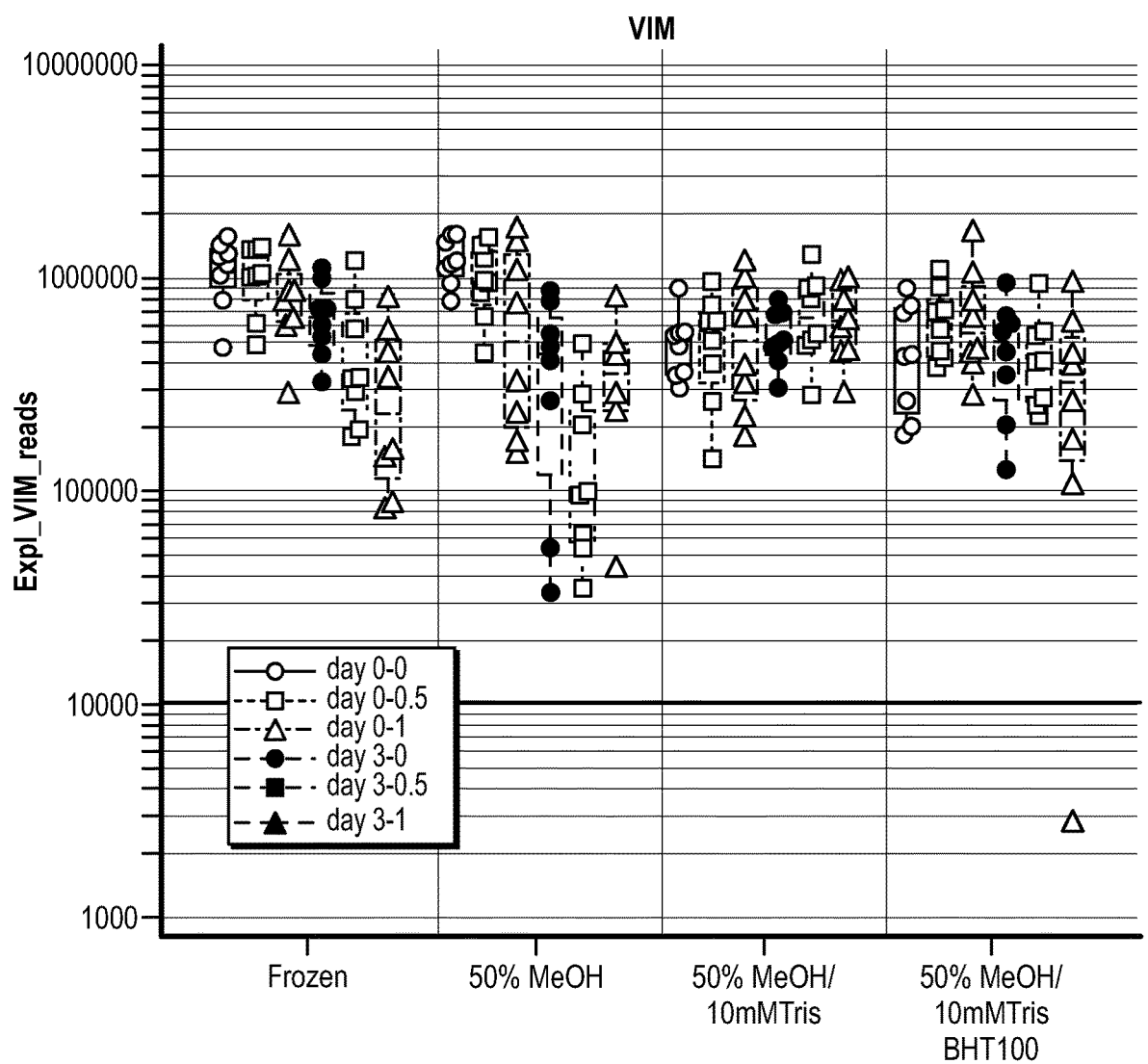
FIG. 25: Total aligned reads to VIM locus obtained after sequencing libraries in Experiment I. "VIM" corresponds to vimentin.
Figure 26:
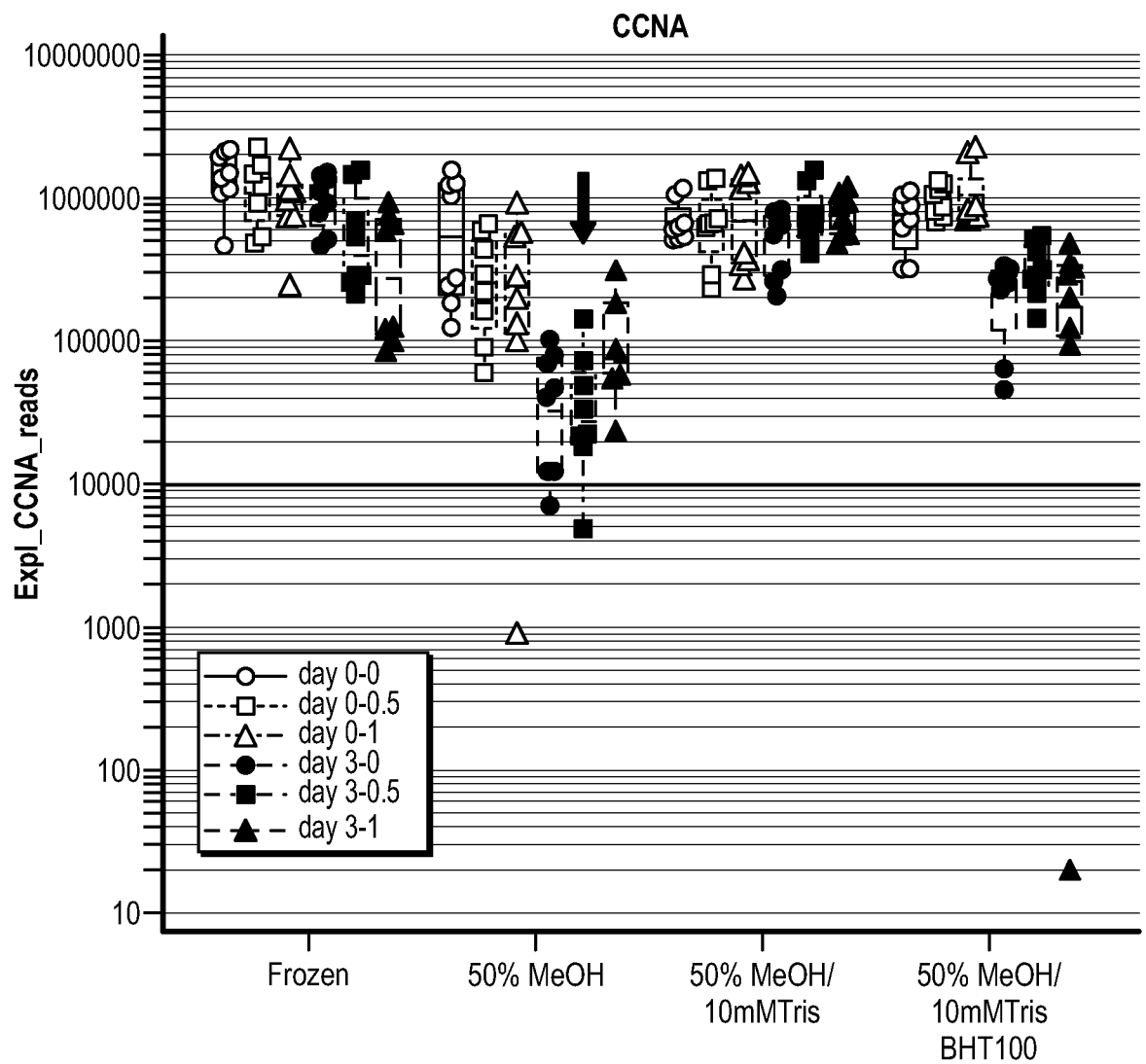
FIG. 26: Total aligned reads to CCNA1 locus obtained after sequencing libraries in Experiment I.

FIGS. 25 and 26 provide the total aligned reads obtained after sequencing the libraries in Experiment I. Number of reads aligned to VIM or CCNA1 locus, FIGS. 25 and 26 respectively, is displayed on the Y axis, while the X axis shows the buffers tested in this experiment. Open circles denote samples with 0% Methyl cell line input at day 0. Open Squares denote input samples with 0.5% methylated cell line, at day 0; Open triangles denote input samples with 1% methylated cell line, also at day 0; Filled circles denote samples with 0% methylated cell line input on day 3; Filled squares denote samples with 0.5% methylated cell line input on day 3; Filled triangles denote samples with 1% methylated cell line input on day 3. A reference line corresponding to 10000 reads (a minimum number required for sample to be considered diagnostic in a clinical assay) is drawn across the graphs for ease of visualization. In these figures, Frozen refers to cell pellet frozen at −80° C. without any buffer addition; 50% MeOH is 50% Methanol; 50% MeOH/10 mM Tris is 50% Methanol/10 mM Tris; 50% MeOH/10 mM Tris BHT100 is 50% methanol/10 mM Tris +100 mg/L BHT. This experiment was done in 50 mL conical tubes, with cells fixed in larger 20 mL volume of buffer.

FIG. 26 shows a decrease of analyzable reads for CCNA1 marker specifically in cells fixed for 3 days in 50% methanol buffer (red arrow) but not in 50% methanol buffer supplemented with Tris (with or without added BHT). This recapitulated the effect noted Experiment H, in cells fixed for 21 days. There was, however, a stochastic element of the effect, as it was not seen in all experiments analyzing cells fixed in 50% methanol.

Figure 27:
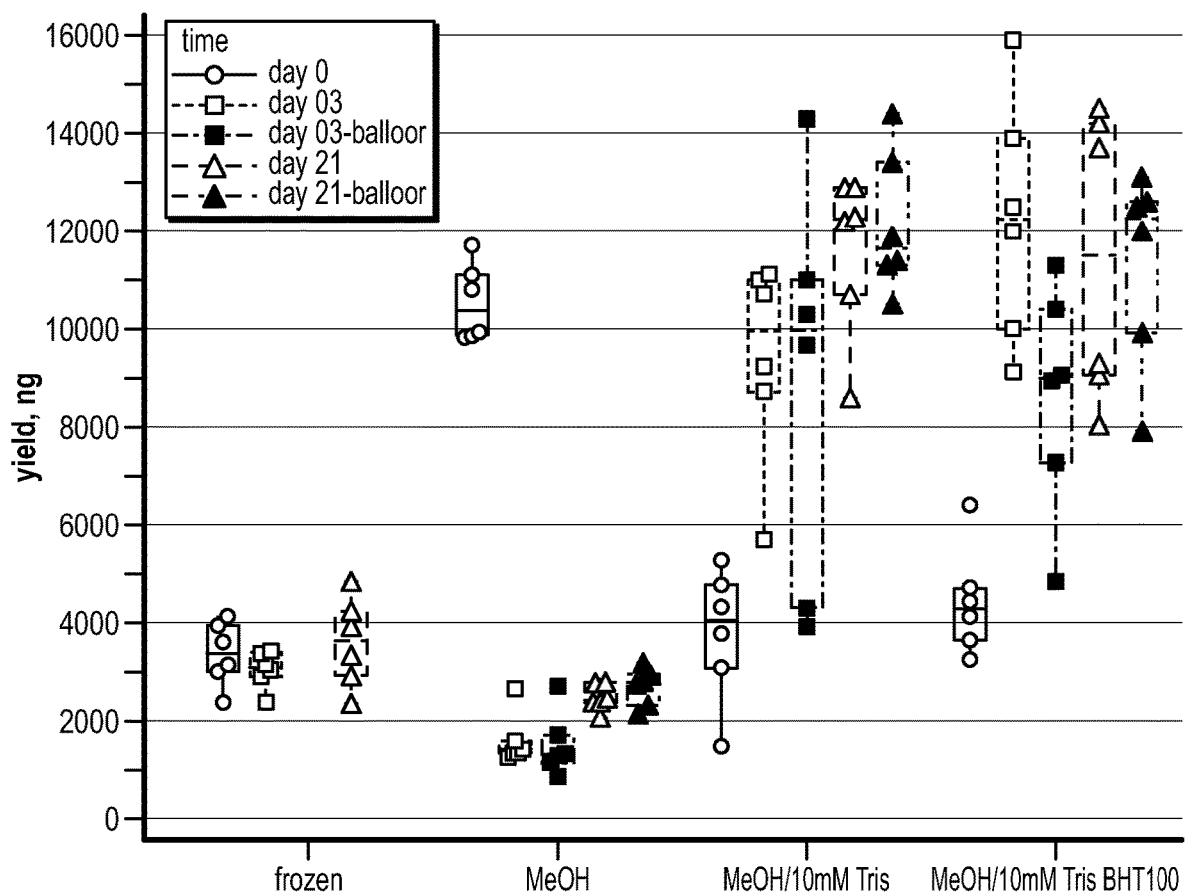
FIG. 27: DNA amount recovered from samples fixed in indicated preservatives from Experiment J.

FIG. 27 shows DNA amount recovered from samples fixed in indicated preservatives in Experiment J. This figure is the summary of total DNA yield from samples processed in Experiment J. The experiment was done in 50 mL conical tubes, with cells fixed in larger 20 mL volume of buffer with and without addition of silicone balloons during incubation. DNA amount in ng is displayed on the Y axis, while the X axis shows the buffers tested in this experiment. Open circles denote samples collected at day 0 timepoint; Open squares correspond to DNA processed after 3 days of incubation in indicated buffers without adding balloons during incubation; Filled squares correspond to DNA processed after 3 days of incubation in indicated buffers in the presence of balloons; Open triangles correspond to DNA processed after 21 days of incubation in indicated buffers without adding balloons during incubation; Filled triangles correspond to DNA processed after 21 days of incubation in indicated buffers in the presence of balloons. In this figure, Frozen refers to cell pellet frozen at −80° C. without any buffer addition; MeOH is 50% Methanol; MeOH/10 mM Tris is 50% Methanol/10 mM Tris; MeOH/10 mM Tris BHT100 is 50% methanol/10 mM Tris +100 mg/L BHT.

FIG. 27 shows that DNA recovery in 50% methanol buffer was, again, lower on day 3, and day 21, compared to day 0 (same effect as observed on day 3 and day 21 in Experiments H and I). The DNA yield from cells fixed in buffers containing methanol plus Tris was increased compared to day zero.

Figure 28:
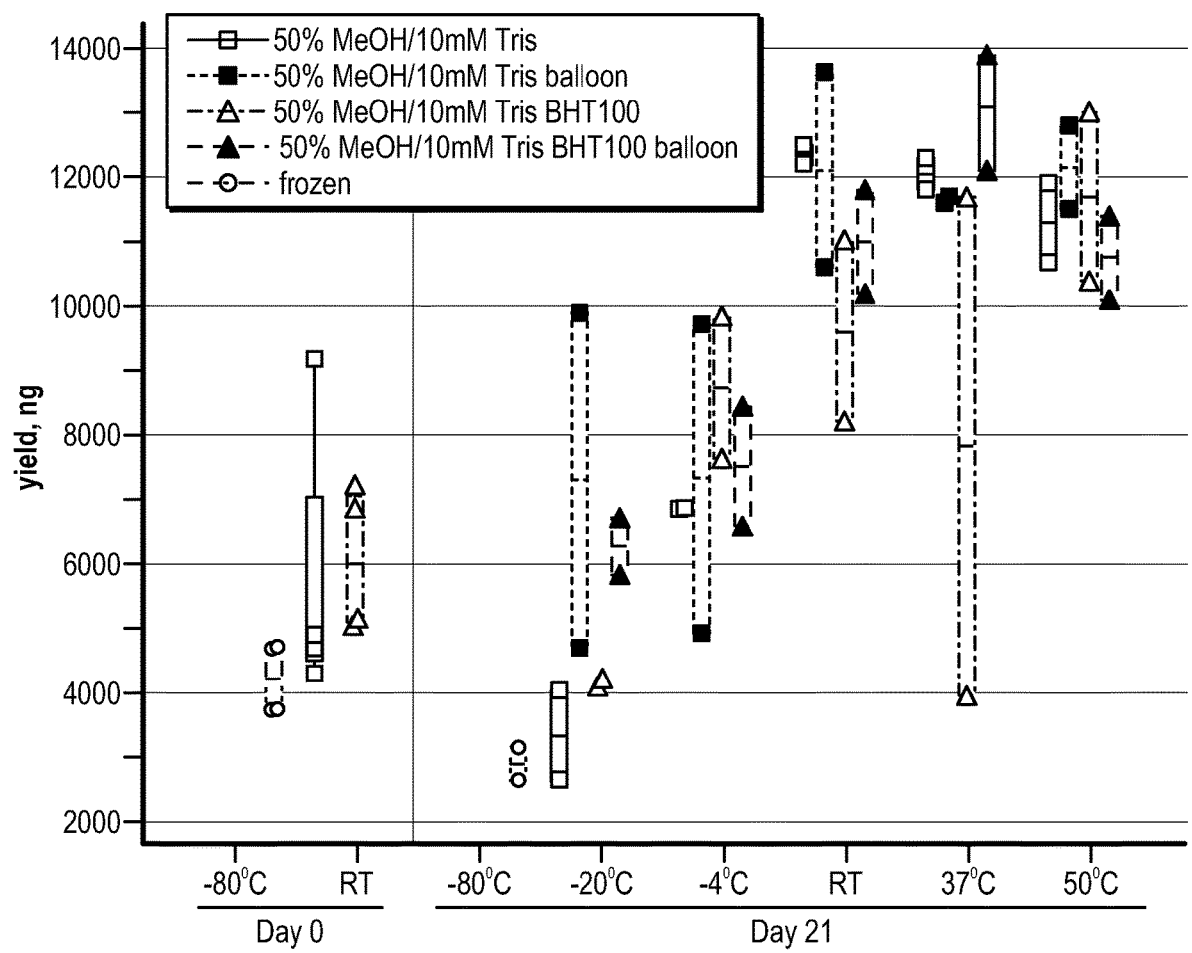
FIG. 28: DNA amount recovered from samples fixed in indicated preservatives from Experiment K.

FIG. 28 shows DNA amount recovered from samples fixed in indicated preservatives in Experiment K. This figure is the summary of total DNA yield from samples processed in Experiment K. This experiment was done in 50 mL conical tubes, with cells fixed in larger 20 mL volume of buffer. In this experiment, cells were incubated in different buffers for a week at a range of temperatures, followed by incubation for 2 more weeks at room temperature, for a total of 22 days in the buffer. Half of the samples had a medical grade silicone balloon added to the buffer during incubation, while the other half had no balloons added. The day 0 timepoint, of samples incubated in the buffer at room temperature for approximately 1 hr is used for comparison. is used for comparison, DNA amount in ng is displayed on the Y axis, while the X axis shows the buffers tested in this experiment. Open circles denote cells frozen at −80° C. without any preservative buffer. Open squares correspond to samples incubated in 50% Methanol/10 mM Tris buffer without balloons; Filled squares correspond to samples incubated in 50% Methanol/10 mM Tris buffer in the presence of balloons; Open triangles correspond to samples incubated in 50% Methanol/10 mM Tris with 100 mg/L BHT buffer without balloons; Filled triangles correspond to samples incubated in 50% Methanol/10 mM Tris with 100 mg/L BHT buffer in the presence of balloons. Incubation temperatures are indicated on the X axis. −80° C. refers to the standard comparator conditions of freezing cell pellet without addition of the preservative buffer (open circles). RT indicates samples incubated at room temperature.

FIG. 28 shows that compared to DNA recovery from cell pellet frozen at −80° C., DNA yield was enhanced in cells incubated in either 50% methanol plus Tris or 50% methanol plus Tris and BHT, across all temperature ranges from −20° C. to 50° C., with the magnitude of the enhancement increasing as the temperature at which the cells were incubated during the first week increased. Further observations are that buffers containing 50% methanol plus Tris with or without addition of BHT remain optically clear after one week of incubation across a temperature range from −20° C. to +50° C.

Figure 29:
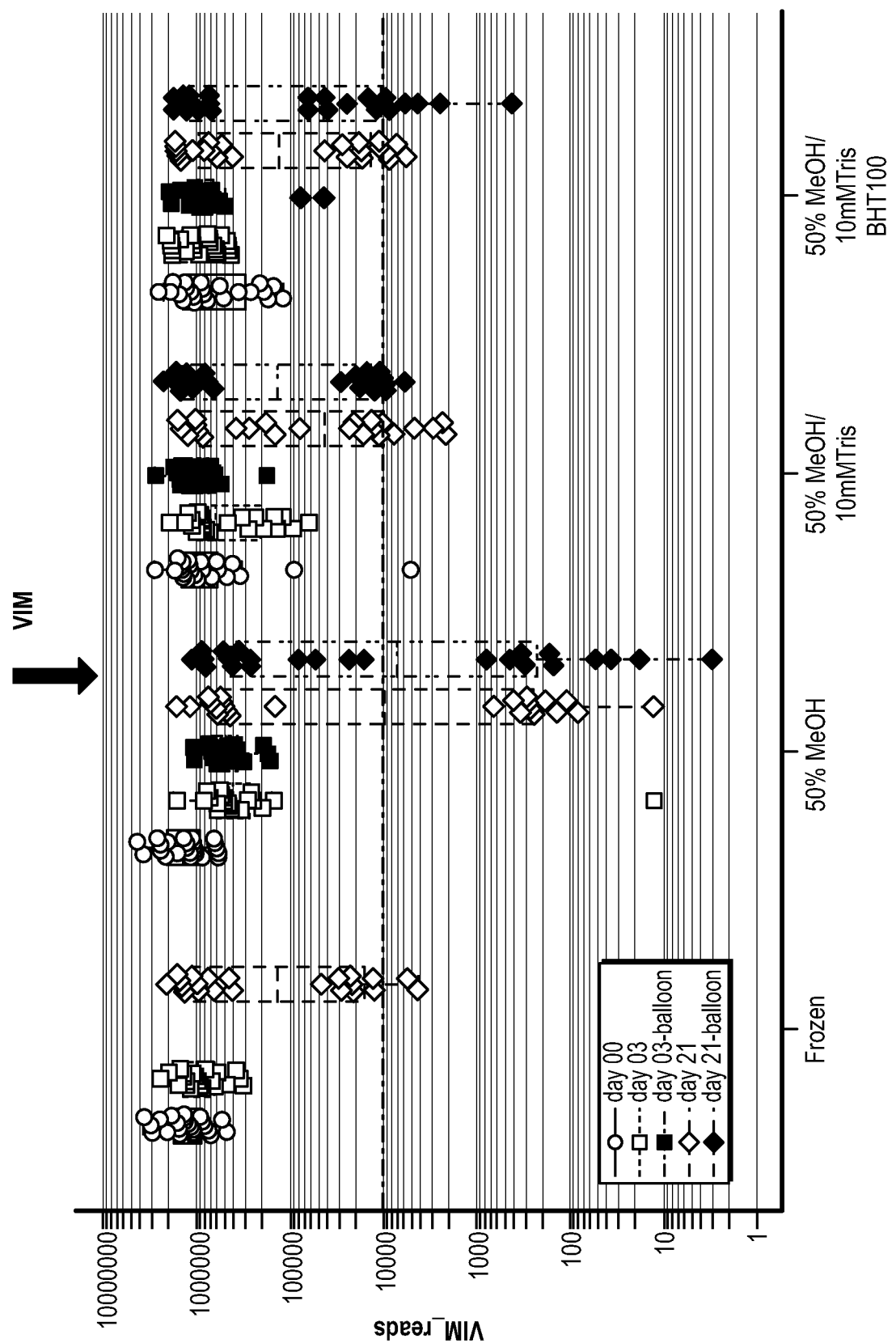
FIG. 29: Total aligned reads to VIM locus obtained after sequencing libraries in Experiment J. "VIM" corresponds to vimentin.
Figure 30:
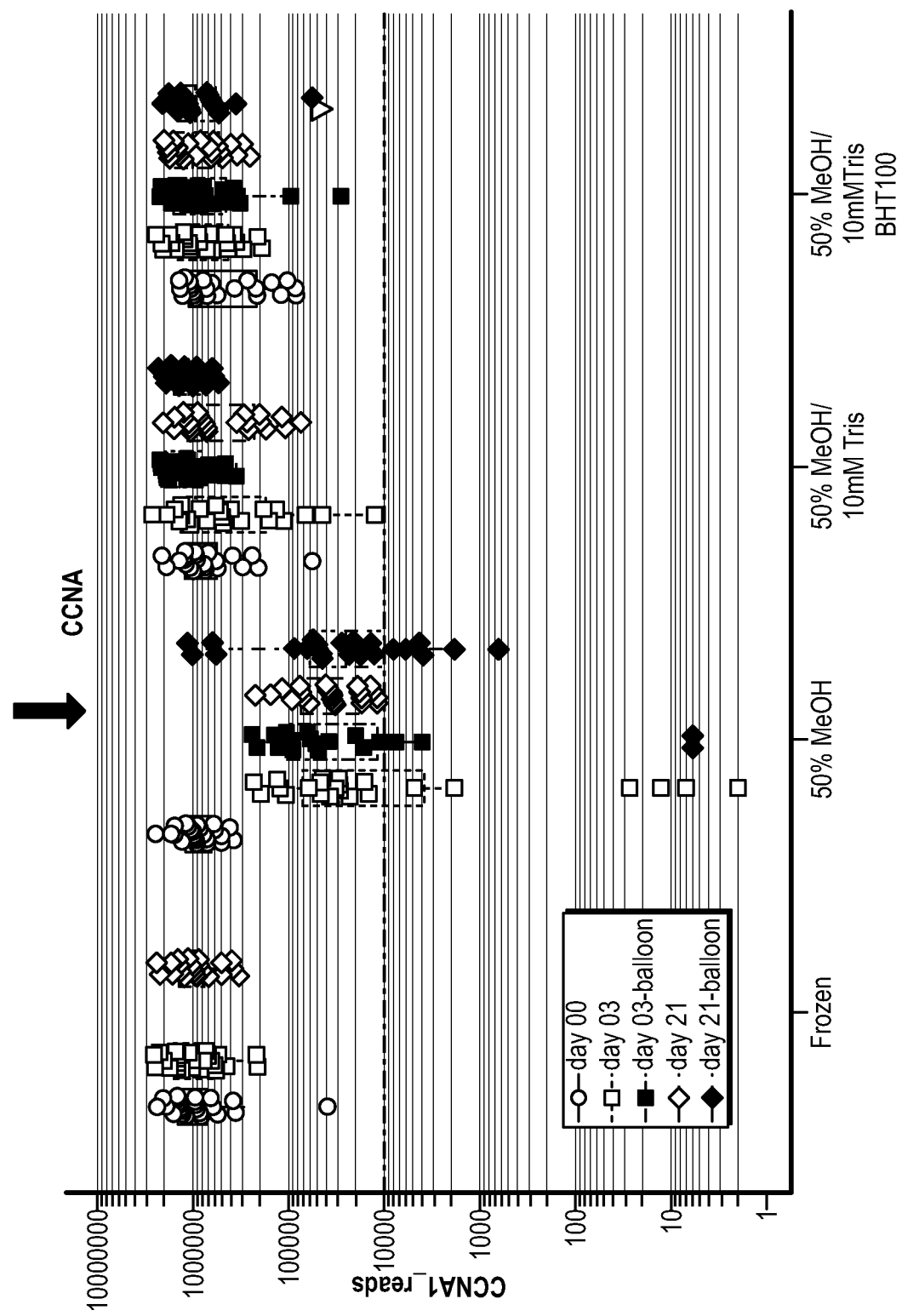
FIG. 30: Total aligned reads to CCNA1 locus obtained after sequencing libraries in Experiment J.

FIGS. 29 and 30 provide the total aligned reads obtained after sequencing the libraries in Experiment J. Number of reads aligned to VIM or CCNA1 locus, FIGS. 29 and 30 respectively, is displayed on the Y axis, while the X axis shows the buffers tested in this experiment. Open circles denote samples at day 0. Open squares denote samples incubated for 3 days, without balloons; filled squares denote samples after 3 day incubation in the presence of balloons. Open triangles denote samples incubated for 21 days without added balloons; filled squares denote samples incubated for 21 days with balloons. A reference line corresponding to 10000 reads (a minimum number required for sample to be considered diagnostic in a clinical assay) is drawn across the graphs for ease of visualization. In these figures, Frozen refers to cell pellet frozen at −80° C. without any buffer addition; 50% MeOH is 50% Methanol; 50% MeOH/10 mM Tris is 50% Methanol/10 mM Tris; 50% MeOH/10 mM Tris BHT100 is 50% methanol/10 mM Tris +100 mg/L BHT. This experiment was done in 50 mL conical tubes, with cells fixed in larger 20 mL volume of buffer.

FIG. 30 shows a decrease of analyzable reads for CCNA1 marker specifically in cells fixed for 3 days or 21 days in 50% methanol buffer (red arrow) but not in 50% methanol buffer supplemented with Tris (with or without added BHT). This recapitulated the effect noted Experiment H, in cells fixed for 21 days, and experiment I, in cells fixed for 3 days. The samples fixed in 50% methanol also show a decrease of analyzable VIM reads at day 21, but not at day 3 (FIG. 29). There was, however, a stochastic element of the effect, as it was not seen in all experiments analyzing cells fixed in 50% methanol.

Figure 31:
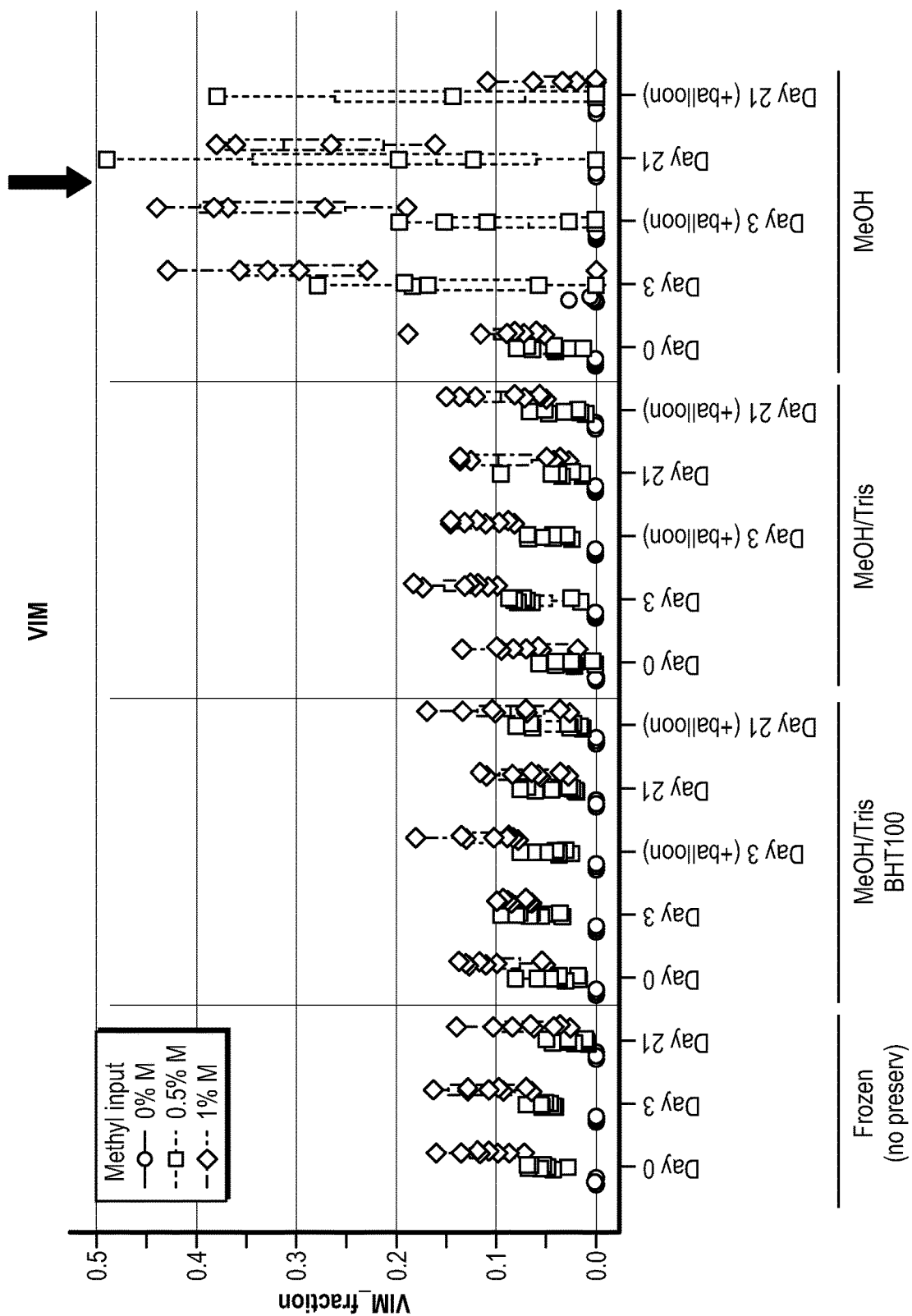
FIG. 31: VIM methylation level assay results in cells fixed in various buffers from Experiment J. "VIM" corresponds to vimentin.
Figure 32:
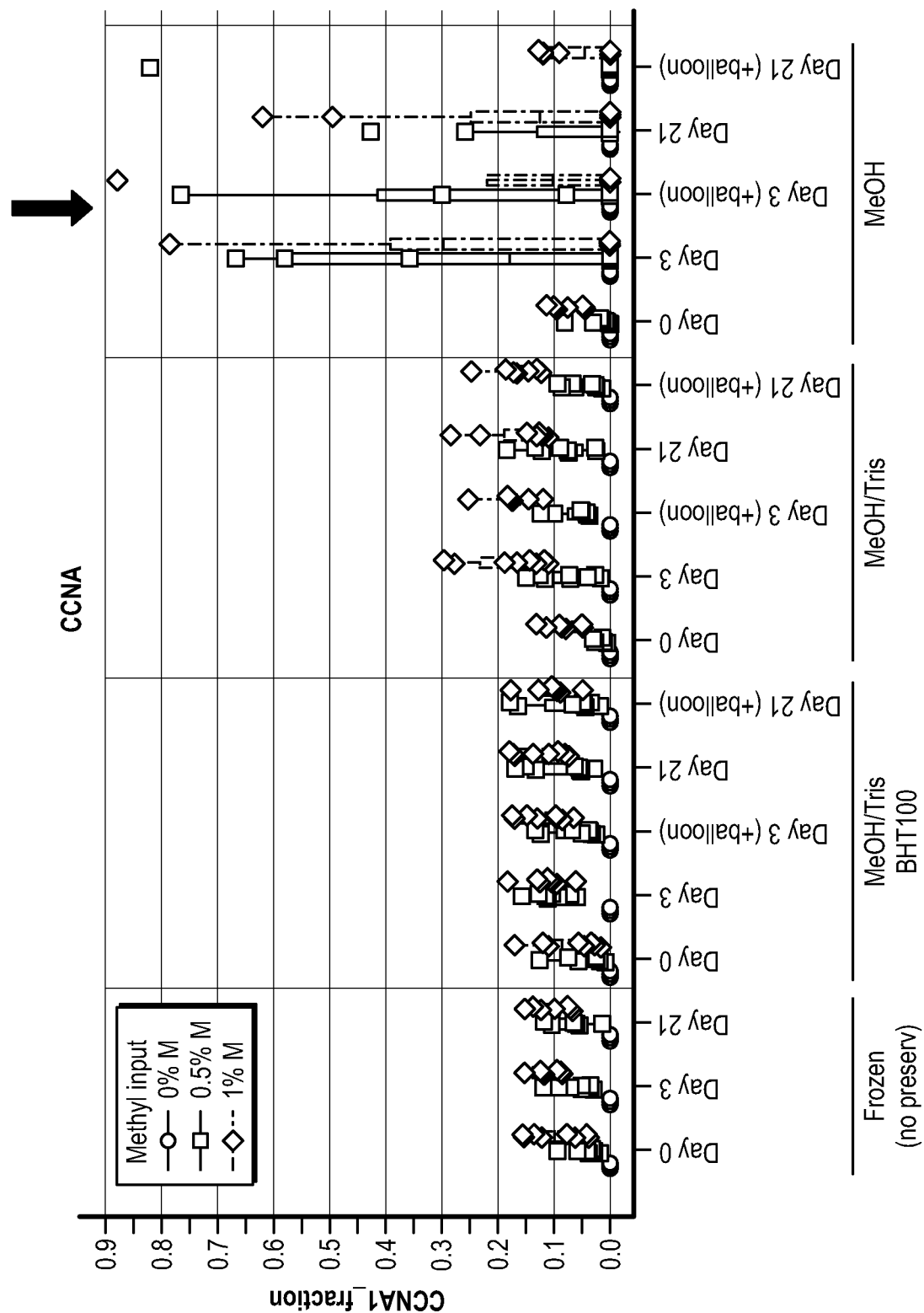
FIG. 32: CCNA1 methylation level assay results in cells fixed in various buffers from Experiment J.

FIGS. 31 and 32 provide methylation level assay results for VIM and CCNA, respectively, in Experiment J. Methylation signal (fraction) is plotted on the Y axis. Open circles denote samples with 0% Methyl cell line input. Open squares denote samples with 0.5% methylated cell line input; filled diamonds denote samples with 1% methylated cell line input. In these figures, Frozen refers to cell pellet frozen at −80° C. without any buffer addition; 50% MeOH is 50% Methanol; 50% MeOH/10 mM Tris is 50% Methanol/10 mM Tris; 50% MeOH/10 mM Tris BHT100 is 50% methanol/10 mM Tris +100 mg/L BHT. This experiment was done in 50 mL tubes, with cells fixed in larger 20 mL volume of buffer.

FIGS. 31 and 32 show an artifactual increase of VIM and CCNA1 methylation signal, respectively, after 3 and 21 days of incubation in 50% Methanol buffer (red arrows), along with a marked increase in variability in these samples. Both effects were much less evident in buffers supplemented with 10 mM Tris. In this experiment, the presence of BHT further brought the methylation signal for CCNA1 at 3 and 21 days closer to that observed in the frozen samples. The presence of balloons during the incubation had no effect on the methylation signal.

In summary, experiment J shows that unbuffered 50% methanol was associated with loss of DNA yield in incubations with cells of as short as 3 days. This effect is substantially prevented with addition of Tris. Experiment J shows that unbuffered 50% methanol produced artifactual increases in DNA methylation at the Vim and CCNA1 loci in incubations with cells of as short as 3 days. This effect is substantially prevented with addition of Tris, with further improvement noted with addition of both Tris and BHT.

Figure 33:
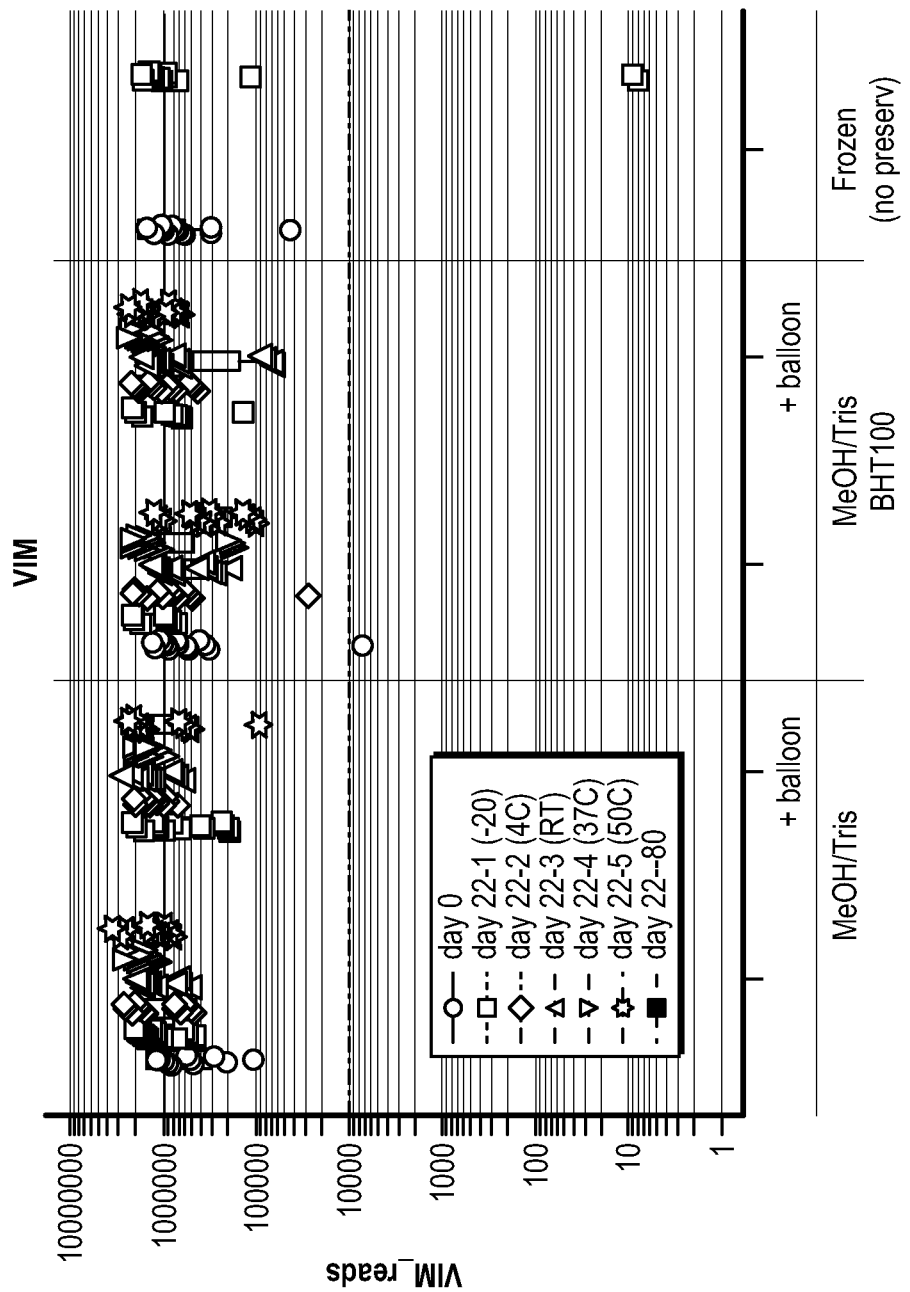
FIG. 33: Total aligned reads to VIM locus obtained after sequencing libraries in Experiment K. "VIM" corresponds to vimentin.
Figure 34:
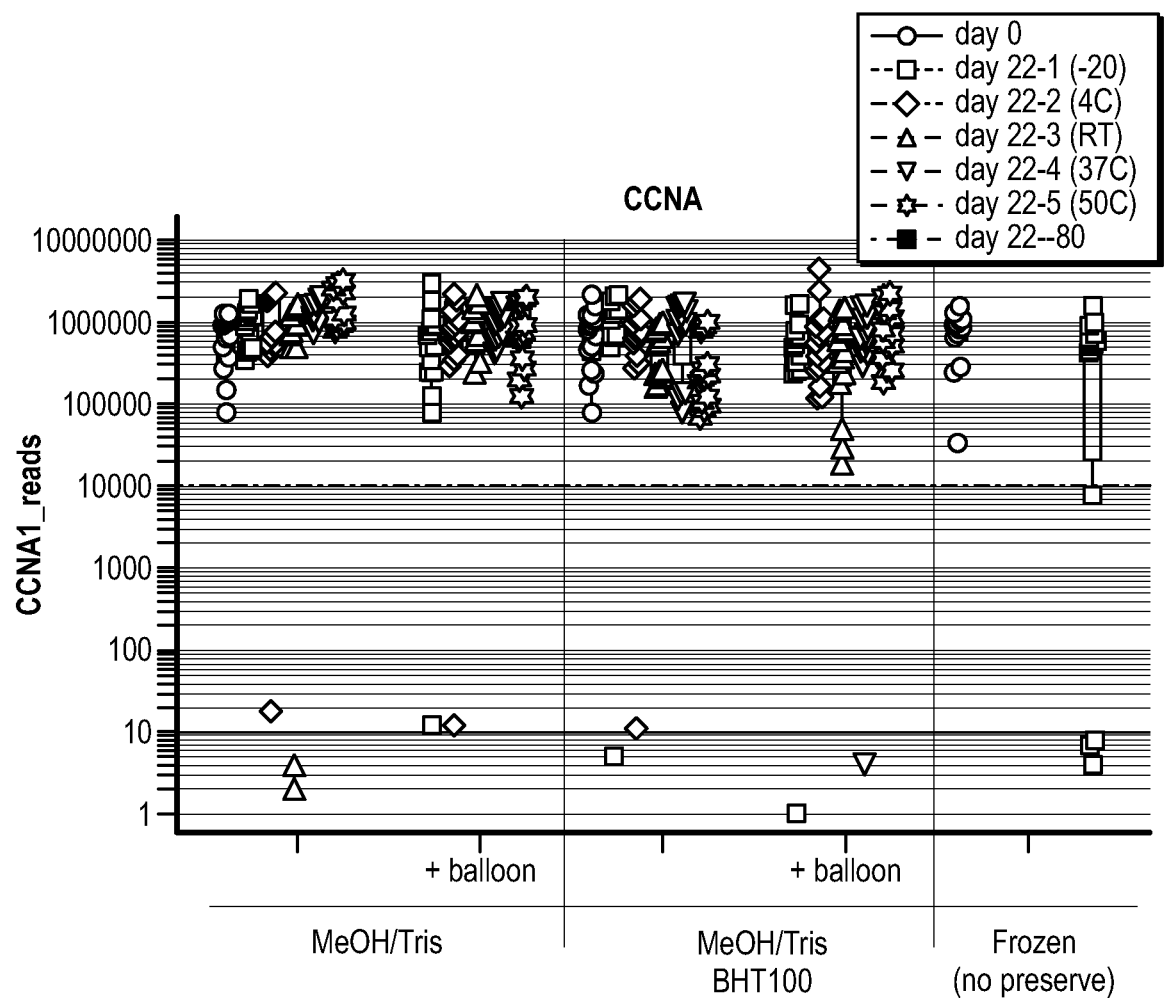
FIG. 34: Total aligned reads to CCNA1 locus obtained after sequencing libraries in Experiment K.

FIGS. 33 and 34 provide the total aligned reads obtained after sequencing the libraries in Experiment K. Number of reads aligned to VIM or CCNA1 locus, FIGS. 33 and 34 respectively, is displayed on the Y axis, while the X axis shows the buffers tested in this experiment. Open circles denote samples at day 0. Open squares denote samples incubated for 7 days at −20° C., followed by 2 weeks of incubation at room temperature. Filled diamonds denote samples incubated for 7 days at 4° C., followed by 2 weeks of incubation at room temperature. Open triangles denote samples incubated for 21 days at room temperature. Upside-down filled triangles denote samples incubated for 7 days at 37° C., followed by 2 weeks of incubation at room temperature. Filled stars denote samples incubated for 7 days at 50° C., followed by 2 weeks of incubation at room temperature. Filled squares denote flash-frozen samples that were kept at −80° C. for 3 weeks without addition of preservative buffer. A reference line corresponding to 10000 reads (a minimum number required for sample to be considered diagnostic in a clinical assay) is drawn across the graphs for ease of visualization. In these figures, Frozen refers to cell pellet frozen at −80° C. without any buffer addition; 50% MeOH/10 mM Tris is 50% Methanol/10 mM Tris; 50% MeOH/10 mM Tris BHT100 is 50% methanol/10 mM Tris +100 mg/L BHT. This experiment was done in 50 mL conical tubes, with cells fixed in larger 20 mL volume of buffer.

FIGS. 33 and 34 shows no appreciable variation of analyzable reads for VIM or CCNA1 markers after 21 days in 50% methanol buffer supplemented with Tris (with or without added BHT). This recapitulated the effect noted Experiment H and J, with room temperature incubation, and showed that incubation at different temperatures showed no appreciable effect on the number of analyseable reads for VIM or CCNA, after cell incubation in buffered methanol, compared to flash frozen samples. Alternatively stated, in comparison to experiment J, the results of experiment K show that addition of Tris to 50% methanol protects from the collapse of read counts in bisulfite sequencing assays of DNA prepared from cell samples incubated in methanol based buffers, and this protection extends to cells incubated in buffers at temperatures as high as 50° C.

Figure 35:
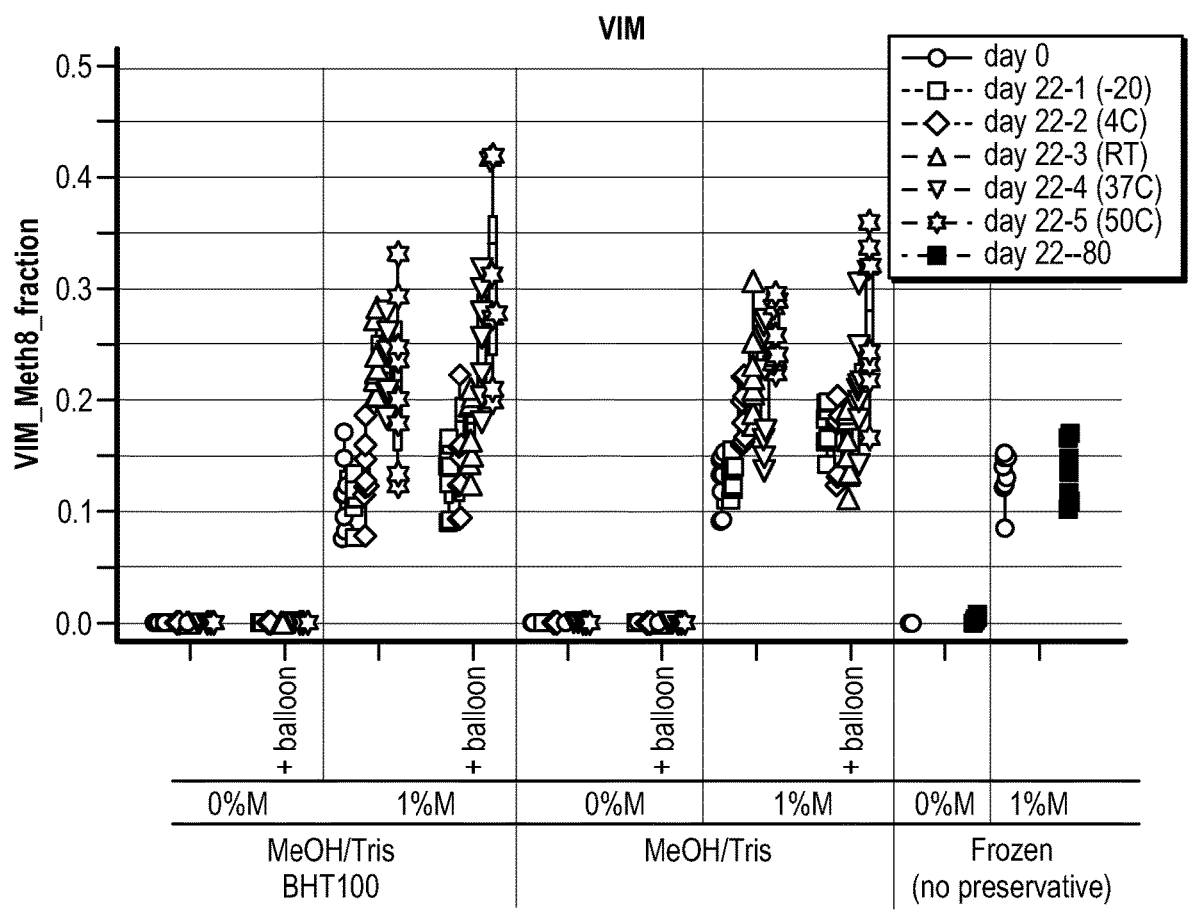
FIG. 35: VIM methylation level assay results in cells fixed in various buffers from Experiment K. "VIM" corresponds to vimentin.
Figure 36:
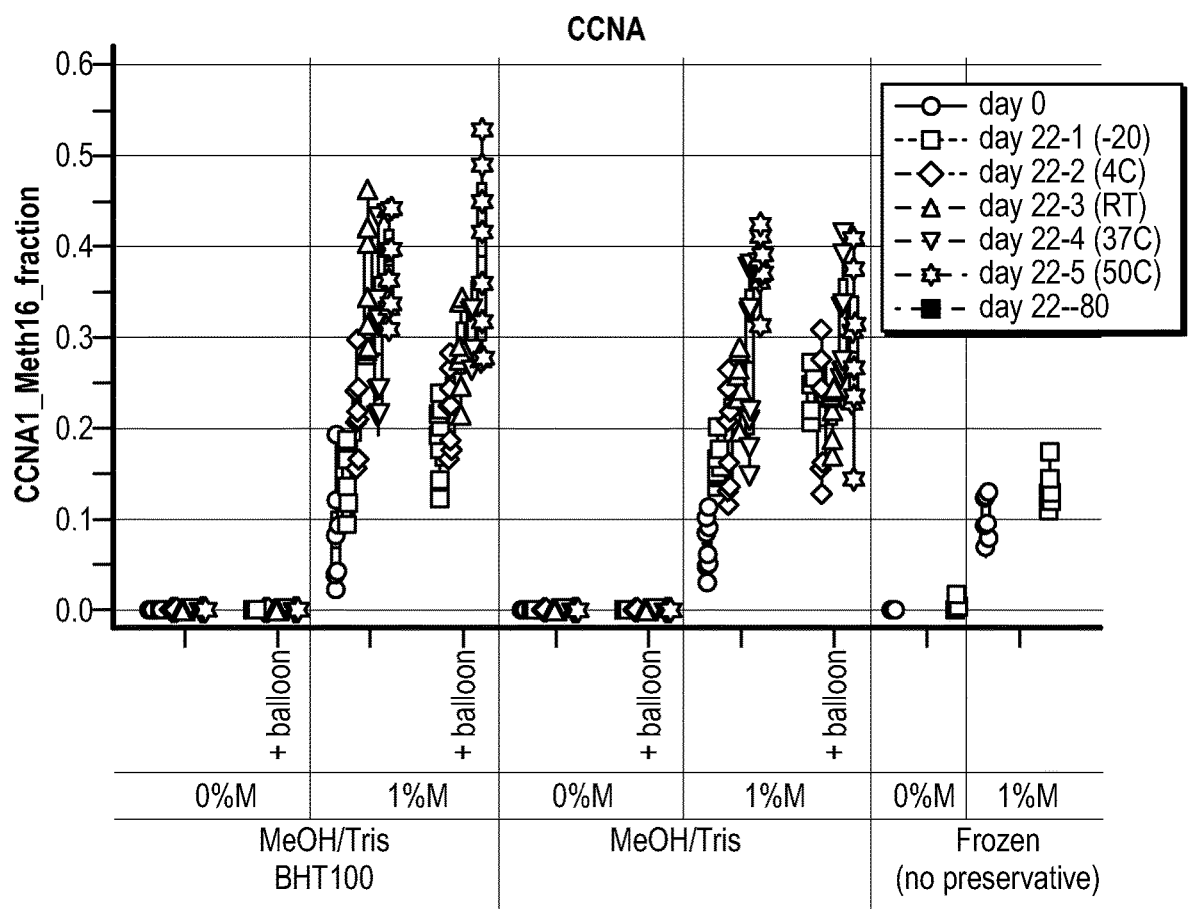
FIG. 36: CCNA1 methylation level assay results in cells fixed in various buffers from Experiment K.

FIGS. 35 and 36 provide methylation level assay results for VIM and CCNA, respectively, in Experiment K. Methylation signal (fraction) is plotted on the Y axis. Open circles denote samples at day 0. Open squares denote samples incubated for 7 days at −20° C., followed by 2 weeks of incubation at room temperature. Filled diamonds denote samples incubated for 7 days at 4° C., followed by 2 weeks of incubation at room temperature. Open triangles denote samples incubated for 21 days at room temperature; Upsidedown filled triangles denote samples incubated for 7 days at 37° C., followed by 2 weeks of incubation at room temperature. Filled stars denote samples incubated for 7 days at 50° C., followed by 2 weeks of incubation at room temperature. Filled squares denote flash-frozen samples that were kept at −80° C. for 3 weeks without addition of preservative buffer. In these figures, Frozen refers to cell pellet frozen at −80° C. without any buffer addition; 50% MeOH/10 mM Tris is 50% Methanol/10 mM Tris; 50% MeOH/10 mM Tris BHT100 is 50% methanol/10 mM Tris +100 mg/L BHT. This experiment was done in 50 mL tubes, with cells fixed in larger 20 mL volume of buffer.

FIGS. 35 and 36 show an artifactual increase of VIM and CCNA1 methylation signal, respectively, after 37° C. and 50° C. incubation in 50% Methanol buffer supplemented with Tris, or Tris-BHT, compared to flash-frozen samples. The presence of balloons during the incubation had no effect on the methylation signal.

Figure 37:
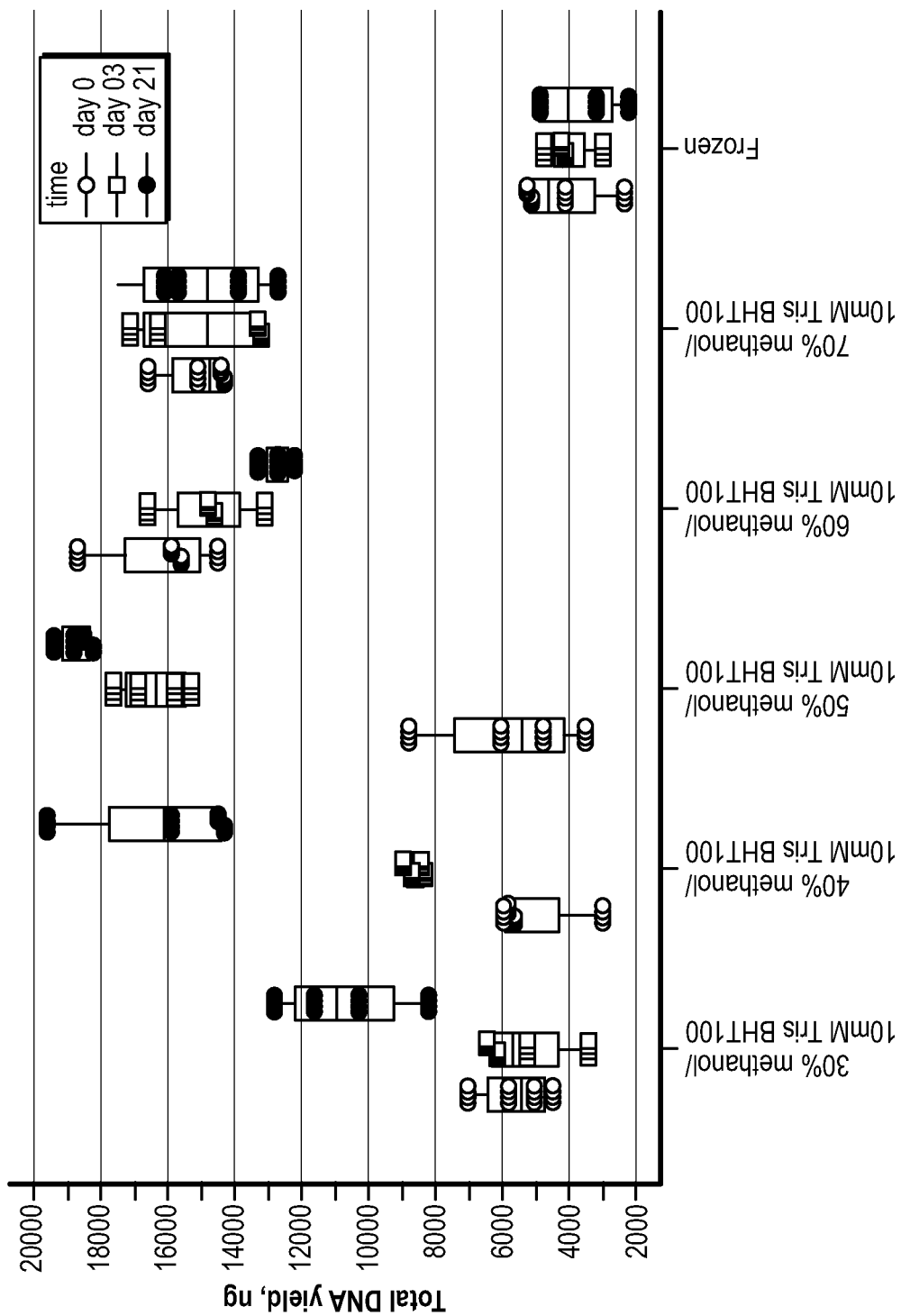
FIG. 37: DNA amount recovered from samples fixed in indicated preservatives from Experiment L.

FIG. 37 shows DNA amount recovered from samples fixed in indicated preservatives containing 10 mM Tris, 100 mg/L BHT and methanol at a range spanning 30%-70% (30%, 40%, 50%, 60%, 70%) in Experiment L. This figure is the summary of total DNA yield from samples processed in Experiment L. This experiment was done in 50 mL conical tubes, with cells fixed in larger 20 mL volume of buffer. In this experiment, cells were incubated in different buffers for 1 hr (day zero), 3 days, or 21 days in indicated buffers. All of the day 3 and day 21 samples, except for frozen no-preservative control had a medical grade silicone balloon added to the buffer during incubation. The day 0 timepoint, of samples incubated in the buffer at room temperature for approximately 1 hr is used for comparison. DNA amount in ng is displayed on the Y axis, while the X axis shows the buffers tested in this experiment. Open circles denote cells cell incubated for 1 hr (day zero). Open squares correspond to samples incubated for 3 days. Filled circles correspond to samples incubated for 21 days.

FIG. 37 shows that compared to DNA recovery from cell pellet frozen at −80° C., DNA yield was enhanced in cells incubated at a range of methanol concentrations, with the yield comparable at 21 days, in all methanol buffers. In 30% methanol, the increase was observed at day 21, but not after 3 days of incubation. In 40% and 50% methanol there is a time-dependent increase of DNA recovery, with the yield increased after 3 days, and further increased after 21 days. At methanol concentration of 60% or higher, the DNA recovery yield was increased after as little as 1 hr of incubation (conditions on Day 0), but then appeared to decrease slightly with longer incubation period.

Figure 38:
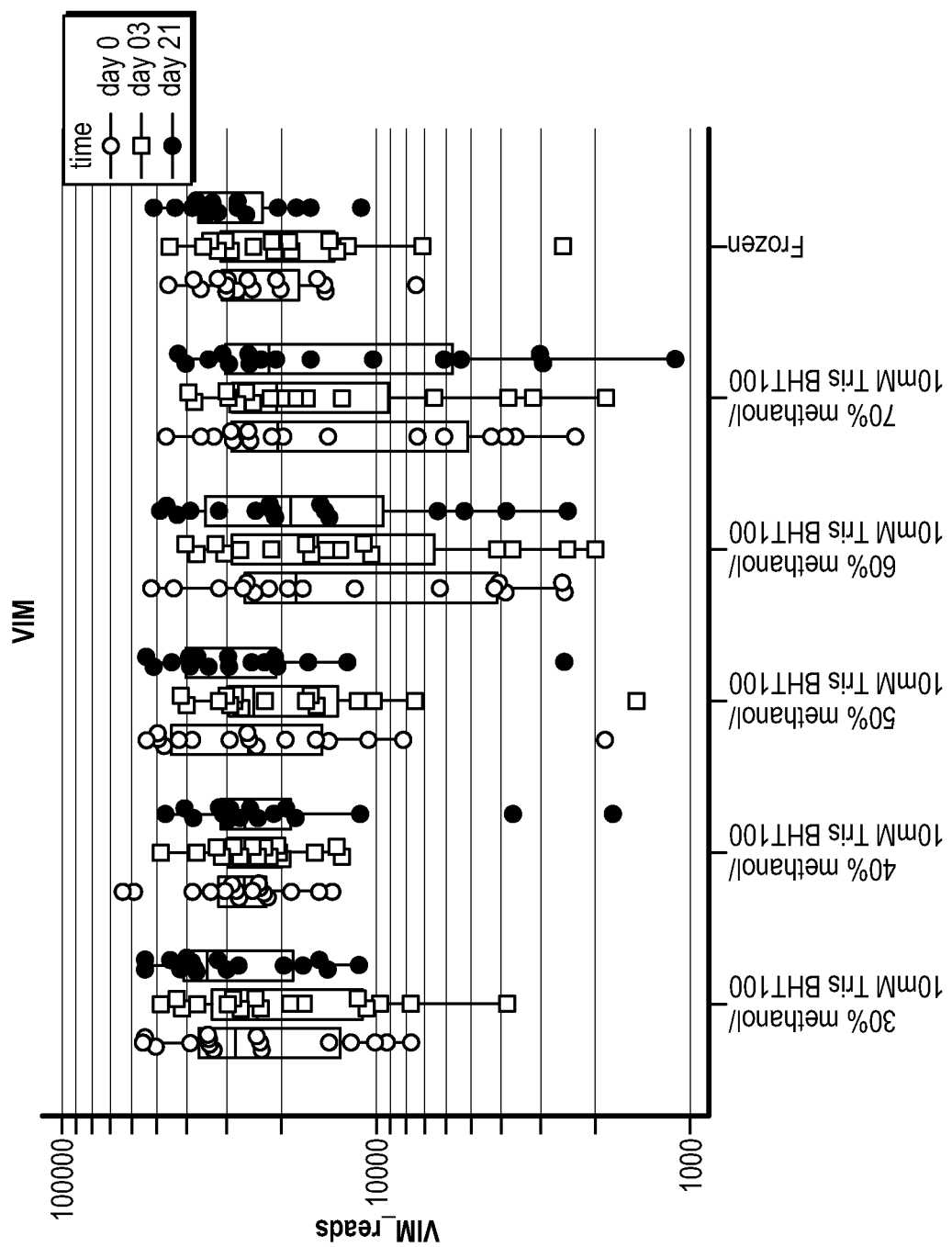
FIG. 38: Total aligned reads to VIM locus obtained after sequencing libraries in Experiment L. "VIM" corresponds to vimentin.
Figure 39:
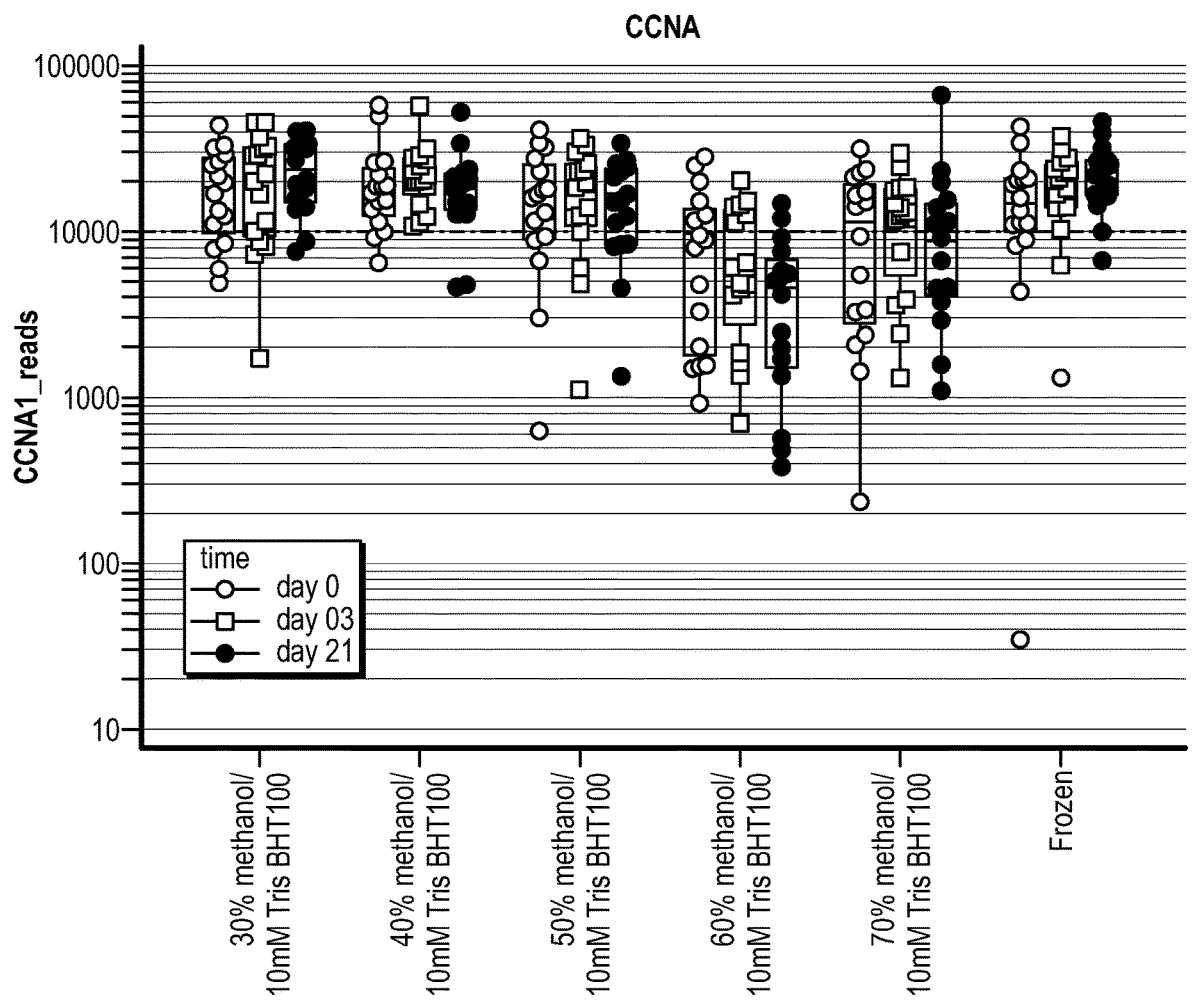
FIG. 39: Total aligned reads to CCNA1 locus obtained after sequencing libraries in Experiment L.

FIGS. 38 and 39 provide the total aligned reads obtained after sequencing the libraries in Experiment L. Number of reads aligned to VIM or CCNA1 locus, FIGS. 38 and 39 respectively, is displayed on the Y axis, while the X axis shows the buffers tested in this experiment. Open circles denote samples at day 0. Open squares denote samples incubated for 3 days. Filled circles denote samples incubated for 21 days. A reference line corresponding to 10000 reads (a minimum number required for sample to be considered diagnostic in a clinical assay) is drawn across the graphs for ease of visualization. In these figures, Frozen refers to cell pellet frozen at −80° C. without any buffer addition; 30% MeOH/10 mM Tris BHT100 is 30% Methanol/10 mM Tris+100 mg/L BHT; 40% MeOH/10 mM Tris BHT100 is 40% Methanol/10 mM Tris+100 mg/L BHT; 50% MeOH/10 mM Tris BHT100 is 50% methanol/10 mM Tris +100 mg/L BHT: 60% MeOH/10 mM Tris BHT100 is 60% Methanol/10 mM Tris+100 mg/L BHT; 70% MeOH/10 mM Tris BHT100 is 70% Methanol/10 mM Tris+100 mg/L BHT. This experiment was done in 50 mL conical tubes, with cells fixed in larger 20 mL volume of buffer.

FIGS. 38 and 39 shows no appreciable variation of analyzable reads for VIM or CCNA1 markers after 3 or 21 days in methanol buffer supplemented with Tris and BHT, when methanol concentration was kept in 30-50% range. At higher methanol concentration of 60 or 70% there is increased variability, and moderate decrease in the number of the analyzable reads.

Figure 40:
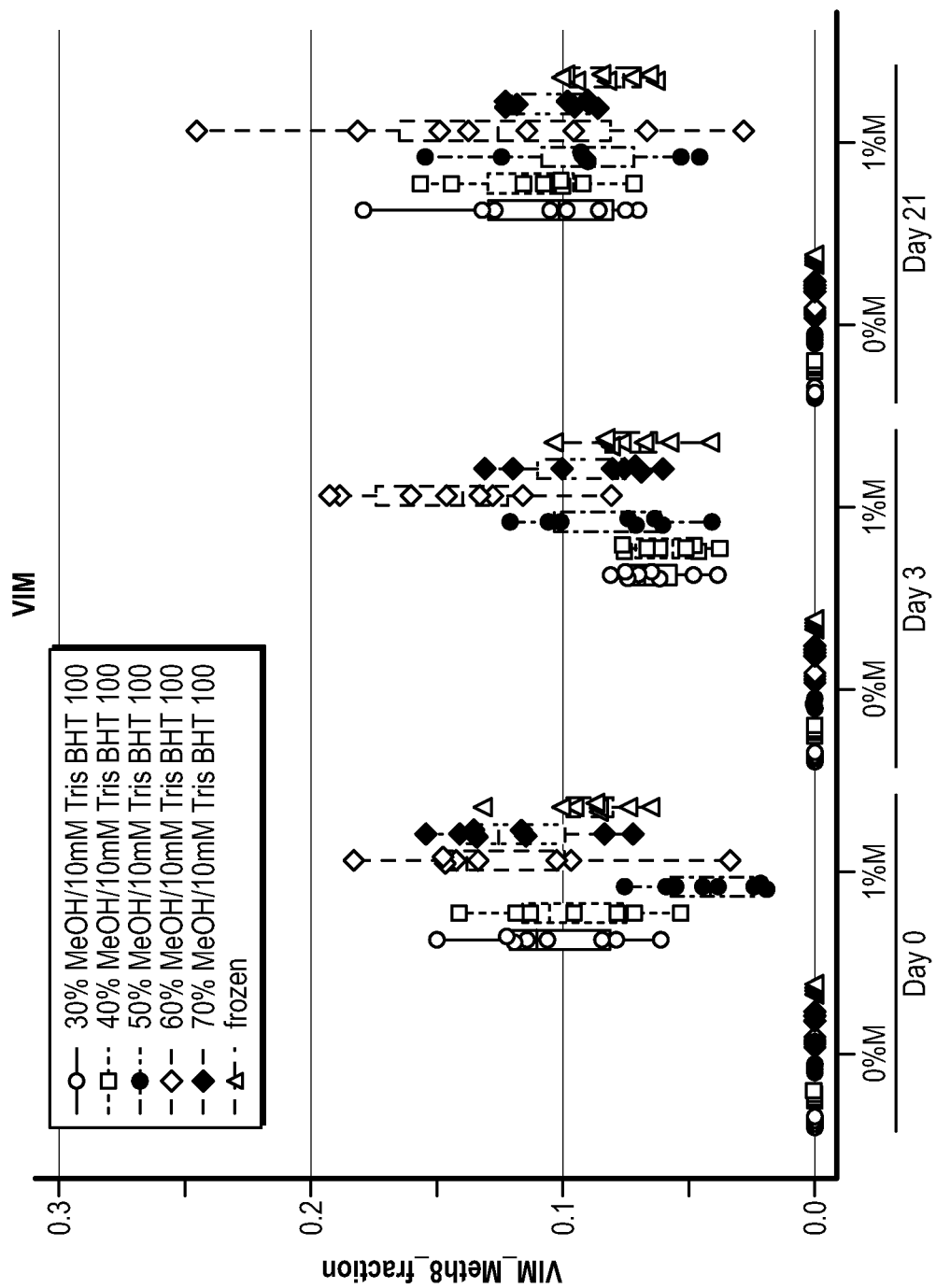
FIG. 40: VIM methylation level assay results in cells fixed in various buffers from Experiment L. "VIM" corresponds to vimentin.
Figure 41:
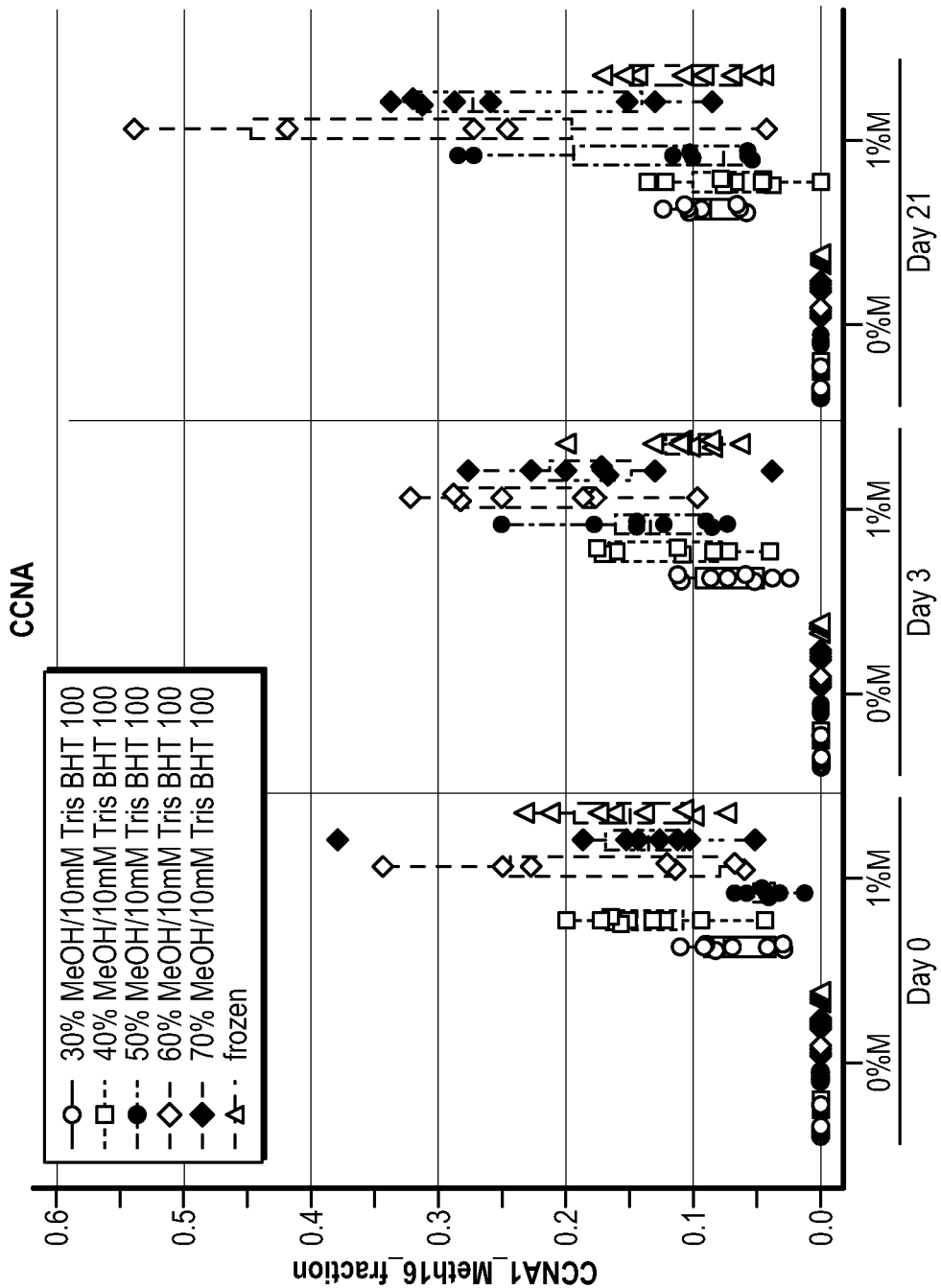
FIG. 41: CCNA1 methylation level assay results in cells fixed in various buffers from Experiment L.

FIGS. 40 and 41 provide methylation level assay results for VIM and CCNA, respectively, in Experiment L. Methylation signal (fraction) is plotted on the Y axis. Open circles denote samples fixed in 30% MeOH/10 mM Tris+100 mg/L BHT. Open squares denote samples fixed in 40% MeOH/10 mM Tris+100 mg/L BHT. Filled circles denote samples fixed in 50% MeOH/10 mM Tris+100 mg/L BHT. Open diamonds denote samples fixed in 60% MeOH/10 mM Tris+100 mg/L BHT. Filled diamonds denote samples fixed in 70% MeOH/10 mM Tris+100 mg/L BHT. Open triangles denote that were kept at −80° C. without addition of preservative buffer. This experiment was done in 50 mL tubes, with cells fixed in larger 20 mL volume of buffer. All of the day 3 and day 21 samples, except for frozen no-preservative control had a medical grade silicone balloon added to the buffer during incubation.

FIGS. 40 and 41 show that methylation signal remains stable in buffers methanol based buffers that are comprised of Tris and BHT across a range of methanol concentrations of from 30% to 70%, after 3 or 21 days of incubation.

In summary, experiment L, as compared to the above experiments, demonstrates that when cells are incubated in Tris buffered methanol, with the inclusion of BHT, the Tris buffered methanol is associated with improved DNA yield and with preservation of DNA methylation marks, and that these effects are observed in buffers spanning a methanol concentration of from 30%-70%.

SEQUENCE LISTING:

SEQ ID NO: 1-Exemplary Vimentin Nucleotide Sequence (corresponding to Hg19 coordinates: chr10:17,270,838-17,271,183)
tctgagggat tccttactct ttcctcttcc cgctcctttg cccgcgggtc tccccgcctg
accgcagccc cgaggccgcc gcgcacctcc tcccacgccc ctttggcgtg gtgccaccgg
acccctctgg ttcagtccca ggcggacccc cccctcaccg cgcgaccccg ccttttttcag
cacccccaggg tgagcccagc tcagactatc atccggaaag ccccccaaaag tcccagccca
gcgctgaagt aacgggacca tgcccagtcc cacgccccgg agcaggaagg ctcgaggcgc
ccccaccccca cccgcccacc ctccccgctt ctcgctaggt cccga SEQ ID NO: 2-Exemplary Vimentin Nucleotide Sequence (corresponding to Hg19 coordinates: chr10:17,271,348-17,271,717)
ccctcgttcg cctcttctcc gggagccagt ccgcgccacc gccgccgccc aggccatcgc
caccctccgc agccatgtcc accaggtccg tgtcctcgtc ctcctaccgc aggatgttcg
gcggccgggg caccgcgagc cggccgagct ccagccggag ctacgtgact acgtccaccc
gcacctacag cctgggcagc gcgctgcgcc ccagcaccag ccgcagcctc tacgcctcgt
ccccgggcgg cgtgtatgcc acgcgctcct ctgccgtgcg cctgcggagc agcgtgcccg
gggtgcggct cctgcaggac tcggtggact ctcgctggc cgacgccatc aacaccgagt
tcaagaacac SEQ ID NO: 3-Exemplary Vimentin Nucleotide Sequence
gcttcctgga gcagcagaat aagatcctgc tggccgagct cgagcagctc aagggccaag
gcaagtcgcg cctaggggac ctctacgagg aggagatgcg ggagctgcgc cggcaggtgg
accagctaac caacgacaaa gcccgcgtcg aggtggagcg cgacaacctg ccgaggaca
tcatgcgcct ccgggagaag taaggctgcg cccatgcaag tagctgggcc tcgggagggg
gctggagga gagggaacg ccccccggc cccgcgaga gctgccacgc ccttgggat
gtggccgggg ggaggcctgc cagggagaca gcggagagcg gggctgtggc tgtggtggcg
cagccccgcc cagaacccag accttgcagt tcgcatttcc tcctctgtcc ccacacattg
cccaaggacg ct SEQ ID NO: 4-Exemplary Vimentin Nucleotide Sequence (corresponding to Hg19 coordinates: chr10:17,270,838-17,271,347)
tctgagggat tccttactct ttcctcttcc cgctcctttg cccgcgggtc tccccgcctg
accgcagccc cgaggccgcc gcgcacctcc tcccacgccc ctttggcgtg gtgccaccgg
acccctctgg ttcagtccca ggcggacccc cccctcaccg cgcgaccccg ccttttttcag
cacccccaggg tgagcccagc tcagactatc atccggaaag ccccccaaaag tcccagccca
gcgctgaagt aacgggacca tgcccagtcc cacgccccgg agcaggaagg ctcgaggcgc
ccccaccccca cccgcccacc ctccccgctt ctcgctaggt cccgattggc tggggcgctc
cgcggctggg atgcagtgg gaggggaccc tctttcctaa cggggttata aaaacagcgc
cctcggcggg gtccagtcct ctgccactct cgctccgagg tccccgcgcc agagacgcag
ccgcgctccc accacccaca cccaccgcg SEQ ID NO: 5-Exemplary Vimentin Nucleotide Sequence (corresponding to Hg19 coordinates: chr10:17271442-17271547)
CTCGTCCTCCTACCGCAGGATGTTCGGCGGCCCGGGCACCGCGAGCCGGCCGA
GCTCCAGCCGGAGCTACGTGACTACGTCCACCCGCACCTACAGCCTGGGCAGC SEQ ID NO: 6-Exemplary CCNA1 Nucleotide Sequence (corresponding to Hg19 coordinates: chr13:37005856-37006031)
GCGACTGCACTTGGGGCAGCCCCGCCGCGTCCCAGCCGCCTCCCGGCAGGAA
GCGTAGGTGTGTGAGCCGACCCGGAGCGAGCCGCGCCCTCGGGCCAGCGTGG
GCAGGGCGCCGCAGCCTGCGCAGCCCCGAGGACCCCGCGTCGCTCTCCCGAG
CCAGGGTTCTCAGGAGCGGG SEQ ID NO: 7-Exemplary CCNA1 Nucleotide Sequence (corresponding to Hg19 coordinates: chr13:37005805-37006194)
CGGGGCAGGCGCGGCCCGCAAGGACCCCCGCGATGGAGACGCAACACTGCCG
CGACTGCACTTGGGGCAGCCCCGCCGCGTCCCAGCCGCCTCCCGGCAGGAAGC
GTAGGTGTGTGAGCCGACCCGGAGCGAGCCGCGCCCTCGGGCCAGCGTGGGC
AGGGCGCCGCAGCCTGCGCAGCCCCGAGGACCCCGCGTCGCTCTCCCGAGCC
AGGGTTCTCAGGAGCGGGCCGCGCAGGAGACGTTAGAGGGGGTTGTTAGCGG
CTGTTGGGAGAACGGGTCACGGAAACAGTCCCTTCCAAAGCCGGGGCCATCG
TGGGGTGGGCGAGTCCGCCCTCCCAGGCCGGGGCGCGGACCAGAGGGGACG
TGTGCAGACGGCCGCGGTCAGCCCC SEQ ID NO: 8-Exemplary Up10 nucleotide sequence
ccgtgactct ccctacctcc ccgactcccc aggcttctta cagtgacctc ttaccgtgcc
ccactccatg aatcgccaga gctattcgtc cctaaatttc aaaccttgcg caatgtccct
tcacagaccc ctccaggtat cacgcagccc cgagccccga gcccgcccc ggggggcctca
tcccgcccct tcgcgtccgc ggctcgtttt ccccactga gcgcccagct cccgcagttt
cccggccgt cgagcgccgt gggcggggct ccagggcggc ggcgcctcgc ggggagggtc
ctccgtgctg ggggcgaggc caccccgaggc agctcccggc ccgcccccaa ccccgccccg
ctctcggagc ctataaaggg aggcgacccg cggcccgccc ggctggcatc ccccagccgc
cgccagcccc gccgagggga gccagcgccg tctctgaggg gcgtccggcg ccggagccat
gaccctccgc cgactcagga agctgcagca aaggaggag gcggcggcca ccccggaccc
cgccgcccgg actcccgact cggaagtcgc gcccgccgct ccggtcccga ccccgggacc
ccctgccgca gccgc SEQ ID NO: 9-Exemplary Up10 nucleotide sequence
gcggctgcgg caggggggtcc cggggtcggg accggagcgg cgggcgcgac ttccgagtcg -continued

SEQUENCE LISTING:

ggagtccggg cggcggggtc cggggtggcc gccgcctcct ccttctgctg cagcttcctg
agtcggcgga gggtcatggc tccggcgccg acgccctc agagacgcg ctggctcccc
tcggcgggc tggcggcggc tggggatgc cagccggcg ggccgcgggt cgcctcccttt
tataggctcc gagagcgggg cggggttggg ggcgggcggg gagctgcctc gggtggcctc
gccccagca cggaggaccc tccccgcgag gcgccgccgc cctggagccc cgcccacggc
gctcgacggc cggggaaact gcgggagctg ggcgctcagt gggggaaaac gagccgcgga
cgcgaagggg cgggatgagg ccccgggc ggggctcggg gctcggggct gcgtgatacc
tggaggggtc tgtgaaggga cattgcgcaa ggtttgaaat ttagggacga atagctctgg
cgattcatgg agtggggcac ggtaagaggt cactgtaaga agcctgggga gtcggggagg
tagggagagt cacgg SEQ ID NO: 10-Exemplary Up10 nucleotide sequence
aaaccttgcg caatgtccct tcacagaccc ctccaggtat cacgcagccc cgagccccga
gccccgcccc gggggcctca tcccgcccct tcgcgtccgc ggctcgtttt ccccactga
gcgcccagct cccgcagttt ccccggccgt cgagcgccgt gggcggggct ccagggcggc
ggcgcctcgc ggggagggtc ctccgtgctg ggggcgaggc cacccgaggc agctccccgc
ccgcccccaa ccccgccccg ctctcggagc ctataaaggg aggcgacc SEQ ID NO: 11-Exemplary Up10 nucleotide sequence
ggtcgcctcc ctttataggc tccgagagcg gggcggggt gggggcgggc ggggagctgc
ctcgggtggc ctcgcccca gcacggagga ccctccccgc gaggcgccgc cgccctggag
ccccgcccac ggcgctcgac ggccgggaa actgcgggag ctgggcgctc agtggggggaa
aacgagccgc ggacgcgaag gggcgggatg aggcccccgg ggcggggctc ggggctcggg
gctgcgtgat acctggaggg gtctgtgaag ggacattgcg caaggtt SEQ ID NO: 12-Exemplary Up35-1/Up35-2 nucleotide sequence
tctggcccca tgctcagctc cgcggccatc gctgaagcga ggcgcagccg ccgctgccgc
ccgggaaact ttgcggccgg ccggagcgcg ccgagccaag cgcggggggg aagagcggag
aagagctggg gaggcgggga gcgagggcgc agcgggccgg ggccgccggc caagcctttg
tctggggacg cggcggcgcg ccggagagtc ccgaggctgc ctgcaccgcc ccagagctct
gggctgtgcc cgcgcaggga ccgggccggg tagagtcggg cggggtggag aggcaagcgg
agcgcgcggt ggggctgagg ggaggcgtgg ggcgagtgcc cgttgctcgc tctctagctc
tcttgctctt acgctctctc gctcgcagcc gctcgcagct cggcggtgca gctgtgctgg
atccggcggc gccgcagcct tttatcgcct cctgatgtca ctggggtgcg ggggcccggg
cggcccggtg cgcggggcca tagctgcacg gcctccgcgg cccagcggcg cagggcgggg
cgcgcctgac agctcccccg ccccccgcgt cagctgactg gcggcccgag cggccccgga
gcggcggagg cctggcggag cgctggagcg gagtgggacg gccagcctgg gcccacccc
gtaccctgca ggtcccggcc cacgcacgct cgcctggagt gcgcgcccca cctctaggcc
aaatcaccgc tttcccctcc tcgcgcactc tcctccctca gttcccttg caccccaccc
ccatcccgtg tcaccccaa ggaggctcag aatgagcgcc gggacaacgc ctcctgggcc
ctttgttccc aagcggcccc cgcccagtgg gcgacgctct gtgtgtcctc gcggcttctg
gccgtgtgtg tcgtgcgttc ctgtttctgt agatctgcgc gtatttgtat gttggggagg
gcgggctcga ggctccgaga gttgtgttca gacccaactc ttaacctcag gggacctttc
tcaggccaag cgagggcccc tcctggcggg tgcagtcgca gagccctgag gttcgactcc
actggccccg ccgctccccg cgttcaccc accgcacaat gttcacagtg aaggcgacgg
gaaaagcagc agcccaaagg ctctgaattc ctcttcccg ccacacgcac ggaatcctga
gccccggag cctcggggcc gaggccggcc cgggacggtg ctccgagtag ctctccactg
ctggggagcc ggccctgttt ttgtttgaac gttttgtaac gattaagcag atcccggcgt
cagcccgccg cggagaggct caaacaggca taaagtgcga ccccaagtgg ccactgtgcg
caaaggcgcc gcgaccgccc ggcccacggc cggaaggctt ggacggcgcc tcgtacccag
ccaggtctcc cctacctggc ccaacccaag ccagcccaga acgcatacta tgtgtgcacc
agagcccagg acaggttccc ctcgagcgat gtacaggtc SEQ ID NO: 13-Exemplary Up35-1/Up35-2 nucleotide sequence
gacctgtaca tcgctcgagg ggaacctgtc ctgggctctg gtgcacacat agtatgcgtt
ctgggctggc ttgggttggg ccaggtaggg gagacctggc tggtacgag gcgccgtcca
agccttccgg ccgtgggccg ggcggtcgcg gcgcctttgc gcacagtggc cacttggggt
cgcactttat gcctgtttga gcctctccgc ggcgggctga cgccgggatc tgcttaatcg
ttacaaaacg ttcaaacaaa aacagggccg gctccccagc agtggagagc tactcggagc
accgtcccgg gccggcctcg gccccgaggc tccgggggct caggattccg tgcgtgtggc
ggggaagagg aattcagagc ctttgggctg ctgcttttcc cgtcgccttc actgtgaaca
ttgtcggtg gggtgaacgc gggagcggc ggggccagtg gagtcgaacc tcagggctct
gcgactgcac ccgccaggag gggccctcgc ttggcctgag aaaggtcccc tgaggttaag
agttgggtct gaacacaact ctcggagcct cgagcccgcc ctccccaaca tacaaatacg
cgcagatctc cagaaacagg aacgcacgac acacacggcc agaagccgcg aggacacaca
gagcgtcgcc cactgggcgg gggccgcttg gaacaaagg gcccaggagg cgttgtcccg
gcgctcattc tgagcctcct tgggggtgac acgggatggg ggtgggtgc aaagggaact
gagggaggag agtgcgcgag gaggggaaag cggtgatttg gcctagaggt ggggcgcgca
ctccaggcga gcgtgcgtgg gccgggacct gcagggtacg ggggtgggcc caggctggcc
gtcccactcc gctccagcgc tccgccaggc ctccgccgct ccggggccgc tcgggccgcc
agtcagctga cgcgggggc gggagctg tcaggcgcgc cccgccctgc gccgctgggc
gcggaggcc gtgcagctat tggccccgcg accgggccgc ccgggcccc gcaccccagt
gacatcagga ggcgataaaa ggctgcggcc ccgccggatc cagcacagct gcaccgccga
gctgcgagcg gctgcgagcg agagagcgta agagcaagag agctagagag cgagcaacgg
gcactcgccc cacgcctccc ctcagcccca ccgcgcgctc cgcttgcctc tccaccccgc
ccgactctac ccggccggt ccctgcgcgg gcacagccca gagctctggg gcggtgcagg
cagcctcggg actctccggc gcgccgccgc gtccccagac aaaggcttgg ccggcggccc

```
cggcccgctg cgccctcgct ccccgcctcc ccagctcttc tccgctcttc ccccccgcgc
ttggctcggc gcgctccggc cggccgcaaa gtttcccggg cggcagcggc ggctgcgcct
cgcttcagcg atggccgcgg agctgagcat ggggccaga SEQ ID NO: 14-Exemplary Up35-1 nucleotide sequence
cctgcaccgc cccagagctc tgggctgtgc ccgcgcaggg accgggccgg gtagagtcgg
gcggggtgga gaggcaagcg gagcgcgcgg tggggctgag gggaggcgtg gggcgagtgc
ccgttgctcg ctctctagct ctcttgctct tacgctctct cgctcgcagc cgctcgcagc
tcggcggtgc agctgtgctg gatccggcgg cgccgcagcc ttttatcgcc tcctgatgtc
actggggtgc gggg SEQ ID NO: 15-Exemplary Up35-1 nucleotide sequence
ccccgcaccc cagtgacatc aggaggcgat aaaaggctgc ggcgccgccg gatccagcac
agctgcaccg ccgagctgcg agcggctgcg agcgagagag cgtaagagca agagagctag
agagcgagca acgggcactc gccccacgcc tcccctcagc cccaccgcgc gctccgcttg
cctctccacc ccgcccgact ctacccggcc cggtccctgc gcgggcacag cccagagctc
tggggcggtg cagg SEQ ID NO: 16-Exemplary Up 35-2 nucleotide sequence
gggaaaagca gcagcccaaa ggctctgaat tcctcttccc cgccacacgc acggaatcct
gagccccgg agcctcgggg ccgaggccgg cccgggacgg tgctccgagt agctctccac
tgctggggag ccggccctgt ttttgtttga acgttttgta acgattaagc agatcccggc
gtcagcccgc cgcggagagg ctcaaacagg cataaagtgc SEQ ID NO: 17-Exemplary Up 35-2 nucleotide sequence
gcactttatg cctgtttgag cctctccgcg gcgggctgac gccgggatct gcttaatcgt
tacaaaacgt tcaaacaaaa acagggccgg ctccccagca gtggagagct actcggagca
ccgtcccggg ccggcctcgg ccccgaggct cggggggctc aggattccgt gcgtgtggcg
gggaagagga attcagagcc tttgggctgc tgcttttccc SEQ ID NO: 18-Exemplary vimentin nucleotide sequence (corresponding to hg19_dna
range = chr10:17270838-17271717)
TCTGAGGGATTCCTTACTCTTTCCTCTTCCCGCTCCTTTGCCCGCGGGTCTCCCC
GCCTGACCGCAGCCCCGAGACCGCCGCGCACCTCCTCCCACGCCCCTTTGGCG
TGGTGCCACCGGACCCCTCTGGTTCAGTCCCAGGCGGACCCCCCCCTCACCGC
GCGACCCCGCCTTTTTCAGCACCCCAGGGTGAGCCCAGCTCAGACTATCATCC
GGAAAGCCCCCAAAAGTCCCAGCCCAGCGCTGAAGTAACGGGACCATGCCCA
GTCCCAGGCCCCGGAGCAGGAAGGCTCGAGGGCGCCCCCACCCCACCCGCCC
ACCCTCCCCGCTTCTCGCTAGGTCCCTATTGGCTGGCGCGCTCCGCGGCTGGG
ATGGCAGTGGGAGGGGACCCTCTTTCCTAACGGGGTTATAAAAACAGCGCCCT
CGGCGGGGTCCAGTCCTCTGCCACTCTCGCTCCGAGGTCCCCGCCGCCAGAGAC
GCAGCCGCGCTCCCACCACCCACACCCACCGCGCCCTCGTTCGCCTCTTCTCCG
GGAGCCAGTCCGCGCCACCGCCGCCGCCCAGGCCATCGCCACCCTCCGCAGCC
ATGTCCACCAGGTCCGTGTCCTCGTCCTCCTACCGCAGGATGTTCGGCGGCCC
GGGCACCGCGAGCCGGCCGAGCTCCAGCCGGAGCTACGTGACTACGTCCACC
CGCACCTACAGCCTGGGCAGCGCGCTGCGCCCCAGCACCAGCCGCAGCCTCTA
CGCCTCGTCCCCGGGCGGCGTGTATGCCACGCGCTCCTCTGCCGTGCGCCTGC
GGAGCAGCGTGCCCGGGGTGCGGCTCCTGCAGGACTCGGTGGACTTCTCGCTG
GCCGACGCCATCAACACCGAGTTCAAGAACAC SEQ ID NO: 19-Exemplary ADCY1 nucleotide sequence (corresponding to hg19_dna
range = chr7:45613877-45614572)
CGGGGCTCGGCTGTCGCAGCGCGGTCGCCGCCGAGGACCACGGTCGGGGCGC
GGGCGGGCTCCAGTGCGCAGGCGCGGCGGGCGGGAGGGGACGCGCTCCGGGC
GCGCGCGCGGGGCAGCCGGCGCCCCAACTCCGCCCGCCCCGCGCCCCGCGCC
CCGGCGCCTCGCCGCCCGCCGCCCGCCCGCCCGGCGCCGCCGCCCGCGCCCC
GGCGCCCCGGGCCGGCGAGGGGCGCGCCCGCGGCCGCGGCCGCTGCATGGCG
CTGAGATGGCGGGGGCGCCGCGCGGCGGAGGCGGCGGCGGAGGCGGCGCGG
GCGAGCCCGGGGCGCCGAGCGGGCGGCCGGGACAAGCCGCCGGCGCGGGCT
CCGGGCGTGCGACGAGGAGTTCGCTTGCCCAGAGCTGGAGGCGCTGTTCCGCG
GCTACACGCTGCGGCTGGAGCAGGCGGCCACGCTGAAGGCGCTGGCCGTTCTC
AGCCTGCTGGCGGCGCGCTGGCGCTGGCCGAGCTGCTGGGCGCGCCGGGGC
CCGCGCCCGGCCTGGCCAAGGGCTCACACCCGGTGCACTGCGTCCTCTTCCTG
GCGCTGCTCGTGGTAACCAACGTCCGGTCCCTGCAGGTGCCCCAGCTGCAGCA
GGTCGGCCAGCTGGCGCTGCTCTTCAGCCTCACCTTCGCGCTGCTCTGCTGTCC
TTTCGCGCTGGGCG SEQ ID NO: 20-Exemplary BMP3 nucleotide sequence (corresponding to hg19_dna
range = chr4:81952348-81952402)
GTTCAACCCTCGGCTCCGCCGCCGGCTCCTTGCGCCTTCGGAGTGTCCCGCAG
CG SEQ ID NO: 21-Exemplary BMP3 nucleotide sequence (corresponding to hg19_dna
range = chr4:81031173-81031262)
CTAAATAAATACACTTTCCTTTGTGTTCCCATATACTCCTTGTTCCCATGTCAA
CTATAACACATACGCTACCATTTTATAATTACTTAA
```

SEQUENCE LISTING:

SEQ ID NO: 22-Exemplary CD1D nucleotide sequence (corresponding to hg19_dna range = chr1:158150797-158151205)
CGGAAAGGGACGTGAGCTGAGCGGCGGGGGAGAAGAGTGCGCAGGTCAGAG
GGCGGCGCGCAGCGGCGCTCCGCGAGGTCCCCACGCCGGGCGATATGGGGTG
CCTGCTGTTTCTGCTGCTCTGGGCGCTCCTCCAGGCTTGGGGAAGCGCTGAAG
GTGGGTGGAACGAGGGCGCTTGAGTGCACTCGCGGGAGGGCGGAGAGAGGG
AGCTGGGTAGGGACGGGGAGGGCAACGCCTGATGGGGACTGGTGAGACCCGG
GACGCACTGGCGCGATCTAGGTAGAAAACTCGCTGCTCCCTGGCTCCGGGGAG
AGGCAGCGCGGCACAGAGTTCGCTGGCATCAGCCGCCTCCTGAAGCTCATCTC
CTCTTGTTTCTTTCTTCCTTCTCTTTATGCTGGCTGCTCTCCCG SEQ ID NO: 23-Exemplary CDKN2A nucleotide sequence (corresponding to hg19_dna range = chr9:21974710-21974763)
GTTGGGCAGCGCCCCCGCCTCCAGCAGCGCCCGCACCTCCTCTACCCGACCCC
G SEQ ID NO: 24- Exemplary CDKN2A nucleotide sequence (corresponding hg19_dna range = chr9:21975053-21975199)
GAGCACTTAGCGAATGTGGCACCCCTGAAGTCGCCCCAGGTTGGGTCTCCCCC
GGGGGCACCAGCCGGAAGCAGCCCTCGCCAGAGCCAGCGTTGGCAAGGAAGG
AGGACTGGGCTCCTCCCCACCTGCCCCCCACACCGCCCTCCG SEQ ID NO: 25-Exemplary DIO3 nucleotide sequence (corresponding to hg19_dna range = chr14:102026104-102026145)
GCCCGCGCTCTACCGAGCCCAGCCAGCTCCTACCTCGGCCCG SEQ ID NO: 26-Exemplary DOCK10 nucleotide sequence (corresponding to hg19_dna range = chr2:225907226-225907322 5'pad = 0 3'pad = 0 strand = + repeatMasking = none
GCAAGAGGCGGGTTTTTCTCTCTTGCACCCCCACTCTTCCCACCCCCTTCCCTC
CTCTGAAGCTTCTCGAAGACTTTCCAAACTCTGCGCTCCCCCG SEQ ID NO: 27-Exemplary ELMO1 nucleotide sequence (corresponding to hg19_dna range = chr7:37487755-37488477)
CGGGGGATTCCCTCCCATCCCCGAGTGCAGGAGAAGACGCCGAGTCTGAGCC
GCAGCCGCTTCTCTAGCTCTATAGGAATCTTGACTCCAAGATCCCAGCCCCAC
ATCCCCCGTCCCCAGTAACCCCGCGCCAGCGTCGCAACCCTCCCGCGCCCCCC
CTCCCGCAGACCCTGGTCGAAATGTCTCGGCGGGCTCCCGGGCCCGGGCCCT
GCGCTTCATCCGCGGGCGCCGCACCTCCAGCGCCCCCTCCCTCCGCTCCCACTC
CCACTCCCGCCATCCCCGGAGCTCAGACTTCCCCAACTGCAGAGCGCCCCGAC
GCGCCCGCAGCCCTCACCCTGCCGAGCGCGGCGGCCACCCCGCCCGAGCCGC
GGCGCCCCCAGGGAGGAAACAAAAGTGTCTCCGCGGCGCCCGGAGTCCCCCG
GAGCAGGACGCCTCCTCCCGGCCCCAGTCCCGGCCCCCTCCCCTGCCGCGCCG
AGGTCAGCGAGTCGGGGCGCGGCGCCAGCCCAGGAAACTTTACGAACCTGCT
TGGGGTCGCAGGACAGCAGCGGCAAGGGTTCCCGGCGATCAGAGCTCCGGCG
ACCCGCCACCATTGAAGGGGAACTGGAGGCTCTGTCGCCCAGCGTGGGGCCG
CGGCGGCGTGGGTGGCTCTGCCTCTATCCTGTGCCCATCCTCGCCCGCTCCCGC
TCGCCCCAGCACACGCACTTACACTCTGGGTCGGCCG SEQ ID NO: 28-Exemplary ELOVL2 nucleotide sequence (corresponding to hg19_dna range = chr6:11044395-11044834)
CGGTGCGTGGGTCCAGGAGAGAAAGAAAGCGCGGCGGTGTCGGTGGCGGCGC
GCGGCCCCACTCACCATGATCCGCAGCGGCTGTGGCGCGGCGACCCGGGCGG
GCGGCGATGCGCTGTCCAGGGTAGCCGGGTCCCTCTGCCCGGCGCTATCTCGG
CGCCCGCGCCGGTTACCCCCACCCACACCCACGCCCGGCGCGCGCACACCCGC
CCGCGCCTCCCCGCCCCCTCGGGCTCGCGCCGCCGCCGCGCGGCGCTCCGAGC
CTCGGGGCCGTTTCGTCCCCGCCCCCTCTCCCACAGGGGCCTCGCCGGCCGCC
GCGCCAGGAGGGCGCGCGGGGGAGGGGCGCAGGGCAAGTGAGGCGGCGCCC
CCCGCCCCTGCGGCCTCGCGCGCCCCTCCTGGGCGACCGACCTCGCCCTCGC
GTCCGCGGCGTCCCCTGCCG SEQ ID NO: 29-Exemplary FER1L4 nucleotide sequence (corresponding to hg19_dna range = chr20:34189488-34189693)
CGGCACGTGCGTAGCGAGTGCCGCGTCGACCAGGGGCGCGTCGTCCCGCAGC
TGCAGGCGGAGGCTGCGCGTCAGCGGCGGGAAGAGCTCCACGAAGCTCAGCT
GCTCGTTCCATTCGGGCGCCGCCGCCTCGGCGCTCACCGACGTCTCGCCCTGA
AGGTGGCGTTAAAGACAGGAGAAGGGAGATCAGCGCGGAGTCGGGGCCG SEQ ID NO: 30-Exemplary HUNK nucleotide sequence (corresponding to hg19_dna range = chr21:33246580-33246650)
CGGCAGGGGGGGATCCGTGGCGAGGCGGGAACCAGGGCTAGAGGAGGT
GGGCTCTTATGTCGGGGGGC SEQ ID NO: 31-Exemplary LRRC4 nucleotide sequence (corresponding to hg19_dna range = chr7:127671993-127672310)
CGGAGCCCAGGAACATAGTCCCCGCTGGCTAGCGGCGGCAGCAGCAGCAGCG
GGGCCCCTGCGCGCGGCGCCCACCGTCTCCTCCTCGCGCCGGGCTCGCGGTGT
TGCAGGCGGCAGCCACGCAGACTGCTCTCTCATCCTTTTGTCCTTCAGTCAGA

```
ACGTGAATGTACTGCTGACGCATACTGTTCTGGGAGAAGATTAGCGTGATGCA
GTGCTCTTATGTATTAGCGCCGCTCCCCCTCCGTCGCCTGCCTCGCGGGGTTAA
CGCCGGCGCCTTCCAGCGCCGCGCCGGCCGGCGCCGCGCAGCCCCGCGCCTCC
```

SEQ ID NO: 32-Exemplary NDRG4 nucleotide sequence (corresponding to hg19_dna
range = chr16:58497395-58497451)
```
CGGTCCCCGCTCGCCCTCCCGCCCGCCCACCGGGCACCCCAGCCGCGCAGAAG
GCGG
```

SEQ ID NO: 33-Exemplary SFMBT2 nucleotide sequence (corresponding to hg19_dna
range = chr10:7452885-7452956)
```
CGGCCTCGCTCGCTTGCTCGCTCGCCCGCCCTTGCCCGCTCGCTCCCCGCCCGC
CGCCTCCCTCGCGCGCCC
```

SEQ ID NO: 34-Exemplary SFMBT2 nucleotide sequence (corresponding to hg19_dna
range = chr10:7451771-7451869)
```
GCCATATTGAAACTGGCACGGTTTCTAAAGACTCCTTCCCCGCAGTTGTGGCG
CTTCCAAGAAAACACGAGTACGGATCAGGCTCTGGATGAGTGTCCG
```

SEQ ID NO: 35-Exemplary SFMBT2 nucleotide sequence (corresponding to hg19_dna
range = chr10:7452029-7452452)
```
GCACGCATATTAAAAAATAAACTCCAGAACCAGCTCAAGTCAGCAATTTTGAA
AGGGGGTCGAATAAGAGGAGACAACCGGAAAGCCCCTAAGTGACAGGATATT
ACTTTAAAGAGAAAATAATGAACAAAAAGACCATCCTCGCTGGAGCACGCTC
CAAAACTACTACTGCCAATTTTATTTCAGTTGCTCAGGCAAATGTTTCCAAGG
GAGCGATTCCGAATGTCTGCACGATTTTTACCCCCATGCCGGTCTCCGATTCC
CGTCCTCACCATCTTTTTCTCCCACCCAAACCAAAAGAAAGGGGAGACCCCAG
CGCGGAGGAGACGCGGGAGCGCGGGGTAGGTAGCAGCGGCGGCTGCGTCGCT
AAAATGAGTGCAGAAACGAGGAAGGTGGGCGGCGGGAGGGGACAGGCTGCG
CCCG
```

SEQ ID NO: 36-Exemplary SFMBT2 nucleotide sequence (corresponding to hg19_dna
range = chr10:7450242-7450831)
```
CGGCGTGTCGCCATCGTTCAGCCTCGCTGCCCAGGTGGGAGGGGTCACCTGCC
GCGGGGTCTCCAAGCCAGTGCCGCTTGCTCCCGGCCCCACCCACTGACAGCA
CGGCGTCCGAGTGACCCTGTCTAGCCTCGTTCTGCGCTCCTGCAAACCACGTT
GCTGCGCTAACTACAAACCTGGCCAACATGTCTTTGTAACCCTATCATTTAAA
AACGCTTCCAGGCACCTGGCCGCTGCCAGATCAGGTTCGCGGGCCCGGAGGA
GGTCCTCCCACCTGCCCCCGCCAGCCCCGGGGACCGTGCGCGGCCTCCGTGTG
GCCCCCGCCCACGAGGTCCCTCGGGCAGGAACCGCCGCGCGACCCTCTGTTCAG
CGGCCGCGTCCTGGCCACGGGCGACCCCTGTCGGGAACCCTGTTCCCGGCTAA
GCTGCGTTCCCGCATTCCGGTGGCTCTCACCCGAGCTCGCGTTTGCTGGCTTTC
CCTCTGGCTCCTCTGCCTGACCCCGATTTTGTCTCCGAACTCCACTCCCAGATC
CTCCCCGCCCTGGAACGCCGACCTTTCCCCCGCACTTCGCCGCCCACTCACATC
CCCCG
```

SEQ ID NO: 37-Exemplary ST8SIA1 nucleotide sequence (corresponding to hg19_dna
range = chr12:22487528-22487620)
```
CGGGAGAAGGCTCGGCTCCCTCCTAAACATGTGGCCCGTGGCGTCCCCTTGTC
CCCTCCGAGCGATGCTCCTGCGCCCTTCGCCGCCTCCCGC
```

SEQ ID NO: 38-Exemplary TSPYL5 nucleotide sequence (corresponding to hg19_dna
range = chr8:98289858-98290220)
```
CGGAGGAGCTGCGCGGACGCAGCGGCTTCCAGGCCACCCCACCCCGCGCCAG
CCTGCACCTGTGCCGCCTGGGTGTCTTCCCCGAGACTCTGGTACTGTGAAGGG
TCCGGGTCGCGCGGGGCGTCGTCCGGAGCAGGGCGGACTCGGGCTTTGGCGC
GGCCTTTGCCCCGGTTTTTGGCGCGGGAGGACTTTCGACCCCGACTTCGGCCG
CTCATGGTGGCGGCGGAGGCAGCTTCAAAGACACGCTGTGACCCTGCGGCTCC
TGACGCCAGCTCTCGGTCGGGACCGAGCGGGTCTCTCCACGGCAACCGCCGAC
GTCACGAACGTACAACTGTACCGTCGCGAGAGGACGTGATGCGCCCG
```

SEQ ID NO: 39-Exemplary VAV3 nucleotide sequence (corresponding to hg19_dna
range = chr1:108507608-108507679)
```
CGCGCGGGATCGAGGGAGCAGGAGCCGCGGCTGACGGGTCGCGGGCGCCGCG
CTAGGCTCGGCTCCGGTCCC
```

SEQ ID NO: 40-Exemplary ZNF568 nucleotide sequence (corresponding to hg19_dna
range = chr19:37407197-37407284)
```
CGGAAGTTGAGTGGGGCCGCGGGGCCTGCTGGGAGGTGTTGTCCTCGGAAAC
GTCGCTGGCGCGGAGGGATGGTTCGGCGCTTTAGGC
```

SEQ ID NO: 41- Exemplary ZNF568 nucleotide sequence (corresponding to hg19_dna
range = chr19:37407197-37407365)
```
CGGAAGTTGAGTGGGGCCGCGGGGCCTGCTGGGAGGTGTTGTCCTCGGAAAC
GTCGCTGGCGCGGAGGGATGGTTCGGCGCTTTAGGCGTCGTCGTCACAGACCTAT
CTGCGGGTCGCCTTCACCCAGCATCTCAGAAACTGCGCGCGGGATGAACATTC
GGGTGTTTCCG
```

SEQUENCE LISTING:

SEQ ID NO: 42-Exemplary SNF569 nucleotide sequence (corresponding to hg19_dna range = chr19:37957760-37958046)
CGGGGCCACACTCAGCCAGACGAATGTCTGGCAAATGACAGTCACTTCACGCC
AGACTCTCACAGTCCTTCACACGCCACTCCCACTGCCTCAGGGAACCACAAGC
ACAGGCATCGCCCCGCCCGGCGTCCTCCTCCAAAGATTGGGGCACCAGGACCG
CGGGCCCCCACTCCCACCCAGCACAAAGAGTCCGGCGCTCAGAGCTAGCGGTT
TCCCGAGGACTCACCACCAAGCCCGCGGACACAGGCCCCGATTCCACACTTAA
CGCTGCCAAAGTGGCAGAGCCG SEQ ID NO: 43-Exemplary ZNF610 nucleotide sequence (corresponding to hg19_dna range = chr19:52839503-52840013)
CGGAAGCGGATCGCGTGGGTAGAAGGTCACACCGCAGCGCGTCAGTTTCCCTT
TGTTTAGATTCAATCTGGGCTTCCCAGCTCCCCCGCGCTTCTGTACCCGGGATC
TGAGAGTCAACACAGACCTTGAAATCCCCGCACCGCTCCCTCCACCCCGTGTA
AATTCAGGCGTCTCCGTGAGAGTCCGGCGCTCGCTTCCCTGTGTGTTAAAATC
GCTCGGCGACGGGTCCTGTCCCCGCTCGTTCTGCCTTGGGCCAGGTAAACACG
GATTTTCGAGACTCCTTTCCGCTTAAAACTCTTTACTGACCCAACGTCCTGCCC
CGCGCTTTTAAAAGTCCTTACCGCAAGGTGGATTCCCGCCCGGGGAGCCTCCC
AACCCTCGCCCCCGGCCCCTGAAGCGCAGCGCCGCAGCCCCAGTCCCGGCGGG
GGAGGCCGCGTCCTGTACTGGGTCCTGGGACCCTTGAGACCCCACACTTCTAA
TAATTCAGCCCCACCCTTTTCCTCCTTGATCCG SEQ ID NO: 44-Exemplary ZNF671 nucleotide sequence (corresponding to hg19_dna range = chr19:58238810-58238955)
CGGGAGCGGCAGGCGTCTCGATCGGGGACGCAGGCACTTCCGTCCCTGCAGA
GCATCAGACGCGTCTCGGGACACTGGGGACAACATCTCCTCCGCGCTTTCCA
ACACCTCCACCTGCGGCCCACACAAGCGTTACAGAACCCCG ZNF682
SEQ ID NO: 45-Exemplary ZNF682 nucleotide sequence (corresponding to hg19_dna range = chr19:20149796-20149923)
CGGGATCACAGCACTTCCCACGCACAAACCACACACGGGGTCTGGACTCTGCC
CTGAGGACGCTTCCATTGTCCCCGCAGTCGGGGCAGACGCAAGAACGCGCGC
GGCTCTTCCCAGGGTGGGCTCCG

We claim:

1. A method of preserving the methylation pattern of methylated DNA molecule in a biological sample, comprising treating the biological sample with a storage solution, wherein the storage solution comprises methanol and tris, and wherein the methylation pattern is preserved at room temperature.

2. The method of claim 1, wherein the storage solution further comprises BHT.

3. The method of claim 2, wherein the BHT is present in an amount from 1 to 500 ppm, 20 to 200 ppm or 25 to 100 ppm.

4. A method of preserving the methylation pattern of methylated DNA molecule in a biological sample, comprising treating the biological sample with a storage solution, wherein the storage solution comprises methanol and BHT, and wherein the methylation pattern is preserved at room temperature.

5. The method of claim 4, wherein the BHT is present in an amount from 1 to 500 ppm, 20 to 200 ppm or 25 to 100 ppm.

6. The method of claim 1, wherein the storage solution does not comprise EDTA.

7. The method of claim 1, wherein the methylation pattern is preserved for at least 2 weeks or for at least 3 weeks.

8. The method of claim 1, wherein the methylation pattern of the biological sample in the storage solution is preserved by at least 65% in comparison to the methylation pattern in the biological sample prior to storage.

9. The method of claim 1, wherein the biological sample is stored in the storage solution.

10. The method of claim 1, wherein the biological sample is a sample from any of: gastrointestinal tract, aerodigestive tract, respiratory tract, genitourinary tract, or a body fluid, or wherein the biological sample is a sample from any of: esophagus, stomach, colon, small intestine, pancreas, liver, oral cavity, oropharynx, trachea, bronchial tree, lung, or breast.

11. The method of claim 10, wherein the body fluid is any of: blood, urine, sputum, saliva, stool, bile, pancreatic juice, nasal secretions, tears, semen, vaginal secretions, cerebrospinal fluid, pleural fluid, peritoneal fluid, gastric juice, pericardial fluid, sweat, lymph, cyst fluid, pancreatic cyst fluid, synovial fluid, joint fluid, menstrual fluid, endometrial washing, breast aspirate, or amniotic fluid.

12. The method of claim 1, wherein the methanol comprises 100% methanol or from 10% to 100%, 10% to 90%, 20% to 90%, 30% to 90%, 30% to 80%, 30% to 70%, 40% to 60% methanol admixed with water.

13. The method of claim 1, wherein the methanol is peroxide free or at a level less than or equal to 0.001%.

14. The method of claim 12, wherein the water is free of DNAse and/or RNAse activity.

15. The method of claim 1, wherein the pattern of DNA methylation is assayed within a differentially methylated domain of the vimentin gene or a differentially methylated domain of the CCNA1 gene.

16. The method of claim 15, wherein the differentially methylated domain of vimentin comprises a nucleotide sequence that is at least 60%, 65%, 70%, 75%, 80%, 85%, 90%, 91%, 92%, 93%, 94%, 95%, 96%, 97%, 98%, 99%, or 100% identical to any one of SEQ ID NOs: 1-5, or SEQ ID NO: 18 or complements and/or fragments thereof; or the differentially methylated domain of CCNA1 comprises a nucleotide sequence that is at least 60%, 65%, 70%, 75%, 80%, 85%, 90%, 91%, 92%, 93%, 94%, 95%, 96%, 97%, 98%, 99%, or 100% identical to SEQ ID NO: 6 or 7, a complement thereof, or a fragment thereof.

17. The method of claim 1, wherein the pattern of DNA methylation is assayed by a step that includes treatment of the DNA with a bisulfite compound that converts cytosine bases to uracil.

18. The method of claim 9, wherein the methylated DNA patterns are preserved for at least 1 hour, 2 hours, 3 hours, 4 hours, 5 hours, 6 hours, 7 hours, 10 hours, 12 hours, 16 hours, 20 hours, 24 hours, 2 days, 3 days, 4 days, 5 days, 6 days, 7 days, 10 days, two weeks, 15 days, 16 days, 17 days, 18 days, 19 days, 20 days, 21 days, 22 days, 23 days, 24 days, 25 days, 26 days, 27 days, 28 days, 29 days, 30 days, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 1 year, 18 months or 2 years in the composition when stored at room temperature (23° C.), at 4° C., between −30° C. to 50° C., between −30° C. to 30° C. or between −10° C. to 30° C.

\* \* \* \* \*

SEQUENCE LISTING

<160> NUMBER OF SEQ ID NOS: 45

<210> SEQ ID NO 1
<211> LENGTH: 345
<212> TYPE: DNA
<213> ORGANISM: Homo sapiens

<400> SEQUENCE: 1
tctgagggat tccttactct ttcctcttcc cgctcctttg cccgcgggtc tccccgcctg     60
accgcagccc cgaggccgcc gcgcacctcc tcccacgccc cttttggcgtg gtgccaccgg    120 acccctctgg ttcagtccca ggcggacccc cccctcaccg cgcgacccccg ccttttttcag  180 cacccccaggg tgagcccagc tcagactatc atccggaaag cccccaaaag tcccagccca  240
gcgctgaagt aacgggacca tgcccagtcc cacgccccgg agcaggaagg ctcgaggcgc   300 ccccaccccca cccgcccacc ctccccgctt ctcgctaggt cccga               345

<210> SEQ ID NO 2
<211> LENGTH: 370
<212> TYPE: DNA
<213> ORGANISM: Homo sapiens

<400> SEQUENCE: 2
ccctcgttcg cctcttctcc gggagccagt ccgcgccacc gccgccgccc aggccatcgc     60
caccctccgc agccatgtcc accaggtccg tgtcctcgtc ctcctaccgc aggatgttcg    120
gcggcccggg caccgcgagc cggccgagct ccagccggag ctacgtgact acgtccaccc   180

| | | |
|---|---|---|
| gcacctacag cctgggcagc gcgctgcgcc ccagcaccag ccgcagcctc tacgcctcgt | 240 | |
| ccccgggcgg cgtgtatgcc acgcgctcct ctgccgtgcg cctgcggagc agcgtgcccg | 300 | |
| gggtgcggct cctgcaggac tcggtggact tctcgctggc cgacgccatc aacaccgagt | 360 | |
| tcaagaacac | 370 | |

<210> SEQ ID NO 3
<211> LENGTH: 432
<212> TYPE: DNA
<213> ORGANISM: Unknown
<220> FEATURE:
<223> OTHER INFORMATION: Description of Unknown:
      Vimentin Nucleotide Sequence

<400> SEQUENCE: 3

| | | |
|---|---|---|
| gcttcctgga gcagcagaat aagatcctgc tggccgagct cgagcagctc aagggccaag | 60 | |
| gcaagtcgcg cctaggggac ctctacgagg aggagatgcg ggagctgcgc cggcaggtgg | 120 | |
| accagctaac caacgacaaa gcccgcgtcg aggtggagcg cgacaacctg gccgaggaca | 180 | |
| tcatgcgcct ccgggagaag taaggctgcg cccatgcaag tagctgggcc tcgggagggg | 240 | |
| gctggaggga gaggggaacg ccccccccggc ccccgcgaga gctgccacgc ccttggggat | 300 | |
| gtggccgggg ggaggcctgc cagggagaca gcggagagcg gggctgtggc tgtggtggcg | 360 | |
| cagccccgcc cagaacccag accttgcagt tcgcatttcc cctctgtcc ccacacattg | 420 | |
| cccaaggacg ct | 432 | |

<210> SEQ ID NO 4
<211> LENGTH: 509
<212> TYPE: DNA
<213> ORGANISM: Homo sapiens

<400> SEQUENCE: 4

| | | |
|---|---|---|
| tctgagggat tccttactct ttcctcttcc cgctcctttg ccgcggggtc tccccgcctg | 60 | |
| accgcagccc cgaggccgcc gcgcacctcc tcccacgccc ctttggcgtg gtgccaccgg | 120 | |
| acccctctgg ttcagtccca ggcggacccc ccctcaccg cgcgacccg ccttttttcag | 180 | |
| caccccaggg tgagcccagc tcagactatc atccggaaag ccccccaaaag tcccagccca | 240 | |
| gcgctgaagt aacgggacca tgcccagtcc cacgccccgg agcaggaagg ctcgaggcgc | 300 | |
| ccccacccca cccgcccacc ctccccgctt ctcgctaggt cccgattggc tggggcgctc | 360 | |
| cgcggctggg atggcagtgg gaggggaccc tctttcctaa cggggttata aaaacagcgc | 420 | |
| cctcggcggg gtccagtcct ctgccactct cgctccgagg tccccgcgcc agagacgcag | 480 | |
| ccgcgctccc accacccaca cccaccgcg | 509 | |

<210> SEQ ID NO 5
<211> LENGTH: 106
<212> TYPE: DNA
<213> ORGANISM: Homo sapiens

<400> SEQUENCE: 5

| | | |
|---|---|---|
| ctcgtcctcc taccgcagga tgttcggcgg cccgggcacc gcgagccggc cgagctccag | 60 | |
| ccggagctac gtgactacgt ccacccgcac ctacagcctg ggcagc | 106 | |

<210> SEQ ID NO 6
<211> LENGTH: 176
<212> TYPE: DNA
<213> ORGANISM: Homo sapiens

```
<400> SEQUENCE: 6
gcgactgcac ttggggcagc cccgccgcgt cccagccgcc tcccggcagg aagcgtaggt      60
gtgtgagccg acccggagcg agccgcgccc tcgggccagc gtgggcaggg cgccgcagcc     120
tgcgcagccc cgaggacccc gcgtcgctct cccgagccag ggttctcagg agcggg        176

<210> SEQ ID NO 7
<211> LENGTH: 390
<212> TYPE: DNA
<213> ORGANISM: Homo sapiens

<400> SEQUENCE: 7
cggggcaggc gcggcccgca aggacccccg cgatggagac gcaacactgc cgcgactgca      60
cttggggcag ccccgccgcg tcccagccgc ctcccggcag gaagcgtagg tgtgtgagcc     120
gacccggagc gagccgcgcc ctcgggccag cgtgggcagg gcgccgcagc ctgcgcagcc     180
ccgaggaccc cgcgtcgctc tcccgagcca gggttctcag gagcgggccg cgcaggagac     240
gttagagggg gttgttagcg gctgttggga gaacgggtca cggaaacagt cccttccaaa     300
gccggggcca tcgtggggtg ggcgagtccg ccctcccagg ccgggggcgc ggaccagagg     360
ggacgtgtgc agacggccgc ggtcagcccc                                     390

<210> SEQ ID NO 8
<211> LENGTH: 615
<212> TYPE: DNA
<213> ORGANISM: Unknown
<220> FEATURE:
<223> OTHER INFORMATION: Description of Unknown:
      Up10 nucleotide sequence

<400> SEQUENCE: 8
ccgtgactct ccctacctcc ccgactcccc aggcttctta cagtgacctc ttaccgtgcc      60
ccactccatg aatcgccaga gctattcgtc cctaaatttc aaaccttgcg caatgtccct     120
tcacagaccc ctccaggtat cacgcagccc gagccccga gccccgcccc ggggcctca      180 tcccgcccct tcgcgtccgc ggctcgtttt ccccactga gcgcccagct cccgcagttt     240
ccccggccgt cgagcgccgt gggcggggct ccagggcggg ggcgcctcgc ggggagggtc     300
ctccgtgctg ggggcgaggc cacccgaggc agctccccgc ccgcccccaa ccccgccccg     360
ctctcggagc ctataaaggg aggcgacccg cggcccgccc ggctggcatc cccagccgc     420 cgccagcccc gccgagggga gccagcgccg tctctgaggg gcgtccggcg ccggagccat     480
gaccctccgc cgactcagga agctgcagca gaaggaggag gcggcggcca ccccggaccc     540
cgccgcccgg actcccgact cggaagtcgc gccgccgct ccggtcccga ccccgggacc     600
ccctgccgca gccgc                                                     615

<210> SEQ ID NO 9
<211> LENGTH: 615
<212> TYPE: DNA
<213> ORGANISM: Unknown
<220> FEATURE:
<223> OTHER INFORMATION: Description of Unknown:
      Up10 nucleotide sequence

<400> SEQUENCE: 9
gcggctgcgg caggggggtcc cggggtcggg accggagcgg cgggcgcgac ttccgagtcg      60
ggagtccggg cggcggggtc cggggtggcc gccgcctcct ccttctgctg cagcttcctg     120
agtcggcgga gggtcatggc tccggcgccg gacgcccctc agagacggcg ctggctcccc     180
```

```
tcggcgggc  tggcggcggc  tgggggatgc  cagccgggcg  ggccgcgggt  cgcctcccct     240
tataggctcc  gagagcgggg  cggggttggg  ggcgggcggg  gagctgcctc  gggtggcctc     300
gcccccagca  cggaggaccc  tccccgcgag  gcgccgccgc  cctggagccc  cgcccacggc     360
gctcgacggc  cggggaaact  gcgggagctg  ggcgctcagt  gggggaaaac  gagccgcgga     420
cgcgaagggg  cgggatgagg  ccccggggc   ggggctcggg  gctcggggct  gcgtgatacc     480
tggaggggtc  tgtgaaggga  cattgcgcaa  ggtttgaaat  ttaggacga   atagctctgg     540 cgattcatgg  agtggggcac  ggtaagaggt  cactgtaaga  agcctgggga  gtcggggagg     600
tagggagagt  cacgg                                                           615

<210> SEQ ID NO 10
<211> LENGTH: 288
<212> TYPE: DNA
<213> ORGANISM: Unknown
<220> FEATURE:
<223> OTHER INFORMATION: Description of Unknown:
      Up10 nucleotide sequence

<400> SEQUENCE: 10
aaaccttgcg  caatgtccct  tcacagaccc  ctccaggtat  cacgcagccc  cgagccccga     60
gccccgcccc  gggggcctca  tcccgcccct  tcgcgtccgc  ggctcgtttt  ccccactga     120 gcgcccagct  cccgcagttt  cccggccgt   cgagcgccgt  gggcgggct   ccagggcggc    180 ggcgcctcgc  ggggagggtc  ctccgtgctg  ggggcgaggc  cacccgaggc  agctccccgc    240
ccgcccccaa  ccccgccccg  ctctcggagc  ctataaaggg  aggcgacc                  288

<210> SEQ ID NO 11
<211> LENGTH: 287
<212> TYPE: DNA
<213> ORGANISM: Unknown
<220> FEATURE:
<223> OTHER INFORMATION: Description of Unknown:
      Up10 nucleotide sequence

<400> SEQUENCE: 11
ggtcgcctcc  ctttataggc  tccgagagcg  gggcgggtt   ggggcgggc   ggggagctgc     60 ctcgggtggc  ctcgcccca   gcacggagga  ccctccccgc  gaggcgccgc  cgccctggag    120
ccccgcccac  ggcgctcgac  ggccggggaa  actgcgggag  ctgggcgctc  agtggggga    180 aacgagccgc  ggacgcgaag  gggcgggatg  aggccccgg   ggcggggctc  ggggctcggg    240
gctgcgtgat  acctggaggg  gtctgtgaag  ggacattgcg  caaggtt                    287

<210> SEQ ID NO 12
<211> LENGTH: 1539
<212> TYPE: DNA
<213> ORGANISM: Unknown
<220> FEATURE:
<223> OTHER INFORMATION: Description of Unknown:
      Up35-1/Up35-2 nucleotide sequence

<400> SEQUENCE: 12
tctggcccca  tgctcagctc  cgcggccatc  gctgaagcga  ggcgcagccg  ccgctgccgc     60
ccgggaaact  ttgcggccgg  ccggagcgcg  ccgagccaag  cgcggggggg  aagagcggag    120
aagagctggg  gaggcggga   gcgagggcgc  agcgggccgg  ggccgccggc  caagcctttg    180
tctggggacg  cggcggcgcg  ccggagagtc  ccgaggctgc  ctgcaccgcc  ccagagctct    240
gggctgtgcc  cgcgcaggga  ccgggccggg  tagagtcggg  cggggtggag  aggcaagcgg    300
```

```
agcgcgcggt ggggctgagg ggaggcgtgg ggcgagtgcc cgttgctcgc tctctagctc    360
tcttgctctt acgctctctc gctcgcagcc gctcgcagct cggcggtgca gctgtgctgg    420
atccggcggc gccgcagcct tttatcgcct cctgatgtca ctggggtgcg ggggcccggg    480
cggcccggtg cgcgggccaa tagctgcacg gcctccgcgg cccagcggcg cagggcgggg    540
cgcgcctgac agctcccccg ccccccgcgt cagctgactg gcggcccgag cggccccgga    600
gcggcggagg cctggcggag cgctggagcg gagtgggacg gccagcctgg gcccacccca    660
gtaccctgca ggtcccggcc cacgcacgct cgcctggagt gcgcgcccca cctctaggcc    720
aaatcaccgc tttcccctcc tcgcgcactc tcctccctca gttcccttfg cacccaccc    780 ccatcccgtg tcaccccaaa ggaggctcag aatgagcgcc gggacaacgc ctcctgggcc    840
ctttgttccc aagcggcccc cgcccagtgg gcgacgctct gtgtgtcctc gcggcttctg    900
gccgtgtgtg tcgtgcgttc ctgtttctgg agatctgcgc gtatttgtat gttggggagg    960
gcgggctcga ggctccgaga gttgtgttca gacccaactc ttaacctcag ggaccttfc   1020 tcaggccaag cgagggcccc tcctggcggg tgcagtcgca gagccctgag gttcgactcc   1080 actgccccg ccgctccccg cgttcacccc accgcacaat gttcacagtg aaggcgacgg    1140
gaaaagcagc agcccaaagg ctctgaattc ctcttccccg ccacacgcac ggaatcctga   1200 gccccggag cctcggggcc gaggccggcc cgggacggtg ctccgagtag ctctccactg    1260
ctggggagcc ggccctgttt tgtttgaac gttttgtaac gattaagcag atcccggcgt    1320
cagcccgccg cggagaggct caaacaggca taaagtgcga ccccaagtgg ccactgtgcg   1380
caaaggcgcc gcgaccgccc ggcccacggc cggaaggctt ggacggcgcc tcgtacccag   1440
ccaggtctcc cctacctggc ccaacccaag ccagcccaga acgcatacta tgtgtgcacc   1500
agagcccagg acaggttccc ctcgagcgat gtacaggtc                          1539
```

<210> SEQ ID NO 13
<211> LENGTH: 1539
<212> TYPE: DNA
<213> ORGANISM: Unknown
<220> FEATURE:
<223> OTHER INFORMATION: Description of Unknown:
    Up35-1/Up35-2 nucleotide sequence

<400> SEQUENCE: 13

```
gacctgtaca tcgctcgagg ggaacctgtc ctgggctctg gtgcacacat agtatgcgtt     60
ctgggctggc ttgggttggg ccaggtaggg gagacctggc tgggtacgag cgccgtcca    120 agccttccgg ccgtgggccg ggcggtcgcg gcgcctttgc gcacagtggc cacttgggt    180 cgcactttat gcctgtttga gcctctccgc ggcgggctga cgccgggatc tgcttaatcg    240
ttacaaaacg ttcaaacaaa aacagggccg gctcccagc agtggagagc tactcggagc    300
accgtcccgg gccggcctcg gccccgaggc tccgggggct caggattccg tgcgtgtggc    360
ggggaagagg aattcagagc ctttgggctg ctgcttttcc cgtcgccttc actgtgaaca    420
ttgtgcggtg gggtgaacgc ggggagcggc ggggccagtg gagtcgaacc tcagggctct    480
gcgactgcac ccgccaggag gggccctcgc ttggcctgag aaaggtcccc tgaggttaag    540
agttgggtct gaacacaact ctcggagcct cgagcccgcc ctccccaaca tacaaatacg    600
cgcagatctc cagaaacagg aacgcacgac acacacggcc agaagccgcg aggacacaca    660
gagcgtcgcc cactgggcgg gggccgcttg gaacaaagg gccaggagg cgttgtcccg     720 gcgctcattc tgagcctcct tgggggtgac acgggatggg ggtgggtgc aaagggaact     780
```

```
gagggaggag agtgcgcgag gaggggaaag cggtgatttg ccctagaggt ggggcgcgca    840
ctccaggcga gcgtgcgtgg gccgggacct gcagggtacg ggggtgggcc caggctggcc    900
gtcccactcc gctccagcgc tccgccaggc ctccgccgct ccggggccgc tcgggccgcc    960
agtcagctga cgcgggggc ggggagctg tcaggcgcgc ccgccctgc gccgctgggc       1020 cgcggaggcc gtgcagctat tggcccgcgc accgggccgc ccgggccccc gcacccagt    1080 gacatcagga ggcgataaaa ggctgcggcg ccgccggatc cagcacagct gcaccgccga    1140
gctgcgagcg gctgcgagcg agagagcgta agagcaagag agctagagag cgagcaacgg    1200
gcactcgccc cacgcctccc ctcagcccca ccgcgcgctc cgcttgcctc tccacccccgc   1260 ccgactctac ccggcccggt ccctgcgcgg gcacagccca gagctctggg gcggtgcagg    1320
cagcctcggg actctccggc gcgccgccg gtccccagac aaaggcttgg ccggcggccc     1380
cggcccgctg cgccctcgct ccccgcctcc ccagctcttc tccgctcttc cccccgcgc    1440 ttggctcggc gcgctccggc cggccgcaaa gtttcccggg cggcagcggc ggctgcgcct    1500
cgcttcagcg atggccgcgg agctgagcat ggggccaga                          1539

<210> SEQ ID NO 14
<211> LENGTH: 254
<212> TYPE: DNA
<213> ORGANISM: Unknown
<220> FEATURE:
<223> OTHER INFORMATION: Description of Unknown:
      Up35-1 nucleotide sequence

<400> SEQUENCE: 14
cctgcaccgc cccagagctc tgggctgtgc ccgcgcaggg accgggccgg gtagagtcgg     60
gcggggtgga gaggcaagcg gagcgcgcgg tgggctgag gggaggcgtg gggcgagtgc    120
ccgttgctcg ctctctagct ctcttgctct tacgctctct cgctcgcagc cgctcgcagc    180
tcggcggtgc agctgtgctg gatccggcgg cgccgcagcc ttttatcgcc tcctgatgtc    240
actggggtgc gggg                                                     254

<210> SEQ ID NO 15
<211> LENGTH: 254
<212> TYPE: DNA
<213> ORGANISM: Unknown
<220> FEATURE:
<223> OTHER INFORMATION: Description of Unknown:
      Up35-1 nucleotide sequence

<400> SEQUENCE: 15
ccccgcaccc cagtgacatc aggaggcgat aaaaggctgc ggcgccgccg gatccagcac     60
agctgcaccg ccgagctgcg agcggctgcg agcgagagag cgtaagagca agagagctag    120
agagcgagca acgggcactc gccccacgcc tcccctcagc ccaccgcgc gctccgcttg    180 cctctccacc ccgcccgact ctacccggcc cggtccctgc gcgggcacag cccagagctc    240
tggggcggtg cagg                                                     254

<210> SEQ ID NO 16
<211> LENGTH: 220
<212> TYPE: DNA
<213> ORGANISM: Unknown
<220> FEATURE:
<223> OTHER INFORMATION: Description of Unknown:
      Up 35-2 nucleotide sequence

<400> SEQUENCE: 16
```

```
gggaaaagca gcagcccaaa ggctctgaat tcctcttccc cgccacacgc acggaatcct    60
gagcccccgg agcctcgggg ccgaggccgg cccgggacgg tgctccgagt agctctccac   120
tgctggggag ccggccctgt ttttgtttga acgttttgta acgattaagc agatcccggc   180
gtcagcccgc cgcggagagg ctcaaacagg cataaagtgc                         220

<210> SEQ ID NO 17
<211> LENGTH: 220
<212> TYPE: DNA
<213> ORGANISM: Unknown
<220> FEATURE:
<223> OTHER INFORMATION: Description of Unknown:
      Up 35-2 nucleotide sequence

<400> SEQUENCE: 17
gcactttatg cctgtttgag cctctccgcg gcgggctgac gccgggatct gcttaatcgt    60
tacaaaacgt tcaaacaaaa acagggccgg ctccccagca gtggagagct actcggagca   120
ccgtcccggg ccggcctcgg ccccgaggct ccggggctc aggattccgt gcgtgtggcg    180
gggaagagga attcagagcc tttgggctgc tgcttttccc                         220

<210> SEQ ID NO 18
<211> LENGTH: 880
<212> TYPE: DNA
<213> ORGANISM: Homo sapiens

<400> SEQUENCE: 18
tctgagggat tccttactct ttcctcttcc cgctcctttg cccgcgggtc tccccgcctg    60
accgcagccc cgagaccgcc gcgcacctcc tcccacgccc ctttggcgtg gtgccaccgg   120
acccctctgg ttcagtccca ggcggacccc cccctcaccg cgcgaccccg cctttttcag   180
caccccaggg tgagcccagc tcagactatc atccggaaag cccccaaaag tcccagccca   240
gcgctgaagt aacgggacca tgcccagtcc caggccccgg agcaggaagg ctcgagggcg   300
cccccacccc acccgcccac cctccccgct tctcgctagg tccctattgg ctggcgcgct   360
ccgcggctgg gatggcagtg ggaggggacc ctctttccta acggggttat aaaaacagcg   420
ccctcggcgg ggtccagtcc tctgccactc tcgctccgag gtccccgcgc cagagacgca   480
gccgcgctcc caccacccac acccaccgcg ccctcgttcg cctcttctcc gggagccagt   540
ccgcgccacc gccgccgccc aggccatcgc caccctccgc agccatgtcc accaggtccg   600
tgtcctcgtc ctcctaccgc aggatgttcg gcggcccggg caccgcgagc cggccgagct   660
ccagccggag ctacgtgact acgtccaccc gcacctacag cctgggcagc gcgctgcgcc   720
ccagcaccag ccgcagcctc tacgcctcgt ccccgggcgg cgtgtatgcc acgcgctcct   780
ctgccgtgcg cctgcggagc agcgtgcccg gggtgcggct cctgcaggac tcggtggact   840
tctcgctggc cgacgccatc aacaccgagt tcaagaacac                         880

<210> SEQ ID NO 19
<211> LENGTH: 696
<212> TYPE: DNA
<213> ORGANISM: Homo sapiens

<400> SEQUENCE: 19
cggggctcgg ctgtcgcagc gcggtcgccg ccgaggacca cggtcggggc gcgggcgggc    60
tccagtgcgc aggcgcggcg ggcgggaggg gacgcgctcc gggcgcgcgc gcggggcagc   120
cggcgcccca actccgcccg ccccgcgccc cgcgcccgg cgcctcgccg cccgccgccc    180
```

```
gcccgccccg gcgccgccgc ccgcgccccg gcgccccggg ccggcgaggg gcgcgcccgc    240
ggccgcggcc gctgcatggc gctgagatgg cgggggcgcc gcgcggcgga ggcggcggcg    300
gaggcggcgc gggcgagccc gggggcgccg agcgggcggc cgggacaagc cgccggcgcg    360
ggctccgggc gtgcgacgag gagttcgctt gcccagagct ggaggcgctg ttccgcggct    420
acacgctgcg gctggagcag gcggccacgc tgaaggcgct ggccgttctc agcctgctgg    480
cgggcgcgct ggcgctggcc gagctgctgg gcgcgccggg cccgcgccc ggcctggcca    540 agggctcaca cccggtgcac tgcgtcctct tcctggcgct gctcgtggta accaacgtcc    600
ggtccctgca ggtgccccag ctgcagcagg tcggccagct ggcgctgctc ttcagcctca    660
ccttcgcgct gctctgctgt cctttcgcgc tgggcg                             696

<210> SEQ ID NO 20
<211> LENGTH: 55
<212> TYPE: DNA
<213> ORGANISM: Homo sapiens

<400> SEQUENCE: 20
gttcaaccct cggctccgcc gccggctcct tgcgccttcg gagtgtcccg cagcg          55

<210> SEQ ID NO 21
<211> LENGTH: 90
<212> TYPE: DNA
<213> ORGANISM: Homo sapiens

<400> SEQUENCE: 21
ctaaataaat acactttcct ttgtgttccc atatactcct tgttcccatg tcaactataa     60
cacatacgct accattttat aattacttaa                                     90

<210> SEQ ID NO 22
<211> LENGTH: 409
<212> TYPE: DNA
<213> ORGANISM: Homo sapiens

<400> SEQUENCE: 22
cggaaaggga cgtgagctga gcggcggggg agaagagtgc gcaggtcaga gggcggcgcg     60
cagcggcgct ccgcgaggtc cccacgccgg gcgatatggg gtgcctgctg tttctgctgc    120
tctgggcgct cctccaggct tggggaagcg ctgaaggtgg gtggaacgag ggcgcttgag    180
tgcactcgcg ggagggcgga gagggagc tgggtaggga cggggagggc aacgcctgat     240
ggggactggt gagacccggg acgcactggc gcgatctagg tagaaaactc gctgctccct    300
ggctccgggg agaggcagcg cggcacagag ttcgctggca tcagccgcct cctgaagctc    360
atctcctctt gtttctttct tccttctctt tatgctggct gctctcccg               409

<210> SEQ ID NO 23
<211> LENGTH: 54
<212> TYPE: DNA
<213> ORGANISM: Homo sapiens

<400> SEQUENCE: 23
gttgggcagc gcccccgcct ccagcagcgc ccgcacctcc tctacccgac cccg           54

<210> SEQ ID NO 24
<211> LENGTH: 147
<212> TYPE: DNA
<213> ORGANISM: Homo sapiens
```

```
<400> SEQUENCE: 24
gagcacttag cgaatgtggc acccctgaag tcgccccagg ttgggtctcc cccggggggca    60 ccagccggaa gcagccctcg ccagagccag cgttggcaag gaaggaggac tgggctcctc   120
cccacctgcc ccccacaccg ccctccg                                        147

<210> SEQ ID NO 25
<211> LENGTH: 42
<212> TYPE: DNA
<213> ORGANISM: Homo sapiens

<400> SEQUENCE: 25
gcccgcgctc taccgagccc agccagctcc tacctcggcc cg                        42

<210> SEQ ID NO 26
<211> LENGTH: 97
<212> TYPE: DNA
<213> ORGANISM: Homo sapiens

<400> SEQUENCE: 26
gcaagaggcg ggttttctc tcttgcaccc ccactcttcc cacccccttc cctcctctga     60
agcttctcga agactttcca aactctgcgc tcccccg                              97

<210> SEQ ID NO 27
<211> LENGTH: 723
<212> TYPE: DNA
<213> ORGANISM: Homo sapiens

<400> SEQUENCE: 27
cgggggattc cctcccatcc ccgagtgcag gagaagacgc cgagtctgag ccgcagccgc    60
ttctctagct ctataggaat cttgactcca agatcccagc cccacatccc ccgtccccag   120 taacccccgcg ccagcgtcgc aaccctcccg cgcccccct cccgcagacc ctggtcgaaa   180
tgtctcggcg ggctcccggg cccgggcc tgcgcttcat ccgcgggcgc cgcacctcca     240 gcgcccctc cctccgctcc cactcccact cccgccatcc ccggagctca gacttcccca   300
actgcagagc gccccgacgc gcccgcagcc ctcaccctgc cgagcgcggc ggccaccccc   360
gcccgagccg cggcgccccc agggaggaaa caaaagtgtc tccgcggcgc ccggagtccc   420
ccggagcagg acgcctcctc ccggcccag tccggcccc ctcccctgcc gcgccgaggt    480
cagcgagtcg gggcgcggcg ccagcccagg aaactttacg aacctgcttg ggtcgcagg   540 acagcagcgg caagggttcc cggcgatcag agctccggcg accgccacc attgaagggg   600 aactggaggc tctgtcgccc agcgtggggc cgcggcggcg tgggtggctc tgcctctatc   660
ctgtgcccat cctcgcccgc tcccgctcgc cccagcacac gcacttacac tctgggtcgg   720
ccg                                                                  723

<210> SEQ ID NO 28
<211> LENGTH: 440
<212> TYPE: DNA
<213> ORGANISM: Homo sapiens

<400> SEQUENCE: 28
cggtgcgtgg gtccaggaga gaaagaaagc gcggcggtgt cggtggcggc gcgcggcccc    60
actcaccatg atccgcagcg gctgtggcgc ggcgacccgg gcgggcggcg atgcgctgtc   120
cagggtagcc gggtccctct gcccggcgct atctcggcgc ccgcgccggt tacccccacc   180
cacacccacg cccggcgcgc gcacacccgc ccgcgcctcc ccgccccctc gggctcgcgc   240
```

```
cgccgccgcg cggcgctccg agcctcgggg ccgtttcgtc cccgccccct ctcccacagg     300
ggcctcgccg gccgccgcgc caggagggcg cgcggggag gggcgcaggg caagtgaggc      360 ggcgccccc gccctgcgg cctcgcgcgc cccctcctgg gcgaccgacc tcgccctcgc       420
gtccgcggcg tccctgccg                                                  440

<210> SEQ ID NO 29
<211> LENGTH: 206
<212> TYPE: DNA
<213> ORGANISM: Homo sapiens

<400> SEQUENCE: 29
cggcacgtgc gtagcgagtg ccgcgtcgac caggggcgcg tcgtcccgca gctgcaggcg     60
gaggctgcgc gtcagcggcg ggaagagctc cacgaagctc agctgctcgt tccattcggg    120
cgccgccgcc tcggcgctca ccgacgtctc gccctgaagg tggcgttaaa gacaggagaa    180
gggagatcag cgcggagtcg gggccg                                         206

<210> SEQ ID NO 30
<211> LENGTH: 71
<212> TYPE: DNA
<213> ORGANISM: Homo sapiens

<400> SEQUENCE: 30
cggcaggggc ggcggatccg tggcgaggcg ggaaccaggg ctagaggagg tgggctctta    60
tgtcgggggg c                                                          71

<210> SEQ ID NO 31
<211> LENGTH: 318
<212> TYPE: DNA
<213> ORGANISM: Homo sapiens

<400> SEQUENCE: 31
cggagcccag gaacatagtc cccgctggct agcggcggca gcagcagcag cggggcccct    60
gcgcgcggcg cccaccgtct cctcctcgcg ccgggctcgc ggtgttgcag gcggcagcca    120
cgcagactgc tctctcatcc ttttgtcctt cagtcagaac gtgaatgtac tgctgacgca    180
tactgttctg ggagaagatt agcgtgatgc agtgctctta tgtattagcg ccgctccccc    240
tccgtcgcct gcctcgcggg gttaacgccg gcgccttcca gcgccgcgcc ggccggcgcc    300
gcgcagcccc gcgcctcc                                                  318

<210> SEQ ID NO 32
<211> LENGTH: 57
<212> TYPE: DNA
<213> ORGANISM: Homo sapiens

<400> SEQUENCE: 32
cggtccccgc tcgccctccc gcccgcccac cgggcacccc agccgcgcag aaggcgg       57

<210> SEQ ID NO 33
<211> LENGTH: 72
<212> TYPE: DNA
<213> ORGANISM: Homo sapiens

<400> SEQUENCE: 33
cggcctcgct cgcttgctcg ctcgcccgcc cttgcccgct cgctcccgc ccgccgcctc     60 cctcgcgcgc cc                                                         72
```

<210> SEQ ID NO 34
<211> LENGTH: 99
<212> TYPE: DNA
<213> ORGANISM: Homo sapiens

<400> SEQUENCE: 34
gccatattga aactggcacg gtttctaaag actccttccc cgcagttgtg gcgcttccaa    60
gaaaacacga gtacggatca ggctctggat gagtgtccg                           99

<210> SEQ ID NO 35
<211> LENGTH: 424
<212> TYPE: DNA
<213> ORGANISM: Homo sapiens

<400> SEQUENCE: 35
gcacgcatat taaaaaataa actccagaac cagctcaagt cagcaatttt gaaaggggt     60 cgaataagag gagacaaccg gaaagcccct aagtgacagg atattacttt aaagagaaaa   120
taatgaacaa aaagaccatc ctcgctggag cacgctccaa aactactact gccaatttta   180
tttcagttgc tcaggcaaat gtttccaagg gagcgattcc gaatgtctgc acgatttta    240 cccccatgcc ggtctccgat tccccgtcct caccatcttt ttctcccacc caaaccaaaa   300
gaaaggggag accccagcgc ggaggagacg cgggagcgcg gggtaggtag cagcggcggc   360
tgcgtcgcta aaatgagtgc agaaacgagg aaggtgggcg gcgggagggg acaggctgcg   420
cccg                                                                424

<210> SEQ ID NO 36
<211> LENGTH: 590
<212> TYPE: DNA
<213> ORGANISM: Homo sapiens

<400> SEQUENCE: 36
cggcgtgtcg ccatcgttca gcctcgctgc ccaggtggga ggggtcacct gccgcggggt    60
ctccaagcca gtgccgcttg ctcccggccc ccacccactg acagcacggc gtccgagtga   120
ccctgtctag cctcgttctg cgctcctgca aaccacgttg ctgcgctaac tacaaacctg   180
gccaacatgt ctttgtaacc ctatcattta aaaacgcttc caggcacctg gccgctgcca   240
gatcaggttc gcgggcccgg aggaggtcct cccacctgcc ccgccagcc cggggaccg    300 tgcgcggcct ccgtgtggcc cccgcccacg aggtccctcg ggcaggaacc gccgcgcgac   360
ctctgttcag cggccgcgtc ctggccacgg gcgacccctg tcgggaaccc tgttcccggc   420
taagctgcgt tcccgcattc cggtggctct cacccgagct cgcgtttgct ggctttccct   480
ctggctcctc tgcctgaccc cgattttgtc tccgaactcc actccagat cctccccgcc    540 ctggaacgcc gacctttccc ccgcacttcg ccgcccactc acatccccg               590

<210> SEQ ID NO 37
<211> LENGTH: 93
<212> TYPE: DNA
<213> ORGANISM: Homo sapiens

<400> SEQUENCE: 37
cgggagaagg ctcggctccc tcctaaacat gtggcccgtg gcgtcccctt gtccctccg     60 agcgatgctc ctgcgccctt cgccgcctcc cgc                                 93

<210> SEQ ID NO 38
<211> LENGTH: 363

<212> TYPE: DNA
<213> ORGANISM: Homo sapiens

<400> SEQUENCE: 38
cggaggagct gcgcggacgc agcggcttcc aggccacccc accccgcgcc agcctgcacc    60
tgtgccgcct gggtgtcttc cccgagactc tggtactgtg aagggtccgg gtcgcgcggg   120
gcgtcgtccg gagcagggcg gactcgggct ttggcgcggc ctttgccccg gtttttggcg   180
cgggaggact ttcgacgggg acttcggccg ctcatggtgg cggcggaggc agcttcaaag   240
acacgctgtg accctgcggc tcctgacgcc agctctcggt cgggaccgag cgggtctctc   300
cacggcaacc gccgacgtca cgaacgtaca actgtaccgt cgcgagagga cgtgatgcgc   360
ccg                                                                  363

<210> SEQ ID NO 39
<211> LENGTH: 72
<212> TYPE: DNA
<213> ORGANISM: Homo sapiens

<400> SEQUENCE: 39
cgcgcgggat cgagggagca ggagccgcgg ctgacgggtc gcgggcgccg cgctaggctc    60
ggctccggtc cc                                                        72

<210> SEQ ID NO 40
<211> LENGTH: 88
<212> TYPE: DNA
<213> ORGANISM: Homo sapiens

<400> SEQUENCE: 40
cggaagttga gtggggccgc ggggcctgct gggaggtgtt gtcctcggaa acgtcgctgg    60
cgcggaggga tggttcggcg ctttaggc                                       88

<210> SEQ ID NO 41
<211> LENGTH: 169
<212> TYPE: DNA
<213> ORGANISM: Homo sapiens

<400> SEQUENCE: 41
cggaagttga gtggggccgc ggggcctgct gggaggtgtt gtcctcggaa acgtcgctgg    60
cgcggaggga tggttcggcg ctttaggcgt ctgtcacaga cctatctgcg ggtcgccttc   120
acccagcatc tcagaaactg cgcgcgggat gaacattcgg gtgtttccg               169

<210> SEQ ID NO 42
<211> LENGTH: 287
<212> TYPE: DNA
<213> ORGANISM: Homo sapiens

<400> SEQUENCE: 42
cggggccaca ctcagccaga cgaatgtctg gcaaatgaca gtcacttcac gccagactct    60
cacagtcctt cacacgccac tcccactgcc tcagggaacc acaagcacag gcatcgcccc   120
gcccggcgtc ctcctccaaa gattggggca ccaggaccgc gggcccccac tcccacccag   180
cacaaagagt ccggcgctca gagctagcgg tttcccgagg actcaccacc aagcccgcgg   240
acacaggccc cgattccaca cttaacgctg ccaaagtggc agagccg                 287

<210> SEQ ID NO 43
<211> LENGTH: 511
<212> TYPE: DNA

```
<213> ORGANISM: Homo sapiens

<400> SEQUENCE: 43
cggaagcgga tcgcgtgggt agaaggtcac accgcagcgc gtcagtttcc ctttgtttag        60
attcaatctg ggcttcccag ctcccccgcg cttctgtacc cgggatctga gagtcaacac       120
agaccttgaa atccccgcac cgctccctcc accccgtgta aattcaggcg tctccgtgag       180
agtccggcgc tcgcttccct gtgtgttaaa atcgctcggc gacgggtcct gtccccgctc       240
gttctgcctt gggccaggta aacacggatt ttcgagactc ctttccgctt aaaactcttt       300
actgacccaa cgtcctgccc cgcgctttta aaagtcctta ccgcaaggtg gattcccgcc       360
cggggagcct cccaacctcg cccccggccc ctgaagcgca gcgccgcagc cccagtcccg       420 gcggggagg ccgcgtcctg tactgggtcc tgggaccctt gagaccccac acttctaata       480
attcagcccc accctttcc tccttgatcc g                                       511

<210> SEQ ID NO 44
<211> LENGTH: 146
<212> TYPE: DNA
<213> ORGANISM: Homo sapiens

<400> SEQUENCE: 44
cgggagcggc aggcgtctcg atcggggacg caggcacttc cgtccctgca gagcatcaga        60
cgcgtctcgg gacactgggg acaacatctc ctccgcgctt tcccaacacc tccacctgcg       120
gcccacacaa gcgttacaga accccg                                            146

<210> SEQ ID NO 45
<211> LENGTH: 128
<212> TYPE: DNA
<213> ORGANISM: Homo sapiens

<400> SEQUENCE: 45
cgggatcaca gcacttccca cgcacaaacc acacacgggg tctggactct gccctgagga        60
cgcttccatt gtccccgcag tcggggcaga cgcaagaacg cgcgcggctc ttcccagggt       120
gggctccg                                                                128
```